US007456335B2

(12) United States Patent
Kogel et al.

(10) Patent No.: US 7,456,335 B2
(45) Date of Patent: Nov. 25, 2008

(54) NUCLEIC ACID SEQUENCES AND THEIR USE IN METHODS FOR ACHIEVING PATHOGEN RESISTANCE IN PLANTS

(75) Inventors: Karl-Heinz Kogel, Lollar (DE); Ralph Hückelhoven, Giessen (DE); Holger Schultheiss, Freidberg (DE); Markus Frank, Mannheim (DE)

(73) Assignee: BASF Plant Science GmbH (DE)

( * ) Notice: Subject to any disclaimer, the term of this patent is extended or adjusted under 35 U.S.C. 154(b) by 238 days.

(21) Appl. No.: 10/488,222

(22) PCT Filed: Aug. 3, 2002

(86) PCT No.: PCT/EP02/09719

§ 371 (c)(1),
(2), (4) Date: Mar. 2, 2004

(87) PCT Pub. No.: WO03/020939

PCT Pub. Date: Mar. 13, 2003

(65) Prior Publication Data
US 2005/0132439 A1 Jun. 16, 2005

(30) Foreign Application Priority Data
Sep. 3, 2001 (DE) ................ 101 42 579
Jul. 2, 2002 (DE) ................ 102 29 729

(51) Int. Cl.
C12N 15/09 (2006.01)
C12N 15/82 (2006.01)
C12N 15/29 (2006.01)
A01H 5/00 (2006.01)

(52) U.S. Cl. ............ 800/279; 800/278; 800/286; 800/317; 800/320; 800/298; 435/320.1; 435/468; 435/419; 536/23.6; 536/24.5

(58) Field of Classification Search ............ 800/279
See application file for complete search history.

(56) References Cited

U.S. PATENT DOCUMENTS

| 4,801,340 | A | 1/1989 | Inoue et al. |
|---|---|---|---|
| 4,962,028 | A | 10/1990 | Bedbrook et al. |
| 4,987,071 | A | 1/1991 | Cech et al. |
| 5,034,323 | A | 7/1991 | Jorgensen et al. |
| 5,116,742 | A | 5/1992 | Cech et al. |
| 5,187,267 | A | 2/1993 | Comai et al. |
| 5,352,605 | A | 10/1994 | Fraley et al. |
| 5,428,148 | A | 6/1995 | Reddy et al. |
| 5,504,200 | A | 4/1996 | Hall et al. |
| 5,565,350 | A | 10/1996 | Kmiec |
| 5,593,874 | A | 1/1997 | Brown et al. |
| 5,608,152 | A | 3/1997 | Kridl et al. |
| 5,683,439 | A | 11/1997 | Jensen |
| 5,689,049 | A | 11/1997 | Cigan et al. |
| 5,689,051 | A | 11/1997 | Cigan et al. |
| 5,698,425 | A | 12/1997 | Ligon et al. |
| 5,712,135 | A | 1/1998 | D'Halluin et al. |
| 5,789,214 | A | 8/1998 | Ryals et al. |
| 5,804,693 | A | 9/1998 | Gaffney et al. |
| 6,100,451 | A | 8/2000 | Chappell et al. |
| 6,110,736 | A | 8/2000 | Hodges et al. |
| 6,555,732 | B1 * | 4/2003 | Duvick et al. ............ 800/279 |
| 6,806,085 | B1 | 10/2004 | Sonnewald et al. |
| 2005/0100907 | A1 | 5/2005 | Kreutzer et al. |

FOREIGN PATENT DOCUMENTS

| CA | 2 348 888 A1 | 5/2000 |
|---|---|---|
| EP | 0 375 091 A1 | 12/1988 |
| EP | 0 332 104 A2 | 9/1989 |
| EP | 0 335 528 A2 | 10/1989 |
| EP | 0 388 186 A1 | 9/1990 |
| EP | 0 409 625 A1 | 1/1991 |
| EP | 0 120 516 B1 | 10/1991 |
| EP | 0 321 201 B1 | 12/1994 |
| EP | 0 291 533 B1 | 10/1995 |
| EP | 0 360 257 B1 | 11/1996 |
| EP | 1 041 148 A1 | 10/2000 |
| WO | WO-84/02913 A1 | 8/1984 |
| WO | WO-91/13980 A1 | 9/1991 |
| WO | WO-91/13991 A1 | 9/1991 |
| WO | WO-92/16635 A1 | 10/1992 |
| WO | WO-93/21334 A1 | 10/1993 |

(Continued)

OTHER PUBLICATIONS

Schweizer et al. The Plant J. (2000) 24(6), pp. 895-903.*
Zheng et al. Plant Mol. Biol. 44, pp. 1-9 (2000).*
Schiene et al. Mol Gen Genet (2000) 263:761-770.*
Altschul et al., Gapped Blast and PSI-Blast: a new generation of protein database search programs. *Nucleic Acids Research*, vol. 25, No. 17, pp. 3389-3402 (Aug. 15, 1997).
An et al., New cloning vehicles for transformation of higher plants. *The EMBO Journal*, vol. 4, No. 2, pp. 277-284 (1985).
Anandalakshmi et al., A viral suppressor of gene silencing in plants. *Proc. Natl. Acad. Sci. USA*, vol. 95, pp. 13079-13084 (Oct. 1998).
Angell et al., Potato virus X amplicon-mediated silencing of nuclear genes. *The Plant Journal*, vol. 20, No. 3, pp. 357-362 (1999).
Ansari et al., Towards a motif for artificial transcriptional activators. *Chem & Biol.*, vol. 8, pp. 583-592 (2001).

(Continued)

*Primary Examiner*—Medina A Ibrahim
(74) *Attorney, Agent, or Firm*—Connolly Bove Lodge & Hutz LLP

(57) ABSTRACT

The invention relates to novel RacB cDNA sequences from barley and to expression cassettes and vectors comprising these promoter sequences. The invention furthermore relates to transgenic plants transformed with these expression cassettes or vectors, to cultures, parts or transgenic propagation material derived from them, and to their use for the production of foodstuffs, feeding stuffs, seed, pharmaceuticals or fine chemicals. The invention furthermore relates to methods of generating or increasing a pathogen resistance in plants by reducing the expression of an RacB protein or of a functional equivalent thereof.

41 Claims, 7 Drawing Sheets

FOREIGN PATENT DOCUMENTS

| WO | WO-94/21794 A1 | 9/1994 |
|----|----------------|--------|
| WO | WO-95/15389 A2 | 6/1995 |
| WO | WO-95/19443 A2 | 7/1995 |
| WO | WO-95/23230 A1 | 8/1995 |
| WO | WO-96/12814 A1 | 5/1996 |
| WO | WO-96/28561 A1 | 9/1996 |
| WO | WO-96/34949 A1 | 11/1996 |
| WO | WO-97/05900 A1 | 2/1997 |
| WO | WO-97/32016 A1 | 9/1997 |
| WO | WO-97/41228 A3 | 11/1997 |
| WO | WO-98/03536 A1 | 1/1998 |
| WO | WO-98/04586 A2 | 2/1998 |
| WO | WO-98/22593 A1 | 5/1998 |
| WO | WO-98/45456 A1 | 10/1998 |
| WO | WO-98/45461 A1 | 10/1998 |
| WO | WO-99/16890 A2 | 4/1999 |
| WO | WO-99/27114 A1 | 6/1999 |
| WO | WO-99/32619 A1 | 7/1999 |
| WO | WO-99/47552 A2 | 9/1999 |
| WO | WO-99/50428 A2 | 10/1999 |
| WO | WO-99/53050 A1 | 10/1999 |
| WO | WO-99/66057 A2 | 12/1999 |
| WO | WO-00/01722 A1 | 1/2000 |
| WO | WO-00/01830 A1 | 1/2000 |
| WO | WO-00/15815 A1 | 3/2000 |
| WO | WO-00/26388 A2 | 5/2000 |
| WO | WO-00/44895 A1 | 8/2000 |
| WO | WO-00/44914 A1 | 8/2000 |
| WO | WO-00/49035 A1 | 8/2000 |
| WO | WO-00/60086 A1 | 10/2000 |
| WO | WO-00/63364 A2 | 10/2000 |
| WO | WO-00/68374 A1 | 11/2000 |

OTHER PUBLICATIONS

Bartel et al., Isolation of New Ribozymes from a Large Pool of Random Sequences. *Science*, vol. 261, pp. 1411-1418 (Sep. 10, 1993).

Baumlein et al., A novel seed protein gene from *Vicia faba* is developmentally regulated in transgenic tobacco and *Arabidopsis* plants. *Mol Gen Genet*, vol. 225, pp. 459-467 (1991).

Baumlein et al., Database NCBI Gen Bank, Accession No. X03677. 1, May 24, 1995.

Baumlein et al., Upstream sequences regulating legumin gene expression in heterologous transgenic plants. *Mol Gen Genet*, vol. 225, pp. 121-128 (1991).

Baumlein, Cis-analysis of a seed protein gene promoter: the conservative RY repeat CATGCATG within the legumin box is essential for tissue-specific expression of a legumin gene. *The Plant Journal*, vol. 2, No. 2, pp. 233-239 (1992).

Bayley et al., Exchange of gene activity in transgenic plants catalyzed by the Cre-*lox* site-specific recombination system. *Plant Molecular Biology*, vol. 18, pp. 353-361 (1992).

Bechtold et al., *In plantar Agro bacterium* mediated gene transfer by infiltration of adult *Arabidopsis thaliana* plants. *C. R. Acad. Sic. Paris*, vol. 316, pp. 1194-1199 (1993).

Beerli et al., Chemically Regulated Zinc Finger Transcription Factors. *The Journal of Biological Chemistry*, vol. 275, No. 42, pp. 32617-32627 (Oct. 20, 2000).

Beerli et al., Positive and negative regulation of endogenous genes by designed transcription factors. *Proc. Natl. Acad. Sci. USA*, vol. 97, No. 4, pp. 1495-1500 (Feb. 15, 2000).

Beerli et al., Toward controlling gene expression at will: Specific regulation of the *erB-2/HER*-2 promoter by using polydactyl zinc finger proteins constructed from modular building blocks. *Proc. Natl. Acad. Sci. USA*, vol. 95, pp. 14628-14633 (Dec. 1998).

Benard et al., Characterization of Rac and Cdc42 in Chemoattractant-stimulated Human Neutrophils Using a Novel Assay for Active GTPases. *The Journal of Biological Chemistry*, vol. 274, pp. 13198-13204 (May 7, 1999).

Benfey et al., The CaMV 35S enhancer contains at least two domains which can confer different developmental and tissue-specific expression patterns. *The EMBO Journal*, vol. 8, No. 8, pp. 2195-2202 (1989).

Berger et al., Expression in transgenic plants of a viral gene product that mediates insect transmission of polyviruses. *Proc. Natl. Acad. Sci. USA*, vol. 86, pp. 8402-8406 (Nov. 1989).

Bevan, M., Binary *Agrobacterium* vectors for plant transformation. *Nucleic Acids Research*, vol. 12, No. 22, pp. 8711-8721 (Nov. 22, 1984).

Bilang et al., The 3'-terminal region of the hygromycin-B-resistance gene is important for its activity in *Escherichia coli* and *Nicotiana tabacum*. Gene, vol. 100, pp. 247-250 (1991).

Bremer et al., Inhibition of Major Groove DNA Binding bZIP Proteins by Positive Patch Polyamides. *Bioorganic and Medical Chemistry*, vol. 9, pp. 2093-2103 (2001).

Broglie et al., Transgenic Plants with enhanced resistance to the Fungal Pathogen *Rhizoctonia solani* . . . *Science*, vol. 254, pp. 1194-1197 (Nov. 1991).

Bruce et al., Photoregulation of a phytochrome gene promoter from oat transferred into rice by particle bombardment. *Proc. Natl. Acad. Sci. USA*, vol. 86, pp. 9692-9696 (Dec. 1989).

Buchel et al., The *PR-1a* promoter contains a number of elements that bind GT-1-like nuclear factors with different affinity. *Plant Molecular Biology*, vol. 30, pp. 493-504 (1996).

Burstein et al., The ras-related GTPases rac1 regulates a proliferative pathway selectively utilized by G-protein coupled receptors. *Oncogene*, vol. 17, No. 2, pp. 1617-1623 (Sep. 1998).

Bushchges et al., The Barley *Mlo* Gene: A Novel Control Element of Plant Pathogen Resistance. *Cell*, vol. 88, pp. 695-705 (Mar. 7, 1997).

Bustos et al., Regulation of β-Glucuronidase Expression in Transgenic Tobacco Plants by an A/T-Rich, *cis*-Acting Sequence Found Upstream of a French Bean β-Phaseolin Gene. *The Plant Cell*, vol. 1, pp. 839-853 (Sep. 1989).

Chandra et al., The Pto kinase mediates a signaling pathway leading to the oxidative burst in tomato. *Proc. Natl. Acad. Sci. USA*, vol. 93, pp. 13393-13397 (Nov. 1996).

Chen et al., The promoter of a $H_2O_2$-inducible, *Arabidopsis* gluthatione *S*-transferase gene contains closely linked OBF- and OBP1-binding sites. *The Plant Journal*, vol. 10, No. 6, pp. 955-966 (1996).

Chiang et al., Targeting the Ets Binding Site of the HER2/*neu* Promoter with Pyrrole-Imidazole Polyamides. *J. Biol. Chem.*, vol. 275, No. 32 (Aug. 11, 2000).

Chiu et al., Engineered GFP as a vital reporter in plants. *Current Biology*, vol. 6, No. 3, pp. 325-330 (1996).

Christensen et al., Maize polyubiquitin genes: structure, thermal perturbation of expression and transcript splicing, and promoter activity following transfer to protoplasts by electroporation. *Plant Molecular Biology*. vol. 18, pp. 675-689 (1992).

Chua et al., A novel RU486 inducible system for the activation and repression of genes. *Adv. Drug Delivery Rev.*, vol. 30, No. (1,3) pp. 23-31 (Mar. 2, 1998).

Clough et al., Floral dip: a simplified method for *Agrobacterium*-mediated transformation of *Arabidopsis thalina*. *The Plant Journal*, vol. 16, No. 6, pp. 735-743 (1998).

Cole-Strauss et al., Targeted gene repair directed by the chimeric RNA/DNA oligonucleotide in a mammalian cell-free extract. *Nucleic Acids Research*, vol. 27, No. 5, pp. 1323-1330 (1999).

Cordero et al., Expression of a maize proteinase inhibitor gene is induced in response to wounding and fungal infection: systemic wound-response of a monocot gene. *The Plant Journal*, vol. 6, No. 2, pp. 141-150 (1994).

De Block et al., Transformation of *Brassica napus* and *Brassica oleracea* Using *Agrobacterium tumefaciens* and the expression of the *bar* and *neo* Genes in the Transgenic Plants. *Plant Physiol.*, vol. 91, pp. 694-701 (1989).

De Feyter et al., A ribozyme gene and an antisense gene are equally effective in conferring resistance to tobacco mosaic virus on transgenic tobacco. *Mol Gen Genet*, vol. 250, pp. 329-338 (1996).

Dellaporta et al., Molecular Cloning of the Maize *R-nj* Allele by Transposon Tagging with *Ac. In Chromosome Structure and Function: Impact of New Concepts, 18th Stadler Genetics Symposium*, vol. 11, pp. 263-282 (1988).

Dervan et al., Sequence-specific DNA recognition by polyamides. *Current Opinion in Chem. Biol.*, vol. 3, No. 6, pp. 688-693 (Dec. 1999).

Devoto et al., Topology, Subcellular Localization, and Sequence Diversity of the Mlo Family in Plants. *The Journal of Biological Chemistry*, vol. 274, pp. 34993-35004 (Dec. 3, 1999).

Diekmann et al., Interaction of Rac with $p67^{phox}$ and Regulation of Phagocytic NADPH Oxidase Activity. *Science*, vol. 265, pp. 531-533 (Jul. 22, 1994).

Dreier et al., Insights into the Molecular Recognition of the 5'-GNN-3' Family of DNA Sequences by Zinc Finger Domains. *J. Mol. Biol.*, vol. 303, pp. 489-502 (2000).

Dreier et al., Development of Zinc Finger Domains for Recognition of the 5'-ANN-3' Family of DNA Sequences and Their Use in the Construction of Artificial Transcription Factors. *The Journal of Biological Chemistry*, vol. 276, No. 31, pp. 29466-29478 (Aug. 3, 2001).

Duan et al., Transgenic rice plants harboring an introduced potato proteinase inhibitor II gene are insect resistant. *Nature Biotechnology*, vol. 14, pp. 494-498 (Apr. 1996).

Dunwell et al., Transgenic approaches to crop improvement. *Journal of Experimental Biology*, vol. 51, pp. 487-496 (Feb. 2000).

Dusi et al., Mechanisms of NADPH oxidase activation: translocation of $p40_{phox}$, $^{Rac1}$ and rac2 from the cytosol to the membranes in human neutrophlis lacking $p47_{phox}$ or $p67_{phox}$. *Biochem. J.*, vol. 314, pp. 409-412 (1996).

Eckelkamp et al., Wound-induced systemic accumulation of a transcript coding for a Bowman-Birk tryspin inhibitor-related protein in maize (*Zea mays* L.). *FEBS*, vol. 323, No. 1,2, pp. 73-76 (May 1993).

Fagard et al., Systemic silencing signal(s). *Plant Molecular Biology*, vol. 43, pp. 285-293 (2000).

Famulok et al., Aptamers as Tools in Molecular Biology and Immunology. *Combinational Chemistry in Biology*, vol. 243, pp. 123-136 (1999).

Fennell et al., Electroporation and PEG delivery of DNA into maize microspores. *Plant Cell Reports*, vol. 11, pp. 567-570 (1992).

Fire et al., Potent and specific genetic interference by double-stranded RNA in *Caenorhabditis elegans*, *Nature*, vol. 391, pp. 806-811 (Feb. 1998).

Fowler et al., Database NCBI Gen Bank, Accession No. AF380335.1, May 22, 2001.

Fowler et al., Database NCBI Gen Bank, Accession No. AJ278665.1, Aug. 2, 2001.

Franck et al., Nucleotide Sequence of Cauliflower Mosaic Virus DNA. *Cell*, vol. 21, pp. 285-294 (Aug. 1980).

Franken et al., Recombinant proteins from transgenic plants. *Current Opinion in Biotechnology*, vol. 8, pp. 411-416 (1997).

Fredricksen et al., Database NCBI Gen Bank, Accession No. BM816965, Mar. 5, 2002.

Freialdehoven et al., Indentification of Genes Required for the Function of Non-Race-Specific *mlo* Resistance to Powdery Mildew in Barley. *The Plant Cell*, vol. 8, pp. 5-14 (Jan. 1996).

Friedrich et al., A benzothiadazole derivative induces systematic acquired resistance in tobacco. *The Plant Journal*, vol. 10(1), pp. 61-70 (1996).

Gallie et al., A comparison of eukaryotic viral 5'-leader sequences as enhancers of mRNA expression *in vivo*. *Nucleic Acids Research*, vol. 15, No. 21, pp. 8693-8711 (1987).

Gardner et al., Potato spindle tuber virois infections mediated by the Ti plasmid of *Agrobacterium tumefaciens*. *Plant Molecular Biology*, vol. 6, pp. 221-228 (1986).

Gatz et al., Stringent repression and homogeneous de-repression by tetracycline of a modified CaMV 35S promoter in intact transgenic tobacco plants. *The Plant Journal*, vol. 2, No. 3, pp. 397-404 (1992).

Gatz, C., Chemical Control of Gene Expression, *Annu. Rev. Plant Physoil Mol. Biol.*, vol. 48, pp. 89-108 (1997).

Gautier et al., α-DNA IV: α-anomeric and β-anomeric tetrathymidylates covalently linked to intercalating oxazolopyridocarbazole. *Nucleic Acids Research*, vol. 15, No. 16 pp. 6625-6641 (1987).

Gielen et al., The complete nucleotide sequence of the TL-DNA of the *Agrobacterium tumefaciens* plasmid PTiAch5. *The EMBO Journal*, vol. 3, No. 4, pp. 825-846 (1984).

Goring et al., Transformation of a partial nopaline synthase gene into tobacco suppresses the expression of a resident wild-type gene. *Proc. Natl. Acad. Sci.* USA, vol. 88, pp. 1770-1774 (Mar. 1991).

Gottesfeld et al., Chemical Approaches to Control Gene Expression. *Gene Expression*, vol. 9, No. 1/2, pp. 77-91 (2000).

Gottesfeld, Sequence-specific Recognition of DNA in the Nucleosome by Pyrrole-Imidazole Polyamides. *J. Mol. Biol.*, vol. 309, No. 3, pp. 615-629 (2001).

Greulich et al., Single cell and single molecule laser biotechnology. *SPIE*, vol. 2629, pp. 62-69 (1993).

Groom et al., *rbohA*, a rice homologue of the mammalian *gp91phox* respiratory burst oxidase gene. *The Plant Journal*, vol. 10, No. 3, pp. 515-522 (1996).

Guerche et al., Direct Gene Transfer by Electroporation in *Brassica napus*. *Plant Science*, vol. 52, pp. 111-116 (1987).

Haseloff et al., Removal of a cryptic and subcellular localization of green fluorescent protein are required to mark transgenic *Arabidopsis* plants brightly. *Proc. Natl. Acad, Sci.* USA, vol. 94, pp. 2122-2127 (Mar. 1997).

Haseloff et al., Simple RNA enzymes with new and highly specific endoribonuclease activities. *Nature*, vol. 334, pp. 585-591 (Aug. 1988).

Hassanain et al., Database NCBI Gen Bank, Accession No. AF126052.1, Jun. 2, 1999.

Hassanain et al., Plant Rac Proteins Induce Superoxide Production In Mammalian Cells. *Biochemical and Biophysical Communications*, vol. 272, pp. 783-788 (2000).

Hassanian et al., Database NCBI Gen Bank, Accession No. AF126053.1, Jun. 2, 1999.

Helene et al., Control of Gene Expression of Triple Helix-Forming Oligonucleotides. *Annals N.Y. Acad. of Sciences*, vol. 660, pp. 27-36 (1992).

Helene, C., The anti-gene strategy: control of gene expression by triplex-forming-oligonucleotides. *Anti-Cancer Drug Design*, vol. 6, pp. 569-584 (Aug. 1991).

Herskowitz, I., Functional inactivation of genes by dominant negative mutations. *Nature*, vol. 329, pp. 219-222 (Sep. 17, 1987).

Hill et al., The Rho family GTPases RhoA, Rac1, and CDC42Hs Regulate Transcriptional Activation by SRF. *Cell*, vol. 81, pp. 1159-1170 (Jun. 30, 1995).

Hillebrand et al., Database NCBI Gen Bank, Accession No. Y07648.2, Dec. 20, 1999.

Hillebrand et al., Structure of the gene encoding nitrilase 1 from *Arabidopsis thaliana*. *Gene*, vol. 170, pp. 197-200 (1996).

Hohn et al. Gene therapy in plants. *Proc. Natl. Acad. Sci.* USA, vol. 96, pp. 8321-8323 (Jul. 1999).

Holsters et al., Transfection and Transformation of *Agrobacterium tumefaciens*. *Molec. Gen. Genet.*, vol. 163, pp. 181-187 (1978).

Holtorf et al., Comparison of different constitutive and inducible promoters for the overexpression of transgenes in *Arabidopsis thalina*. *Plant Molecular Biology*, vol. 29, pp. 637-646 (1995).

Hood et al., Plant-based production of xenogenic proteins. *Current Opinion in Biotechnology*, vol. 10, No. 4, pp. 382-386 (Aug. 1999).

Horsch et al., SA simple and General Method for Transferring Genes into Plants. *Science*, vol. 227, No. 4689, pp. 1229-1231 (Feb. 22, 1985).

Howell et al., Cloned Cauliflower Mosaic Virus DNA Infects Turnips (*Brassica rapa*). *Science*, vol. 208, No. 4449, pp. 1265-1267 (Jun. 13, 1980).

Huckelhoven et al., Differential expression of putative cell death regulator genes in near-isogenic, resistant and susceptible barley lines during interaction with the powdery mildew fungus. *Plant Molecular Biology*, vol. 47, pp. 739-748 (2001).

Inoue et al., Sequence-dependent hydrolysis of RNA using modified oligonucleotide splints and RNase H. *Federal of European Biochemical Societies*, vol. 215, No. 2, pp. 327-330 (May 1987).

Inoue et al., Synthesis and hybridization studies on two complementary nona(2'-O-methyl)ribonucleotides. *Nucleic Acids Research*, vol. 15, No. 15, pp. 6131-6148 (1987).

Irani et al., Mitogenic Signaling Mediated by Oxidants in Ras-Transformed Fibroblasts. *Science*, vol. 275, pp. 1649-1652 (Mar. 14, 1997).

Irani et al., Ras, Superoxide and Signal Transduction. *Biochemical Pharmacology*, vol. 55, pp. 1339-1346 (1998).

Jahne et al., Regeneration of transgenic, microspore-derived, fertile barley. *Theor. Appl. Genet.* vol. 89, pp. 525-533 (1994).

Jarosch et al., The Ambivalence of the Barley *Mlo* Locus: Mutations Conferring Resistance.

Against Powdery Mildew (*Blumeria graminis f.* sp. *hordei*) Enhance Susceptibility to the Rice Blast Fungus *Magnaporthe grisea.*. *Mol Plant Microbe Interact*, vol. 12, No. 6, pp. 508-514 (Jan. 1999).

Jefferson et al., GUS fusions: β-glucuronidase as a sensitive and versatile gene fusion marker in higher plants. *The EMBO Journal*, vol. 6, No. 13, pp. 3910-3907 (1987).

Jenes et al., Techniques for Gene Transfer. *Transgenic Plants*, vol. 1, pp. 125-146 (Academic Press 1993).

Jorgensen et al., Chalcone synthase cosuppression phenotypes in petunia flowers: comparison of sense vs. antisense constructs and single-copy vs. complex T-DNA sequences. *Plant Molecular Biology*, vol. 31, pp. 957-973 (1996).

Jorgensen et al., Primary Infection by Erysiphe graminis f. sp. hordei of Barley Mutants with Resistance Genes in the ml-o Locus. *Phytopathology*, vol. 67, pp. 678-685 (May 1997).

Jorgensen, J.H., Spectrum of Resistance Conferred by Mlo Powdery Mildew Resistance Genes in Barley. *Euphytica*, vol. 26, pp. 55-62 (1997).

Josefsson et al., Structure of a Gene encoding the 1.7 S Storage Protein, Napin from *Brassica napus*. *J. Biol. Chem.*, vol. 262, No. 25, pp. 12196-12201 (Sep. 1987).

Kang et al., Zinc Finger Proteins as Designer Transcription Factors. *J. Biol. Chem.*, vol. 275, No. 12, pp. 8742-8748 (Mar. 24, 2000).

Kawasaki et al., The small GTP-binding protein Rac is a regulator of cell death in plants. *Proc. Natl. Acad. Sci.* USA, vol. 96, pp. 10922-10926 (Sep. 1999).

Keown et al., Methods for Introducing DNA into Mammalian Cells, *Methods in Enzymology*, vol. 18, pp. 527-537 (1990).

Kim et al., Design of TATA box-binding protein / zinc finger fusions for targeted regulation of gene expression. *Proc. Natl. Acad. Sci.* USA, vol. 94, pp. 3616-3620 (Apr. 1997).

Klein et al., High-velocity microprojectiles for delivering nucleic acids into living cells. *Nature*, vol. 327, pp. 70-73 (May 1987).

Kleinberg et al. p21rac Does Not Participate in the Early Interaction between p47-*phox* and Cytochrome $b_{558}$ That Leads to Phagocyte NADPH Oxidase Activation in Vitro. *Biochemistry*, vol. 33, pp. 2490-2495 (1994).

Klug, A., Zinc Finger Peptides for the Regulation of Gene Expression. *J. Mol. Biol.*, vol. 293, pp. 215-218 (1999).

Kmeic, E., Gene Therapy. *American Scientist*, vol. 87, No. 3, pp. 240-247 (May-Jun. 1999).

Kogel et al., Acquired Resistance in Barley. *Plant Physiol.*, vol. 106, pp. 1269-1277 (1994).

Kolster et al., Near-Isogenic Barley Lines with genes for Resistance to Powdery Mildew. *Crop Science*, vol. 26, No. 5, pp. 903-907 (Sep.-Oct. 1986).

Koncz et al., T-DNA insertional mutagenesis in *Arabidopsis. Plant Molecular Biology*, vol. 20, pp. 963-976 (1992).

Kumar et al., A Compromised Mlo Pathway Affects the Response of Barley to the Necrotrophic Fungus *Biopolaris sorokiniana* (Teleomorph: *Cochliobolus sativus*) and Its Toxins. *Phytopathology*, vol. 91, No. 2, pp. 127-133 (2001).

Kwong et. al., Characterization of the Effector-specifying Domain of Rac Involved in NADPH Oxidase Activation. *The Journal of Biological Chemistry*, vol. 270, No. 34, pp. 19868-19872 (Aug. 25, 1995).

Lagna et al., Use of Dominant Negative Constructs to Modulate Gene Expression. *Current Topics in Developmental Biology*, vol. 36, pp. 75-98 (1998).

Lam et al., Tetramer of a 21-Base Pair Synthetic Element Confers Seed Expression and Transcriptional Enhancement in response to Water Stress and Abscisic Acid. *J. Biol. Chem.*, vol. 266, No. 26, pp. 17131-17135 (Sep. 15, 1991).

Lawton et al., Benzothiadiazole induces disease resistance in *Arabidopsis* by activation of the systemic acquired resistance signal transduction pathway. *The Plant Journal*, vol. 10(1), pp. 71-82 (1996).

Lefell et al., Applications of Green Fluorescent Protein in Plants. *BioTechniques*, vol. 23, No. 5, pp. 912-918 (1997).

Lin et al., Inhibition of Pollen Tube Elongation by Microinjected Anti-Rop1Ps Antibodies Suggests a Crucial Role for Rho-Type GTPases in the Control of Tip Growth. *The Plant Cell*, vol. 9, pp. 1647-'659 (Sep. 1997).

Lloyd et al., Functional expression of the yeast FLP/FRT site-specific recombination system in *Nicotiana tabacum. Mol Gen Genet*, vol. 242, pp. 653-637 (1994).

Loon, L., Pathogenesis-related proteins. *Plant Molecular Biology*, vol. 4, pp. 111-116 (1985).

Low et al., Comparison of the Oxidative Burst Signaling Pathways of Plants and Human Neutrophils. *Advances in Molecular Genetics of Plant-Microbe Interactions*, vol. 3, pp. 361-369 (1994).

Lyngkjaer, M.F., A Japanese powdery isolate with exceptionally large infection efficiency on Mlo-resistant barley. *Plant Pathology*, vol. 44, pp. 786-790 (1995).

Ma et al., Plant Expression Systems for the Production of Vaccines. *Current Topics in Microbiology and Immunology*, vol. 236, pp. 275-292 (1999).

Maher, L., DNA Triple-Helix Formation: An Approach to Artificial Gene Repressors? *Bio Essays*, vol. 14, No. 12, pp. 807-815 (Dec. 1992).

Mapp et al., Activation of gene expression by small molecule transcription factors. *Proc. Natl. Acad. Sci.* USA, vol. 97, No. 8, pp. 3930-3935 (Apr. 11, 2000).

Marineau et al., Differential accumulation of potato tuber mRNAs during the hypersensitive response induced by arachidonic acid elicitor. *Plant Molecular Biology*, vol. 9, pp. 335-342 (1987).

Matton et al., Cloning, Expression, and Sequence Conservation of Pathgenesis-Related Gene Transcripts of Potato. *Molecular Plant-Microbe Interactions*, vol. 2, No. 6, pp. 325-331 (1989).

Matzke et al., Transgene silencing by the host genome defense: implications for the evolution of epigenetic control mechanisms in plant and vertebrates. *Plant Molecular Biology*, vol. 43, pp. 401-415 (2000).

McCormick et al., Leaf disc transformation of cultivated tomato (*L. esculentum*) using *Agrobacterium tumefaciens. Plant Cell Reports*, vol. 5, pp. 81-84 (1986).

McGurl et al., Structure, Expression, and Antisense Inhibition of the Systemin Precursor Gene. *Science*, vol. 255, pp. 1570-1573 (Mar. 20, 1992).

Mehdy et al., Active Oxygen Species in Plant Defense against Pathogens. *Plant Phsiol*, vol. 105, pp. 467-472 (1994).

Mi et al., Database EMBL, Accession No. AF250327.1, Aug. 2, 2000.

Mi et al., Database NCBI Gen Bank, Accession No. AF218381.1, Jan. 31, 2000.

Millar et al., Firefly Luciferase as a Reporter of Regulated Gene Expression in Higher Plants. *Plant Molecular Biology Reporter*, vol. 10, No. 4, pp. 324-337 (1992).

Mol et al., Regulation of plant gene expression by antisense RNA. *Federation of European Biochemical Societies*, vol. 268, No. 2, pp. 427-430 (Aug. 1990).

Napoli et al., Introduction of a Chimeric Chalcone Synthase Gene into Petunia Results in Reversible Co-Suppression of Homologous Genes *in trans. The Plant Cell*, vol. 2, pp. 279-289 (Apr. 1990).

Neuhaus et al., Transgenic rapeseed plants obtained by the microinjection of DNA into microspore-derived embryoids. *Theor. Appl. Genet*, vol. 75, pp. 30-36 (1987).

Norman et al., Isolation and Properties of cDNA Clones Encoding SRF, a Transcription Factor That Binds to the *c-fos* Serum Response Element. *Cell*, vol. 55, pp. 989-1003 (Dec. 23, 1988).

Odell et al., Identification of DNA sequences required for activity of the cauliflower mosaic virus 35S promoter. *Nature*, vol. 313, pp. 810-812 (Feb. 28, 1985).

Odell et al., Site-directed recombination in the genome of transgenic tobacco. *Mol Gen Genet*, vol. 223, pp. 369-378 (1990).

Ono et al., Essential Role of Small GTPase Rac in Disease Resistance of Rice. *PNAS*, vol. 98 No. 2, pp. 759-764 (Jan. 16, 2001).

Ow et al., Transient and Stable Expression of the Firefly Luciferase Gene in Plant Cells and Transgenic Plants. *Science*, vol. 234, pp. 856-859 (Nov. 14, 1986).

Owen et al., Synthesis of a Functional Anti-Phytochrome Single-Chain $F_v$ Protein in Transgenic Tobacco. *Biotechnology*, vol. 10, pp. 790-794 (Jul. 1992).

Perlmutter et al., The use of dominant-negative mutations to elucidate signal transduction pathways in lymphocytes. *Current Opinion in Immunology*, vol. 8, No. 2, pp. 285-290 (Apr. 1996).

Peterhansel et al., Interaction Analyses of Genes Required for Resistance Responses to Powdery Mildew in Barley Reveal Distinct Pathways Leading to Leaf Cell Death. *The Plant Cell*, vol. 9, pp. 1397-1409 (Aug. 1997).

Potrykus, I., Gene Transfer to Plant: Assessment of Published Approaches and Results. *Annu. Rev. Plant. Physiol.*, vol. 42, pp. 205-225 (1991).

Prasher et al., Cloning and Expression of the cDNA Coding for Aequorin, a Bioluminescent Calcium-binding Protein. *Biochemical and Biophysical Research Communications*, vol. 126, No. 3, pp. 1259-1268 (1985).

Prigmore et al., A 68-kDa Kinase and NADPH Oxidase Component p67$^{phox}$ Are Targets for Cdc42Hs and Rac1 in Neutrophils. *Journal of Biological Chemistry*, vol. 270, No. 18, pp. 10717-10722 (1995).

Pugin et al., Early Events Induced by the Elicitor Cryptogein in Tobacco Cells: Involvement of a Plasma Membrane NADPH Oxidase and Activation of Glycolysis and the Pentose Phosphate Pathway. *The Plant Cell*, vol. 9, pp. 2077-2091 (Nov. 1997).

Ratcliff et al., Tobacco rattle virus as a vector for analysis of gene function by silencing. *The Plant Journal*, vol. 25, No. 2, pp. 237-245 (2001).

Rathore et al., Use of *bar* as a selectable marker gene and for the production of herbicide-resistant rice plants from photoplasts. *Plant Molecular Biology*, vol. 21, pp. 871-884 (1993).

Rebmann et al., Cloning and sequencing of cDNAs encoding a pathogen-induced putative peroxidase of wheat (*Tritcum aestivum* L.). *Plant Molecular Biology*, vol. 16, pp. 329-331 (1991).

Redolfi, Occurrence of pathogenesis-related (b) and similar proteins in different plant species. *Neth. J. Pl. Path.* vol. 89, pp. 245-254 (1983).

Reichel et al., Enhanced green fluorescence by the expression of an *Aequorea victoria* green fluorescent protein mutant in mono- and dicotyledonous plant cells. *Proc. Natl. Acad. Sci.* USA, vol. 93, pp. 5888, 5893 (Jun. 1996).

Rohrmeier et al., *WIP1*, a wound-inducible gene from maize with homology to Bowman-Birk proteinase inhibitors. *Plant Molecular Biology*, vol. 22, pp. 783-792 (1993).

Rogers et al., Improved Vectors for Plant Transformation: Expression Cassette Vectors and New Selectable Markers. *Methods in Enzymology*, vol. 153, pp. 253-277 (1987).

Rouster et al., The untranslated leader sequence of the barley *lipoxygenase 1 (Lox1)* gene confers embryo-specific expression. *The Plant Journal*, vol. 15, No. 3, pp. 435-440 (1998).

Ruiz et al., Initiation and Maintenance of Virus-Induced Gene Silencing. *The Plant Cell*, vol. 10, pp. 937-946 (Jun. 1998).

Rushton et al., Synthetic Plant Promoters Containing Defined Regulatory Elements Provide Novel Insights into Pathogen- and Wound-Induced Signaling. *The Plant Cell*, vol. 14, pp. 749-762 (Apr. 2002).

Ryan, C., Protease Inhibitors in Plants: Genes for Improving Defenses Against Insects and Pathogens. *Annu. Rev. Phytopathol*, vol. 28, pp. 425-449 (1990).

Sambrook et al., Molecular Cloning (A Laboratory Manual), pp. 9.31-9.57. (2ed., Cold Springs Harbor Laboratory Press 1989).

Sauer, B., Inducible Gene Targeting in Mice Using the Cre/*lox* System. *Methods: A Companion to Methods in Enzymology*, vol. 14, pp. 381-392 (1998).

Schardl et al., Design and Construction of a versatile system for the expression of foreign genes in plants. *Gene*, vol. 61, pp. 1-11 (1987).

Scheid et al., Reversible inactivation of a transgene in *Arabidopsis thaliana*. *Mol Gen Genet*, vol. 228, pp. 104-112 (1991).

Schenborn et al., Reporter Gene Vectors and Assays. *Molecular Bioltechnology*, vol. 13, Sec. 1, pp. 29-44 (1999).

Schoffl et al., The function of plant heat shock promoter elements in the regulated expression of chimaeric genes in transgenic tobacco. *Mol Gen Genet*, vol. 217, pp. 246-253 (1989).

Schubert et al., An ozone-responsive region of the grapevine resveratrol synthase promoter differs from the basal pathogen-responsive sequence. *Plant Molecular Biology*, vol. 34, pp. 417-426 (1997).

Schulthesis et al., A Small GTP-Binding Host Protein Is Required for Entry of Powdery Mildew Fungus into Epidermal Cells of Barley. *Plant Physiology*, vol. 128, pp. 1447-1454 (Apr. 2002).

Schulze-Lefert et al., Closing the ranks to attack by powdery mildew. *Trends in Plant Science*, vol. 5, pp. 343-348 (Aug. 2000).

Schweizer et al., A Transient Assay System for the Function Assessment of Defense-Related Genes in Wheat. *Mol. Plant Microbe Intract.* vol. 12, No. 8, pp. 647-654 (1999).

Schweizer et al., Double-stranded RNA interferes with gene function at the single-cell level in cereals. *The Plant Journal*, vol. 24, No. 6, pp. 895-903 (2000).

Schweizer et al., Jasmonate-Inducible Genes Are Activated in Rice by Pathogen Attack without a Concomitant Increase in Endogenous Jasmonic Acid Levels. *Plant Phsiol.*, vol. 144, pp. 79-88 (1997).

Segal et al., Design of novel sequence-specific DNA-binding proteins. *Curr. Opinion Chem. Biol.*, vol. 4, No. 1, pp. 34-39 (Feb. 2000).

Sharrocks et al., The ETS-domain Transcription Factor Family. *Int. J. Biochem. Cell Biol.*, vol. 29, No. 12, pp. 1371-1387 (1997).

Sheehy et al., Reduction of polygalacturonase activity in tomato fruit by antisense RNA. *Proc. Natl. Acad. Sci.* USA, vol. 85, pp. 8805-8809 (Dec. 1988).

Sheen et al., Green-fluorescent protein as a new vital marker in plant cells. *The Plant Journal*, vol. 8, No. 5, pp. 777-784 (1995).

Sheppard, D., Dominant Negative Mutants: Tools for the Study of Protein Function In Vitro and In Vivo. *American Journal of Resipiratory Cell and Molecular Biology*. vol. 11, No. 1, pp. 1-6 (Jul. 1994).

Shewmaker et al., Transcription of Cauliflower Mosaic Virus Integrated in Plant genomes. *Virology*, vol. 140, pp. 281-288 (1985).

Shinshi et al., Structure of tobacco endochitinase gene: evidence that different chitinase genes arise by transposition of sequences encoding a cysteine-rich domain. *Plant Molecular Biology*, vol. 14, pp. 357-368 (1990).

Shirsat et al., Sequences responsible for the tissue specific promoter activity of a pea legumin gene in tobacco. *Mol Gen Genet*, vol. 215, pp. 326-331 (1989).

Siebertz et al., *cis*-Analysis of the Wound-Inducible Promoter *wun1* in Transgenic Tobacco Plants and Histochemical Localization of Its Expression. *The Plant Cell*, vol. 1, pp. 961-968 (Oct. 1989).

Smith et al., Expression of a truncated tomato polygalacturonase gene inhibits expression of the endogenous gene in transgenic plants. *Mol Gen Genet*, vol. 224, pp. 447-481 (1990).

Somssich et al., Rapid activation by fungal elicitor of genes encoding "pathogenesis-related" proteins in cultured parsley cells. *Proc. Natl. Acad. Sci. USA*, vol. 83, pp. 2427-2430 (Apr. 1986).

Stalberg et al., Disruption of an overlapping E-box / ABRE motif abolished high transcription of the *napA* storage-protein promoter in transgenic *Brassica napus* seeds. *Planta*, vol. 199, pp. 515-519 (1996).

Stanford et al., Differential expression within a family of novel wound-induced genes in a potato. *Mol Gen Genet*, vol. 215, pp. 200-208 (1989).

Steinecke et al., Expression of a chimeric ribozyme gene results in endonucleolytic cleavage of target mRNA and a concomitant reduction of gene expression in vivo. *The EMBO Journal*, vol. 11, No. 4, pp. 1525-1530 (1992).

Steinecke et al., Ribozymes, *Methods in Cell Biology*, vol. 50, pp. 449-460 (Academic Press 1995).

Stockhaus et al., Correlation of the expression of the nuclear photosynthetic gene ST-LS1 with the presence of chloroplasts. *The EMBO Journal*, vol. 8, No. 9, pp. 2445-2451 (1989).

Stoger et al., Plant transformation by particle bombardment of embryogenic pollen. *Plant Cell Reports*, vol. 14, pp. 273-278 (1995).

Strepp et al., Plant Nuclear gene knockout reveals a role in plastid division for the homolog of the bacterial cell division protein FtsZ, an ancestral tubuloin. *Proc. Natl. Acad. Sci.* USA, vol. 95, pp. 4368-4373 (Apr. 1998).

Sundaresan et al., Regulation of reactive-oxygen-species generation in fibroblasts by Rac1. *Biochem. J.*, vol. 318, pp. 379-382 (1996).

Symons, M., Rho family GTPases: the cytoskeleton and beyond. *TIBS*, vol. 21, pp. 178-181 (May 1996).

Tanner, N., Ribozymes: the characteristics and properties of catalytic RNAs. *FEMS Microbiology Reviews*, vol. 23, pp. 257-275 (1999).

Thomas et al., Site-Directed Mutagenesis by Gene Targeting in Mouse Embryo-Derived Stem Cells. *Cell*, vol. 51, pp. 503-512 (Nov. 6, 1987).

Tian et al., Expression of the green fluorescent protein gene in conifer tissues. *Plant Cell Reports*, vol. 16, pp. 267-271 (1997).

Uknes et al., Acquired Resistance in *Arabidopsis*. *The Plant Cell*, vol. 4, pp. 645-656 (Jun. 1992).

Urbach et al., Toward rules for 1:1 polyamide: DNA recognition. *PNAS*, vol. 98, No. 8, pp. 4343-4348 (Apr. 10, 2001).

Vaeck et al., Transgenic plants protected from insect attack. *Nature*, vol. 328, pp. 33-37 (Jul. 1987).

Valster et al., Plant GTPases: the Rhos in bloom. *Trends in Cell Biology*, vol. 10, pp. 141-146 (Apr. 2000).

Van der Krol et al., Flavonoid Genes in Petunia: Addition of a Limited Number of Gene Copies May Lead to a Suppression of Gene Expression. *The Plant Cell*, vol. 2, pp. 291-299 (Apr. 1990).

Voet et al., Biochemistry. 2nd ed., p. 896 (Wiley Press N.Y.).

Von Wintzingerode et al., Database NCBI Gen Bank, Accession No. AJ290240.1, Apr. 18, 2001.

Wang et al., Expanding the Recognition of the Minor Groove of DNA by Incorporation of β-Alanine in Hairpin Polyamides. *Bioorganic and Medicinal Chemistry*, vol. 9 (2001), 653-657.

Ward et al., Chemical regulation of transgene expression in plants. *Plant Molecular Biology*, vol. 22, pp. 361-366 (1993).

Ward et al., Coordinate Gene Activity in Response to Agents That Induce Systemic Acquired Resistance. *The Plant Cell*, vol. 3, pp. 1085-1094 (Oct. 1991).

Warmer et al., Isolation of an asparagus intracellular *PR* gene (*AoPR1*) wound-responsive promoter by the inverse polymerase chain reaction and its characterization in transgenic tobacco. *The Plant Journal*, vol. 3, No. 2, pp. 191-201 (1993).

Waterhouse et al., Virus resistance and gene silencing in plants can be induced by simultaneous expression of sense and antisense RNA. *Proc. Natl. Acad. Sci.* USA, vol. 95, pp. 13959-13964 (Nov. 1998).

Wei et al., An epidermis/papilla-specific oxalate oxidase-like protein in the defence response of barley attacked by the powdery mildew fungus. *Plant Molecular Biology*, vol. 36, pp. 101-112 (1998).

Weinberger et al., Database NCBI Gen Bank, Accession No. NM000461.1, Nov. 5, 2002.

Whitelam et al., Antibody expression in transgenic plants. *Trends in Plant Science*, vol. 1, No. 8, pp. 286-272 (Aug. 1996).

Wiberg, A., Genetical studies of spontaneous sources of resistance to powdery mildew in barley. *Hereditas*, vol. 77, pp. 89-148 (1974).

Winge et al., Cloning and characterization of rac-like cDNAs from *Arabidopsis thaliana*.. *Plant Molecular Biology*, vol. 35, pp. 483-495 (1997).

Wolter et al., The *mlo* resistance alleles to powdery mildew infection in barley trigger a developmentally controlled defence mimic phenotype. *Mol Gen Genet*, vol. 239, pp. 122-128 (1993).

Wurtz et al., Fmoc Solid Phase Synthesis of Polyamides Containing Pyrrole and Imidazole Amino Acids. *Organic Letters*, vol. 3, No. 8, pp. 1201-1203 (2001).

Zhang et al., ocs element promoter sequences are activated by auxin and salicylic acid in *Arabddopsis*. *Proc. Natl. Acad. Sci.* USA, vol. 91, pp. 2507-2511 (Mar. 1994).

Zhang et al., Synthetic Zinc Finger Transcription Factor Action at an Endogenous Chromosomal Site. *J. Biol. Chem.*, vol. 275, No. 43, pp. 33850-33860 (Oct. 27, 2000).

Zhu et al., Engineering herbicide-resistant maize using chimeric RNA/DNA oligonucleotides. *Nature Biotechnology*, vol. 18, No. 5, pp. 555-558 (May 2000).

Ivanchenko et al., Database NCBI Gen Bank, Accession No. AJ278665, Aug. 2, 2001.

\* cited by examiner

```
                                           ▼
RACB_H.vul._   MSASRFIKCVTVGDGAVGKTCMLISYTSNTFPTDYVPTVFDNFSANVVVDGNTVNLGLWD  60
RACB_Z.mays_   MSASRFIKCVTVGDGAVGKTCMLISYTSNTFPTDYVPTVFDNFSANVVVDGNTVNLGLWD  60
RACB_O.sat.    MSASRFIKCVTVGDGAVGKTCMLISYTSNTFPTDYVPTVFDNFSANVVVDGNTVNLGLWD  60
RAC2_H.sap.    MQA---IKCVVVGDGAVGKTCLLISYTTNAFPGEYIPTVFDNYSANVMVDSKPVNLGLWD  57
RAC1_H.sap.    MQA---IKCVVVGDGAVGKTCLLISYTTNAFPGEYIPTVFDNYSANVMVDGKPVNLGLWD  57
                 *   ****  ********* * **** *  * ****** **** **  *******

RACB_H.vul._   TAGQEDYNRLRPLSYRGADVFLLAFSLISKASYENVSKKWIPELKHYAPGVPIILVGTKL 120
RACB_Z.mays_   TAGQEDYNRLRPLSYRGADVFLLAFSLISKASYENVSKKWIPELKHYAPGVPIILVGTKL 120
RACB_O.sat.    TAGQEDYNRLRPLSYRGADVFLLAFSLISKASYENVSKKWIPELKHYAPGVPIILVGTKL 120
RAC2_H.sap.    TAGQEDYDRLRPLSYPQTDVFLICFSLVSPASYENVRAKWFPEVRHHCPSTPIILVGTKL 117
RAC1_H.sap.    TAGQEDYDRLRPLSYPQTDVFLICFSLVSPASFENVRAKWYPEVRHHCPNTPIILVGTKL 117
               ******  ******    **** **** *  * *** ***  **  **   ********

RACB_H.vul._   DLRDDKQFFVDHPG--AVPITTAQGEELKKLIGAPYYIECSSKTQLNVKGVFDAAIKVVL 178
RACB_Z.mays_   DLRDDKQFFVDHPG--AVPITTAQGEELRKQIGAPYYIECSSKTQLNVKGVFDAAIKVVL 178
RACB_O.sat.    DLRDDKQFFVDHPG--AVPITTAQGEELRKQIGAPYYIECSSKTQLNVKGVFDAAIKVVL 178
RAC2_H.sap.    DLRDDKDTIEKLKEKKLAPITYPQGLALAKEIDSVKYLECSALTQRGLKTVFDEAIRAVL 177
RAC1_H.sap.    DLRDDKDTIEKLKEKKLTPITYPQGLAMAKEIGAVKYLECSALTQRGLKTVFDEAIRAVL 177
               ******      ***    *       * **   **     * *** **

RACB_H.vul.    QPPKAKKKKKAQRGACSIL 197
RACB_Z.mays_   QPPKAKKKKKVQRGACSIL 197
RACB_O.sat.    QPPKAKKKKKAQRGACSIL 197
RAC2_H.sap.    CPQPTRQQKR----ACSLL 192
RAC1_H.sap.    CPPPVKKRKR----KCLLL 192
                *       *     *  *
```

Fig. 1

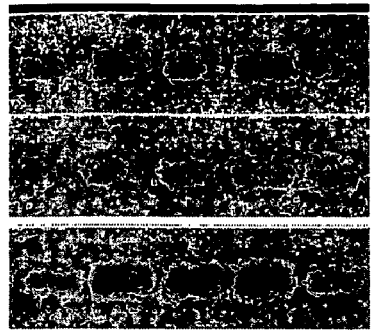
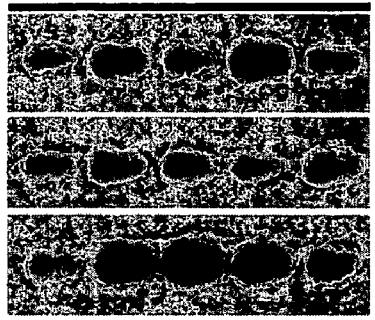
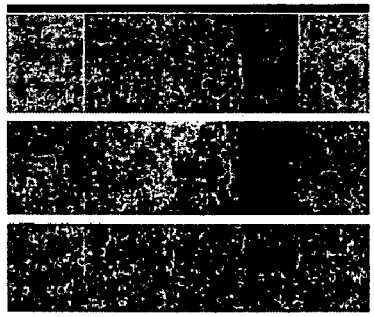
Fig. 3

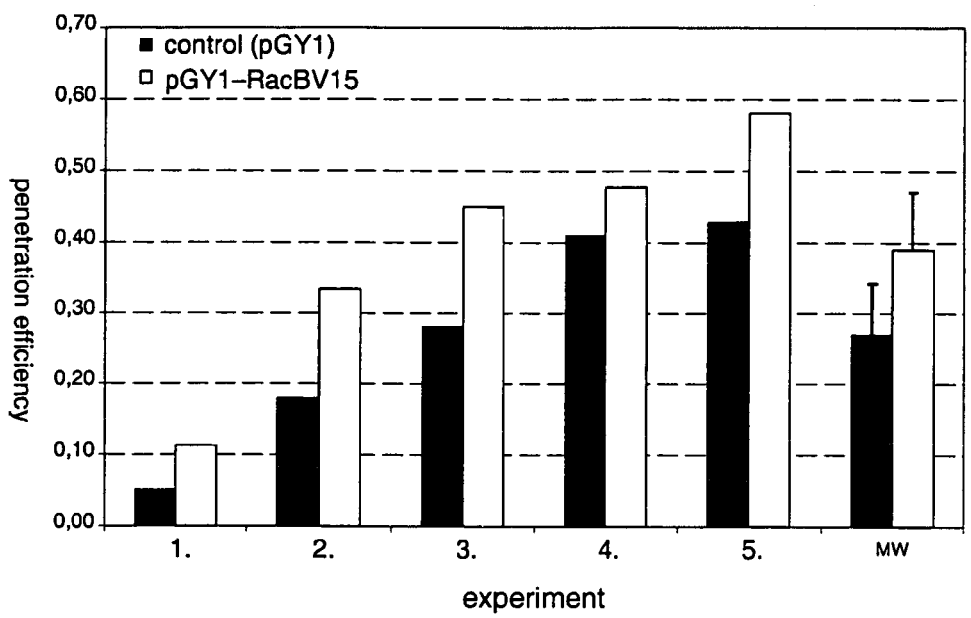
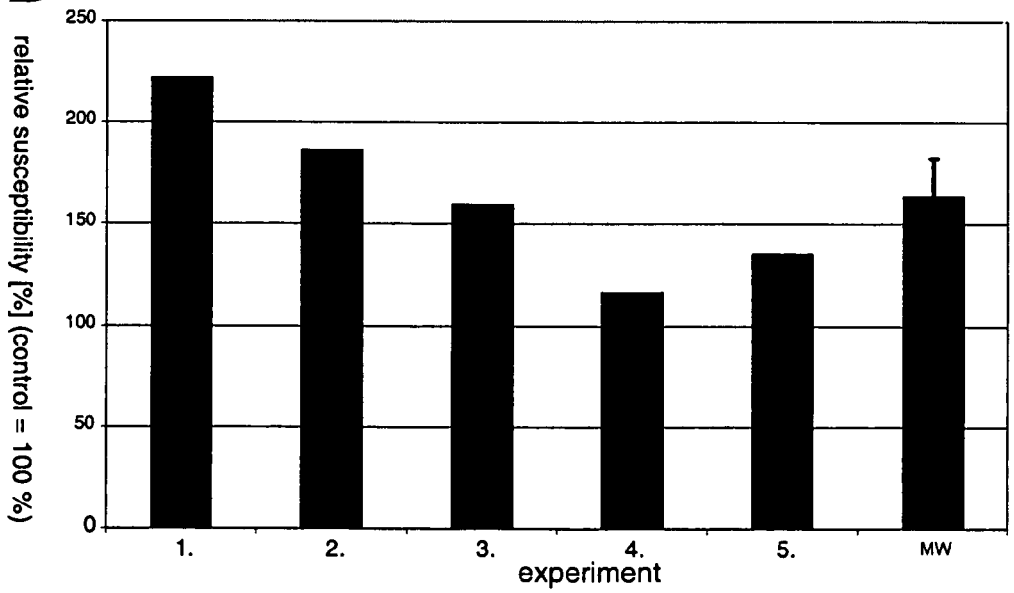
Fig.6

NUCLEIC ACID SEQUENCES AND THEIR USE IN METHODS FOR ACHIEVING PATHOGEN RESISTANCE IN PLANTS

RELATED APPLICATIONS

This application is a national stage application (under 35 U.S.C. 371) of PCT/EP02/09719 filed Aug. 30, 2002, which claims the benefit of German application 101 42 579.1 filed Sep. 3, 2001, and German application 102 29 729.0 filed Jul. 2, 2002.

FIELD OF THE INVENTION

The invention relates to novel RacB cDNA sequences from barley and to expression cassettes and vectors comprising these sequences. The invention furthermore relates to transgenic plants transformed with these expression cassettes or vectors, to cultures, parts or transgenic propagation material derived from them, and to their use for the production of foodstuffs, feeding stuffs, seed, pharmaceuticals or fine chemicals. The invention furthermore relates to methods of generating or increasing a pathogen resistance in plants by reducing the expression of an RacB protein or of a functional equivalent thereof.

DESCRIPTION OF THE BACKGROUND

The aim of plant biotechnology work is the generation of plants with advantageous novel properties, for example for increasing agricultural productivity, increasing the quality in the case of foodstuffs, or for producing specific chemicals or pharmaceuticals (Dunwell J M (2000) J Exp Bot 51 Spec No:487-96). The plant's natural defense mechanisms against pathogens are frequently insufficient. Fungal diseases alone result in annual yield losses of many billions of US$. The introduction of foreign genes from plants, animals or microbial sources can increase the defenses. Examples are the protection of tobacco against feeding damage by insects by expressing *Bacillus thuringiensis* endotoxins under the control of the 35S CaMV promoter (Vaeck et al. (1987) Nature 328:33-37) or the protection of tobacco against fungal infection by expressing a bean chitinase under the control of the CaMV promoter (Broglie et al. (1991) Science 254:1194-1197). However, most of the approaches described only offer resistance to a single pathogen or a narrow spectrum of pathogens.

Only a few approaches exist which impart a resistance to a broader spectrum of pathogens, in particular fungal pathogens, to plants. Systemic acquired resistance (SAR)—a defense mechanism in a variety of plant/pathogen interactions—can be mediated by the application of endogenous messenger substances such as jasmonate (JA) or salicylic acid (SA) (Ward, et al. (1991) Plant Cell 3:1085-1094; Uknes, et al. (1992) Plant Cell 4(6):645-656). Similar effects can also be achieved by synthetic compounds such as 2,6-dichloroisonicotinic acid (INA) or S-methyl benzo(1,2,3)thiadiazole-7-thiocarboxylate (BTH; Bion®) (Friedrich et al. (1996) Plant J 10(1):61-70; Lawton et al. (1996) Plant J. 10:71-82). The expression of pathogenesis-related (PR) proteins, which are highly regulated in the case of an SAR, may also cause pathogen resistance in some cases.

In barley, the Mlo locus has been described for some time as a negative regulator of plant defense. The loss, or loss of function, of the Mlo gene causes an increased and, above all, race-unspecific resistance for example against a large number of mildews (Büschges R et al. (1997) Cell 88:695-705; Jorgensen J H (1977) Euphytica 26:55-62; Lyngkjaer M F et al. (1995) Plant Pathol 44:786-790). The Mlo phenotype is inherited recessively, which also suggests a function as a susceptibility gene. Mlo-deficient barley varieties obtained by traditional breeding are already being widely used in agriculture. Although these varieties are being grown intensively, this resistance has proved to be extraordinarily durable, probably owing to the recessivity. Resistance breakdown has not been observed as yet. Mlo-like resistances in other plants, especially in cereal species, have not been described even though wheat, rye and other cereals are also attacked by comparable mildew pathogens. The reason in the case of wheat may be, for example, the existence of a hexaploid genome, which makes the identification of mutants in which each of the six copies of the gene has been inactivated extremely difficult.

The Mlo gene has only recently been cloned (Büschges R et al. (1997) Cell 88:695-705; WO 98/04586; Schulze-Lefert P, Vogel J (2000) Trends Plant Sci. 5:343-348). As a consequence, various homologs have been isolated from other cereal species. Various methods for obtaining pathogen resistance using these genes have been described (WO 98/04586; WO 00/01722; WO 99/47552).

Mlo resistance of a plant to mildew pathogens manifests itself in two important events, both of which bring about resistance to penetration: cell wall apposition (CWA) underneath the penetration site of the pathogen in the epidermal cell wall. Spreading of this fungal pathogen is almost exclusively restricted to this subcellular structure (Jorgensen J H and Mortensen K (1977) Phytopathology 67:678-685; Freialdenhoven A et al. (1996) Plant Cell 8:5-14). This reaction is caused by the genes Ror1 and Ror2, which are required for the effect of Mlo (Peterhänsel C et al. (1997) 9:1397-1409).

The disadvantage in Mlo pathogen resistance is that Mlo-deficient plants—even in the absence of a pathogen—initiate a defense mechanism which manifests itself for example in the spontaneous death of leaf cells (Wolter M et al. (1993) Mol Gen Genet 239:122-128). A further disadvantage is that the Mlo-deficient genotypes are hypersusceptible to hemibiotrophic pathogens such as *Magnaporte grisea* (*M. grisea*) and *Cochliobolus sativus* (*Bipolaris sorokiniana*) (Jarosch B et al. (1999) Mol Plant Microbe Interact 12:508-514; Kumar J et al. (2001) Phytopathology 91:127-133). The Mlo gene therefore appears to be a negative regulator of cell death. Again, the cause is probably the induction of cell death in the absence of the Mlo gene, which increases the susceptibility to these fairly necrotrophic pathogens. This ambivalent effect, which limits the biotechnological use of Mlo, is probably due to the fact that necrotrophic fungi are capable of exploiting the more pronounced HR of the Mlo-deficient host plant for their infection process. A resistance comparable to Mlo deficiency, but without the characteristic of inducing cell death, would be desirable.

The proteins Rho, Rac and Cdc42 are members of the small GTP (guanosine triphosphate) binding protein family and regulate a large number of intracellular processes as "molecular switches", both in plant and animal organisms. As elements of signal transduction, they play an important role in the conversion of extracellular stimuli. For example, they regulate NADPH oxidase and thus the release of reactive oxygen molecules ("oxidative burst"). Animal or human Rac1 is essential for the formation of the active NADPH oxidase complex which, in turn, is important for the formation of superoxide, thus contributing to plant defense (Irani K and Goldschmidt-Clermont P J (1998) Biochem Pharmacol 55: 1339-1346). The function in plant defense in plants and animals is largely analogous (Kwong et al. (1995) J Biol Chem 270(34): 19868-19872; Dusi et al. (1996) Biochem J 314:409-412; Diekmann et al. (1994) Science 265:531-533; Purgin et al. (1997) The Plant Cell 9:2077-2091; Kleinberg et al. (1994) Biochemistry 33:2490-2495; Prigmore et al. (1995) Journal of Biol Chem 27(18): 10717-10722; Irani et al. (1997) Science 275:1649-1652; Low et al. (1994) Advances in Molecular Genetics of Plant-Microbe Interactions 3:361-369 (1994) eds. M J Daniels, Kluwer Acadmic Publishers, Netherlands; Mehdy et al. (1994) Plant Physiol 105: 467-472; Sundaresan et al. (1996) Biochem J 318:379-382). Moreover, GTP binding proteins function in restructuring the cytoskeleton and in cell transformation (Symon M. (1996) TIBS 21: 178-181), and also in the activation of transcription (Hill et al. (1995) Cell 81:1159-1170; Chandra et al. (1996) Proc Natl Acad Sci USA 93:13393-13397).

In plants, there exists a substantial family of Rac-like proteins (Winge et al. (1997) Plant Mol Biol 35:483-495), which is also termed Rop family (Lin et al. (1997) The Plant Cell 9:1647-1659). In plants, the Rac proteins appear to have a function in the release of reactive oxygen molecules as the consequence of pathogen infection (Groom Q J et al. (1996) Plant J 10: 515-522; Hassanain HH et al. (2000) Biochem Biophys Res Commun 272(3):783-788; Ono E et al. (2001) Proc Natl Acad Sci USA 98: 759-764). Rac modulates, inter alia, cell wall architecture, signal transduction in the meristem and the defense against pathogens (Valster A H et al. (2000) Trends Cell Biol 10(4):141-146). When the constitutively active form is overexpressed, Rac1 from rice is capable of inducing a hypersensitive response (HR) at the sites of *M. grisea* attack, thus causing pathogen resistance. Analogously, the expression of a negative dominant form of Rac1 brings about an increased susceptibility to *M. grisea* (Kawasaki T et al. (1999) Proc Natl Acad Sci USA 96:10922-10926; Ono E et al. (2001) Proc Natl Acad Sci USA 98: 759-764). These findings suggest that an overexpression of Rac proteins in the plant can bring about advantageous effects with regard to plant defense.

WO 00/15815 describes five Rac genes from maize. Although methods for both an up regulation and a down regulation of Rac proteins are described and speculatively discussed in connection with obtaining a resistance to pathogens (p. 55/line 25 et seq.), the only technical teaching, which describes this use in real terms, concerns merely an overexpression of the claimed Rac genes for obtaining pathogen resistance (p. 60/line 21 et seq.). The author postulates quite unambiguously and in agreement with the situation described in the prior art (p. 60/line 31 et seq.): "Thus the present invention is useful in protecting plants from pathogens. Once a plant is transformed with a polynucleotide sequence encoding an Rac polypeptide, expression of the polypeptide in the plant confers resistance to infection by plant pathogens." The rationale behind this hypothesis (plants defense via reactive oxygen molecules) is explained hereinbelow and supported by a large number of references. Beyond this, no differentiation is being made between the five claimed Rac genes.

SUMMARY OF THE INVENTION

One embodiment of the invention is directed to methods for generating or increasing a resistance to at least one pathogen in plants comprising reducing an amount, activity or function of a RacB protein in a plant or a tissue, organ, part or cell thereof. Preferably reducing is performed by introducing to the plant or the tissue, organ, part or cell thereof a molecule of or an expression cassette that contains a double-stranded RacB RNA, an RacB antisense RNA, an RACB sense RNA, an RacB antisense RNA in combination with a ribozyme, a nucleic acid that encodes a dominant-negative RacB protein or a DNA- or protein binding factor, a viral nucleic acid that causes RacB degradation, a construct for inducing homologous recombination, or a combination thereof Another embodiment of the invention is directed to methods for generating or increasing a resistance to at least one pathogen in a plant comprising stably transforming the plant with a recombinant expression cassettes comprising a dsRNA encoding a RacB protein, a RacB antisense RNA which may be combined with a ribozyme, ,a RacB sense RNA for inducing cosuppression a dominant-negative RacB protein, a DNA- or protein-binding factor against RacB genes, RacB RNA or RacB protein, or a viral nucleic acid that causes RacB degradation, or a combination thereof.

Another embodiment of the invention is directed to an isolated RacB protein or nucleic acid encoding a RacB protein. Preferred sequences of the protein include SEQ ID NO 2, 7, 35, 37 and 39. Preferred sequences of the nucleic acid include SEQ ID NO 1, 3, 5, 34, 36, 38, 40, 42, 44, 46, 48, 49, 51, 53, 55, 57, 61, 63, 65, 67 and 69, as well as sequences complementary thereto, and sequences derived from any of these sequence through degeneracy of the genetic code.

Another embodiment of the invention is directed to double-stranded RNA molecules that are capable of reducing the expression of a RacB protein in a cell. Preferred dsRNA includes a sense strand comprising a sequence, which is essentially identical to at least part of the sense RNA transcript of a sequence encoding the RacB protein, and an antisense strand, which is essentially complementary to the sense strand. Also preferred are dsRNA molecule wherein the two RNA strands are linked covalently to each other.

Additional embodiments of the invention are directed to expression cassettes, vectors, and transgenic organisms containing nucleic acid sequences and proteins of the invention.

Other embodiments and advantages of the invention are set forth in part in the description, which follows, and in part, may be obvious from this description, or may be learned from the practice of the invention.

DESCRIPTION OF THE FIGURES

FIG. 1. Alignment of the amino acid sequences of barley RacB, rice RacB, maize RacB, and human Rac1 and Rac2 proteins.

FIG. 3. RacB expressed constitutively in various resistant barley lines.

FIG. 6. Overexpression of a constitutively active RacB mutant in barley cv. Pallas.

DESCRIPTION OF THE INVENTION

Figure 2:
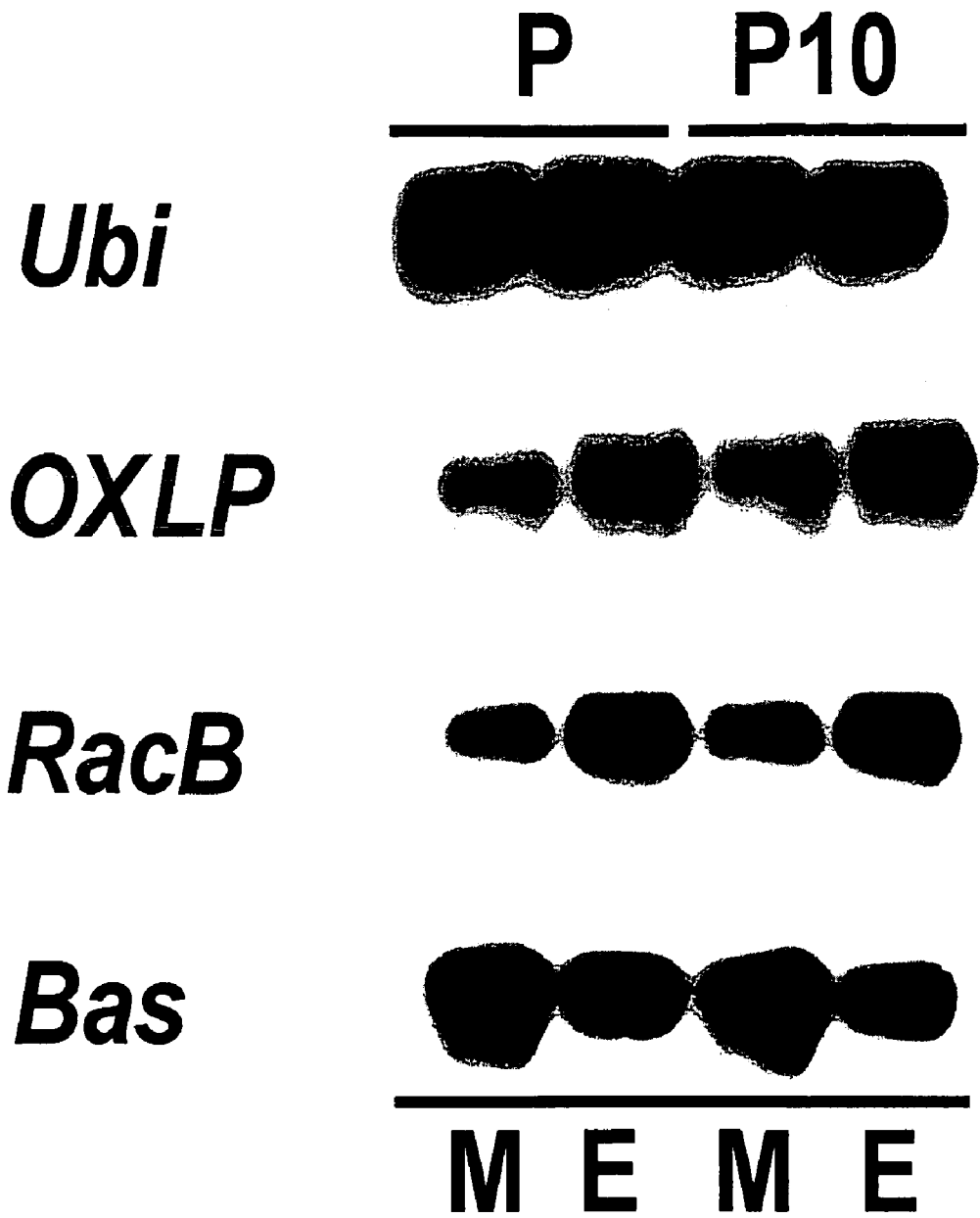
FIG. 2. Expression of RacB in epidermal tissue.

It is an object of the present invention to provide novel methods of plant defense against pathogens which bring about an effective defense against as broad a spectrum of pathogens as possible in as large a number of plant species as possible, preferably the crop plants used in agriculture. We have found that this object is achieved by the method according to the invention.

The invention firstly comprises a method of generating or increasing the resistance to at least one pathogen in plants, which comprises the following steps a) reducing the amount, activity or function of an RacB protein in a plant or a tissue, organ, part or cell thereof, and b) selecting those plants in which, as opposed or as compared to the original plant, the resistance to at least one pathogen exists or is increased.

Surprisingly, the Rac homolog RacB from barley (*Hordeum vulgare*) (SEQ ID NO: 1) (hereinbelow: hvRacB), despite a great similarity with rice Rac1, has a negative control function upon attack by powdery mildew of barley *Blumeria* (syn. *Erysiphe*) *graminis* f.sp. *hordei* (Bgh), as opposed to the former: reducing the hvRacB expression in the epidermal cell by a sequence-specific RNA interference approach using double-stranded hvRacB dsRNA ("gene silencing") significantly prevented the development of haustoria owing to Bgh infection. Further experiments demonstrated (cf. Example 7) that this phenotype cannot be observed in an mlo5-ror1-mutant genotype, namely barley A89. This suggests that RacB is linked operably to Mlo or Ror1 or both, that is to say they probably act within a signal cascade.

Similarly to the loss of function of Mlo, that of HvRacB confers broad resistance to various Blumeria graminis f.sp. hordei isolates. In transient gene silencing experiments, HvRacB reduced the penetration efficiency (development of haustoria) of Bgh by 44% (cf. Example 7), an effect whose magnitude corresponds to the effect achieved by Mlo dsRNA (Schweizer P et al. (2000) Plant J 24:895-903). In the wild-type barley variety Ingrid, approximately 60% of the fungal penetrations resulted in the development of haustoria, while the penetration rate in BCIngrid-mlo5 is virtually 0%. The barley variety A89 (mlo-ror1 dual mutant) shows a penetration efficiency of approximately 20 to 35%. An altered RacB expression owing to Bgh inoculation was observed in none of these variants (cf. Example 7; FIG. 3). The fact that only a penetration of approximately 50% can be observed even in pathogen-sensitive wild-type varieties, such as Pallas or Ingrid, can be attributed to the basal resistance which is always present.

Interestingly, the gene silencing of hvRacB only enhances cell wall apposition, but apparently not the spontaneous cell death of the plant, which is in contrast to Mlo. Thus, HvRacB differs from OsRac1, a rice homolog of Rac1 (Ono E et al. (2001) Proc Natl Acad Sci USA 98: 759-764). HvRacB acts predominantly as negative regulator of cell wall apposition. This difference is of outstanding importance for its use for obtaining pathogen resistance in plants. As already described above, Mlo resistance to biotrophic fungi (for example mildew fungi) is indeed caused, inter alia, by increased cell wall apposition, but the trade-off is a higher susceptibility to necrotrophic fungi (Jarosch B et al. (1999) Mol Plant Microbe Interact 12:508-514; Kumar J et al. (2001) Phytopathology 91:127-133). Since HvRacB only affects cell all apposition, this problem of ambivalence can be circumvented.

Owing to the above findings, RacB must be considered as a key element for the successful penetration of a pathogen such as Bgh into the plant cell. Accordingly, the method according to the invention has all the advantages of Mlo deficiency without simultaneously showing its biggest shortcoming, namely increased spontaneous cell death.

Moreover, the method outperforms all those methods in which a pathogen-resistant phenotype is realized by overexpressing a resistance-conferring protein. Switching off a gene can be realized without expressing a (foreign) protein. In an ideal case, all that needs doing is to deactivate the endogenous gene. This has not inconsiderable advantages for approval and acceptance by the consumer, who is frequently apprehensive toward plants with foreign proteins. Very especially advantageous in this context is the use of inducible promoters for reducing the amount, activity or function of RacB protein, which, for example when using pathogen-inducible promoters, allows expression only when required (i.e. pathogen infection).

A partial sequence of the barley RacB cDNA (HvRacB-cDNA) (GenBank Acc. No.: AJ290240), which is highly conserved relative to rice RacB (GenBank Acc. No.: AF250327) and maize RacB (GenBank Acc. No.: AF126053) and very similar to rice Rac1 has been described. Maize RacB is also one of the five Rac genes in the abovementioned application WO 00/15815 (Sequence No. 3). The complete coding sequence of the HvRacB protein has not been described as yet (see Example 1). Barley RacB has a homology of 95% identity with rice RacB and maize RacB and is over 55% identical to human RAC1 or RAC2 (Hassanain et al. 2000, FIG. 1). HvRacB is expressed constitutively in primary leaves of barley (epidermis-specifically) and its expression level is not affected substantially by Bgh infection. Expression thus takes place in the tissue which interacts directly with the Bgh pathogen.

In principle, the method according to the invention can be applied to all plant species, preferably to those in which an RacB protein or a functional equivalent thereof is expressed naturally. Since the function of RacB is closely connected functionally to the Mlo gene and the latter has been identified in a large number of plants, including dicots (Devoto A et al. (1999) J Biol Chem 274(49):34993-5004), it can be assumed that RacB and its homologs are similarly widely distributed. The sequences from other plants (for example *Arabidopsis thaliana*) which are homologous to the RacB sequences disclosed within the scope of the present invention can be found readily for example by database searches or by screening genetic libraries using the RacB sequences as search sequence or probe.

The term "plant" as used herein refers to all genera and species of higher and lower plants of the Plant Kingdom. The term includes the mature plants, seed, shoots and seedlings and their derived parts, propagation material, plant organs, tissue, protoplasts, callus and other cultures, for example cell cultures, and any other type of plant cell grouping to give functional or structural units. Mature plants refers to plants at any desired developmental stage beyond that of the seedling. Seedling refers to a young immature plant at an early developmental stage. "Plant" comprises all annual and perennial monocotyledonous and dicotyledonous plants and includes by way of example but not by limitation those of the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solarium, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea* and *Populus*.

The term "plant" preferably comprises monocotyledonous crop plants such as, for example, cereal species such as wheat, barley, millet, rye, triticale, maize, rice, sorghum or oats and also sugar cane.

The term furthermore comprises dicotyledonous crop plants such as, for example,

*Brassicacae* such as oilseed rape, canola, cress, *Arabidopsis*, cabbages or canola, *Leguminosae* such as soybean, alfalfa, pea, beans or peanut Solanaceae such as potato, tobacco, tomato, egg plant or pepper, *Asteraceae* such as sunflower, Tagetes, lettuce or Calendula,

*Cucurbitaceae* such as melon, pumpkin/squash or zucchini, and also linseed, cotton, hemp, clover, spinach, flax, red pepper, carrot, beet, radish, sugar beet, sweet potato, cucumber, chicory, cauliflower, broccoli, asparagus, onion, garlic, celery/celeriac, strawberry, raspberry, blackberry, pineapple, avocado and the various tree, bush, nut and vine species. Tree species preferably comprise plum, cherry, peach, nectarine, apricot, banana, papaya, mango, apple, pear, quince.

Also comprised are ornamental plants, useful trees, ornamental trees, flowers, cut flowers, shrubs or lawns such as by way of example but not by limitation the families of the *Rosaceae* such as rose, *Ericaceae* such as rhododendrons and azaleas, *Euphorbiaceae* such as poinsettias and croton, *Caryophyllaceae* such as carnations, *Solanaceae* such as petunias, *Gesneriaceae* such as African violet, *Balsaminaceae* such as touch-me-not, *Orchidaceae* such as orchids, *Iridaceae* such as gladioli, iris, freesia and crocus, *Compositae* such as calendula, *Geraniaceae* such as geraniums, *Liliaceae* such as dracaena, *Moraceae* such as ficus, *Araceae* such as philodendron and many others.

Preferred within the scope of the invention are those plants which are employed as foodstuffs or feeding stuffs, very especially preferaby monocotyledonous genera and species like the above-described cereal species.

The method is applied very especially preferably to monocotyledonous plants, most preferably to agriculturally important plants such as wheat, oats, millet, barley, rye, maize, rice, buckwheat, sorghum, triticale, spelt, linseed or sugar cane.

"Pathogen resistance" denotes the reduction or weakening of disease symptoms of a plant following infection by a pathogen. The symptoms can be manifold, but preferably comprise those which directly or indirectly have an adverse effect on the quality of the plant, the quantity of the yield, the suitability for use as feeding stuff or foodstuff, or else which make sowing, planting, harvesting or processing of the crop difficult.

"Conferring", "existing", "generating" or "increasing" a pathogen resistance means that the defense mechanisms of a specific plant species or variety is increasingly resistant to one or more pathogens due to the use of the method according to the invention in comparison with the wild type of the plant ("original plant"), to which the method according to the invention has not been applied, under otherwise identical conditions (such as, for example, climatic conditions, growing conditions, pathogen species and the like). The increased resistance manifests itself preferably in a reduced manifestation of the disease symptoms, disease symptoms comprising—in addition to the above-mentioned adverse effects—for example also the penetration efficiency of a pathogen into the plant or plant cells or the proliferation efficiency in or on the same. In this context, the disease symptoms are preferably reduced by at least 10% or at least 20%, especially preferably by at least 40% or 60%, very especially preferably by at least 70% or 80% and most preferably by at least 90% or 95%.

"Selection" with regard to plants in which—as opposed or as compared to the original plant—resistance to at least one pathogen exists or is increased means all those methods which a are suitable for recognizing an existing or increased resistance to pathogens. These may be symptoms of pathogen infection (for example the development of haustoria in the case of fungal infection), but may also comprise the above-described symptoms which relate to the quality of the plant, the quantity of the yield, the suitability for use as feeding stuff or foodstuff and the like.

"Pathogen" within the scope of the invention means by way of example but not by limitation viruses or viroids, bacteria, fungi, animal pests such as, for example, insects or nematodes. Especially preferred are fungi such as, for example, mildew. However, it can be assumed that a reduced expression of an RacB protein, its activity or function also brings about resistance to other pathogens. Changes in the cell wall structure can constitute a prime mechanism of pathogen resistance.

The following pathogens may be mentioned by way of example but not by limitation:

1. Fungal Pathogens or Fungus-Like Pathogens:

Fungal pathogens or fungus-like pathogens (e.g. Chromista) are preferably from the group comprising the *Plasmodiophoramycota, Oomycota, Ascomycota, Chytridiomycetes, Zygomycetes, Basidiomycota* and *Deuteromycetes (Fungi Imperfecti)*. The pathogens mentioned in Tables 1 and 2 and the diseases with which they are associated may be mentioned by way of example but not by limitation.

TABLE 1

Fungal plant diseases

| Disease | Pathogen |
|---|---|
| Leag rust | *Puccinia recondita* |
| Yellow rust | *P. striiformis* |
| Powdery mildew | *Erysiphe graminis/Blumeria graminis* |
| Glume blotch | *Septoria nodorum* |
| Leaf blotch | *Septoria tritici* |
| Ear fusarioses | *Fusarium* spp. |
| Eyespot | *Pseudocercosporella herpotrichoides* |
| Smut | *Ustilago* spp. |
| Bunt | *Tilletia caries* |
| Take-all | *Gaeumannomyces graminis* |
| Anthrocnose leaf blight | *Colletotrichum graminicola* |
| Anthracnose stalk rot | (teleomorph: *Glomerella graminicola* Politis); *Glomerella tucumanensis* (anamorph: *Glomerella falcatum* Went) |
| *Aspergillus* ear and kernel rot | *Aspergillus flavus* |
| Banded leaf and sheath spot | *Rhizoctonia solani* Kuhn = *Rhizoctonia microsclerotia* J. Matz (telomorph: *Thanatephorus cucumeris*) |
| Black bundle disease | *Acremonium strictum* W. Gams = *Cephalosporium acremonium* Auct. non Corda |
| Black kernel rot | *Lasiodiplodia theobromae* = *Botryodiplodia theobromae* |
| Borde blanco | *Marasmiellus* sp. |
| Brown spot (black spot, stalk rot) | *Physoderma maydis* |
| *Cephalosporium* kernel rot | *Acremonium strictum* = *Cephalosporium acremonium* |
| Charcoal rot | *Macrophomina phaseolina* |
| *Corticium* ear rot | *Thanatephorus cucumeris* = *Corticium sasakii* |
| *Curvularia* leaf spot | *Curvularia clavata, C. eragrostidis,* = *C. maculans* (teleomorph: *Cochliobolus eragrostidis*), *Curvularia inaequalis, C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis, C. tuberculata* (teleomorph: *Cochliobolus tuberculatus*) |
| *Didymella* leaf spot | *Didymella exitalis* |
| *Diplodia* ear rot and stalk rot | *Diplodia frumenti* (teleomorph: *Botryosphaeria festucae*) |

TABLE 1-continued

Fungal plant diseases

| Disease | Pathogen |
|---|---|
| *Diplodia* ear rot, stalk rot, seed rot and seedling blight | *Diplodia maydis* = *Stenocarpella maydis* |
| *Diplodia* leaf spot or streak | *Stenocarpella macrospora* = *Diplodialeaf macrospora* |

TABLE 2

Downy mildew

| Disease | Pathogen |
|---|---|
| Brown stripe downy mildew | *Sclerophthora rayssiae* var. *zeae* |
| Crazy top downy mildew | *Sclerophthora macrospora* = *Sclerospora macrospora* |
| Green ear downy mildew (*graminicola* downy mildew) | *Sclerospora graminicola* |
| Java downy mildew | *Peronosclerospora maydis* = *Sclerospora maydis* |
| Philippine downy mildew | *Peronosclerospora philippinensis* = *Sclerospora philippinensis* |
| Sorghum downy mildew | *Peronosclerospora sorghi* = *Sclerospora sorghi* |
| Spontaneum downy mildew | *Peronosclerospora spontanea* = *Sclerospora spontanea* |
| Sugarcane downy mildew | *Peronosclerospora sacchari* = *Sclerospora sacchari* |
| Dry ear rot (cob, kernel and stalk rot) | *Nigrospora oryzae* (teleomorph: *Khuskia oryzae*) |
| Ear rots, minor | *Alternaria alternata* = *A. tenuis*, *Aspergillus glaucus*, *A. niger*, *Aspergillus* spp., *Botrytis cinerea* (teleomorph: *Botryotinia fuckeliana*), *Cunninghamella* sp., *Curvularia pallescens*, *Doratomyces stemonitis* = *Cephalotrichum stemonitis*, *Fusarium culmorum*, *Gonatobotrys simplex*, *Pithomyces maydicus*, *Rhizopus microsporus* Tiegh., *R. stolonifer* = *R. nigricans*, *Scopulariopsis brumptii* |
| Ergot(horse's tooth) | *Claviceps gigantea* (anamorph: *Sphacelia* sp.) |
| Eyespot | *Aureobasidium zeae* = *Kabatiella zeae* |
| *Fusarium* ear and stalk rot | *Fusarium subglutinans* = *F. moniliforme* var. *subglutinans* |
| *Fusarium* kernel, root and stalk rot, seed rot and seedling blight | *Fusarium moniliforme* (teleomorph: *Gibberella fujikuroi*) |
| *Fusarium* stalk rot, seedling root rot | *Fusarium avenaceum* (teleomorph: *Gibberlla avenacea*) |
| *Gibberella* ear and stalk rot | *Gibberella zeae* (anamorph: *Fusarium graminearum*) |
| Gray ear rot | *Botryosphaeria zeae* = *Physalospora zeae* (anamorph: *Macrophoma zeae*) |
| Gray leaf spot (*Cercospora* leaf spot) | *Cercospora sorghi* = *C. sorghi* var. *maydis*, *C. zeae-maydis* |
| *Helminthosporium* root rot | *Exserohilum pedicellatum* = *Helminthosporium pedicellatum* (teleomorph: *Setosphaeria pedicellata*) |
| *Hormodendrum* ear rot (*Cladosporium* rot) | *Cladosporium cladosporioides* = *Hormodendrum cladosporioides*, *C. herbarum* (teleomorph: *Mycosphaerella tassiana*) |
| *Hyalothyridium* leaf spot | *Hyalothyridium maydis* |
| Late wilt | *Cephalosporium maydis* |
| Leaf spots, minor | *Alternaria alternata*, *Ascochyta maydis*, *A. tritici*, *A. zeicola*, *Bipolaris victoriae* = |

TABLE 2-continued

Downy mildew

| Disease | Pathogen |
|---|---|
| | *Helminthosporium victoriae* (teleomorph: *Cochliobolus victoriae*), *C. sativus* (anamorph: *Bipolaris sorokiniana* = *H. sorokinianum* = *H. sativum*), *Epicoccum nigrum*, *Exserohilum prolatum* = *Drechslera prolata* (teleomorph: *Setosphaeria prolata*) *Graphium penicillioides*, *Leptosphaeria maydis*, *Leptothyrium zeae*, *Ophiosphaerella herpotricha*, (anamorph: *Scolecosporiella* sp.), *Paraphaeosphaeria michotii*, *Phoma* sp., *Septoria zeae*, *S. zeicola*, *S. zeina* |
| Northern corn leaf blight (white blast, crown stalk rot, stripe) | *Setosphaeria turcica* (anarnorph: *Exserohilum turcicum* = *Helminthosporium turcicum*) |
| Northern corn leaf spot *Helminthosporium* ear rot (race 1) | *Cochliobolus carbonum* (anamorph: *Bipolaris zeicola* = *Helminthosporium carbonum*) |
| *Penicillium* ear rot (blue eye, blue mold) | *Penicillium* spp., *P. chrysogenum*, *P. expansum*, *P. oxalicum* |
| *Phaeocytostroma* stalk rot and root rot | *Phaeocytostroma ambiguum*, = *Phaeocytosporella zeae* |
| *Phaeosphaeria* leaf spot | *Phaeosphaeria maydis* = *Sphaerulina maydis* |
| *Physalospora* ear rot (*Botryosphaeria* ear rot) | *Botryosphaeria festucae* = *Physalospora zeicola* (anamorph: *Diplodia frumenti*) |
| Purple leaf sheath | Hemiparasitic bacteria and fungi |
| *Pyrenochaeta* stalk rot and root rot | *Phoma terrestris* = *Pyrenochaeta terrestris* |
| *Pythium* root rot | *Pythium* spp., *P. arrhenomanes*, *P. graminicola* |
| *Pythium* stalk rot | *Pythium aphanidermatum* = *P. butleri* L. |
| Red kernel disease (ear mold, leaf and seed rot) | *Epicoccum nigrum* |
| *Rhizoctonia* ear rot (sclerotial rot) | *Rhizoctonia zeae* (teleomorph: *Waitea circinata*) |
| *Rhizoctonia* root rot and stalk rot | *Rhizoctonia solani*, *Rhizoctonia zeae* |
| Root rots, minor | *Alternaria alternata*, *Cercospora sorghi*, *Dictochaeta fertilis*, *Fusarium acuminatum* (teleomorph: *Gibberella acuminata*), *F. equiseti* (teleomorph: *G. intricans*), *F. oxysporum*, *F. pallidoroseum*, *F. poae*, *F. roseum*, *G. cyanogena*, (anamorph: *F. sulphureum*), *Microdochium bolleyi*, *Mucor* sp., *Periconia circinata*, *Phytophthora cactorum*, *P. drechsleri*, *P. nicotianae* var. *parasitica*, *Rhizopus arrhizus* |
| *Rostratum* leaf spot (*Helminthosporium* leaf disease, ear and stalk rot) | *Setosphaeria rostrata*, (anamorph: *Exserohilum rostratum* = He/minthosporium rostratum*) |
| Rust, common corn | *Puccinia sorghi* |
| Rust, southern corn | *Puccinia polysora* |
| Rust, tropical corn | *Physopella pallescens*, *P. zeae* = *Angiopsora zeae* |
| *Sclerotium* ear rot (southern blight) | *Sclerotium rolfsii* Sacc. (teleomorph: *Athelia rolfsii*) |
| Seed rot-seedling blight | *Bipolaris sorokiniana*, *B. zeicola* = *Helminthosporium carbonum*, *Diplodia maydis*, *Exserohilum pedicillatum*, *Exserohilum turcicum* = *Helminthosporium turcicum*, *Fusarium avenaceum*, *F. culmorum*, *F. moniliforme*, *Gibberella zeae* (anamorph: *F. graminearum*), *Macrophomina phaseolina*, *Penicillium* spp., *Phomopsis* sp., *Pythium* spp., *Rhizoctonia solani*, *R. zeae*, *Sclerotium rolfsii*, *Spicaria* sp. |

TABLE 2-continued

| Downy mildew | |
|---|---|
| Disease | Pathogen |
| *Selenophoma* leaf spot | *Selenophoma* sp. |
| Sheath rot | *Gaeumannomyces graminis* |
| Shuck rot | *Myrothecium gramineum* |
| Silage mold | *Monascus purpureus, M ruber* |
| Smut, common | *Ustilago zeae = U. maydis* |
| Smut, false | *Ustilaginoidea virens* |
| Smut, head | *Sphacelotheca reiliana = Sporisorium holcisorghi* |
| Southern corn leaf blight and stalk rot | *Cochliobolus heterostrophus* (anamorph: *Bipolaris maydis = Helminthosporium maydis*) |
| Southern leaf spot | *Stenocarpella macrospora = Diplodia macrospora* |
| Stalk rots, minor | *Cercospora sorghi, Fusarium episphaeria, F. merismoides, F. oxysporum* Schlechtend, *F. poae, F. roseum, F. solani* (teleomorph: *Nectria haematococca), F. tricinctum, Mariannaea elegans, Mucor* sp., *Rhopographus zeae, Spicaria* sp. |
| Storage rots | *Aspergillus* spp., *Penicillium* spp. and other fungi |
| Tar spot | *Phyllachora maydis* |
| *Trichoderma* ear rot and root rot | *Trichoderma viride = T. lignorum* teleomorph: *Hypocrea* sp. |
| White ear rot, root and stalk rot | *Stenocarpella maydis = Diplodia zeae* |
| Yellow leaf blight | *Ascochyta ischaemi, Phyllosticta maydis* (teleomorph: *Mycosphaerella zeae-maydis*) |
| Zonate leaf spot | *Gloeocercospora sorghi* |

The following are especially preferred:

Plasmodiophoromycota such as *Plasmodiophora brassicae* (clubroot of crucifers), *Spongospora subterranea* (powdery scab of potato tubers), *Polymyxa graminis* (root disease of cereals and grasses), Oomycota such as *Bremia lactucae* (downy mildew of lettuce), *Peronospora* (downy mildew) in snapdragon (*P. antirrhini*), onion (*P. destructor*), spinach (*P. effusa*), soybean (*P. manchurica*), tobacco ("blue-mold"; *P. tabacina*) alfalfa and clover (*P. trifolium*), *Pseudoperonospora humuli* (downy mildew of hops), *Plasmopara* (downy mildew in grapevines) (*P. viticola*) and sunflower (*P. halstedii*), *Sclerophtohra macrospora* (downy mildew in cereals and grasses), *Pythium* (seed rot, seedling damping-off, and root rot and all types of plants, for example damping-off of Beta beet caused by *P. debaryanum*), *Phytophthora infestans* (blight in potato, brown rot in tomato and the like), *Albugo* spec. (white rust on cruciferous plants).

Ascomycota such as *Microdochium nivale* (snow mold of rye and wheat), *Fusarium graminearum, Fusarium culmorum* (partial ear sterility mainly in wheat), *Fusarium oxysporum* (*Fusarium* wilt of tomato), *Blumeria graminis* (powdery mildew of barley (f.sp. *hordei*) and wheat (f.sp. *tritici*)), *Erysiphe pisi* (powdery mildew of pea), *Nectria galligena* (*Nectria* canker of fruit trees), *Unicnula necator* (powdery mildew of grapevine), *Pseudopeziza tracheiphila* (red fire disease of grapevine), *Claviceps purpurea* (ergot on, for example, rye and grasses), *Gaeumannomyces graminis* (take-all on wheat, rye and other grasses), *Magnaporthe grisea* (rice blast disease), *Pyrenophora graminea* (leaf stripe of barley), *Pyrenophora teres* (net blotch of barley), *Pyrenophora tritici-repentis* (leaf blight of wheat), *Venturia inaequalis* (apple scab), *Sclerotinia sclerotium* (stalk break, stem rot), *Pseudopeziza medicaginis* (leaf spot of alfalfa, white and red clover).

Basidiomycetes such as *Typhula incarnata* (*typhula* blight on barley, rye, wheat), *Ustilago maydis* (blister smut on maize), *Ustilago nuda* (loose smut on barley), *Ustilago tritici* (loose smut on wheat, spelt), *Ustilago avenae* (loose smut on oats), *Rhizoctonia solani* (*rhizoctonia* root rot of potato), *Sphacelotheca* spp. (head smut of sorghum), *Melampsora lini* (rust of flax), *Puccinia graminis* (stem rust of wheat, barley, rye, oats), *Puccinia recondita* (leaf rust on wheat), *Puccinia dispersa* (brown rust on rye), *Puccinia hordei* (leaf rust of barley), *Puccinia coronata* (crown rust of oats), *Puccinia striiformis* (yellow rust of wheat, barley, rye and a large number of grasses), *Uromyces appendiculatus* (brown rust of bean), *Sclerotium rolfsii* (root and stem rots of many plants).

Deuteromycetes (*Fungi imperfecti*) such as *Septoria nodorum* (glume blotch) of wheat (*Septoria tritici*), *Pseudocercosporella herpotrichoides* (eyespot of wheat, barley, rye), *Rynchosporium secalis* (leaf spot on rye and barley), *Alternaria solani* (early blight of potato, tomato), *Phoma betae* (blackleg on Beta beet), *Cercospora beticola* (leaf spot on Beta beet), *Alternaria brassicae* (black spot on oilseed rape, cabbage and other crucifers), *Verticillium dahliae* (*verticillium* wilt), *Colletotrichum lindemuthianum* (bean anthracnose), *Phoma lingam* (blackleg of cabbage and oilseed rape), *Botrytis cinerea* (grey mold of grapevine, strawberry, tomato, hops and the like).

Most preferred are *Phytophthora infestans* (potato blight, brown rot in tomato and the like), *Microdochium nivale* (previously *Fusarium* nivale; snow mold of rye and wheat), *Fusarium graminearum, Fusarium culmorum* (partial ear sterility of wheat), *Fusarium oxysporum* (*Fusarium* wilt of tomato), Blumeria graminis (powdery mildew of barley (f. sp. *hordei*) and wheat (f. sp. *tritici*)), *Magnaporthe grisea* (rice blast disease), *Sclerotinia* sclerotium (stalk break, stem rot), *Septoria nodorum* and *Septoria* tritici (glume blotch of wheat), *Alternaria brassicae* (black spot of oilseed rape, cabbage and other crucifers), *Phoma lingam* (blackleg of cabbage and oilseed rape).

2. Bacterial Pathogens:

The pathogens and the diseases associated with them which are mentioned in Table 3 may be mentioned by way of example but not by limitation.

TABLE 3

| Bacterial diseases | |
|---|---|
| Disease | Pathogen |
| Bacterial leaf blight and stalk rot | *Pseudomonas avenae* subsp. *avenae* |
| Bacterial leaf spot | *Xanthomonas campestris* pv. *holcicola* |
| Bacterial stalk rot | *Enterobacter dissolvens = Erwinia dissolvens* |
| Bacterial stalk and top rot | *Erwinia carotovora* subsp. *carotovora, Erwinia chrysanthemi* pv. *zeae* |
| Bacterial stripe | *Pseudomonas andropogonis* |
| Chocolate spot | *Pseudomonas syringae* pv. *coronafaciens* |
| Goss's bacterial wilt and blight (leaf freckles and wilt) | *Clavibacter michiganensis* subsp. *nebraskensis = Corynebacterium michiganense* pv. and *nebraskense* |
| Holcus spot | *Pseudomonas syringae* pv. *syringae* |
| Purple leaf sheath | Hemiparasitic bacteria |

TABLE 3-continued

Bacterial diseases

| Disease | Pathogen |
|---|---|
| Seed rot-seedling blight | Bacillus subtilis |
| Stewart's disease (bacterial wilt) | Pantoea stewartii = Erwinia stewartii |
| Corn stunt (achapparramiento, maize stunt, Mesa Central or Rio Grande maize stunt) | Spiroplasma kunkelii |

The following pathogenic bacteria are very especially preferred: *Corynebacterium sepedonicum* (bacterial ring rot of potato), *Erwinia carotovora* (black leg of potato), *Erwinia amylovora* (fire blight of pear, apple, quince), *Streptomyces scabies* (potato scab), *Pseudomonas syringae* pv. *tabaci* (wildfire of tobacco), *Pseudomonas syringae* pv. *phaseolicola* (grease spot of dwarf bean), *Pseudomonas syringae* pv. tomato (bacterial speck of tomato), *Xanthomonas campestris* pv. *malvacearum* (bacterial blight of cotton) and *Xanthomonas campestris* pv. *oryzae* (bacterial leaf blight of rice and other grasses).

3. Viral Pathogens:

"Viral pathogens" includes all plant viruses such as, for example, tobacco or cucumber mosaic virus, ringspot virus, necrosis virus, maize dwarf mosaic virus and the like.

The pathogens and diseases associated with them which are mentioned in Table 4 may be mentioned by way of example, but not by limitation.

TABLE 4

Viral diseases

| Disease | Pathogen |
|---|---|
| American wheat striate (wheat striate mosaic) | American wheat striate mosaic virus (AWSMV) |
| Barley stripe mosaic | Barley stripe mosaic virus (BSMV) |
| Barley yellow dwarf | Barley yellow dwarf virus (BYDV) |
| Brome mosaic | Brome mosaic virus (BMV) |
| Cereal chlorotic mottle | Cereal chlorotic mottle virus (CCMV) |
| Corn chlorotic vein banding (Brazilian maize mosaic) | Corn chlorotic vein banding virus (CCVBV) |
| Corn lethal necrosis | Virus complex of Maize chlorotic mottle virus (MCMV) and Maize dwarf mosaic virus (MDMV) A or B or Wheat streak mosaic virus(WSMV) |
| Cucumber mosaic | Cucumber mosaic virus (CMV) |
| Cynodon chlorotic streak | Cynodon chlorotic streak virus (CCSV) |
| Johnsongrass mosaic | Johnsongrass mosaic virus (JGMV) |
| Maize bushy stunt | Mycoplasma-like organism (MLO) associated |
| Maize chlorotic dwarf | Maize chlorotic dwarf virus (MCDV) |
| Maize chlorotic mottle | Maize chlorotic mottle virus (MCMV) |
| Maize dwarf mosaic | Maize dwarf mosaic virus (MDMV) strains A, D, E and F |
| Maize leaf fleck | Maize leaf fleck virus (MLFV) |
| Maize line | Maize line virus (MLV) |
| Maize mosaic (corn leaf stripe, enanismo rayado) | Maize mosaic virus (MMV) |
| Maize mottle and chlorotic stunt | Maize mottle and chlorotic stunt virus |
| Maize pellucid ringspot | Maize pellucid ringspot virus (MPRV) |
| Maize raya gruesa | Maize raya gruesa virus (MRGV) |
| Maize rayado fino (fine striping disease) | Maize rayado fino virus (MRFV) |
| Maize red leaf and red stripe | Mollicute |

TABLE 4-continued

Viral diseases

| Disease | Pathogen |
|---|---|
| Maize red stripe | Maize red stripe virus (MRSV) |
| Maize ring mottle | Maize ring mottle virus (MRMV) |
| Maize rio IV | Maize rio cuarto virus (MRCV) |
| Maize rough dwarf (nanismo ruvido) | Maize rough dwarf virus (MRDV) (Cereal tillering disease virus) |
| Maize sterile stunt | Maize sterile stunt virus (strains of barley yellow striate virus) |
| Maize streak | Maize streak virus (MSV) |
| Maize stripe (maize chlorotic stripe, maize hoja blanca) | Maize stripe virus |
| Maize stunting | Maize stunting virus |
| Maize tassel abortion | Maize tassel abortion virus (MTAV) |
| Maize vein enation | Maize vein enation virus (MVEV) |
| Maize wallaby ear | Maize wallaby ear virus (MWEV) |
| Maize white leaf | Maize white leaf virus |
| Maize white line mosaic | Maize white line mosaic virus (MWLMV) |
| Millet red leaf | Millet red leaf virus (MRLV) |
| Northern cereal mosaic | Northern cereal mosaic virus (NCMV) |
| Oat pseudorosette (zakuklivanie) | Oat pseudorosette virus |
| Oat sterile dwarf | Oat sterile dwarf virus (OSDV) |
| Rice black-streaked dwarf | Rice black-streaked dwarf virus (RBSDV) |
| Rice stripe | Rice stripe virus (RSV) |
| Sorghum mosaic | Sorghum mosaic virus (SrMV) (auch: sugarcane mosaic virus (SCMV) Stamme H, I and M) |
| Sugarcane Fiji disease | Sugarcane Fiji disease virus (FDV) |
| Sugarcane mosaic | Sugarcane mosaic virus (SCMV) strains A, B, D, E, SC, BC, Sabi and MB (formerly MDMV-B) |
| Wheat spot mosaic | Wheat spot mosaic virus (WSMV) |

4. Animal Pests 4.1 Insect Pathogens:

The following may be mentioned by way of example, but not by limitation: insects such as, for example, beetles, caterpillars, lice or mites. Preferred insects are those of the genera *Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera*, etc. Especially preferred are coleopteran and lepidopteran insects such as, for example, the European corn borer (ECB), *Diabrotica barberi* (northern corn rootworm), *Diabrotica undecimpunctata* (southern corn rootworm), *Diabrotica virgifera* (Western corn rootworm), *Agrotis ipsilon* (black cutworm), *Crymodes devastator* (glassy cutworm), *Feltia ducens* (dingy cutworm), *Agrotis gladiaria* (claybacked cutworm), *Melanotus* spp., *Aeolus mellillus* (wireworm), *Aeolus mancus* (wheat wireworm), *Horistonotus uhlerii* (sand wireworm), *Sphenophorus maidis* (maize billbug), *Sphenophorus zeae* (timothy billbug), *Sphenophorus parvulus* (bluegrass billbug), *Sphenophorus callosus* (southern corn billbug), *Phyllogphaga* spp. (white grubs), *Anuraphis maidiradicis* (corn root aphid), *Delia platura* (seedcorn maggot), *Colaspis brunnea* (grape colaspis), *Stenolophus lecontei* (seedcorn beetle) and *Clivinia impressifrons* (lender seedcorn beetle).

Other examples are: lema (*Oulema melanopus*), frit fly (*Oscinella frit*), wireworms (*Agrotis lineatus*) and aphids (such as, for example, the oat grain aphid *Rhopalosiphum padi*, the blackberry aphid *Sitobion avenae*).

4.2 Nematodes:

The pathogens and the diseases associated with them mentioned in Table 6 may be mentioned by way of example, but not by limitation.

TABLE 6

Parasitic nematodes

| Damage | Pathogenic nematode |
|---|---|
| Awl | *Dolichodorus* spp., *D. heterocephalus* |
| Bulb and stem nematode disease; Europe | *Ditylenchus dipsaci* |
| Burrowing | *Radopholus similis* |
| Cyst nematode disease | *Heterodera avenae*, *H. zeae*, *Punctodera chalcoensis* |
| Dagger | *Xiphinema* spp., *X. americanum*, *X. mediterraneum* |
| False root-knot | *Nacobbus dorsalis* |
| Lance, Columbia | *Hoplolaimus columbus* |
| Lance | *Hoplolaimus* spp., *H. galeatus* |
| Lesion | *Pratylenchus* spp., *P. brachyurus*, *P. crenatus*, *P. hexincisus*, *P. neglectus*, *P. penetrans*, *P. scribneri*, *P. thornei*, *P. zeae* |
| Needle | *Longidorus* spp., *L. breviannulatus* |
| Ring | *Criconemella* spp., *C. ornata* |
| Root-knot disease | *Meloidogyne* spp., *M. chitwoodi*, *M. incognita*, *M. javanica* |
| Spiral | *Helicotylenchus* spp. |
| Sting | *Belonolaimus* spp., *B. longicaudatus* |
| Stubby-root | *Paratrichodorus* spp., *P. christiei*, *P. minor*, *Quinisulcius acutus*, *Trichodorus* spp. |
| Stunt | *Tylenchorhynchus dubius* |

Very especially preferred are *Globodera rostochiensis* and *G. pallida* (cyst eelworm on potato, tomato and other *Solanaceae*), *Heterodera schachtii* (beet eelworm on sugar and fodder beet, oilseed rape, cabbage and the like), *Heterodera avenae* (oat cyst nematode on oat and other cereal species), *Ditylenchus dipsaci* (stem or bulb eelworm, stem eelworm of rye, oats, maize, clover, tobacco, beet), *Anguina tritici* (grain nematode, cockle disease of wheat (spelt, rye), *Meloidogyne hapla* (root-knot nematode of carrot, cucumber, lettuce, tomato, potato, sugar beet, lucerne).

Examples of preferred fungal or viral pathogens for the individual varieties are:

1. Barley:
   Fungal, bacterial and viral pathogens: *Puccinia graminis* f.sp. *hordei* (barley stem rust), *Blumeria* (*Erysiphe*) *graminis* f.sp. *hordei* (barley powdery mildew), barley yellow dwarf virus (BYDV),
   Pathogenic insects/nematodes: *Ostrinia nubilalis* (European corn borer); *Agrotis ipsilon* (black cutworm); *Schizaphis graminum* (greenbug); *Blissus leucopterus leucopterus* (chinch bug); *Acrosternum hilare* (green stink bug); *Euschistus servus* (brown stink bug); *Delia platura* (seedcorn maggot); *Mayetiola destructor* (Hessian fly); *Petrobia latens* (brown wheat mite).

2. Soybean:
   Fungal, bacterial or viral pathogens: *Phytophthora megasperma* fsp. *glycinea*, *Macrophomina phaseolina*, *Rhizoctonia solani*, *Sclerotinia sclerotiorum*, *Fusarium oxysporum*, *Diaporthe phaseolorum* var. *sojae* (*Phomopsis sojae*), *Diaporthe phaseolorum* var. *caulivora*, *Sclerotium rolfsii*, *Cercospora kikuchii*, *Cercospora sojina*, *Peronospora manshurica*, *Colletotrichum dematium* (*Colletotrichum truncatum*), *Corynespora cassiicola*, *Septoria glycines*, *Phyllosticta sojicola*, *Alternaria alternata*, *Pseudomonas syringae* p.v. *glycinea*, *Xanthomonas campestris* p.v. *phaseoli*, *Microsphaera diffussa*, *Fusarium semitectum*, *Phialophora gregata*, soybean mosaic virus, *Glomerella glycines*, Tobacco Ring spot virus, Tobacco Streak virus, *Phakopsora pachyrhizi*, *Pythium aphanidermatum*, *Pythium ultimum*, *Pythium debaryanum*, Tomato spotted wilt virus, *Heterodera glycines Fusarium solani*.
   Pathogenic insects/nematodes: *Pseudoplusia includens* (soybean looper); *Anticarsia gemmatalis* (velvetbean caterpillar); *Plathypena scabra* (green cloverworm); *Ostrinia nubilalis* (European corn borer); *Agrotis ipsilon* (black cutworm); *Spodoptera exigua* (beet armyworm); *Heliothis virescens* (cotton budworm); *Helicoverpa zea* (cotton bollworm); *Epilachna varivestis* (Mexican bean beetle); *Myzus persicae* (green peach aphid); *Empoasca fabae* (potato leaf hopper); *Acrosternum hilare* (green stink bug); *Melanoplus femurrubrum* (redlegged grasshopper); *Melanoplus differentialis* (differential grasshopper); *Hylemya platura* (seedcorn maggot); *Sericothrips variabilis* (soybean thrips); *Thrips tabaci* (onion thrips); *Tetranychus turkestani* (strawberry spider mite); *Tetranychus urticae* (two-spotted spider mite).

3. Canola:
   Fungal, bacterial or viral pathogens: *Albugo candida*, *Alternaria brassicae*, *Leptosphaeria maculans*, *Rhizoctonia solani*, *Sclerotinia sclerotiorum*, *Mycosphaerella brassiccola*, *Pythium ultimum*, *Peronospora parasitica*, *Fusarium roseum*, *Alternaria alternata*.

4. Alfalfa:
   Fungal, bacterial or viral pathogens: *Clavibater michiganese* subsp. *insidiosum*, *Pythium ultimum*, *Pythium irregulare*, *Pythium splendens*, *Pythium debaryanum*, *Pythium aphanidermatum*, *Phytophthora megasperma*, *Peronospora trifoliorum*, *Phoma medicaginis* var. *medicaginis*, *Cercospora medicaginis*, *Pseudopeziza medicaginis*, *Leptotrochila medicaginis*, *Fusarium*, *Xanthomonas campestris* p.v. *alfalfae*, *Aphanomyces euteiches*, *Stemphylium herbarum*, *Stemphylium alfalfae*.

5. Wheat:
   Fungal, bacterial or viral pathogens: *Pseudomonas syringae* p.v. *atrofaciens*, *Urocystis agropyri*, *Xanthomonas campestris* p.v. *translucens*, *Pseudomonas syringae* p.v. *syringae*, *Alternaria alternata*, *Cladosporium herbarum*, *Fusarium graminearum*, *Fusarium avenaceum*, *Fusarium culmorum*, *Ustilago tritici*, *Ascochyta tritici*, *Cephalosporium gramineum*, *Collotetrichum graminicola*, *Erysiphe graminis* f.sp. *tritici*, *Puccinia graminis* f.sp. *tritici*, *Puccinia recondita* f.sp. *tritici*, *Puccinia striiformis*, *Pyrenophora tritici-repentis*, *Septoria nodorum*, *Septoria tritici*, *Septoria avenae*, *Pseudocercosporella herpotrichoides*, *Rhizoctonia solani*, *Rhizoctonia cerealis*, *Gaeumannomyces graminis* var. *tritici; Pythium aphanidermatum*, *Pythium arrhenomanes*, *Pythium ultimum*, *Bipolaris sorokiniana*, Barley Yellow Dwarf Virus, Brome Mosaic Virus, soil borne wheat mosaic virus, wheat streak mosaic virus, wheat spindle streak virus, American wheat striate virus, *Claviceps purpurea*, *Tilletia tritici*, *Tilletia laevis*, *Ustilago tritici*, *Tilletia indica*, *Rhizoctonia solani*, *Pythium arrhenomannes*, *Pythium gramicola*, *Pythium aphanidermatum*, high plains virus, European wheat striate virus, *Puccinia graminis* f.sp. *tritici* (wheat stem rust), *Blumeria* (*Erysiphe*) *graminis* f.sp. *tritici* (wheat powdery mildew).
   Pathogenic insects/nematodes: *Pseudaletia unipunctata* (armyworm); *Spodoptera, frugiperda* (fall armyworm);

*Elasmopalpus lignosellus* (lesser cornstalk borer); *Agrotis orthogonia* (western cutworm); *Elasmopalpus Zignosellus* (lesser cornstalk borer); *Oulema melanopus* (cereal leaf beetle); *Hypera punctata* (clover leaf weevil); *Diabrotica undecimpunctata howardi* (southern corn rootworm); Russian wheat aphid; *Schizaphis graminum* (greenbug); *Macrosiphum avenae* (English grain aphid); *Melanoplus femurrubrum* (redlegged grasshopper); *Melanoplus differentialis* (differential grasshopper); *Melanoplus sanguinipes* (migratory grasshopper); *Mayetiola destructor* (Hessian fly); *Sitodiplosis mosellana* (wheat midge); *Meromyza americana* (wheat stem maggot); *Hylemya coarctata* (wheat bulb fly); *Frankliniella fusca* (tobacco thrips); *Cephus cinctus* (wheat stem sawfly); *Aceria tulipae* (wheat curl mite).

6. Sunflower:

Fungal, bacterial or viral pathogens: *Plasmophora halstedii, Sclerotinia sclerotiorum*, aster yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* p.v. *Carotovora, Cephalosporium acremonium, Phytophthora cryptogea, Albugo tragopogonis*.

Pathogenic insects/nematodes: *Suleima helianthana* (sunflower bud moth); *Homoeosoma electellum* (sunflower moth); *zygogramma exclamationis* (sunflower beetle); *Bothyrus gibbosus* (carrot beetle); *Neolasioptera murtfeldtiana* (sunflower seed midge).

7. Maize:

Fungal, bacterial or viral pathogens: *Fusarium moniliforme* var. *subglutinans, Erwinia stewartii, Fusarium moniliforme, Gibberella zeae (Fusarium graminearum), Stenocarpella maydi (Diplodia maydis), Pythium irregulare, Pythium debaryanum, Pythium graminicola, Pythium splendens, Pythium ultimum, Pythium aphanidermatum, Aspergillus flavus, Bipolaris maydis 0, T (Cochliobolus heterostrophus), Helminthosporium carbonum I, II & III (Cochliobolus carbonum), Exserohilum turcicum I, II & III, Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganese* subsp. *nebraskense, Trichoderma viride*, maize dwarf mosaic virus A & B, wheat streak mosaic virus, maize chlorotic dwarf virus, *Claviceps sorghi, Pseudonomas avenae, Erwinia chrysanthemi* p.v. *Zea, Erwinia corotovora*, cornstunt spiroplasma, *Diplodia macrospora, Sclerophthora macrospora, Peronosclerospora sorghi, Peronosclerospora philippinesis, Peronosclerospora maydis, Peronosclerospora sacchari, Spacelotheca reiliana, Physopella zeae, Cephalosporium maydis, Caphalosporium acremonium*, maize chlorotic mottle virus, high plains virus, maize mosaic virus, maize rayado fino virus, maize streak virus (MSV), maize stripe virus, maize rough dwarf virus.

Pathogenic insects/nematodes: *Ostrinia nubilalis* (European corn borer); *Agrotis ipsilon* (black cutworm); *Helicoverpa zea* (corn earworm); *Spodoptera frugiperda* (fall armyworm); *Diatraea grandiosella* (Southwestern corn borer); *Elasmopalpus lignosellus* (lesser cornstalk borer); *Diatraea saccharalis* (surgarcane borer); *Diabrotica virgifera* (Western corn rootworm); *Diabrotica longicornis barberi* (Northern corn rootworm); *Diabrotica undecimpunctata howardi* (Southern corn rootworm); *Melanotus* spp. (wireworms); *Cyclocephala borealis* (Northern masked chafer; white grub); *Cyclocephala immaculata* (Southern masked chafer; white grub); *Popillia japonica* (Japanese beetle); *Chaetocnema pulicaria* (corn flea beetle); *Sphenophorus maidis* (maize billbug); *Rhopalosiphum maidis* (corn leaf aphid); *Anuraphis maidiradicis* (corn root aphid); *Blissus leucopterus leucopterus* (chinch bug); *Melanoplus* femur-rubrum (red-legged grasshopper); *Melanoplus sanguinipes* (migratory grasshopper); *Hylemva platura* (seedcorn maggot); *Agromyza parvicornis* (corn blot leafminer); *Anaphothrips obscrurus* (grass thrips); *Solenopsis milesta* (thief ant); *Tetranychus urticae* (two-spotted spider mite).

8. Sorghum:

Fungal, bacterial or viral pathogens: *Exserohilum turcicum, Colletotrichum graminicola (Glomerella graminicola), Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternate, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi*, sugarcane mosaic H, maize dwarf mosaic virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*.

Pathogenic insects/nematodes: *Chilo partellus* (sorghum borer); *Spodoptera frugiperda* (fall armyworm); *Helicoverpa zea* (corn ear-worm); *Elasmopalpus lignosellus* (lesser cornstalk borer); *Feltia subterranea* (granulate cutworm); *Phvllophaga crinita* (white grub); *Eleodes, Conoderus* and *Aeolus* spp. (wireworm); *Oulema melanopus* (cereal leaf beetle); *Chaetocnema pulicaria* (corn flea beetle); *Sphenophorus maidis* (maize billbug); *Rhopalosiphum maidis* (corn leaf aphid); *Siphaflava* (yellow sugarcane aphid); *Blissus leucopterus leucopterus* (chinch bug); *Contarinia sorghicola* (sorghum midge); *Tetranychus cinnabarinus* (carmine spider mite); *Tetranychus urticae* (two-spotted spider mite).

9. Cotton:

Pathogenic insects/nematodes: *Heliothis virescens* (cotton budworm); *Helicoverpa zea* (cotton bollworm); *Spodoptera exigua* (beet armyworm); *Pectinophora gossypiella* (pink bollworm); *Anthonomus grandis grandis* (boll weevil); *Aphis gossypii* (cotton aphid); *Pseudatomoscelis seriatus* (cotton fleahopper); *Trialeurodes abutilonea* (banded-winged whitefly); *Lygus lineolaris* (tarnished plant bug); *Melanoplus femurrubrum* (red-legged grasshopper); *Melanoplus differentialis* (differential grasshopper); *Thrips tabaci* (onion thrips); *Franklinkiella fusca* (tobacco thrips); *Tetranychus cinnabarinus* (carmine spider mite); *Tetranychus urticae* (two-spotted spider mite).

10. Rice:
   Pathogenic insects/nematodes: *Diatraea saccharalis* (sugarcane borer); *Spodoptera frugiperda* (fall armyworm); *Helicoverpa zea* (corn earworm); *Colaspis brunnea* (grape *colaspis*); *Lissorhoptrus oryzophilus* (rice water weevil); *Sitophilus oryzae* (rice weevil); *Nephotettix nigropictus* (rice leafhopper); *Blissus Ieucopterus leucopterus* (chinch bug); *Acrosternum hilare* (green stink bug).
11. Oilseed rape:
   Pathogenic insects/nematodes: *Brevicoryne brassicae* (cabbage aphid); *Phyilotreta cruciferae* (flea beetle); *Mamestra conjgurata* (bertha armyworm); *Plutella xylostella* (diamond-back moth); *Delia* ssp. (root maggots).

For the purposes of the invention, "RacB protein" is understood as meaning the RacB protein from barley as shown in SEQ ID NO: 2, and its homologs from rice (*Oryza sative*) as shown in SEQ ID NO: 4 and maize (*Zea mays*) as shown in SEQ ID NO: 6, and functional equivalents of the abovementioned.

"Amount of protein" is understood as meaning the amount of an RacB polypeptide in an organism, a tissue, a cell or a cell compartment. "Reduction" of the amount of protein means the quantitative reduction of the amount of an RacB protein in an organism, a tissue, a cell or a cell compartment—for example by one of the methods described hereinbelow—in comparison with the wild type of the same genus and species, to which this method had not been applied, under otherwise identical conditions (such as, for example, culture conditions, plant age and the like). The reduction amounts to at least 10%, preferably at least 10% or at least 20%, especially preferably at least 40% or 60%, very especially preferably at least 70% or 80%, most preferably at least 90% or 95%.

"Activity" is preferably understood as meaning the GTPase activity of an RacB polypeptide in an organism, a tissue, a cell or a cell compartment. "Reduction" of the activity is understood as meaning the reduction of the total activity of an RacB protein in an organism, a tissue, a cell or a cell compartment—for example by one of the methods described hereinbelow—in comparison with the wild type of the same genus and species, to which this method had not been applied, under otherwise identical conditions (such as, for example, culture conditions, plant age and the like). The reduction amounts to at least 10%, preferably at least 10% or at least 20%, especially preferably at least 40% or 60%, very especially preferably at least 70% or 80%, most preferably at least 90% or 95%.

"Function" is preferably understood as meaning the substrate-binding capacity of an RacB polypeptide in an organism, a tissue, a cell or a cell compartment. Suitable substrates are low-molecular-weight compounds such as GTP, but also the protein interaction partners of an RacB protein. "Reduction" of the function is understood as meaning, for example, the quantitative reduction of the binding capacity or binding strength of an RacB protein to at least one substrate in an organism, a tissue, a cell or a cell compartment—for example by one of the methods described hereinbelow—in comparison with the wild type of the same genus and species, to which this method had not been applied, under otherwise identical conditions (such as, for example, culture conditions, plant age and the like). Reduction is also understood as meaning the change in substrate specificity as can be expressed for example by the kcat/Km value. The reduction amounts to at least 10%, preferably at least 10% or at least 20%, especially preferably at least 40% or 60%, very especially preferably at least 70% or 80%, most preferably at least 90% or 95%.

Binding partners for RacB can be identified in a manner with which the skilled worker is familiar, for example by the yeast-2-hybrid system.

Methods of determining the amount of protein, the activity of GTPases or the substrate binding capacity are known to the skilled worker and have been described on a number of occasions for GTPases and for Rac proteins from a variety of genera and species (see, inter alia, Benard V et al. (1999) J Biol Chem 274(19):13198-204; Burstein E S (1998) Oncogene. 17(12):1617-23).

"Functional equivalents" of an RacB protein is preferably understood as meaning those sequences which are derived from, or are homologous to, an RacB protein described by SEQ ID NO: 2, 4 or 6 and which have essentially the same properties.

"Essentially the same properties" of a functional equivalent is above all understood as meaning conferring a pathogen-resistant phenotype or conferring or increasing the resistance to at least one pathogen while reducing the amount of protein, activity or function of said functional RacB equivalent in a plant or in a tissue, part or cells of the same. The absence of a spontaneously induced cell death in combination with said reduction of the amount of protein, activity or function of the functional equivalent is furthermore understood as an essential property.

In this context, the efficacy of the pathogen resistance can deviate both downward or upward in comparison with a value obtained when reducing one of the RacB proteins as shown in SEQ ID NO: 2, 4 or 6. Preferred functional equivalents are those in which the efficacy of the pathogen resistance—measured, for example, by the penetration efficacy of a pathogen (formation of haustoria)—differs by not more than 50%, preferably 25%, especially preferably 10% from a comparative value obtained by reducing an RacB protein as shown in NO: 2, 4 or 6. Especially preferred are those sequences where the reduction increases the efficacy of pathogen resistance quantitatively by more than 50%, preferably 100%, especially preferably 500%, very especially preferably 1000% based on a comparative value obtained by reducing one of the RacB protein as shown in SEQ ID NO: 2, 4 or 6.

The comparison is preferably carried out under analogous conditions. "Analogous conditions" means that all conditions such as, for example, culture or growing conditions, assay conditions (such as buffer, temperature, substrates, pathogen concentration and the like) are kept identical between the experiments to be compared and that the set-ups differ only by the sequence of the RacB polypeptides to be compared, their organism of origin and, if appropriate, the pathogen. When choosing the pathogen, each comparison requires that the pathogen be chosen which is most similar to the other equivalent, taking into consideration the species specificity.

"Functional equivalents" is understood as meaning, in particular, natural or artificial mutations of the RacB polypeptides as shown in SEQ ID NO: 2, 4 or 6 and homologous polypeptides from other plants which continue to have essentially the same properties. Homologous polypeptides from the above-described preferred plants are preferred. The sequences from other plants (for example *Arabidopsis thaliana*) which are homologous to the RacB sequences disclosed within the scope of the present invention can be found readily for example by database search or by screening genetic libraries using the RacB sequences as search sequence or probe.

Mutations comprise substitutions, additions, deletions, inversion or insertions of one or more amino acid residues. Thus, the present invention also comprises those polypeptides which are obtained by modification of a polypeptide as shown in SEQ ID NO: 2, 4 or 6.

Homology between two nucleic acid sequences is understood as meaning the identity of the nucleic acid sequence over in each case the entire sequence length which is calculated by comparison with the aid of the program algorithm GAP (Wisconsin Package Version 10.0, University of Wisconsin, Genetics Computer Group (GCG), Madison, USA; Altschul et al. (1997) Nucleic Acids Res. 25:3389 et seq.), setting the following parameters:

| Gap weight: | 50 | Length weight: | 3 |
| Average match: | 10 | Average mismatch: | 0 |

For example a sequence which has at least 80% homology with sequence SEQ ID NO: 1 at the nucleic acid level is understood as meaning a sequence which, upon comparison with the sequence SEQ ID NO: 1 by the above program algorithm with the above parameter set, has at least 80% homology.

Homology between two polypeptides is understood as meaning the identity of the amino acid sequence over in each case the entire sequence length which is calculated by comparison with the aid of the program algorithm GAP (Wisconsin Package Version 10.0, University of Wisconsin, Genetics Computer Group (GCG), Madison, USA), setting the following parameters:

| Gap weight: | 8 | Length weight: | 2 |
| Average match: | 2,912 | Average mismatch: | −2,003 |

For example a sequence which has at least 80% homology with sequence SEQ ID NO: 2 at the protein level is understood as meaning a sequence which, upon comparison with the sequence SEQ ID NO: 2 by the above program algorithm with the above parameter set, has at least 80% homology.

Functional equivalents derived from one of the polypeptide as shown in SEQ ID NO: 2, 4 or 6 according to the invention by substitution, insertion or deletion have at least 60%, preferably at least 80%, by preference at least 90%, especially preferably at least 95%, very especially preferably at least 98%, homology with one of the polypeptide as shown in SEQ ID NO: 2, 4 or 6 according to the invention and are distinguished by essentially the same properties as the polypeptide as shown in SEQ ID NO: 2, 4 or 6.

Functional equivalents derived from the nucleic acid sequence as shown in SEQ ID NO: 1, 3 or 5 according to the invention by substitution, insertion or deletion have at least 60%, preferably at least 80%, by preference at least 90%, especially preferably at least 95%, very especially preferably at least 98%, homology with one of the polypeptides as shown in SEQ ID NO: 1, 3 or 5 according to the invention and encode polypeptides having essentially the same properties as the polypeptide as shown in SEQ ID NO: 2, 4 or 6.

The RacB proteins comprised as functional equivalents preferably have at least one of the following sequence motifs:
a) A G1 element GXXXXGKS/T preferably in the N-terminal region, very especially preferably an element with the sequence GDGAVGKT, most preferably an element with the sequence KCVTVGDGAVGKTC.
b) A G2 effector region comprising a sequence motif with PTVFDN, especially preferably NTFPTDYVPTVFDNF-SANVV.
c) A G3 element comprising LWDTAGQ, especially preferably NLGLWDTAGQEDYN.
d) A G4 element TKXD, especially preferably TKLD, very especially preferably LVGTKLDLRDDKQ.
e) A G5 element EXS, preferably ECSS, very especially preferably ECSSKTG.
f) A C-terminal isoprenylation motif (CXXX, Hassanain H H et al. (2000) Biochem Biophys Res Commun. 272(3):783-8.), especially preferably CSIL.

Especially preferably, at least 2 or 3 of these motifs (a to f) occur in a functionally equivalent RacB protein, very especially preferably at least 4 or 5 of these motifs, most preferably all motifs a to f. Further sequence motifs which are typical for RacB, in particular also motifs which constitute a delimitation against Rac1 proteins, can be deduced readily by the skilled worker from the sequence alignment of the known RacB (or Rac1) proteins, as shown in FIG. 1.

Examples of the functional equivalents to the RacB proteins as shown in SEQ ID NO: 2, 4 or 6, which equivalents are to be reduced in the method according to the invention, can be identified for example from a variety of organisms whose genomic sequence is known, such as, for example, from *Arabidopsis thaliana*, *Brassica napus*, *Nicotiana tabacum*, *Solanum tuberosum*, or *Helianthinum* from databases of homology comparisons.

The screening of cDNA libraries or genomic libraries of other organisms, preferably of the plant species which are mentioned further below as hosts for the transformation, using the nucleic acid sequences described under SEQ ID NO: 1, 3 or 5 or parts of these as probe is also a method of identifying homologs in other species with which the skilled worker is familiar. In this context, the probes derived from the nucleic acid sequences as shown in SEQ ID NO: 1, 3 or 5 have a length of at least 20 bp, preferably 50 bp, particularly preferably 100 bp, very especially preferably 200 bp, and most preferably 400 bp. A DNA strand which is complementary to the sequences described under SEQ ID NO: 1, 3 or 5 may also be employed for screening the libraries.

Functional equivalents, accordingly, comprise DNA sequences which hybridize under standard conditions with the RacB nucleic acid sequence described by SEQ ID NO: 1, 3 or 5, with the sequence complementary thereto or parts of the abovementioned and which, as complete sequences, encode proteins which have the same properties as the proteins described under SEQ ID NO: 2, 4 or 6.

"Standard hybridization conditions" is to be understood in the broad sense and means stringent or else less stringent hybridization conditions. Such hybridization conditions are described, inter alia, by Sambrook J, Fritsch E F, Maniatis T et al., in Molecular Cloning (A Laboratory Manual), 2nd Edition, Cold Spring Harbor Laboratory Press, 1989, pages 9.31-9.57) or in Current Protocols in Molecular Biology, John Wiley & Sons, N.Y. (1989), 6.3.1-6.3.6.

For example, the conditions during the wash step can be selected from the range of conditions delimited by low-stringency conditions (approximately 2×SSC at 50° C.) and high-stringency conditions (approximately 0.2×SSC at 50° C., preferably at 65° C.): (20×SSC: 0.3M sodium citrate, 3 M NaCl, pH 7.0). In addition, the temperature during the wash step can be raised from low-stringency conditions at room temperature, approximately 22° C., to higher-stringency conditions at approximately 65° C. Both of the parameters salt concentration and temperature can be varied simultaneously, or else one of the two parameters can be kept constant while only the other is varied. Denaturants, for example formamide or SDS, may also be employed during the hybridization.

In the presence of 50% formamide, hybridization is preferably effected at 42° C. Some examples of conditions for hybridization and wash step are shown hereinbelow:

(1) Hybridization conditions be selected, for example, from the following conditions:
  a) 4×SSC at 65° C.,
  b) 6×SSC at 45° C.,
  c) 6×SSC, 100 μg/ml denatured fragmented fish sperm DNA at 68° C.,
  d) 6×SSC, 0.5% SDS, 100 μg/ml denatured salmon sperm DNA at 68° C.,
  e) 6×SSC, 0.5% SDS, 100 μg/ml denatured fragmented salmon sperm DNA, 50% formamide at 42° C.,
  f) 50% formamide, 4×SSC at 42° C., or
  g) 50% (vol/vol) formamide, 0.1% bovine serum albumin, 0.1% Ficoll, 0.1% polyvinylpyrrolidone, 50 mM sodium phosphate buffer pH 6.5, 750 mM NaCl, 75 mM sodium citrates at 42° C., or
  h) 2× or 4×SSC at 50° C. (low-stringency condition),
  i) 30 to 40% formamide, 2× or 4×SSC at 42° C. (low-stringency condition).

(2) Wash steps can be selected, for example, from the following conditions:
  a) 0.015 M NaCl/0.0015 M sodium citrate/0.1% SDS at 50° C.
  b) 0.1×SSC at 65° C.
  c) 0.1×SSC, 0.5% SDS at 68° C.
  d) 0.1×SSC, 0.5% SDS, 50% formamide, at 42° C.
  e) 0.2×SSC, 0.1% SDS at 42° C.
  f) 2×SSC at 65° C. (low-stringency condition).

Functional equivalents derived from a polypeptide as shown in SEQ ID NO: 2, 4 or 6 comprises in particular also the proteins having the SEQ ID NO: 35, 37, 39, 41, 43, 45, 47, 50, 52, 54, 56, 58, 60, 62, 64, 66, 68 or 70. "Functional equivalents" is to be understood as meaning, in particular, proteins encoded by a nucleic acid sequence having the SEQ ID NO: 34, 36, 38, 40, 42, 44, 46, 48, 49, 51, 53, 55, 57, 61, 63, 65, 67 or 69.

The reduction of the expression of an RacB protein, the RacB activity or the RacB function can be realized in many ways.

"Reduction" or "reducing" in connection with an RacB protein, an RacB activity or an RacB function is to be interpreted in the wide sense and comprises the partial or essentially complete inhibition or blocking of the functionality of an RacB protein in a plant or a part, tissue, organ, cells or seeds thereof, which inhibition or blocking is based on a variety of cytobiological mechanisms.

For the purposes of the invention, a reduction also comprises a quantitative reduction of an RacB protein down to the essential complete absence of the RacB protein (i.e. lacking detectability of RacB activity or RacB function, or lacking immunological detectability of the RacB protein). In this context, the expression of a particular RacB protein, or the RacB activity or RacB function, in a cell or an organism is preferably reduced by more than 50%, especially preferably by more than 80%, very especially preferably by more than 90%.

A variety of strategies for reducing the expression of an RacB protein, the RacB activity or RacB function are comprised in accordance with the invention. The skilled worker is aware of a series of different methods being available for influencing the expression of an RacB protein, the RacB activity or the RacB function in the desired manner.

A reduction of the RacB activity or the RacB function is preferably achieved by reduced expression of an endogenous RacB protein.

A reduction of the amount of RacB protein, the RacB activity or the RacB function can be effected using the following methods:
  a) Introduction of a double-stranded RacB RNA nucleic acid sequence (RacB dsRNA) or an expression cassette (s) ensuring the expression thereof
  b) Introduction of an RacB antisense nucleic acid sequences or an expression cassette ensuring expression thereof comprised are those methods in which the antisense nucleic acid sequence is directed against an RacB gene (i.e. genomic DNA sequences) or an RacB gene transcript (i.e. RNA sequences). α-Anomeric nucleic acid sequences are also comprised
  c) Introduction of an RacB antisense nucleic acid sequences in combination with a ribozyme or an expression cassette ensuring expression thereof
  d) Introduction of RacB sense nucleic acid sequences for inducing cosuppression or an expression cassette ensuring expression thereof
  e) Introduction of a nucleic acid sequence encoding dominant-negative RacB protein or an expression cassette ensuring expression thereof
  f) Introduction of DNA- or protein-binding factors against RacB genes, RacB RNAs or RacB proteins or an expression cassette ensuring expression thereof
  g) Introduction of viral nucleic acid sequences and expression constructs causing RacB RNA degradation or an expression cassette ensuring expression thereof
  h) Introduction of constructs for inducing a homologous recombination on endogenous RacB genes, for example for generating knock-out mutants
  i) Introduction of mutations into endogenous RacB genes for generating a loss of function (for example generation of stop codons, reading-frame shifts and the like).

In this context, each and every of these methods may bring about a reduction of the RacB expression, RacB activity or RacB function for the purposes of the invention. A combined use is also feasible. Further methods are known to the skilled worker and can comprise the hindering or prevention of RacB protein processing, of the RacB protein or RacB mRNA transport, inhibition of ribosome attachment, inhibition of RNA splicing, induction of an RacB-RNA-degrading enzyme and/or inhibition of translational elongation or termination.

The individual processes which are preferred may be described in greater detail hereinbelow:

a) Introduction of a Double-Stranded RacB RNA Nucleic Acid Sequence (RacB dsRNA)

The method of regulating genes by means of double-stranded RNA ("double-stranded RNA interference"; dsRNAi) has been described repeatedly for animal and plant organisms (for example Matzke M A et al. (2000) Plant Mol Biol 43:401-415; Fire A. et al (1998) Nature 391:806-811; WO 99/32619; WO 99/53050; WO 00/68374; WO 00/44914; WO 00/44895; WO 00/49035; WO 00/63364). Express reference is made to the processes and methods described in the above references. Effective gene suppression can also be demonstrated upon transient expression or following transient transformation for example as the consequence of biolistic transformation (Schweizer P et al. (2000) Plant J 2000 24: 895-903). dsRNAi methods are based on the phenomenon that the simultaneous introduction of complementary strand and counterstrand of a gene transcript causes the expression of the gene in question to be suppressed in a highly efficient manner. The phenotype caused greatly resembles a corresponding knock-out mutant (Waterhouse P M et al. (1998) Proc Natl Acad Sci USA 95:13959-64).

The dsRNAi method has proved to be particularly effective and advantageous for reducing the RacB expression. As described, inter alia, in WO 99/32619, dsRNAi approaches are markedly superior to traditional antisense approaches.

The invention therefore furthermore relates to double-stranded RNA molecules (dsRNA molecules) which, upon introduction into a plant (or a cell, tissue, organ or seed derived therefrom), bring about the reduction of an RacB.

In the double-stranded RNA molecule for reducing the expression of an RacB protein,
  a) one of the two RNA strands is essentially identical to at least a portion of an RacB nucleic acid sequence, and
  b) the corresponding other RNA strand is essentially identical to at least a portion of the complementary strand of an RacB nucleic acid sequence.

In a further preferred embodiment, the double-stranded RNA molecule for reducing the expression of an RacB protein comprises
  a) a sense RNA strand comprising at least one ribonucleotide sequence which is essentially identical to at least part of the sense RNA transcript of a nucleic acid sequence encoding an RacB protein, and
  b) an antisense RNA strand which is essentially—preferably completely—complementary to the RNA sense strand under a).

With respect to the double-stranded RNA molecules, RacB nucleic acid sequence is to be understood as meaning, preferably, a sequence as shown in SEQ ID NO: 1, 3 or 5 or a functional equivalent thereof as shown in SEQ ID NO: 34, 36, 38, 40, 42, 44, 46, 48, 49, 51, 53, 55, 57, 61, 63, 65, 67 or 69.

"Essentially identical" means that the dsRNA sequence can also show insertions, deletions or individual point mutations compared with the RacB target sequence or a functionally equivalent target sequence while still bringing about an effective reduction of the expression. The homology in accordance with the above definition preferably amounts to at least 75%, preferably at least 80%, very especially preferably at least 90%, most preferably 100%, between the sense strand of an inhibitory dsRNA and at least part of the sense RNA transcript of a nucleic acid sequence encoding an RacB protein or a functional equivalent thereof (or between the antisense strand of the complementary strand of a nucleic acid sequence encoding an RacB protein or a functional equivalent thereof).

The length of the part-segment amounts to at least 10 bases, preferably at least 25 bases, especially preferably at least 50 bases, very especially preferably at least 100 bases, most preferably at least 200 bases or at least 300 bases.

As an alternative, an "essentially identical" dsRNA can also be defined as a nucleic acid sequence which is capable of hybridizing with part of a storage protein gene transcript (for example in 400 mM NaCl, 40 mM PIPES pH 6.4, 1 mM EDTA at 50° C. or 70° C. for 12 to 16 h).

"Essentially complementary" is to be understood as meaning that the antisense RNA strand may also contain insertions, deletions and individual point mutations, compared to the complement of the sense RNA strand. Preferably, the homology between the antisense RNA strand and the complement of the sense RNA strand is at least 80%, preferably at least 90%, very particularly preferably at least 95%, most preferably 100%.

"Part of the sense RNA transcript" of a nucleic acid sequence encoding an RacB protein or a functional equivalent thereof is to be understood as meaning fragments of an RNA or mRNA transcribed from a nucleic acid sequence, preferably an RacB gene, encoding an RacB protein or a functional equivalent thereof. Here, the fragments preferably have a sequence length of at least 20 bases, preferably at least 50 bases, particularly preferably at least 100 bases, very particularly preferably at least 200 bases, most preferably at least 500 bases. Also comprised is the complete transcribed RNA or mRNA.

Also comprised is the use of the dsRNA molecules according to the invention in the methods according to the invention for generating a pathogen resistance in plants.

The dsRNA can be composed of one or more strands of polymerized ribonucleotides. Modifications both of the sugar-phosphate backbone and of the nucleosides may be present. For example, the phosphodiester bonds of the natural RNA can be modified in such a way that they comprise at least one nitrogen or sulfur hetero atom. Bases can be modified in such a way that the activity of, for example, adenosine deaminase is restricted. These and other modifications are described hereinbelow in the methods of stabilizing antisense RNA.

To achieve the same purpose, it is, of course, also possible to introduce a plurality of individual dsRNA molecules each comprising one of the ribonucleotide sequence sections defined above into the cell or the organism.

The dsRNA can be generated enzymatically or fully or partially synthesized chemically.

The double-stranded dsRNA structure can be formed starting from two complementary, separate RNA strands or, preferably, strands starting from an individual self-complementary RNA strand.

In a single self-complementary strand, sense and antisense sequence may be linked by a linking sequence ("linker") and can form for example a hairpin structure. The linking sequence can preferably be an intron which is spliced out after the dsRNA has been synthesized.

The nucleic acid sequence encoding a dsRNA can comprise further elements such as, for example, transcription termination signals or polyadenylation signals.

If the two dsRNA strands are to be combined in a cell or plant, this can be effected in various ways:
  a) transformation of the cell or plant with a vector comprising both expression cassettes,
  b) cotransformation of the cell or plant with two vectors, one of them comprising the expression cassettes with the sense strand and the other comprising the expression cassettes with the antisense strand,
  c) hybridizing two plants, each of which has been transformed with one vector, one of the vectors comprising the expression cassettes with the sense strand and the other comprising the expression cassettes with the antisense strand.

The formation of the RNA duplex can be initiated either outside or within the cell. Like in WO 99/53050, the dsRNA can also comprise a hairpin structure by linking sense and antisense strand by means of a linker (for example an intron). The self-complementary dsRNA structures are preferred since they only require the expression of one construct and always comprise the complementary strands in an equimolar ratio.

The expression cassettes encoding the antisense or sense strand of a dsRNA or the self-complementary strand of the dsRNA are preferably inserted into a vector and, using the methods described hereinbelow, stably inserted into the genome of a plant in order to ensure permanent expression of the dsRNA, using selection markers for example.

The dsRNA can be introduced using a quantity which allows at least one copy per cell. Greater quantities (for example at least 5, 10, 100, 500 or 1000 copies per cell) may bring about a more effective reduction.

As already described, 100% sequence identity between dsRNA and an RacB gene transcript or the gene transcript of a functionally equivalent gene is not necessarily required in order to bring about an effective reduction of the RacB expression. Accordingly, there is the advantage that the method is tolerant with regard to sequence deviations as may exist as the consequence of genetic mutations, polymorphisms or evolutionary divergence. Thus, for example, it is possible to use the dsRNA generated on the basis of the RacB sequence of one organism to suppress the RacB expression in another organism. The high sequence homology between the RacB sequences from rice, maize and barley allows the conclusion that this protein is conserved to a high degree within plants, so that the expression of a dsRNA derived from one of the disclosed RacB sequences as shown in SEQ ID NO: 1, 3 or 5 appears to have an advantageous effect in other plant species as well.

Furthermore, owing to the high homology between the individual RacB proteins and their functional equivalents, it is possible using a single dsRNA generated from a certain RacB sequence of an organism to suppress the expression of further homologous RacB proteins and/or their functional equivalents of the same organism or else the expression of RacB proteins in other related species. For this purpose, the dsRNA preferably comprises sequence regions of RacB gene transcripts which correspond to conserved regions. Said conserved regions can easily be found by comparing sequences.

The dsRNA can be synthesized either in vivo or in vitro. To this end, a DNA sequence encoding a dsRNA can be brought into an expression cassette under the control of at least one genetic control element (such as, for example, promoter, enhancer, silencer, splice donor or splice acceptor or polyadenylation signal). Suitable advantageous constructions are described hereinbelow. Polyadenylation is not required, nor do elements for initiating translation have to be present.

A dsRNA can be synthesized chemically or enzymatically. Cellular RNA polymerases or bacteriophage RNA polymerases (such as, for example, T3, T7 or SP6 RNA polymerase) can be used for this purpose. Suitable methods for expression of RNA in vitro are described (WO 97/32016; U.S. Pat. No. 5,593,874; U.S. Pat. No. 5,698, 425, U.S. Pat. No. 5,712,135, U.S. Pat. No. 5,789,214, U.S. Pat. No. 5,804,693). A dsRNA which has been synthesized in vitro chemically or enzymatically can be isolated completely or to some degree from the reaction mixture, for example by extraction, precipitation, electrophoresis, chromatography or combinations of these methods, before being introduced into a cell, tissue or organism. The dsRNA can be introduced directly into the cell or else be applied extracellularly (for example into the interstitial space).

However, it is preferred to transform the plant stably with an expression construct which brings about the expression of the dsRNA. Suitable methods are described hereinbelow.

b) Introduction of an RacB Antisense Nucleic Acid Sequence

Methods for suppressing a specific protein by preventing its mRNA from accumulating by means of antisense technology have been described in many instances, including in the case of plants (Sheehy et al. (1988) Proc Natl Acad Sci USA 85: 8805-8809; U.S. Pat. No. 4,801, 340; Mol JN et al. (1990) FEBS Lett 268(2):427-430). The antisense nucleic acid molecule hybridizes, or binds, with the cellular mRNA and/or genomic DNA encoding the RacB target protein to be suppressed. This suppresses the transcription and/or translation of the target protein. Hybridization can originate conventionally by the formation of a stable duplex or—in the case of genomic DNA—by the antisense nucleic acid molecule binding to the duplex of the genomic DNA by specific interaction in the major groove of the DNA helix.

An antisense nucleic acid sequence suitable for reducing an RacB protein can be deduced using the nucleic acid sequence encoding this protein, for example the nucleic acid sequence as shown in SEQ ID NO: 1, 3 or 5, or the nucleic acid sequence encoding a functional equivalent thereof, for example a sequence as shown in SEQ ID NO: 34, 36, 38, 40, 42, 44, 46, 48, 49, 51, 53, 55, 57, 61, 63, 65, 67 or 69, following Watson and Crick's base pairing rules. The antisense nucleic acid sequence can be complementary to all of the transcribed mRNA of said protein, be limited to the coding region, or else only be composed of a nucleotide, which is partially complementary to the coding or noncoding sequence of the mRNA. Thus, for example, the oligonucleotide can be complementary to the region comprising the translation start for said protein. Antisense nucleic acid sequences can be, for example, 5, 10, 15, 20, 25, 30, 35, 40, 45 or 50 nucleotides in length, but may also be longer and comprise at least 100, 200, 500, 1000, 2000 or 5000 nucleotides. Antisense nucleic acid sequences can be expressed recombinantly or synthesized chemically or enzymatically using methods known to the skilled worker. In the case of chemical synthesis, natural or modified nucleotides may be used. Modified nucleotides can impart an increased biochemical stability to the antisense nucleic acid sequence and lead to an increased physical stability of the duplex formed of antisense nucleic acid sequence and sense target sequence. The following can be used: for example phosphorothioate derivatives and acridine-substituted nucleotides such as 5-fluorouracil., 5-bromouracil, 5-chlorouracil, 5-iodouracil, hypoxanthin, xanthin, 4-acetylcytosine, 5-(carboxyhydroxylmethyl)uracil, 5-carboxymethylaminomethyl-2-thiouridine, 5-carboxymethylaminomethyluracil, dihydrouracil, β-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, β-D-mannosylqueosine, 5'-methoxycarboxymethyluracil, 5-methoxyuracil, 2-methylthio-N-6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid, 5-methyl-2-thiouracil, 3-(3-amino-3-N-2-carboxypropyl)uracil and 2,6-diaminopurine.

In a further preferred embodiment, the expression of an RacB protein can be inhibited by nucleotide sequences which are complementary to the regulatory region of an RacB gene (for example an RacB promoter and/or enhancer) and which form triple-helical structures with that DNA double helix so that the transcription of the RacB gene is reduced. Such methods have been described (Helene C (1991) Anticancer Drug Res 6(6):569-84; Helene C et al. (1992) Ann NY Acad Sci 660:27-36; Maher L J (1992) Bioassays 14(12):807-815). In a further embodiment, the antisense nucleic acid molecule can be an α-anomeric nucleic acid. Such α-anomeric nucleic acid molecules form specific double-stranded hybrids with complementary RNA in which—as opposed to the conventional β-nucleic acids—the two strands run parallel to one another (Gautier C et al. (1987) Nucleic Acids Res 15:6625-6641). The antisense nucleic acid molecule can furthermore also comprise 2'-O-methylribonucleotides (Inoue et al. (1987) Nucleic Acids Res 15:6131-6148) or chimeric RNA/DNA analogs (Inoue et al. (1987) FEBS Lett 215:327-330).

c) Introduction of an RacB Antisense Nucleic Acid Sequence in Combination with a Ribozyme The above-described antisense strategy can be combined advantageously with a ribozyme method. Catalytic RNA molecules or ribozymes can be adapted to suit any target RNA and cleave the phosphodiester backbone at specific positions, functionally deactivating the target RNA (Tanner N K (1999) FEMS Microbiol Rev 23(3):257-275). The ribozyme itself is not modified thereby, but is capable of cleaving further target RNA molecules analogously, thereby assuming the qualities of an enzyme. The incorporation of ribozyme sequences into antisense RNAs confers this enzyme-like RNA-cleaving quality to precisely these antisense RNAs, thus increasing their efficacy in inactivating the target RNA. The generation and the use of such ribozyme antisense RNA molecules is described, for example, in Haseloff et al. (1988) Nature 334: 585-591.

In this manner, ribozymes (for example "hammerhead" ribozymes; Haselhoff and Gerlach (1988) Nature 334: 585-591) can be used catalytically to cleave the mRNA of an enzyme to be suppressed, for example RacB, and to prevent translation. The ribozyme technique can increase the efficacy of an antisense strategy. Methods of expressing ribozymes for reducing specific proteins are described in (EP 0 291 533, EP 0 321 201, EP 0 360 257). The expression of ribozyme in plant cells has also been described (Steinecke P et al. (1992) EMBO J. 11(4):1525-1530; de Feyter R et al. (1996) Mol Gen Genet. 250(3):329-338). Suitable target sequences and ribozymes can be determined as described for example by "Steinecke P, Ribozymes, Methods in Cell Biology 50, Galbraith et al. eds, Academic Press, Inc. (1995), pp. 449-460" by calculating the secondary structure of ribozyme RNA and target RNA as well as by their interaction (Bayley CC et al. (1992) Plant Mol. Biol. 18(2):353-361; Lloyd A M and Davis R W et al. (1994) Mol Gen Genet. 242(6):653-657). For example, derivatives of the Tetrahymena L-19 IVS RNA with regions which are complementary to the mRNA of the RacB protein to be suppressed can be constructed (see also U.S. Pat. No. 4,987,071 and U.S. Pat. No. 5,116,742). As an alternative, such ribozymes can also be identified from a library of diverse ribozymes via a selection process (Bartel D and Szostak J W (1993) Science 261:1411-1418).

d) Introduction of an RacB Sense Nucleic Acid Sequence for Inducing Cosuppression The expression of an RacB nucleic acid sequence in sense orientation can lead to cosuppression of the corresponding homologous endogenous gene. The expression of sense RNA with homology with an endogenous gene can reduce or switch off the expression of the former, similarly to what has been described for antisense approaches (Jorgensen et al. (1996) Plant Mol Biol 31(5):957-973; Goring et al. (1991) Proc Natl Acad Sci USA 88:1770-1774; Smith et al. (1990) Mol Gen Genet 224:447-481; Napoli et al. (1990) Plant Cell 2:279-289; Van der Krol et al. (1990) Plant Cell 2:291-99). In this context, the homologous gene to be reduced can be represented either fully or only in part by the construct introduced. The possibility of translation is not required. The application of this technique to plants is described, for example, by Napoli et al. (1990) The Plant Cell 2: 279-289 and in U.S. Pat. No. 5,034,323.

The cosuppression is preferably realized by using a sequence essentially identical to at least part of the nucleic acid sequence encoding an RacB protein or a functional equivalent thereof, for example the nucleic acid sequence as shown in SEQ ID NO: 1, 3 or 5, or the nucleic acid sequence encoding a functional equivalent thereof, for example a sequence as shown in SEQ ID NO: 34, 36, 38, 40, 42, 44, 46, 48, 49, 51, 53, 55, 57, 61, 63, 65, 67 or 69.

e) Introduction of Nucleic Acid Sequences Encoding a Dominant-Negative RacB Protein The function or activity of an RacB protein can also be brought about efficiently by expressing a dominant-negative variant of this RacB protein. Methods of reducing the function or activity of a protein by coexpressing its dominant-negative form are known to the skilled worker (Lagna G and Hemmati-Brivanlou A (1998) Current Topics in Developmental Biology 36:75-98; Perlmutter R M and Alberola-Ila J (1996) Current Opinion in Immunology 8(2):285-90; Sheppard D (1994) American Journal of Respiratory Cell & Molecular Biology. 11(1):1-6; Herskowitz I (1987) Nature 329(6136):219-22).

For example, a dominant-negative RacB variant can be brought about by modifying the amino acid threonine at position 20 in the RacB proteins from maize, rice or barley to, preferably, aspartic acid. The threonine which is preferably to be mutated, or, if appropriate, also serine (similarly to threonine at position 20 in RacB from maize, rice or barley) in RacB homologs from other species can be determined for example by computer-aided comparison ("alignment"). These mutations for achieving a dominant-negative RacB variant are preferably carried out at the level of the nucleic acid sequence encoding RacB proteins. A corresponding mutation can be brought about for example by PCR-mediated in-vitro mutagenesis using suitable oligonucleotide primers, by which the desired mutation is introduced. This is done using methods known to the skilled worker; for example, the "LA PCR in vitro Mutagenesis Kit" (Takara Shuzo, Kyoto) may be used for this purpose. A method of generating a dominant-negative variant of the maize RacB protein is also described in WO 00/15815 (Example 4, p. 69).

Especially preferred are the dominant-negative variants of the RacB proteins from barley, rice or maize described under SEQ ID NO: 7, 8 and 9.

f) Introduction of DNA—or Protein-Binding Factors Against RacB Genes, RacB RNAs or RacB Proteins RacB gene expression may also be reduced using specific DNA-binding factors, for example factors of the zinc finger transcription factor type. These factors attach to the genomic sequence of the endogenous target gene, preferably in the regulatory regions, and bring about repression of the endogenous gene. The use of such a method makes possible the reduction of the expression of an endogenous RacB gene without it being necessary to recombinantly manipulate its sequence. Suitable methods for the preparation of suitable factors have been described (Dreier B et al. (2001) J Biol Chem 276(31): 29466-78; Dreier B et al. (2000) J Mol Biol 303(4):489-502; Beerli RR et al. (2000) Proc Natl Acad Sci USA 97 (4):1495-1500; Beerli RR et al. (2000) J Biol Chem 275(42):32617-32627; Segal D J and Barbas C F 3rd. (2000) Curr Opin Chem Biol 4(1):34-39; Kang J S and Kim J S (2000) J Biol Chem 275(12):8742-8748; Beerli RR et al. (1998) Proc Natl Acad Sci USA 95(25):14628-14633; Kim JS et al. (1997) Proc Natl Acad Sci USA 94(8):3616-3620; Klug A (1999) J Mol Biol 293(2):215-218; Tsai S Y et al. (1998) Adv Drug Deliv Rev 30(1-3):23-31; Mapp A K et al. (2000) Proc Natl Acad Sci USA 97(8):3930-3935; Sharrocks A D et al. (1997) Int J Biochem Cell Biol 29(12):1371-1387; Zhang L et al. (2000) J Biol Chem 275(43):33850-33860).

These factors can be selected using any desired portion of an RacB gene. This segment is preferably located in the promoter region. For gene suppression, however, it may also be in the region of the coding exons or introns. The segments in question can be obtained by the skilled worker from Genbank by database search or, starting from an RacB cDNA whose gene is not present in Genbank, by screening a genomic library for corresponding genomic clones. The skilled worker is familiar with the methods required therefor.

Furthermore, it is possible to introduce, into cells, factors which inhibit the RacB target protein itself. The protein-binding factors can be, for example, aptamers (Famulok M and Mayer G (1999) Curr Top Microbiol Immunol 243:123-36) or antibodies or antibody fragments or single-chain antibodies. Methods for obtaining these factors have been described and are known to the skilled worker. For example, a cytoplasmic scFv antibody was employed to modulate the activity of the phytochrome A protein in genetically modified tobacco plants (Owen M et al. (1992) Biotechnology (N Y) 10(7):790-794; Franken E et al. (1997) Curr Opin Biotechnol 8(4):411-416; Whitelam (1996) Trend Plant Sci 1:286-272).

Gene expression may also be suppressed by tailor-made low-molecular-weight synthetic compounds, for example of the polyamide type (Dervan P B and Bürli R W (1999) Current Opinion in Chemical Biology 3:688-693; Gottesfeld J M et al. (2000) Gene Expr 9(1-2):77-91). These oligomers are composed of the units 3-(dimethylamino)propylamine, N-methyl-3-hydroxypyrrole, N-methylimidazole and N-methylpyrrole and can be adapted to any piece of double-stranded DNA in such a way that they bind into the major groove in a sequence-specific manner and block the expression of these gene sequences. Suitable methods have been described (see, inter alia, Bremer R E et al. (2001) Bioorg Med Chem. 9(8):2093-103; Ansari A Z et al. (2001) Chem Biol. 8(6):583-92; Gottesfeld J M et al. (2001) J. Mol. Biol. 309(3):615-29; Wurtz N R et al. (2001) Org Lett 3(8): 1201-3; Wang CC et al. (2001) Bioorg Med Chem 9(3): 653-7; Urbach A R and Dervan PB (2001) Proc Natl Acad Sci USA 98(8):4343-8; Chiang S Y et al. (2000) J. Biol. Chem. 275(32):24246-54).

g) Introduction of Viral Nucleic Acid Sequences and Expression Constructs which Cause RacB RNA Degradation RacB expression can also be brought about efficiently by inducing the specific RacB RNA degradation by the plant with the aid of a viral expression system (amplicon) (Angell, S M et al. (1999) Plant J. 20(3):357-362). These systems—also termed "VIGS" (viral induced gene silencing)—introduce, into the plant, nucleic acid sequences with homology to the transcripts to be suppressed, with the aid of viral vectors. Then, transcription is switched off, probably mediated by plant defense mechanisms against viruses. Suitable techniques and methods have been described (Ratcliff F et al. (2001) Plant J 25(2):237-45; Fagard M and Vaucheret H (2000) Plant Mol Biol 43(2-3):285-93; Anandalakshmi R et al. (1998) Proc Natl Acad Sci USA 95(22):13079-84; Ruiz M T (1998) Plant Cell 10(6): 937-46).

h) Introduction of Constructs for Inducing a Homologous Recombination on Endogenous RacB Genes, for Example for Generating Knock-Out Mutants An example of what is used for generating a homologously recombinant organism with reduced RacB activity is a nucleic acid construct comprising at least part of an endogenous RacB gene which is modified by a deletion, addition or substitution of at least one nucleotide in such a way that its functionality is reduced or fully destroyed. The modification may also relate to the regulatory elements (for example the promoter) of the gene, so that the coding sequence remains unmodified, but expression (transcription and/or translation) does not take place and is reduced.

In the case of conventional homologous recombination, the modified region is flanked at its 5' and 3' end by further nucleic acid sequences which must be sufficient in length for making possible recombination. They are, as a rule, in the range of several hundred bases to several kilobases in length (Thomas K R and Capecchi M R (1987). Cell 51:503; Strepp et al. (1998) Proc Natl Acad Sci USA 95(8):4368-4373). For homologous recombination, the host organism—for example a plant—is transformed with the recombination construct using the methods described hereinbelow, and clones which have successfully undergone recombination are selected, for example using a resistance to antibiotics or herbicides.

Homologous recombination is a relatively rare event in higher eukaryotes, especially in plants. Random integrations into the host genome predominate. One possibility of eliminating the randomly integrated sequences and thus increasing the number of cell clones with a correct homologous recombination is the use of a sequence-specific recombination system as described in U.S. Pat. No. 6,110,736, by which unspecifically integrated sequences can be deleted again, which simplifies the selection of events which have integrated successfully via homologous recombination. A large number of sequence-specific recombination systems can be used, examples being the Cre/lox system of bacteriophage P1, the FLP/FRT system of yeast, the Gin recombinase of phage Mu, the Pin recombinase from *E. coli*, and the R/RS system of the pSR1 plasmid. The bacteriophage P1 Cre/10x and the yeast FLP/FRT system are preferred. The FLP/FRT and cre/lox recombinase system has already been applied to plant systems (Odell et al. (1990) Mol Gen Genet 223: 369-378).

i) Introduction of Mutations into Endogenous RacB Genes for Generating a Loss of Function (For Example Generation of Stop Codons, Reading-Frame Shifts and the Like)

Further suitable methods for reducing the RacB activity are the introduction of nonsense mutations into endogenous RacB genes, for example by introducing RNA/DNA oligonucleotides into the plant (Zhu et al. (2000) Nat Biotechnol 18(5):555-558) and the generation of knockout mutants with the aid of, for example, T-DNA mutagenesis (Koncz et al. (1992) Plant Mol Biol 20(5): 963-976), ENU (N-ethyl-N-nitrosourea) mutagenesis or homologous recombination (Hohn B and Puchta (1999) H Proc Natl Acad Sci USA 96:8321-8323.). Point mutations can also be generated by means of DNA-RNA hybrids also known under the name "chimeraplasty" (Cole-Strauss-et al. (1999) Nucl Acids Res. 27(5):1323-1330; Kmiec (1999) Gene therapy American Scientist 87(3):240-247).

The methods of dsRNAi, cosuppression by means of sense RNA and "VIGS" ("virus induced gene silencing") are also termed "post-transcriptional gene silencing" (PTGS). PTGS methods, like the reduction of the RacB function or activity with dominant-negative RacB variants, are especially advantageous because the demands regarding the homology between the endogenous gene to be suppressed and the sense or dsRNA nucleic acid sequence expressed recombinantly (or between the endogenous gene and its dominant-negative variant) are lower than, for example, in the case of a traditional antisense approach. Such criteria with regard to homology are mentioned in the description of the dsRNAI method and can generally be applied to PTGS methods or dominant-negative approaches. Owing to the high degree of homology between the RacB proteins from maize, rice and barley, a high degree of conservation of this protein in plants can be assumed. Thus, using the RacB nucleic acid sequences from barley, maize or rice, it is presumably also possible efficiently to suppress the expression of homologous RacB proteins in other species without the isolation and structure elucidation of the RacB homologs occurring therein being required. Considerably less labor is therefore required. Similarly, the use of dominant-negative variants of an RacB protein from rice, maize or barley can presumably also efficiently reduce or suppress the function/activity of its homolog in other plant species.

All of the substances and compounds which directly or indirectly bring about a reduction in protein quantity, RNA quantity, gene activity or protein activity of an RacB protein shall subsequently be combined in the term "anti-RacB" compounds. The term "anti-RacB" compound explicitly includes the nucleic acid sequences, peptides, proteins or other factors employed in the above-described methods.

For the purposes of the invention, "introduction" comprises all of the methods which are capable of directly or indirectly introducing an "anti-RacB" compound into a plant or a cell, compartment, tissue, organ or seed thereof, or of generating such a compound there. Direct and indirect methods are comprised. The introduction can lead to a transient presence of an "anti-RacB" compound (for example a dsRNA) or else to its stable presence.

Owing to the different nature of the above-described approaches, the "anti-RacB" compound can exert its function directly (for example by insertion into an endogenous RacB gene). However, its function can also be exerted indirectly following transcription into an RNA (for example in the case of antisense approaches) or following transcription and translation into a protein (for example in the case of binding factors). The invention comprises both directly and indirectly acting "anti-RacB" compounds.

The term "introducing" comprises for example methods such as transfection, transduction or transformation.

"Anti-RacB" compounds therefore also comprises recombinant expression constructs which bring about expression (i.e. transcription and, if appropriate, translation), for example of an RacB dsRNA or an RacB "antisense" RNA, preferably in a plant or a part, tissue, organ or seed thereof.

In said expression constructs, a nucleic acid molecule whose expression (transcription and, if appropriate, translation) generates an "anti-RacB" compound is preferably operably linked to at least one genetic control element (for example a promoter) which ensures expression in an organism, preferably in plants. If the expression construct is to be introduced directly into a plant and the "anti-RacB" compound (for example the RacB dsRNA) is to be generated therein in plantae, plant-specific genetic control elements (for example promoters) are preferred. However, the "anti-RacB" compound may also be generated in other organisms or in vitro and then be introduced into the plant (as described in Examples 6 and 7). Preferred in this context are all of the prokaryotic or eukaryotic genetic control elements (for example promoters) which permit the expression in the organism chosen in each case for the preparation.

Operable linkage is to be understood as meaning, for example, the sequential arrangement of a promoter with the nucleic acid sequence to be expressed (for example an "anti-RacB" compound) and, if appropriate, further regulatory elements such as, for example, a terminator in such a way that each of the regulatory elements can fulfil its function when the nucleic acid sequence is expressed recombinantly, depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly is preferably less than 200 base pairs, especially preferably less than 100 base pairs, very especially preferably less than 50 base pairs.

Operable linkage, and an expression cassette, can be generated by means of customary recombination and cloning techniques as are described, for example, in Maniatis T, Fritsch E F and Sambrook J (1989) Molecular Cloning: A Laboratory Manual, Cold Spring Harbor Laboratory, Cold Spring Harbor (NY), in Silhavy T J, Berman M L and Enquist L W (1984) Experiments with Gene Fusions, Cold Spring Harbor Laboratory, Cold Spring Harbor (NY), in Ausubel F M et al. (1987) Current Protocols in Molecular Biology, Greene Publishing Assoc. and Wiley Interscience and in Gelvin et al. (1990) In: Plant Molecular Biology Manual. However, further sequences which, for example, act as a linker with specific cleavage sites for restriction enzymes, or as a signal peptide, may also be positioned between the two sequences. The insertion of sequences may also lead to the expression of fusion proteins. Preferably, the expression cassette, consisting of a linkage of promoter and nucleic acid sequence to be expressed, can exist in a vector-integrated form and be inserted into a plant genome, for example by transformation.

However, expression cassette also denotes those constructions in which a promoter is positioned behind an endogenous RacB gene, for example by means of homologous recombination, and the reduction according to the invention of an RacB protein is brought about by the expression of an antisense RacB RNA.

Analogously, an "anti-RacB" compound (for example a nucleic acid sequence encoding an RacB dsRNA or an RacB antisense RNA) can be positioned behind an endogenous promoter in such a way that the same effect is manifested. Both approaches lead to inventive expression cassettes.

The term plant-specific promoters is understood as meaning, in principle, any promoter which is capable of governing the expression of genes, in particular foreign genes, in plants or plant parts, plant cells, plant tissues or plant cultures. In this context, expression can be, for example, constitutive, inducible or development-dependent.

The following are preferred:

a) Constitutive Promoters

Preferred vectors are those which make possible constitutive expression in plants (Benfey et al. (1989) EMBO J. 8:2195-2202). "Constitutive" promoter is understood as meaning those promoters which ensure expression in a large number of, preferably all, tissues over a substantial period of plant development, preferably at all stages of plant development. In particular a plant promoter or a promoter derived from a plant virus are preferably used. Particularly preferred is the promoter of the CaMV cauliflower mosaic virus $^{35}$S transcript (Franck et al. (1980) Cell 21:285-294; Odell et al. (1985) Nature 313:810-812; Shewmaker et al. (1985) Virology 140:281-288; Gardner et al. (1986) Plant Mol Biol 6:221-228) or the 19S CaMV promoter (U.S. Pat. No. 5,352,605; WO 84/02913; Benfey et al. (1989) EMBO J. 8:2195-2202). Another suitable constitutive promoter is the "Rubisco small subunit (SSU)" promoter (U.S. Pat. No. 4,962,028), the leguminB promoter (GenBank Acc. No. X03677), the *Agrobacterium nopaline* synthase promoter, the TR dual promoter, the *Agrobacterium* OCS (octopine synthase) promoter, the ubiquitin promoter (Holtorf S et al. (1995) Plant Mol Biol 29:637-649), the ubiquitin 1 promoter (Christensen et al. (1992) Plant Mol Biol 18:675-689; Bruce et al. (1989) Proc Natl Acad Sci USA 86:9692-9696), the Smas promoter, the cinnamyl alcohol dehydrogenase promoter (U.S. Pat. No. 5,683,439), the promoters of the vacuolar ATPase subunits or the promoter of a proline-rich protein from wheat (WO 91/13991), and further promoters of genes whose constitutive expression in plants is known to the skilled worker. A particularly preferred constitutive promoter is the promoter of the nitrilase-1 (nit1) gene from *A. thaliana* (GenBank Acc.-No.: Y07648.2, nucleotides 2456-4340, Hillebrand et al. (1996) Gene 170:197-200).

b) Tissue-Specific Promoters

Preferred are furthermore promoters with specificity for the anthers, ovaries, flowers, leaves, stems, roots and seeds.

Seed-specific promoters such as, for example, the phaseolin promoter (U.S. Pat. No. 5,504,200; Bustos MM et al. (1989) Plant Cell 1(9):839-53), the 2S albumin gene promoter (Joseffson L G et al. (1987) J Biol Chem 262: 12196-12201), the legumin promoter (Shirsat A et al. (1989) Mol Gen Genet 215(2): 326-331), the USP (unknown seed protein) promoter (Baumlein H et al. (1991) Mol Gen Genet 225(3):459-67), the napin gene promoter (U.S. Pat. No. 5,608,152; Stalberg K et al. (1996) L Planta 199:515-519), the sucrose binding protein promoter (WO 00/26388) or the legumin B4 promoter (LeB4; Bäumlein H et al. (1991) Mol Gen Genet 225: 121-128; Baeumlein et al. (1992) Plant Journal 2(2): 233-9; Fiedler U et al. (1995) Biotechnology (NY) 13(10):1090f), the *Arabidopsis oleosin* promoter (WO 98/45461), the *Brassica* Bce4 promoter (WO 91/13980). Further suitable seed-specific promoters are those of the genes encoding the high-molecular-weight glutenin (HMWG), gliadin, branching enzyme, ADP glucose pyrophosphatase (AGPase) or starch synthase. Furthermore preferred are promoters which permit seed-specific expression in monocots such as maize, barley, wheat, rye, rice and the like. The following can be employed advantageously: the promoter of the lpt2 or lpt1 gene (WO 95/15389, WO 95/23230) or the promoters described in WO 99/16890 (promoters of the *hordein* gene, the glutelin gene, the oryzin gene, the prolamin gene, the gliadin gene, the glutelin gene, the zein gene, the kasirin gene or the secalin gene).

Tuber-, storage-root- or root-specific promoters such as, for example, the patatin promoter class I (B33), the potato cathepsin D inhibitor promoter.

Leaf-specific promoters such as the potato cytosolic FBPase promoter (WO 97/05900), the Rubisco (ribulose-1,5-bisphosphate carboxylase) SSU (small subunit) promoter or the ST-LSI promoter from potato (Stockhaus et al. (1989) EMBO J. 8:2445-2451). Very especially preferred are epidermis-specific promoters such as, for example, the OXLP gene (oxalate-oxidase-like protein) promoter (Wei et al. (1998) Plant Mol. Biol. 36:101-112).

Flower-specific promoters such as, for example, the phytoene synthase promoter (WO 92/16635) or the promoter of the P-rr gene (WO 98/22593).

Anther-specific promoters such as the 5126 promoter (U.S. Pat. No. 5,689,049, U.S. Pat. No. 5,689,051), the glob-1 promoter and the γ-zein promoter.

c) Chemically Inducible Promoters

The expression cassettes can also comprise a chemically inducible promoter (review article: Gatz et al. (1997) Annu Rev Plant Physiol Plant Mol Biol 48:89-108), by which the expression of the exogenous gene in the plant at a particular point in time can be controlled. Such promoters such as, for example, the PRP1 promoter (Ward et al. (1993) Plant Mol Biol 22:361-366), a salicylic-acid-inducible promoter (WO 95/19443), a benzenesulfonamide-inducible promoter (EP 0 388.186), a tetracyclin-inducible promoter (Gatz et al. (1992) Plant J 2:397-404)., an abscisic-acid-inducible promoter (EP 0 335 528) or an ethanol- or cyclohexanone-inducible promoter (WO 93/21334) can likewise be used.

d) Stress- or Pathogen-Inducible Promoters

Further preferred promoters are those which are induced by biotic or abiotic stress such as, for example, the pathogen-inducible promoter of the PRP1 gene (or gst1 promoter) e.g. from potato (WO 96/28561; Ward et al. (1993) Plant Mol Biol 22:361-366), the tomato high-temperature-inducible hsp70 or hsp80 promoter (U.S. Pat. No. 5,187,267), the potato low-temperature-inducible alpha-amylase promoter (WO 96/12814), the light-inducible PPDK promoter, or the wounding-induced pinII promoter (EP-A 0 375 091).

Further pathogen-inducible promoters comprise the Fis1 promoter from flax (WO 96/34949), the Vst1 promoter (Schubert et al. (1997) Plant Mol Biol 34:417-426) and the EAS4 sesquiterpene cyclase promoter from tobacco (U.S. Pat. No. 6,100,451).

Pathogen-inducible promoters comprise those of genes which are induced as a consequence of infection by pathogens, such as, for example, genes of PR proteins, SAR proteins, β-1,3-glucanase, chitinase and the like (for example Redolfi et al. (1983) Neth J Plant Pathol 89:245-254; Uknes, et al. (1992) The Plant Cell 4:645-656; Van Loon (1985) Plant Mol Viral 4:111-116; Marineau et al. (1987) Plant Mol Biol 9:335-342; Matton et al. (1987) Molecular Plant-Microbe Interactions 2:325-342; Somssich et al. (1986) Proc Natl Acad Sci USA 83:2427-2430; Somssich et al. (1988) Mol Gen Genetics 2:93-98; Chen et al. (1996) Plant J 10:955-966; Zhang and Sing (1994) Proc Natl Acad Sci USA 91:2507-2511; Warner, et al. (1993) Plant J 3:191-201; Siebertz et al. (1989) Plant Cell 1:961-968(1989).

Also comprised are wounding-inducible promoters such as that of the pinII gene (Ryan (1990) Ann Rev Phytopath 28:425-449; Duan et al. (1996) Nat Biotech 14:494-498), of the wun1 and wun2 gene (U.S. Pat. No. 5,428,148), of the win1 and win2 gene (Stanford et al. (1989) Mol Gen Genet 215:200-208), of system in (McGurl et al. (1992) Science 225:1570-1573), of the WIP1 gene (Rohmeier et al. (1993) Plant Mol Biol 22:783-792; Eckelkamp et al. (1993). FEBS Letters 323:73-76), of the MPI gene (Corderok et al. (1994) Plant J 6(2):141-150) and the like.

A source of further pathogen-inducible promoters is the PR gene family. A number of elements in these promoters have been found to be advantageous. Thus, the region −364 to −288 in the promoter of PR-2d provides salicylate specificity (Buchel et al. (1996) Plant Mol Biol 30, 493-504). The sequence 5'-TCATCTTCTT-3' is encountered repeatedly in the promoter of barley β-1,3-glucanase and more than 30 further stress-induced genes. In tobacco, this region binds a nuclear protein whose abundance is increased by salicylate. The PR-1 promoters from tobacco and *Arabidopsis* (EP-A 0 332 104, WO 98/03536) are likewise suitable for use as pathogen-inducible promoters. "Acidic PR-5"-(aPR5)-promoters from barley (Schweizer et al. (1997) Plant Physiol 114: 79-88) and wheat (Rebmann et al. (1991) Plant Mol Biol 16:329-331) are preferred, since they are particularly specifically pathogen-induced. aPR5 proteins accumulate within about 4 to 6 hours after pathogen attack and have only very limited background expression (WO 99/66057). One approach to achieve higher pathogen-induced specificity is the preparation of synthetic promoters from combinations of known pathogen-responsive elements (Rushton et al. (2002) Plant Cell 14, 749-762; WO 00/01830; WO 99/66057). Further pathogen-inducible promoters from different species are known to the person skilled in the art (EP-A 1 165 794; EP-A 1 062 356; EP-A 1 041 148; EP-A 1 032 684;

e) Development-Dependent Promoters

Further suitable promoters are, for example, fruit-maturation-specific promoters such as, for example, the tomato fruit-maturation-specific promoter (WO 94/21794, EP 409 625). Development-dependent promoters comprise partly the tissue-specific promoters, since individual tissues develop by nature in a development-dependent fashion.

Especially preferred are constitutive promoters and leaf- and/or stem-specific, pathogen-inducible and epidermis-specific promoters, with pathogen-inducible and epidermis-specific promoters being most preferred.

Furthermore, further promoters may be linked operably to the nucleic acid sequence to be expressed, which promoters make possible the expression in further plant tissues or in other organisms, such as, for example, *E. coli* bacteria. Suitable plant promoters are, in principle, all of the above-described promoters.

The nucleic acid sequences present in the expression cassettes or vectors according to the invention can be linked operably to further genetic control sequences in addition to a promoter. The term "genetic control sequences" is to be understood in the broad sense and refers to all those sequences which have an effect on the materialization or the function of the expression cassette according to the invention. For example, genetic control sequences modify the transcription and translation in prokaryotic or eukaryotic organisms. Preferably, the expression cassettes according to the invention comprise the promoter with specificity for the embryonal epidermis and/or the flower 5'-upstream of the nucleic acid sequence in question to be expressed recombinantly, and 3'-downstream a terminator sequence as additional genetic control sequence and, if appropriate, further customary regulatory elements, in each case linked operably to the nucleic acid sequence to be expressed recombinantly.

Genetic control sequences also comprise further promoters, promoter elements or minimal promoters, all of which can modify the expression-governing properties. Thus, for example, the tissue-specific expression may additionally depend on certain stressors, owing to genetic control sequences. Such elements have been described, for example, for water stress, abscisic acid (Lam E and Chua N H, J Biol Chem 1991; 266(26): 17131-17135) and heat stress (Schoffl F et al., Molecular & General Genetics 217(2-3):246-53, 1989).

Further advantageous control sequences are, for example, in the Gram-positive promoters amy and SPO2, and in the yeast or fungal promoters ADC1, MFa, AC, P-60, CYC1, GAPDH, TEF, rp28, ADH.

In principle, all natural promoters with their regulatory sequences like those mentioned above may be used for the method according to the invention. In addition, synthetic promoters may also be used advantageously.

Genetic control sequences furthermore also comprise the 5'-untranslated regions, introns or noncoding 3'-region of genes, such as, for example, the actin-1 intron, or the Adh1-S introns 1, 2 and 6 (general reference: The Maize Handbook, Chapter 116, Freeling and Walbot, Eds., Springer, New York (1994)). It has been demonstrated that they may play a significant roles in the regulation of gene expression. Thus, it has been demonstrated that 5'-untranslated sequences can enhance the transient expression of heterologous genes. Examples of translation enhancers which may be mentioned are the tobacco mosaic virus 5' leader sequence (Gallie et al. (1987) Nucl Acids Res 15:8693-8711) and the like. Furthermore, they may promote tissue specificity (Rouster J et al. (1998) Plant J 15:435-440).

The expression cassette may advantageously comprise one or more of what are known as enhancer sequences, linked operably to the promoter, which make possible an increased recombinant expression of the nucleic acid sequence. Additional advantageous sequences, such as further regulatory elements or terminators, may also be inserted at the 3' end of the nucleic acid sequences to be expressed recombinantly.

One or more copies of the nucleic acid sequences to be expressed recombinantly may be present in the gene construct.

Polyadenylation signals which are suitable as control sequences are plant polyadenylation signals, preferably those which essentially correspond to T-DNA polyadenylation signals from *Agrobacterium tumefaciens*, in particular gene 3 of the T-DNA (octopin synthase) of the Ti plasmid pTiACHS (Gielen et al. (1984) EMBO J. 3:835 et seq.) or functional equivalents thereof. Examples of terminator sequences which are especially suitable are the OCS (octopin synthase) terminator and the NOS (nopalin synthase) terminator.

Control sequences are furthermore to be understood as those which make possible homologous recombination or insertion into the genome of a host organism or which permit removal from the genome. In the case of homologous recombination, for example the natural promoter of a particular gene may be exchanged for a promoter with specificity for the embryonal epidermis and/or the flower. Methods such as the cre/lox technology permit a tissue-specific, if appropriate inducible, removal of the expression cassette from the genome of the host organism (Sauer B (1998) Methods. 14(4):381-92). In this method, specific flanking sequences (lox sequences), which later allow removal by means of cre recombinase, are attached to the target gene.

An expression cassettes and the vectors derived from it may comprise further functional elements. The term functional element is to be understood in the broad sense and refers to all those elements which have an effect on the generation, amplification or function of the expression cassettes, vectors or transgenic organisms according to the invention. The following may be mentioned by way of example, but not by limitation:

a) Selection markers which confer a resistance to a metabolism inhibitor such as 2-deoxyglucose-6-phosphate (WO 98/45456), antibiotics or biocides, preferably herbicides, such as, for example, kanamycin, G 418, bleomycin or hygromycin, or else phosphinothricin and the like. Especially preferred selection markers are those which confer resistance to herbicides. Examples which may be mentioned are: DNA sequences which encode phosphinothricin acetyl transferases (PAT) and which inactivate glutamin synthase inhibitors (bar and pat genes), 5-enolpyruvylshikimate-3-phosphate synthase genes (EPSP synthase genes), which confer resistance to Glyphosate® (N-(phosphonomethyl)glycine), the gox gene, which encodes Glyphosate®-degrading enzymes (Glyphosate oxidoreductase), the deh gene (encoding a dehalogenase which inactivates dalapon), sulfonylurea- and imidazolinone-inactivating acetolactate synthases, and bxn genes, which encode bromoxynil-degrading nitrilase enzymes, the aasa gene, which confers resistance to the antibiotic apectinomycin, the streptomycin phosphotransferase (SPT) gene, which allows resistance to streptomycin, the neomycin phosphotransferase (NP-TII) gene, which confers resistance to kanamycin or geneticidin, the hygromycin phosphotransferase (HPT) gene, which mediates resistance to hygromycin, the acetolactate synthase gene (ALS), which confers resistance to sulfonylurea herbicides (for example mutated ALS variants with, for example, the S4 and/or Hra mutation).

b) Reporter genes which encode readily quantifiable proteins and, via their color or enzyme activity, make possible an assessment of the transformation efficacy, the site of expression or the time of expression. Very especially preferred in this context are genes encoding reporter proteins (Schenborn E, Groskreutz D. Mol Biotechnol. 1999; 13(1):29-44) such as the green fluorescent protein (GFP). (Sheen et al. (1995) Plant Journal 8(5):777-784; Haseloff et al. (1997) Proc Natl Acad Sci USA 94(6):2122-2127; Reichel et al. (1996) Proc Natl Acad Sci USA 93(12):5888-5893; Tian et al. (1997) Plant Cell Rep 16:267-271; WO 97/41228; Chui WL et al. (1996) Curr Biol 6:325-330; Leffel SM et al. (1997) Biotechniques. 23(5):912-8), chloramphenicol transferase, a luciferase (Ow et al. (1986) Science 234:856-859; Millar et al. (1992) Plant Mol Biol Rep 10:324-414), the aequorin gene (Prasher et al. (1985) Biochem Biophys Res Commun 126(3):1259-1268), β-galactosidase, R locus gene (encoding a protein which regulates the production of anthocyanin pigments (red coloring) in plant tissue and thus makes possible the direct analysis of the promoter activity without addition of further auxiliary substances or chromogenic substrates; Dellaporta et al., In: Chromosome Structure and Function: Impact of New Concepts, 18th Stadler Genetics Symposium, 11:263-282, 1988), with β-glucuronidase being very especially preferred (Jefferson et al., EMBO J. 1987, 6, 3901-3907).

c) Origins of replication, which ensure amplification of the expression cassettes or vectors according to the invention in, for example, *E. coli*. Examples which may be mentioned are ORI (origin of DNA replication), the pBR322 ori or the P15A ori (Sambrook et al.: Molecular Cloning. A Laboratory Manual, 2nd ed. Cold Spring Harbor Laboratory Press, Cold Spring Harbor, N.Y., 1989).

d) Elements which are necessary for *Agrobacterium*-mediated plant transformation, such as, for example, the right or left border of the T-DNA or the vir region.

To select cells which have successfully undergone homologous recombination, or else to select transformed cells, it is, as a rule, necessary additionally to introduce a selectable marker, which confers resistance to a biocide (for example herbicide), a metabolism inhibitor such as 2-deoxyglucose-6-phosphate (WO 98/45456) or an antibiotic to the cells which have successfully undergone recombination. The selection marker permits the selection of the transformed cells from untransformed ones (McCormick et al. (1986) Plant Cell Reports 5:81-84).

The introduction of an expression cassette according to the invention into an organism or cells, tissues, organs, parts or seeds thereof (preferably into plants or plant cells, tissue, organs, parts or seeds) can be effected advantageously using vectors which comprise the expression cassettes. The expression cassette can be introduced into the vector (for example a plasmid) via a suitable restriction cleavage site. The plasmid formed is first introduced into *E. coli*. Correctly transformed *E. coli* are selected, grown, and the recombinant plasmid is obtained by the methods familiar to the skilled worker. Restriction analysis and sequencing may serve to verify the cloning step.

Examples of vectors may be plasmids, cosmids, phages, viruses or else *agrobacteria*. In an advantageous embodiment, the expression cassette is introduced by means of plasmid vectors. Preferred vectors are those which make possible stable integration of the expression cassette into the host genome.

The generation of a transformed organism (or of a transformed cell or tissue) requires introducing the DNA, RNA or protein in question into the relevant host cell.

A multiplicity of methods are available for this procedure, which is termed transformation (or transduction or transfection) (Keown et al. (1990) Methods in Enzymology 185:527-537). For example, the DNA or RNA can be introduced directly by microinjection or by bombardment with DNA-coated microparticles. Also, the cell can be permeabilized chemically, for example using polyethylene glycol, so that DNA can enter the cell by diffusion. The DNA can also be introduced by protoplast fusion with other DNA-containing units such as minicells, cells, lysosomes or liposomes. Another suitable method of introducing DNA is electroporation, where the cells are permeabilized reversibly by an electrical pulse. Suitable methods have been described (for example by Bilang et al. (1991) Gene 100:247-250; Scheid et al. (1991) Mol Gen Genet 228:104-112; Guerche et al. (1987) Plant Science 52:111-116; Neuhause et al. (1987) Theor Appl Genet 75:30-36; Klein et al. (1987) Nature 327:70-73; Howell et al. (1980) Science 208:1265; Horsch et al. (1985) Science 227:1229-1231; DeBlock et al. (1989) Plant Physiology 91:694-701; Methods for Plant Molecular Biology (Weissbach and Weissbach, eds.) Academic Press Inc. (1988); and Methods in Plant Molecular Biology (Schuler and Zielinski, eds.) Academic Press Inc. (1989)).

In plants, the above-described methods of transforming and regenerating plants from plant tissues or plant cells are exploited for transient or stable transformation. Suitable methods are especially protoplast transformation by polyethylene-glycol-induced DNA uptake, the biolistic method with the gene gun, what is known as the particle bombardment method, electroporation, incubation of dry embryos in DNA-containing solution, and microinjection.

In addition to these "direct" transformation techniques, transformation can also be effected by bacterial infection by means of *Agrobacterium tumefaciens* or *Agrobacterium rhizogenes*. The *Agrobacterium*-mediated transformation is best suited to dicotyledonous plant cells. The methods are described, for example, by Horsch RB et al. (1985) Science 225: 1229f.

When *agrobacteria* are used, the expression cassette must be integrated into specific plasmids, either into a shuttle or intermediate vector, or into a binary vector. If a Ti or Ri plasmid is to be used for the transformation, at least the right border, but in most cases the right and left border, of the Ti or Ri plasmid T-DNA is linked to the expression cassette to be introduced in the form of a flanking region.

Binary vectors are preferably used. Binary vectors are capable of replication both in *E. coli* and in *Agrobacterium*. As a rule, they comprise a selection marker gene and a linker or polylinker flanked by the right and left T-DNA border sequence. They can be transferred directly into *Agrobacterium* (Holsters et al. (1978) Mol Gen Genet 163:181-187). The selection marker gene permits the selection of transformed *agrobacteria* and is, for example, the nptII gene, which confers resistance to kanamycin. The *Agrobacterium* which acts as host organism in this case should already contain a plasmid with the vir region. The latter is required for transferring the T-DNA to the plant cell. An *Agrobacterium* transformed in this way can be used for transforming plant cells. The use of T-DNA for transforming plant cells has been studied and described intensively (EP 120 516; Hoekema, In: The Binary Plant Vector System, Offsetdrukkerij Kanters B. V., Alblasserdam, Chapter V; An et al. (1985) EMBO J. 4:277-287). Various binary vectors are known, some of which are commercially available such as, for example, pBI101.2 or pBIN19 (Clontech Laboratories, Inc. USA).

Further promoters which are suitable for expression in plants have been described (Rogers et al. (1987) Meth in Enzymol 153:253-277; Schardl et al. (1987) Gene 61:1-11; Berger et al. (1989) Proc Natl Acad Sci USA 86:8402-8406).

Direct transformation techniques are suitable for any organism and cell type.

The plasmid used need not meet any particular requirements in the case of the injection or electroporation of DNA or RNA into plant cells. Simple plasmids such as those of the pUC series can be used. If complete plants are to be regenerated from the transformed cells, it is necessary for an additional selectable marker gene to be located on the plasmid.

Stably transformed cells, i.e. those which contain the introduced DNA integrated into the DNA of the host cell, can be selected from untransformed cells when a selectable marker is part of the DNA introduced. Examples of genes which can act as markers are all those which are capable of conferring resistance to antibiotics or herbicides (such as kanamycin, G 418, bleomycin, hygromycin or phosphinothricin) (see above). Transformed cells which express such marker genes are capable of surviving in the presence of concentrations of a corresponding antibiotic or herbicide which kill an untransformed wild type. Examples are mentioned above and preferably comprise the bar gene, which confers resistance to the herbicide phosphinothricin (Rathore K S et al. (1993) Plant Mol Biol 21(5):871-884), the nptII gene, which confers resistance to kanamycin, the hpt gene, which confers resistance to hygromycin, or the EPSP gene, which confers resistance to the herbicide Glyphosate. The selection marker permits the selection of transformed cells from untransformed cells (McCormick et al. (1986) Plant Cell Reports 5:81-84). The resulting plants can be bred and hybridized in the customary fashion. Two or more generations should be grown in order to ensure that the genomic integration is stable and hereditary.

The abovementioned methods are described, for example, in Jenes B et al. (1993) Techniques for Gene Transfer, in: Transgenic Plants, Vol. 1, Engineering and Utilization, edited by SD Kung and R Wu, Academic Press, pp. 128-143 and in Potrykus (1991) Annu Rev Plant Physiol Plant Molec Biol 42:205-225). The construct to be expressed is preferably cloned into a vector which is suitable for the transformation of *Agrobacterium tumefaciens*, for example pBin19 (Bevan et al. (1984) Nucl Acids Res 12:8711f).

As soon as a transformed plant cell has been generated, a complete plant can be obtained using methods known to the skilled worker. For example, callus cultures are used as starting material. The development of shoot and root can be induced in this as yet undifferentiated cell biomass in a known fashion. The shoots obtained can be planted out and bred.

The skilled worker is familiar with such methods of regenerating plant parts and intact plants from plant cells. Methods to do so are described, for example, by Fennell et al. (1992) Plant Cell Rep. 11: 567-570; Stoeger et al (1995) Plant Cell Rep. 14:273-278; Jahne et al. (1994) Theor Appl Genet 89:525-533.

The method according to the invention can advantageously be combined with further methods which bring about pathogen resistance (for example to insects, fungi, bacteria, nematodes and the like), stress resistance or another improvement of the plant properties. Examples are mentioned, inter alia, by Dunwell J M, Transgenic approaches to crop improvement, J Exp Bot. 2000;51 Spec No; pages 487-96.

The invention furthermore relates to the barley RacB protein as shown in SEQ ID NO: 2, and to dominant-negative variant thereof, for example described by SEQ ID NO: 7.

The invention furthermore relates to nucleic acid sequences encoding the barley RacB protein, preferably the nucleic acid sequence as shown in SEQ ID NO: 1, the nucleic acid sequence complementary thereto, and the sequences derived owing to degeneracy of the genetic code.

The invention furthermore relates to the polypeptide encoding functional equivalents of the RacB protein from barley as shown in SEQ ID NO: 35, 37 or 39.

The invention furthermore relates to nucleic acid sequences encoding functional equivalents of the RacB protein from barley, preferably the nucleic acid sequence as shown in SEQ ID NO: 34, 36 or 38, the nucleic acid sequence complementary thereto and the sequences derived by degeneration of the genetic code.

The invention furthermore relates to transgenic expression cassettes comprising one of the nucleic acid sequences according to the invention. In the transgenic expression cassettes according to the invention, the nucleic acid sequence encoding the barley RacB protein is linked to at least one genetic control element as defined above in such a manner that it is capable of expression (transcription and, if appropriate, translation) in any organism, preferably in plants. Suitable genetic control elements are described above. The transgenic expression cassettes may also comprise further functional elements in accordance with the above definition. The inserted nucleic acid sequence encoding a barley RacB protein can be inserted in the expression cassette in sense or antisense orientation and thus lead to the expression of sense or antisense RNA. Transgenic vectors comprising the transgenic expression cassettes are also in accordance with the invention.

"Transgenic", for example regarding a nucleic acid sequence, an expression cassette or a vector comprising said nucleic acid sequence or an organism transformed with said nucleic acid sequence, expression cassette or vector, refers to all those constructs originating by recombinant methods in which either a) the RacB nucleic acid sequence, or b) a genetic control sequence linked operably to the RacB nucleic acid sequence, for example a promoter, or c) (a) and (b) are not located in their natural genetic environment or have been modified by recombinant methods, an example of a modification being a substitutions, additions, deletions, inversion or insertions of one or more nucleotide residues. Natural genetic environment refers to the natural chromosomal locus in the organism of origin, or to the presence in a genomic library. In the case of a genomic library, the natural genetic environment of the nucleic acid sequence is preferably retained, at least in part. The environment flanks the nucleic acid sequence at least at one side and has a sequence of at least 50 bp, preferably at least 500 bp, especially preferably at least 1000 bp, very especially preferably at least 5000 bp, in length. A naturally occurring expression cassette—for example the naturally occurring combination of the RacB promoter with the corresponding RacB gene—becomes a transgenic expression cassette when it is modified by non-natural, synthetic "artificial" methods such as, for example, mutagenization. Such methods have been described (U.S. Pat. No. 5,565,350; WO 00/15815; also see above).

The invention also relates to transgenic organisms transformed with at least one of the nucleic acid sequences according to the invention, expression cassette according to the invention or vector according to the invention, and to cells, cell cultures, tissues, parts—such as, for example, leaves, roots and the like in the case of plant organisms—or propagation material derived from such organisms. The term organism is to be understood in the broad sense and refers to prokaryotic and eukaryotic organisms, preferably bacteria, yeasts, fungi, animal organisms and plant organisms.

The following are preferred:

a) fungi such as *Aspergillus, Eremothecium, Trichoderma, Ashbya, Neurospora, Fusarium, Beauveria* or other fungi described in Indian Chem Eng. Section B. Vol 37, No. 1,2 (1995) on page 15, Table 6. Especially preferred is the filamentous hemiascomycete *Ashbya gossypii* or *Eremothecium ashbyii,* b) yeasts such as *Candida, Saccharomyces, Hansenula* or *Pichia*, with *Saccharomyces cerevisiae* or *Pichia pastoris* (ATCC Accession No. 201178) being especially preferred, c) plants in accordance with the above definition of "plants", d) vertebrates and invertebrates. Especially preferred vertebrates are nonhuman mammals such as in dog, cat, sheep, goat, chicken, mouse, rat, cattle or horse. Preferred animal cells comprise CHO, COS and HEK293 cells. Preferred invertebrates comprise insect cells such as *Drosophila* S2 and *Spodoptera* Sf9 or Sf21 cells, e) prokaryotic organisms such as Gram-positive or Gram-negative bacteria such as *Acetobacter, Gluconobacter, Corynebacterium, Brevibacterium, Bacillus, Clostridium, Cyanobacter, Escherichia* (mainly *Escherichia coli*), *Serratia, Staphylococcus, Aerobacter, Alcaligenes, Penicillium* or *Klebsiella.*

Host or starting organisms which are preferred as transgenic organisms are mainly plants in accordance with the above definition. Included within the scope of the invention are all genera and species of higher and lower plants of the Plant Kingdom. Furthermore included are the mature plants, seed, shoots and seedlings, and parts, propagation material and cultures derived therefrom, for example cell cultures. Mature plants refers to plants at any developmental stage beyond that of the seedling. The term seedling refers to a young immature plant in an early developmental stage. Plants preferred as host organisms are in particular plants which can be used for the process according to the invention to obtain a pathogen resistance according to the criteria mentioned above. Very particularly preferred are monocotyledbnous plants, such as wheat, oats, millet, barley, rye, maize, rice, buckwheat, sorghum, triticale, spelt, linseed, sugar cane, as dicotyledonous crop plants, such as oil seed rape, canola, cress, *Arabidopsis*, cabbages, soya, alfalfa, pea, beans, peanut, potato, tobacco, tomato, eggplant, bell pepper, sunflower, Tagetes, lettuce, *Calendula*, melon, pumpkin/squash or zucchini.

The transgenic organisms can be generated with the above-described methods for the transformation or transfection of organisms.

The invention furthermore relates to the use of the transgenic organisms according to the invention and of the cells, cell cultures, parts—such as, for example, roots, leaves and the like in the case of transgenic plant organisms—derived from them, and to transgenic propagation material such as seeds or fruits, for the production of foodstuffs or feeding stuffs, pharmaceuticals or fine chemicals.

Furthermore preferred is a method for the recombinant production of pharmaceuticals or fine chemicals in host organisms, wherein a host organism is transformed with one of the above-described expression cassettes and this expression cassette comprises one or more structural genes which encode the desired fine chemical or catalyze the biosynthesis of the desired fine chemical, the transformed host organism is cultured, and the desired fine chemical is isolated from the culture medium. This method can be applied widely to fine chemicals such as enzymes, vitamins, amino acids, sugars, fatty acids, and natural and synthetic flavorings, aroma substances and colorants. Especially preferred is the production of tocopherols and tocotrienols and carotenoids. The transformed host organisms are cultured and the products are isolated from the host organisms or the culture medium by methods known to the skilled worker. The production of pharmaceuticals such as, for example, antibodies or vaccines, is described by Hood EE, Jilka J M. (1999) Curr Opin Biotechnol. 10(4):382-6; Ma J K, Vine N D. (1999) Curr Top Microbiol Immunol. 236:275-92.

```
 1. SEQ ID NO: 1    Nucleic acid sequence encoding the barley (Hordeum
                    vulgare) RacB protein.

2. SEQ ID NO: 2    Amino acid sequence encoding the barley (Hordeum
                    vulgare) RacB protein.

3. SEQ ID NO: 3    Nucleic acid sequence encoding the rice
                    (Oryza sativa) RacB protein.

4. SEQ ID NO: 4    Amino acid sequence encoding the
                    rice (Oryza sativa) RacB protein.

5. SEQ ID NO: 5    Nucleic acid sequence encoding the
                    maize (Zea mays) RacB protein.

6. SEQ ID NO: 6    Amino acid sequence encoding the
                    maize (Zea mays) RacB protein.

7. SEQ ID NO: 7    Amino acid sequence encoding a dominant-negative
                    variant of the RacB protein (Hordeum vulgare).

8. SEQ ID NO: 8    Amino acid sequence encoding a dominant-negative
                    variant of the rice (Oryza sativa) RacB protein.

9. SEQ ID NO: 9    Amino acid sequence encoding a dominant-negative
                    variant of the maize (Zea mays) RacB protein.

10. SEQ ID NO: 10   Oligonuceotide primer ONP-1
                    5'-GGATCCGATGAGCGCGTCCAGGTT-3'

11. SEQ ID NO: 11   Oligonucleotide primer ONP-2
                    5'-GTCGACCTTCGCCCTTGTTCTTTGTC-3'

12. SEQ ID NO: 12   RACE-RacB primer
                    5'-gtgggcacatagtcggtggggaaggt-3'

13. SEQ ID NO: 13   GeneRacer ™ 5' primer:
                    5'-CGACTGGAGCACGAGGACACTGA-3

14. SEQ ID NO: 14   GeneRacer ™ 5' nested primer:
                    5'-GGACACTGACATGGACTGAAGGAGTA-3

15. SEQ ID NO: 15   RacB sense primer
                    5'-gttcatcaagtgcgtcaccgtg-3'

16. SEQ ID NO: 16   RacB antisense primer
                    5'-ttagcttcctcagttcttccctg-3'

17. SEQ ID NO: 17   BAS sense primer
                    5'-cgcgccgcagccgagtacgac-3'

18. SEQ ID NO: 18   BAS antisense primer
                    5'-gtcacaaaaacacatgtaacc-3'

19. SEQ ID NO: 19   OXLP sense primer
                    5'-ggccgacatgcattcaccag-3'

20. SEQ ID NO: 20   OXLP antisense primer
                    5'-catctgatattgctgggtctg-3'

21. SEQ ID NO: 21   UBI sense primer
                    5'-ccaagatgcagatcttcgtga-3'

22. SEQ ID NO: 22   UBI antisense primer
                    5'-ttcgcgataggtaaaagagca-3'

23. SEQ ID NO: 23   M13 fwd primer
                    5'-GTAAAACGACGGCCAGTG-3'

24. SEQ ID NO: 24   M13 rev primer
                    5'-GGAAACAGCTATGACCATG-3'

25. SEQ ID NO: 25   HvRop6 LEFT PRIMER
                    5'-GTGGAGGCGCGGCGAGA-3'
```

-continued

26. SEQ ID NO: 26  HvRop6 RIGHT PRIMER
                   5'-CCATGCTTCATCTCCATAGTCA-3'

27. SEQ ID NO: 27  HvRacD LEFT PRIMER
                   5'-ggatccCGATTCCATCAGGAAAGCAT-3'

28. SEQ ID NO: 28  HvRacD RIGHT PRIMER
                   5'-gtcgacGCGAGACACTGCAAAACAAA-3'

29. SEQ ID NO: 29  HvRop4 LEFT PRIMER
                   5'-GGATCCttctcgtccatttagccggc-3'

30. SEQ ID NO: 30  HvRop4 RIGHT PRIMER
                   5'-GTCGACtgatcacttgaagcatgccag-3'

31. SEQ ID NO: 31  RacB5' BamHI Primer
                   5'-GGATCCGATGAGCGCGTCCAGGTT-3'

32. SEQ ID NO: 32  RacB3' SalI Primer
                   5'-GTCGACCTTCGCCCTTGTTCTTTGTC-3'

33. SEQ ID NO: 33  V15 mutagenesis Primer
                   5'-ACCGTGGGGGACGTCGCCGTCGGCAAGAC-3'

34. SEQ ID NO: 34  Nucleic acid sequence encoding the RacB homolog
                   HvRop6 from barley (*Hordeum vulgare*).

35. SEQ ID NO: 35  Amino acid sequence encoding the RacB homolog
                   HvRop6 from barley (*Hordeum vulgare*).

36. SEQ ID NO: 36  Nucleic acid sequence encoding the RacB homolog
                   HvRacD from barley (*Hordeum vulgare*).

37. SEQ ID NO: 37  Amino acid sequence encoding the RacB homolog
                   HvRacD from barley (*Hordeum vulgare*).

38. SEQ ID NO: 38  Nucleic acid sequence encoding the RacB homolog
                   HvRop4 from barley (*Hordeum vulgare*).

39. SEQ ID NO: 39  Nucleic acid sequence encoding the RacB homolog
                   HvRop4 from barley (*Hordeum vulgare*).

40. SEQ ID NO: 40  Nucleic acid sequence encoding the RacB homolog
                   *Zea mays* ROP6 (GenBank Acc.-No.: AJ278665)

41. SEQ ID NO: 41  Amino acid sequence encoding the
                   RacB homolog *Zea mays* ROP6

42. SEQ ID NO: 42  Nucleic acid sequence encoding the RacB homolog
                   *Oryza sativa* subsp. japonica PACDP (RACD) (GenBank
                   Acc.-No.: AF218381)

43. SEQ ID NO: 43  Amino acid sequence encoding the RacB homolog
                   *Oryza sativa* subsp. japonica RACDP 44. SEQ ID NO: 44  Nucleic acid sequence encoding the RacB homolog
                   *Oryza sativa* ROP4 (GenBank Acc.-No.: AF380335)

45. SEQ ID NO: 45  Amino acid sequence encoding the RacB homolog
                   *Oryza sativa* ROP4

46. SEQ ID NO: 46  Nucleic acid sequence encoding the RacB homolog
                   *Zea mays* RACA (GenBank Acc.-No.: AF126052)

47. SEQ ID NO: 47  Amino acid sequence encoding the
                   RacB homolog *Zea mays* RACA 48. SEQ ID NO: 48  Nucleic acid sequence encoding an RacB homolog
                   from *Hordeum vulgare* (GenBank Acc.-No.: BM816965)

49. SEQ ID NO: 49  Nucleic acid sequence encoding an RacB homolog
                   from *Arabidopsis thaliana* (At3g51300)

50. SEQ ID NO: 50  Amino acid sequence encoding an RacB homolog
                   from *Arabidopsis thaliana* (At3g51300)

51. SEQ ID NO: 51  Nucleic acid sequence encoding an RacB homolog
                   from *Arabidopsis thaliana* (At2g17800)

- continued

52. SEQ ID NO: 52  Amino acid sequence encoding an RacB homolog from *Arabidopsis thaliana* (At2g17800)

53. SEQ ID NO: 53  Nucleic acid sequence encoding an RacB homolog from *Arabidopsis thaliana* (At4g35950)

54. SEQ ID NO: 54  Amino acid sequence encoding an RacB homolog from *Arabidopsis thaliana* (At4g35950)

55. SEQ ID NO: 55  Nucleic acid sequence encoding an RacB homolog from *Arabidopsis thaliana* (At1g75840)

56. SEQ ID NO: 56  Amino acid sequence encoding an RacB homolog from *Arabidopsis thaliana* (At1g75840)

57. SEQ ID NO: 57  Nucleic acid sequence encoding an RacB homolog from *Arabidopsis thaliana* (At4g35020)

58. SEQ ID NO: 58  Amino acid sequence encoding an RacB homolog from *Arabidopsis thaliana* (At4g35020)

59. SEQ ID NO: 59  Nucleic acid sequence encoding an RacB homolog from *Arabidopsis thaliana* (At1g20090)

60. SEQ ID NO: 60  Amino acid sequence encoding an RacB homolog from *Arabidopsis thaliana* (At1g20090)

61. SEQ ID NO: 61  Nucleic acid sequence encoding an RacB homolog from *Arabidopsis thaliana* (At5g45970)

62. SEQ ID NO: 62  Amino acid sequence encoding an RacB homolog from *Arabidopsis thaliana* (At5g45970)

63. SEQ ID NO: 63  Nucleic acid sequence encoding an RacB homolog from *Arabidopsis thaliana* (At3g48040)

64. SEQ ID NO: 64  Amino acid sequence encoding an RacB homolog from *Arabidopsis thaliana* (At3g48040)

65. SEQ ID NO: 65  Nucleic acid sequence encoding an RacB homolog from *Arabidopsis thaliana* (At5g62880)

66. SEQ ID NO: 66  Amino acid sequence encoding an RacB homolog from *Arabidopsis thaliana* (At5g62880)

67. SEQ ID NO: 67  Nucleic acid sequence encoding an RacB homolog from *Arabidopsis thaliana* (At4g28950)

68. SEQ ID NO: 68  Amino acid sequence encoding an RacB homolog from *Arabidopsis thaliana* (At4g28950)

69. SEQ ID NO: 79  Nucleic acid sequence encoding an RacB homolog from *Arabidopsis thaliana* (At2g44690)

70. SEQ ID NO: 70  Amino acid sequence encoding an RacB homolog from *Arabidopsis thaliana* (At2g44690)

71. SEQ ID NO: 71  Oligonucleotide primer Fra 186
    5'-ATGAGCGCGTCCAGGTTCATA-3'

72. SEQ ID NO: 72  Oligonucleotide primer Fra 187
    5'-ATCAAACACGCCCTTCACGTT-3'

73. SEQ ID NO: 73  Transgenic expression vector pSUN3NIT_AtRacB_s for expression of *Arbidopsis thalianan* RacB in sense orientation 74. SEQ ID NO: 74  Transgenic expression vector pSUN3NIT_AtRacB_as for expression of *Arbidopsis thalianan* RacB in antisense orientation 75. SEQ ID NO: 75  Transgenic expression vector pSUN3NIT_HvRacB_s for expression of a barley RacB fragment in sense orientation 76. SEQ ID NO: 76  Transgenic expression vector pSUN3NIT_HvRacB_as for expression of a barley RacB fragment in antisense orientation Figures 1. FIG. 1: Alignment of the amino acid sequences of barley RacB, rice RacB, maize RacB, and human Rac1 and Rac2 proteins.

Regions shaded in gray show the position of the G1 element (GXXXXGKS/T; amino acid 13 to 20), of the G2 effector region (amino acid 29 to 45), of the G3 element (LWDTAGQ; amino acid 58 to 64), of the G4 element (TKXD; amino acid 118 to 121), of the G5 element (EXS) and of the C-terminal isoprenylation motif (CXXX, Hassanain HH et al. (2000) Biochem Biophys Res Commun. 272(3):783-8.). Hyphens indicate sequence gaps. Asterisks denote amino acids which are identical in all homologs. Amino acids which differ between barley on the one hand and maize and rice on the other hand are shown white against black. The position which is advantageously modified to obtain a dominant-negative RacB variant is marked by a black triangle above the sequence.

2. FIG. 2: Expression of RacB in epidermal tissue

RT-PCR of RNA from the barley lines Pallas and BCP-Mla12 (P10) 24 h post-inoculation ("hai" hours after inoculation") with BghA6. To extract the RNA, strips of the abaxial epidermis (E, from inoculated locations of leaves) were removed from the mesophyll and the adaxial epidermis (M). Ubiquitin 1 (Ubi) acted as marker for tissue-unspecific expression, OXLP as positive control for gene expression in the epidermis, and Bas as positive control for gene expression in mesophyll cells. The RT-PCR was carried out over 25 amplification cycles as described hereinbelow. RT-PCR products were denatured in the gel, blotted and detected by means of antisense RNA probes under stringent conditions.

3. FIG. 3: RacB is expressed constitutively in various resistant barley lines.

RNA was isolated from the variety Ingrid (Mlo, Ror1, Bgh-susceptible), BCIngrid-mlo5 (mlo5, Ror1, Bgh-resistant) and A89 (mlo5, ror1, moderately susceptible to BghA6) immediately prior to inoculation (0 Ø) or 8, 15 or 24 h post-inoculation with Bgh and 24 h thereafter from noninoculated control plants (24 Ø). Ubiquitin 1 (Ubi) was used as marker for constitutive expression, OXLP as positive control for Bgh-induced gene expression in the epidermal layer. OXLP expression was detected via Northern blot. The RT-PCR for RacB and Ubi was carried out as described over 25 amplification cycles. The PCR products were denatured in the gel, blotted and detected by means of antisense RNA samples under stringent conditions.

Figure 4:
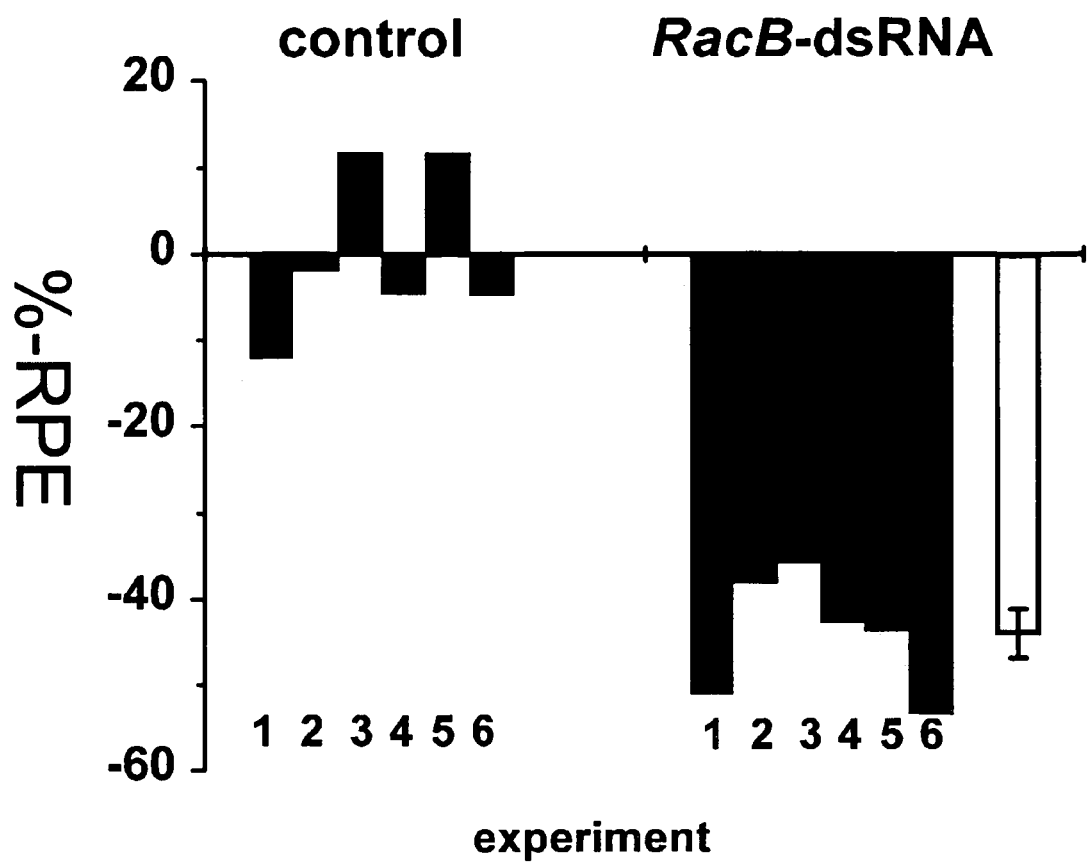
FIG. 4. RNA interference with RacB-dsRNA.

4. FIG. 4: "RNA interference" with RacB-dsRNA reduces the penetration efficacy of barley powdery mildew BghA6 in barley.

The relative penetration efficacy (RPE) was determined in six individual experiments with inoculation with Bgh from barley cv. Pallas. The RPE was calculated as the difference between the penetration efficacy of cells transformed with RacB-dsRNA and the penetration efficacy of cells transformed with control dsRNA (here: average penetration efficacy 57%). The RPE percentage (%-RPE) is calculated from the RPE minus 1, multiplied by 100.

$$RPE = \frac{[PE \text{ of cells transformed with } RacB\text{-}dsRNA]}{[PE \text{ of cells transformed with control } dsRNA]}$$

$$\%\text{-}RPE = 100 * (RPE - 1)$$

The black columns represent the %-RPE upon evaluation of at least 100 interaction sites for in each case one independent experiment. The white column represents the average %-RPE of the experiments with the RacB-dsRNA ("RACB-dsRNA"). The error bar indicates the standard error.

"control" represents the parallel experiments with a control dsRNA.

In cells which had been bombarded with RacB-dsRNA, the %-RPE was markedly reduced in comparison with cells which had been bombarded with a control dsRNA (TR: human thyroid receptor dsRNA).

Figure 5:
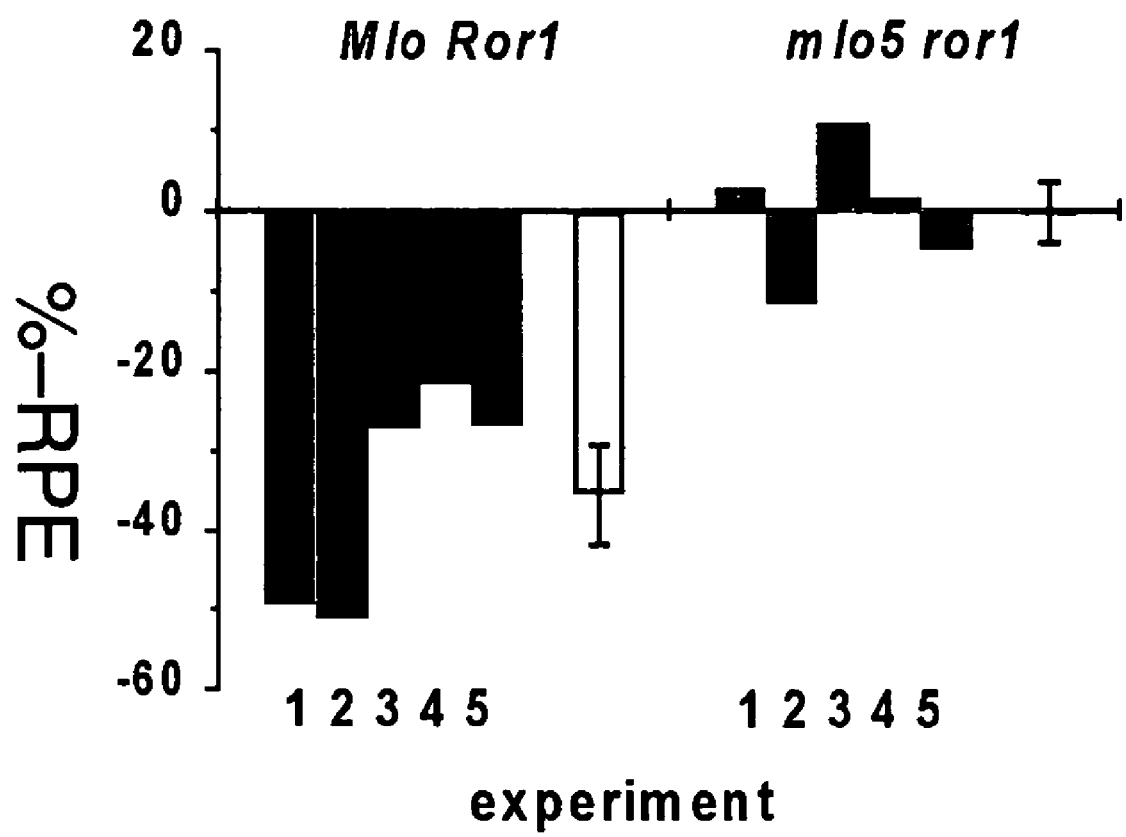
FIG. 5. Effect of the genetic background on RacB function.

5. FIG. 5: Effect of the genetic background on RacB function

The %-RPE was studied in 5 independent experiments by inoculating barley cv. Pallas, Ingrid or A89, which had previously been transformed with RacB-dsRNA, with BghA6.

The %-RPE is markedly reduced in Pallas (Mlo Ror1, black bars, experiments 1 and 2) or Ingrid (Mlo Ror1, black bars, experiments 3, 4 and 5). The %-RPE of the susceptible mutant A89 (mlo5 ror1, black bars, experiments 1 to 5), however, was not reduced. White bars indicate the mean, error bars the standard error.

6. FIG. 6: Overexpression of a constitutively active RacB mutant in barley cv. Pallas A constitutively active mutant of barley RACB (exchange G->V in position 15; RacB-V15) was transiently overexpressed in the barley variety Pallas in 5 independent experiments using the expression construct pGY-RacBV15. For comparison, corresponding experiments were carried out using the vector alone, without RacB insert (pGY).

The expression of a constitutive RacB mutant results in significantly higher susceptibility to pathogen attack by mildew of barley, compared to the controls (FIG. 6-A). In all cases, the relative susceptibility to the fungal pathogen is increased (FIG. 6-B). These results, too, demonstrate the key function of racB in the defense of pathogens.

Figure 7:
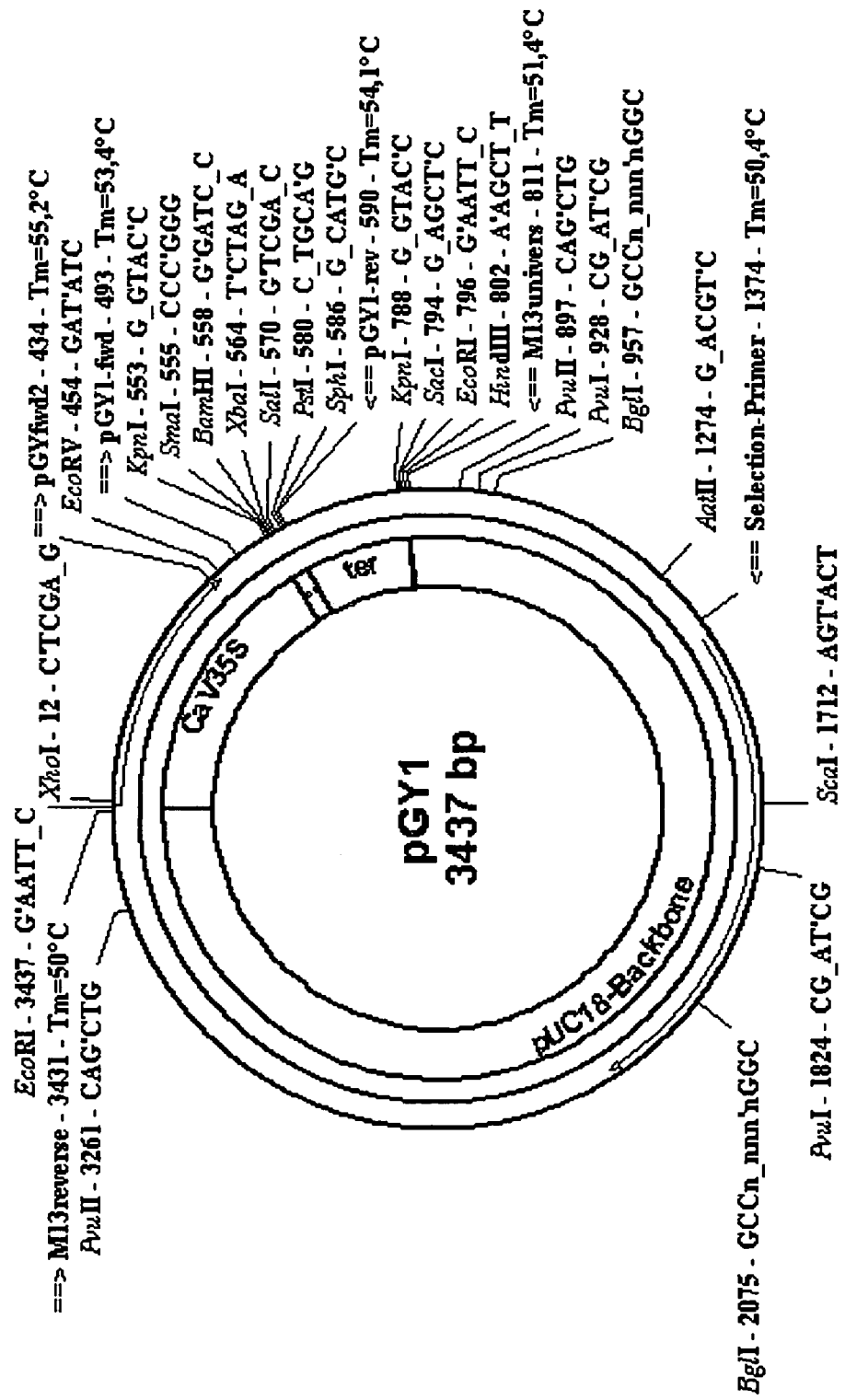
FIG. 7. Plasmid map for expression vector pGY-1.

7. FIG. 7: Plasmid map for expression vector pGY-1 (Schweizer P et al. (1999) Mol Plant Microbe Interact 12: 647-54; Shinshi H et al. (1990) Plant Mol Biol 14:357-368).

EXAMPLES

General Methods:

The chemical synthesis of oligonucleotides can be effected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of *E. coli* cells, growing bacteria, multiplying phages and sequence analysis of recombinant DNA, are carried out as described by Sambrook et al. (1989) Cold Spring Harbor Laboratory Press; ISBN 0-87969-309-6. The sequencing of recombinant DNA molecules is carried out with an MWG-Licor laser fluorescence DNA sequencer following the method of Sanger (Sanger et al. (1977) Proc Natl Acad Sci USA 74:5463-5467).

Example 1

Plants, Pathogens and Inoculation

The barley variety Ingrid is from James McKey, University of Uppsala, Sweden. The variety Pallas and backcrossed line BCIngrid-mlo5 was donated by Lisa Munk, Department of Plant Pathology, Royal Veterinary and Agricultural University, Copenhagen, Denmark. Its production has been described (Kølster P et al. (1986) Crop Sci 26: 903-907). Line A89 was provided by Paul Schulze-Lefert (Max-Plank-Institut für Züchtungsforschung, Cologne, Germany).

Unless otherwise specified, the seed which had been pregerminated on moist filter paper for 12 to 36 hours in the dark was sown along the edge of a square pot (8×8 cm; 5 kernels per pot) in Fruhstorfer soil, type P, covered with soil and watered regularly with tap water. All of the plants were cultured in controlled-environment cabinets or chambers for 5 to 8 days at 16 to 18° C., 50 to 60% relative atmospheric humidity and a 16-hr-light/8-hr-dark rhythm at 3000 or 5000 lux (photon flow density 50 and 60 µmols-$^1$m-$^2$, respectively) and used in the experiments during the seedling stage. In experiments in which applications to the primary leaves were carried out, the latter were developed fully.

Before the transient transfection experiments were carried out, the plants were grown in controlled-environment cabinets or chambers at a daytime temperature of 24° C., a nighttime temperature of 20° C., 50 to 60% relative atmospheric humidity and a 16-hr light/8-hr-dark rhythm at 30 000 lux.

Barley powdery mildew *Blumeria graminis* (DC) Speer f.sp. *hordei* Em. Marchal race A6 (Wiberg A (1974) Hereditas 77: 89-148) (BghA6) was used for the inoculation of barley plants. The fungus was provided by the Department of Biometry, JLU Gießen. Inoculum was grown in controlled-environment cabinets under identical conditions to those described above for the plants by transferring the conidia of infected plant material at a rate of 100 conidia/mm$^2$ to 7-day-old barley plants cv. Golden Promise, which were grown regularly.

The inoculation with BghA6 was carried out using 7-day-old seedlings by shaking off the conidia of already infected plants in an inoculation tower at a rate of approx. 100 conidia/mm$^2$ (unless otherwise specified).

Example 2

RNA Extraction

Total RNA was extracted from 8 to 10 primary leaf segments (length 5 cm) by means of "RNA extraction buffer" (AGS, Heidelberg, Germany).

To this end, the central primary leaf segments 5 cm in length were harvested and homogenized in liquid nitrogen in mortars. The homogenate was stored at −70° C. until the RNA was extracted.

Total RNA was extracted from the deep-frozen leaf material with the aid of an RNA extraction kit (AGS, Heidelberg). To this end, 200 mg of the deep-frozen leaf material were covered with 1.7 ml RNA extraction buffer (AGS) in a microcentrifuge tube (2 ml) and immediately mixed thoroughly. After addition of 200 µl of chloroform, the mixture was again mixed thoroughly and shaken for 45 minutes on a horizontal shaker at 200 rpm at room temperature. To separate the phases, the tubes were subsequently centrifuged for 15 minutes at 20 000 g and 4° C., and the upper, aqueous phase was transferred into a fresh microcentrifuge tube, while the bottom phase was discarded. The aqueous phase was repurified with 900 µl of chloroform by homogenizing for 10 seconds and recentrifuging (see above) and removing the aqueous phase (3 times). Then, 850 µl of 2-propanol were added and the mixture was homogenized and placed on ice for 30 to 60 minutes in order to precipitate the RNA. Thereafter, the mixture was centrifuged for 20 minutes (see above), the supernatant was carefully decanted off, 2 ml of 70% strength ethanol (−20° C.) were pipetted in, and the mixture was mixed and recentrifuged for 10 minutes.

Then, the supernatant was again decanted off, and the pellet was carefully freed from residual fluid, using a pipette, and then dried in a stream of clean air in a clean bench. Then, the RNA was dissolved in 50 µl of DEPC water on ice, mixed and centrifuged for 5 minutes (see above). 40 µl of the supernatant, constituting the RNA solution, were transferred into a fresh microcentrifuge tube and stored at −70° C.

The RNA concentration was determined photometrically. To this end, the RNA solution was diluted 1:99 (v/v) with distilled water, and the absorption was measured at 260 nm (Beckman Photometer DU 7400); ($E_{260}$ 1 at 40 µg RNA/ml). The concentrations of the RNA solutions were subsequently adjusted to 1 µg/µl with DEPC water to match the calculated RNA contents and verified in an agarose gel.

To verify the RNA concentrations in a horizontal agarose gel (1% agarose in 1×MOPS buffer with 0.2 µg/ml ethidium bromide), 1 µl of RNA solution was treated with 1 µl of 10×MOPS, 1 µl of color marker and 7 µl of DEPC water, separated according to size in 1×MOPS running buffer over 1.5 hours at a voltage of 120 V in the gel, and photographed under UV light. Any differences in concentration of the RNA extracts were adjusted with DEPC water, and the adjustment was rechecked in the gel.

Example 3

Cloning the Barley RacB cDNA Sequence

The cDNA fragments required for isolating the HvRacB cDNA, cloning it, sequencing it and generating probes were obtained by means of RT-PCR using the "One Step RT-PCR Kit" (Life Technologies, Karlsruhe, Germany or Qiagen, Hilden, Germany). To this end, total RNA from barley seedlings was used as template.

The RNA was isolated from Pallas 3, 5 and 0.7 days after germination. Moreover, RNA was isolated from Pallas and the backcrossed lines with mlo5, Mlg or Mla12 1, 2 and 5 days after inoculation with BghA6 on day 7 after germination. The following primers are used for the RT-PCR:

```
ONP-1
5'-GGATCCGATGAGCGCGTCCAGGTT-3'    (SEQ ID NO: 10)
and

ONP-2
5'-GTCGACCTTCGCCCTTGTTCTTTGTC-3'  (SEQ ID NO: 11)
```

1000 ng of total RNA, 0.4 mM dNTPs, in each case 0.6 mM OPN-1 and OPN-2 primer, 10 µl of RNase inhibitor and 1 µl of enzyme mix in 1×RT buffer (One Step RT-PCR Kit, Qiagen, Hilden) were employed for each reaction (25 µl batch).

The following temperature program is used (PTC-100TM model 96V; MJ Research, Inc., Watertown, Mass.):

| 1 cycle of | 30 min at 50° C. |
| 1 cycle of | 150 sec at 94° C. |
| 30 cycles of | 45 sec at 94° C., 1 min at 55° C. and 2 min at 72° C. |
| 1 cycle of | 7 min at 72° C. |

The PCR product was separated by 2% w/v agarose gel electrophoresis. This gave an RT-PCR product of in total 642 bp which was composed of the RacB sequence (SEQ ID NO: 1) and terminal sequences encoding restriction endonuclease restriction sites. The fragment encodes a 591 bp open reading frame encoding a polypeptide of 197 amino acids. The corresponding cDNA was isolated from an agarose gel and cloned into vector pGEM-T (Promega, Mannheim, Germany) by means of T-overhang ligation. The cDNAs were sequenced starting from the plasmid DNA using the "Thermo Sequenase Fluorescent Labeled Primer Cycle Sequencing Kit" (Amersham, Freiburg, Germany).

Since a primer has been deduced from the rice RacB sequence as starting primer OPN-1 (GenBank Acc. No.: AF250327), this region (i.e. the 5'-end) of the barley RacB cDNA was reverified by means of RACE technology using the "GeneRacer Kit" (INVITROGENE Life Technologies). To this end, 100 ng of poly-A mRNA, 1 µl of 10×CIP buffer, 10 units of RNAse inhibitor, 10 units of CIP ("calf intestinal phosphatase") and DEPC-treated water were treated for 1 hour at 50° C. in a total volume of 10 µl. To precipitate the RNA, a further 90 µl of DEPC water and 100 µl of phenol: chloroform were added and the mixture was mixed thoroughly for approximately 30 seconds. After centrifugation for 5 minutes at 20 000 g, the top phase was treated with 2 µl of 10 mg/ml mussel glycogen, 10 µl of 3 M sodium acetate (pH 5.2) in a fresh micro reaction vessel. 220 µl of 95% ethanol were added and the mixture was incubated on ice. The RNA was subsequently precipitated by centrifugation for 20 minutes at 20 000 g and 4° C. The supernatant was discarded, 500 µl of 75% ethanol were added, and the mixture was vortexed briefly and recentrifuged for 2 minutes (20 000 g). Again, the supernatant was discarded, and the precipitate was dried in the air for 0.2 minutes at room temperature and subsequently suspended in 6 µl of DEPC water. mRNA CAP structures were removed by adding 1 µl of 10× TAP buffer, 10 units of RNAsin and 1 unit of TAP (tobacco acid pyrophosphatase). The mixture was incubated for 1 h at 37° C. and subsequently cooled on ice. Again, the RNA was precipitated as described above and transferred into a reaction vessel with 0.25 µg of GeneRacer oligonucleotide primer. The oligonucleotide primer was resuspended in the RNA solution, and the mixture was incubated for 5 minutes at 70° C. and then ice-cooled. 1 µl of 10× ligase buffer, 10 mM ATP, 1 unit of RNAsin and 5 units of T4 RNA ligase were added, and the batch was incubated for 1 h at 37° C. Again, the RNA was precipitated as described above and resuspended in 13 µl of DEPC water. 10 pmol of oligo-dT primer were added to the RNA, and the mixture was immediately heated at 70° C. and again cooled on ice. 1 µl of each dNTP solution (25 mM), 2 µl of 10× RT buffer, 5 u (1 µl) of AMV reverse transcriptase and 20 units of RNAsin were added, and the reaction solution was incubated for 1 hour at 42° C. and subsequently for 15 minutes at 85° C. The first-strand cDNA thus prepared was stored at −20° C.

The following primer was used to amplify the 5'-cDNA ends:

```
RACE RacB primer:
5'-gtgggcacatagtcggtggggaaggt-3'   (SEQ ID NO: 12)

GeneRacer ™ 5'-primer:
5'-CGACTGGAGCACGAGGACACTGA-3       (SEQ ID NO: 13)

GeneRacer ™ 5'-nested primer:
5'-GGACACTGACATGGACTGAAGGAGTA-3    (SEQ ID NO: 14)
```

The batch (total volume 25 µl) was composed as follows:
1 µl primer RACE-RacB (5 pmol/µl),
0.5 µl GeneRacer 5'-primer (10 pmol/µl)
2.5 µl 10× buffer Qiagen,
2.5 µl dNTPs (2 mM)
0.5 µl cDNA
0.2 µl QiagenTAG (5 u/µl)
17.8 µl H2O The PCR conditions were:

| 94° C. | denaturation for 5 minutes |
| 5 cycles of | 30 seconds at 70° C. (annealing), |
| | 1 min at 72° C. (extension), |
| | 30 seconds at 94° C. (denaturation) |
| 5 cycles of | 30 seconds at 68° C. (annealing), |
| | 1 min at 72° C. (extension), |
| | 30 seconds at 94° C. (denaturation) |
| 28 cycles of | 30 seconds at 66° C. (annealing), |
| | 1 min at 72° C. (extension), |
| | 30 seconds at 94° C. (denaturation) |
| 72° C. | final extension for 10 minutes |
| 4° C. | cooling until further use |

The PCR gave a product of approx. 400 bp product. Starting from this product, a nested PCR with the RacB-specific oligonucleotide primer and the "GeneRacer nested 5'-primer" was carried out:

| 94° C. | denaturation for 5 minutes |
| 30 cycles of | 30 sec at 64° C. (annealing), |
| | 1 min at 72° C. (extension), |
| | 30 sec at 94° C. (denaturation) |
| 72° C. | final extension for 10 minutes |
| 4° C. | cooling until further use |

The PCR product obtained was isolated via a gel, extracted from the gel, cloned into PGEM-T by means of T-overhang ligation, and sequenced. The sequence in the region of the primer OPN-1 was absolutely identical to the sequence of rice racB, so that no point mutations could be generated by means of primers. Thus, the sequence shown under SEQ ID NO: 1 is identical to the barley RacB sequence.

Example 4

Reverse Transcription Polymerase Chain Reaction (RT-PCR)

The "One Step RT-PCR Kit" (Qiagen, Hilden, Germany) was used for the semi-quantitative RT-PCR. In doing so, RNA (prepared as above) was first translated into cDNA (reverse transcription) and the sought cDNA was amplified in a subsequent PCR reaction using specific primers. To estimate the initial amount of template RNA, the amplification was interrupted during the exponential phase in order to reflect differences in the target RNA. The PCR products were separated by means of an agarose gel, denatured, blotted onto nylon membranes, and detected with specific non-radiolabeled probes under stringent standard conditions. Hybridization, wash steps and immunodetection were carried out as described under "Northern blot".

The following components were combined for the individual reactions (25 µl batch) using the "One Step RT-PCR Kit" (Qiagen, Hilden, Germany):

1000 ng total RNA of a specific sample
0.4 mM dNTPs
0.6 µM of each sense and antisense primer
0.1 µl RNase inhibitor
1 µl enzyme mix in 1×RT buffer cDNA synthesis (reverse transcription) was carried out for 30 minutes at 50° C. The reverse transcriptase was subsequently inactivated for 15 minutes at 95° C., which simultaneously causes activation of DNA polymerase and denaturation of cDNA. A PCR was subsequently carried out with the following program:

| | |
|---|---|
| denaturation for | 1 minute at 94° C. |
| 25 cycles of | 1 minute at 54° C. primer annealing |
| | 1 minute at 72° C. primer extension |
| | 10 minutes at 72° C. completion of the DNA duplexes |
| then: | termination of the reaction at 4° C. |

The PCR products were separated in a 1×TBE agarose gel using ethidium bromide.

The following oligonucleotide primer pairs were used for the amplifications in the individual batches:

a) amplification of a 387 bp fragment of the barley RacB cDNA

RacB sense
5'-gttcatcaagtgcgtcaccgtg-3'        (SEQ ID NO: 15)

RacB antisense
5'-ttagcttcctcagttcttccctg-3'       (SEQ ID NO: 16)

b) amplification of a 674 bp fragment of barley BAS cDNA (GenBank Acc. No. Z34917)

BAS sense     5'-cgcgccgcagccgagtacgac-3'   (SEQ ID NO: 17)

BAS anti-     5'-gtcacaaaaacacatgtaacc-3'   (SEQ ID NO: 18)
sense c) amplification of a 506 bp OXLP cDNA fragment (GenBank Acc. No. X93171)

OXLP sense    5'-ggccgacatgcattcaccag-3'    (SEQ ID NO: 19)

OXLP anti-    5'-catctgatattgctgggtctg-3'   (SEQ ID NO: 20)
sense d) amplification of a 513 bp Ubi cDNA fragment (GenBank accession M60175)

UBI sense     5'-ccaagatgcagatcttcgtga-3'   (SEQ ID NO: 21)

UBI anti-     5'-ttcgcgataggtaaaagagca-3'   (SEQ ID NO: 22)
sense

All of the fragments obtained were additionally ligated into the vector PGEM-T by means of T-overhang ligation and were used as starting plasmids for the generation of probes (for example for Northern blots) or dsRNA. The individual constructs were named pGEMT-RAC1, PGEMT-BAS, pGEMT-OXLP, pGEMT-UBI.

Example 5

Northern Blot Analysis

To prepare the Northern blotting, the RNA was separated in an agarose gel under denaturing conditions. To this end, part of the RNA solution (corresponding to 5 µg of RNA) was mixed with an identical volume of sample buffer (with ethidium bromide), denatured for 5 minutes at 94° C., placed on ice for 5 minutes, centrifuged briefly and applied to the gel. The 1×MOPS gel (1.5% agarose, ultra pure grade) contained 5 percent by volume of concentrated formaldehyde solution (36.5% [v/v]). The RNA was separated for 2 hours at 100 V and subsequently blotted.

Northern blotting was done as an upward capillary RNA transfer. To this end, the gel was first agitated gently for 30 minutes in 25 mM sodium hydrogen/dihydrogen phosphate buffer (pH 6.5) and cut to size. A piece of Whatman paper was prepared in such a way that it rested on a horizontal support and extended on 2 sides into a trough with 25 mM sodium hydrogen/dihydrogen phosphate buffer (pH 6.5). This piece of paper was covered with the gel, uncovered parts of the piece of Whatman paper being covered with a plastic film. The gel was then covered with a positively charged nylon membrane (Boehringer-Mannheim), avoiding air bubbles, whereupon the membrane was recovered to a height of approximately 5 cm with a stack of blotting paper. The blotting paper was additionally weighed down with a sheet of glass and with a 100 g weight. Blotting was carried out overnight at room temperature. The membrane was rinsed briefly in twice-distilled water and irradiated with UV light in a crosslinking apparatus (Biorad) with a light energy of 125 mJ in order to immobilize the RNA. The uniformity of the RNA transfer to the membrane was checked on a UV light bench.

To detect barley mRNA, 10 µg of total RNA from each sample were resolved in an agarose gel and blotted onto a positively charged nylon membrane by capillary transfer. Detection was effected using the DIG system.

Probe preparation: Digogygenin—or fluorescein-labeled RNA probes were prepared for hybridization with the mRNAS to be detected. The probes were generated by in-vitro transcription of a PCR product by means of a T7 or SP6 RNA polymerase, using labeled UTPs. The template for the PCR-aided amplification was provided by the above-described plasmid vectors pGEMT-RAC1, pGEMT-BAS, pGEMT-OXLP, PGEMT-UBI.

Depending on the orientation of the insert, different RNA polymerases were used for generating the antisense strand. T7 RNA polymerase was used for PGEMT-BAS and PGEMT-OXLP, while SP6—RNA polymerase was used for pGEMT-RAC1 and pGEMT-UBI.

The insert of the individual vector was amplified via PCR using flanking standard primers (M13 fwd and rev). The reaction proceeded with the following end concentrations in a total volume of 50 µl of PCR buffer (Silverstar):

```
M13-fwd: 5'-GTAAAACGACGGCCAGTG-3'    (SEQ ID NO: 23)
M13-rev: 5'-GGAAACAGCTATGACCATG-3'   (SEQ ID NO: 24)
```

10% dimethyl sulfoxide (v/v)
2 ng/µl of each primer (M13 forward and reversed)
1.5 mM $MgCl_2$,
0.2 mM dNTPs,
4 units Taq polymerase (Silverstar),
2 ng/µl plasmid DNA.

The amplification was carried out in a Thermocycler (Perkin-Elmar 2400) with the following temperature program:

| | |
|---|---|
| 94° C. | denaturing for 3 minutes |
| 30 cycles of | 30 seconds at 94° C. (denaturing) |
| | 30 seconds at 58° C. (annealing), |
| | 1.2 minutes at 72° C. (extension), |
| 72° C. | final extension for 5 minutes |
| 4° C. | cooling until further use |

The success of the reaction was verified in a 1% agarose gel. The products were subsequently purified using a "High Pure PCR-Product Purification Kit" (Boehringer-Mannheim). This gave approximately 40 µl of column eluate, which was again verified in the gel and stored at −20° C.

The RNA polymerization, the hybridization and the immunodetection were carried out largely following the kit manufacturer's instructions regarding the nonradioactive RNA detection (DIG System User's Guide, DIG-Luminescence detection Kit, Boehringer-Mannheim, Kogel et al. (1994) Plant Physiol 106:1264-1277). 4 µl of purified PCR product were treated with 2 µl of transcription buffer, 2 µl of NTP labeling mix, 2 µl of NTP mix and 10 µl of DEPC water. Then, 2 µl of the T7 RNA polymerase solution were pipetted in. The reaction was then carried out for 2 hours at 37° C. and then made up to 100 µl with DEPC water. The RNA probe was detected in an ethidium bromide gel and stored at −20° C.

To prepare the hybridization, the membranes were first agitated gently for 1 hour at 68° C. in 2×SSC (salt, sodium citrate), 0.1% SDS buffer (sodium dodecyl sulfate), the buffer being renewed twice or 3 times. The membranes were subsequently applied to the internal wall of hybridization tubes preheated at 68° C. and incubated for 30 minutes with 10 ml of Dig-Easy hybridization buffer in a preheated hybridization oven. In the meantime, 10 µl of probe solution were denatured for 5 minutes at 94° C. in 80 µl of hybridization buffer, and the mixture was subsequently placed on ice and centrifuged briefly. For the hybridization, the probe was then transferred into 10 ml of hybridization buffer at a temperature of 68° C., and the buffer in the hybridization tube was replaced by this probe buffer. Hybridization was then carried out overnight, likewise at 68° C.

Prior to the immunodetection of RNA-RNA hybrids, the blots were washed twice under stringent conditions for in each case 20 minutes in 0.1% (w/v) SDS, 0.1×SSC at 68° C.

For the immunodetection, the blots were first agitated twice for 5 minutes in 2×SSC, 0.1% SDS at RT. 2 stringent wash steps were subsequently carried out for in each case 15 minutes at 68° C. in 0.1×SSC, 0.1% SDS. The solution was then replaced by wash buffer without Tween. The reaction mix was shaken for 1 minute and the solution was exchanged for blocking reagent. After a further 30 minutes' shaking, 10 µl of anti-fluorescein antibody solution were added, and shaking was continued for 60 minutes. This was followed by two 15-minute wash steps in Tween-containing wash buffer. The membrane was subsequently equilibrated for 2 minutes in substrate buffer and, after being left to drain, transferred to a sheet of acetate paper. A mixture of 20 µl CDP-Star™ and 2 ml of substrate buffer was then divided uniformly on the "RNA side" of the membrane. The membrane was subsequently covered with a second sheet of acetate paper and the edges were heat-sealed to provide a water-tight seal, avoiding air bubbles. In a dark room, the membrane was then covered for 10 minutes with an X-ray film and the film was subsequently developed. The exposure time was varied as a function of the luminescence reaction.

Unless otherwise specified, the solutions were part of the kit as delivered (DIG-Luminescence detection Kit, Boehringer-Mannheim). All the others were prepared from the following stock solutions by dilution with autoclaved distilled water. Unless otherwise specified, all the stock solutions were made with DEPC (like DEPC water) and subsequently autoclaved.

DEPC water: distilled water is treated overnight at 37° C. with diethyl pyrocarbonate (DEPC, 0.1%, w/v) and subsequently autoclaved.

10×MOPS buffer: 0.2 M MOPS (morpholine-3-propanesulfonic acic), 0.05 M sodium acetate, 0.01 M EDTA, pH brought to 7.0 with 10 M NaOH.

20×SSC (sodium chloride/sodium citrate, salt/sodium citrate): 3 M NaClo, 0.3 M trisodium citrate×$2H_2O$, pH brought to 7.0 with 4 M HCl.

1% SDS (sodium dodecyl sulfate) sodium dodecyl sulfate (w/v), without DEPC.

RNA sample buffer: 760 µl formamide, 260 µl formaldehyde, 100 µl ethidium bromide (10 mg/ml), 80 µl glycerol, 80 µl bromophenol blue (saturated), 160 µl 10×MOPS, 100 µl water.

10×wash buffer without Tween: 1.0 M maleic acid, 1.5 M NaCl; without DEPC, bring to pH 7.5 with NaOH (solid, approx. 77 g) and 10 M NaOH.

Tween-containing wash buffer: made by adding Tween to wash buffer without Tween (0.3%, v/v).

10×blocking reagent: suspend 50 g of blocking powder (Boehringer-Mannheim) in 500 ml of wash buffer without Tween.

Substrate buffer: bring 100 mM Tris (trishydroxymethylaminomethane), 150 mM NaCl to pH 9.5 with 4 M HCl.

10×color marker: 50% glycerol (v/v), 1.0 mM EDTA pH 8.0, 0.25% bromophenol blue (w/v), 0.25% xylene cyanole (w/v).

Example 6

In Vitro Synthesis of the RacB dsRNA

All of the plasmids (pGEMT-RAC1, pGEMT-BAS, pGEMT-OXLP, pGEMT-UBI) which were employed for in-vitro transcription comprise the T7 and SP6 promoters (pGEM-T, Promega) at the respective ends of the nucleic acid sequence inserted, which makes possible the synthesis of sense or antisense RNA. The plasmids can be linearized with suitable restriction enzymes in order to ensure correct transcription of the nucleic acid sequence inserted and to prevent reading being continued into vectorial sequences.

To this end, 10 µg of plasmid DNA were cleaved with in each case at the side of the insert which was located distally from the promoter. The cleaved plasmids are extracted in 200 µl of water with an identical volume of phenol/chloroform/ isoamyl alcohol, transferred into a new Eppendorf reaction vessel (RNAse-free) and centrifuged for 5 minutes at 20 000 g. 180 µl of the plasmid solution were treated with 420 µl of ethanol, and the mixture was placed on ice and subsequently precipitated by centrifugation for 30 minutes at 20 000 g and −4° C. The precipitate was taken up in 10 µl of TE buffer.

To prepare the RacB dsRNA, the plasmid pGEMT-Rac1 was digested with SpeI, and sense RNA was transcribed using T7 RNA polymerase.

Furthermore, pGEMT-Rac1 was digested with NcoI, and antisense RNA was transcribed using SP6 RNA polymerase. RNA polymerases were obtained from Roche Molecular Biology, Mannheim, Germany.

Each transcription reaction contained the following in a volume of 40 µl:
 2 µl of linearized plasmid DNA (1 µg)
 2 µl of NTPs (25 mM) (1.25 mM of each NTP)
 4 µl of 10× reaction buffer (Roche Molecular Biology),
 1 µl of RNAsin RNAsin (27 units; Roche Molecular Biology),
 2 µl of RNA polymerase (40 units)
 29 µl of DEPC water Following incubation for 2 hours at 37° C., part of the reactions from the transcription of the sense and antisense strand, respectively, were mixed, denatured for 5 minutes at 95° C. and subsequently hybridized (annealed) by cooling to a final temperature of 37° C. over 30 minutes. Alternatively, it is also possible first to denature the mixture of sense and antisense strand and then to cool it for 30 minutes at −20° C. The protein precipitate which formed during denaturing and hybridization was removed by briefly centrifuging the reaction at 20 800 g, and the supernatant was used directly for coating tungsten particles (see hereinbelow). For analysis, 1 µl of each RNA strand and of the dsRNA were resolved on a nondenaturing agarose gel. Successful hybridization manifested itself by a band shift toward higher molecular weight in comparison with the single strands.

4 µl of the dsRNA were ethanol-precipitated (by adding 6 µl of water, 1 µl of 3M sodium acetate solution and 25 µl of ethanol, and centrifugation for at least 5 minutes at 20 000 g and 4° C.) and the pellet was resuspended in 500 µl of water. The absorption spectrum between 230 and 300 nm was measured or the absorption at 280 and 260 nm was determined in order to determine the purity and concentration of the dsRNA. As a rule, 80 to 100 µl of dsRNA with an $OD_{260}/OD_{280}$ ratio of 1.80 to 1.95 were obtained. Digestion with DNase I can optionally be carried out, but has no significant effect on the results which follow.

The control dsRNA used was the human thyroid receptor dsRNA (starting vector pT7betaSal (Norman C et al. (1988) Cell 55(6):989-1003), provided by Dr. Baniahmad, Department of Genetics, Gießen, Germany; the sequence of the insert is described under the GenBank Acc. No.: NM_000461). To generate the sense RNA, the plasmid was digested with PvuII, to generate the antisense RNA, it was digested with HindIII, and the RNA was then transcribed with T7 and SP6 RNA polymerase, respectively. The individual process steps for generating the control dsRNA are carried out analogously to those described above for the RacB dsRNA.

Example 7

Transient Transformation, RNAi, and Evaluation of the Development of the Fungal Pathogen Barley cv. Pallas leaf segments were transformed with an RacB dsRNA together with a GFP expression vector. The leaves were subsequently inoculated with Bgh, and the result was analyzed after 48 hours by light and fluorescence microscopy. The penetration into GFP-expressing cells was assessed by detecting haustoria in live cells and by assessing the fungal development on precisely these cells. In all six experiments, bombardment of barley cv. Pallas with RacB dsRNA resulted in a reduced number of successfully Bgh-penetrated cells in comparison with cells which had been bombarded with a foreign control dsRNA (human thyroid hormone receptor dsRNA, TR). The resistance-inducing effect of the RacB dsRNA caused an average reduction in Bgh penetration efficacy by 44% (FIG. 4).

A method was employed for the transient transformation which had already been described for the biolistic introduction of dsRNA into epidermal cells of barley leaves (Schweizer P et al. (1999) Mol Plant Microbe Interact 12:647-54; Schweizer P et al. (2000) Plant J 2000 24: 895-903). Tungsten particles with a diameter of 1.1 µm (particle density 25 mg/ml) were coated with dsRNA (preparation see above) together with plasmid DNA of the vector pGFP (GFP under the control of the CaMV $^{35}$S promoter) as transformation marker. For each bombardment, the following amounts of dsRNA and reporter plasmid were used for coating: 1 µg of pGFP and 2 µg of dsRNA. Double-stranded RNA was synthesized in vitro by annealing sense and antisense RNA (see above).

To prepare microcarriers, 55 mg of tungsten particles (M 17, diameter 1.1 µm; Bio-Rad, Munich) were washed twice with 1 ml of autoclaved distilled water and once with 1 ml of absolute ethanol, dried and taken up in 1 ml of 50% strength glycerol (approx. 50 mg/ml stock solution). The solution was diluted to 25 mg/ml with 50% strength glycerol, mixed thoroughly prior to use, and suspended in an ultrasonic bath. To coat the microcarriers for each bombardment, 1 µg of plasmid, 2 µg of dsRNA (1 µl), 12.5 µl of tungsten particle suspension (25 mg/ml), 12.5 µl of 1 M $Ca(NO_3)_2$ solution (pH 10) were combined dropwise with constant mixing, the mixture was left to stand for 10 minutes at RT and then briefly centrifuged, and 20 µl of the supernatant were drawn off. The remainder with the tungsten particles is resuspended (ultrasonic bath) and employed in the experiment.

Segments (approx. 4 cm in length) of barley primary leaves were used. The tissue was placed on 0.5% Phytagar (Gibco-BRL™ Life Technologies™, Karlsruhe) supplemented with 20 µg/ml benzimidazole in Petri dishes (diameter 6.5 cm), and the edges were covered directly prior to particle bombardment with a stencil provided with a rectangular opening of 2.2 cm×2.3 cm. One after the other, the dishes were placed on the bottom of the vacuum chamber (Schweizer P et al. (1999) Mol Plant Microbe Interact 12:647-54) over which a nylon mesh (mesh size 0.2 mm, Millipore, Eschborn) on an apertured plate had been inserted (5 cm above the bottom, 11 cm underneath the macrocarrier, see hereinbelow) to act as diffuser in order to disperse particle aggregates and to slow down the particle stream. For each bombardment, the macrocarrier (plastic syringe filter holder, 13 mm, Gelman Sciences, Swinney, UK), which was attached at the top of the chamber, was loaded with 5.8 µl of DNA-coated tungsten particles (microcarrier, see hereinbelow). The pressure in the chamber was reduced by 0.9 bar using a diaphragm vacuum pump (Vacuubrand, Wertheim), and the surface of the plant tissue was bombarded with the tungsten particles at a helium gas pressure of 9 bar. The chamber was aerated immediately thereafter. To label transformed cells, the leaves were bombarded with the plasmid (pGFP; vector pUC18-based, CaMV $^{35}$S promoter/terminator cassette with inserted GFP gene; Schweizer P et al. (1999) Mol Plant Microbe Interact 12:647-

54; provided by Dr. P. Schweizer Schweizer P, Institut für Pflanzengenetik [Department of Plant Genetics] IPK, Gatersleben, Germany). Each time before another plasmid was used for the bombardment, the macrocarrier was cleaned thoroughly with water. Following incubation for four hours after the bombardment with slightly open Petri dishes, RT and daylight, the leaves were inoculated with 100 conidia/mm$^2$ of the barley powdery mildew fungus (race A6) and incubated for a further 36 to 48 hours under identical conditions.

Leaf segments were bombarded with the coated particles using a particle inflow gun. 312 µg of tungsten particles were applied per bombardment. 4 hours after bombardment, the leaf segments were inoculation inoculated with *Blumeria graminis* f.sp. *hordei* mildew (race A6) and, after a further 40 hours, evaluated with regard to infection symptoms. The result (for example the penetration efficacy, defined as percentage of attacked cells with a mature haustorium and a secondary hypha (secondary elongating hyphae) was analyzed by fluorescence and light microscopy. Inoculation with 100 conidia/mm$^2$ results in an attack frequency of approximately 50% of the transformed cells. A minimum of 100 interaction sites were evaluated for each individual experiment. Transformed (GFP-expressing) cells were identified under excitation with blue light. Three different categories of transformed cells were distinguished:
1. Penetrated cells comprising a readily recognizable haustorium. A cell with more than one haustorium counted as one cell.
2. Cells which were attacked by a fungal appressorium, but comprise no haustorium. A cell which was attacked repeatedly by Bgh, but contains no haustorium, counted as one cell.
3. Cells which are not attacked by Bgh.

Stomatal cells and subsidiary cells were excluded from the evaluation. Surface structures of Bgh were analyzed by light microscopy or fluorescent staining of the fungus with 0.1% Calcofluor (w/v in water) for 30 sec. The fungal development can be evaluated readily by staining with Calcofluor followed by fluorescence microscopy. While the fungus develops a primary germ tube and an appressorial germ tube in cells transformed with RacB dsRNA, it fails to develop a haustorium. The development of haustoria is a precondition for the development of a secondary hyphae.

The relative penetration efficacies (RPEs) were calculated as the difference between the penetration efficacies in transformed cells (transformation with RacB dsRNA or control dsRNA) and the penetration efficacies of untransformed cells (here: average penetration efficacy 57%). The percentage RPE (%-RPE) is calculated from the RPE minus 1, multiplied by 100.

$$RPE = \frac{[PE \text{ of cells transformed with } RacB \text{ } dsRNA]}{[PE \text{ of cells transformed with control } dsRNA]}$$

$$\%\text{-}RPE = 100 * (RPE\text{-}1)$$

The %-RPE value (deviation from the average penetration efficacy of the control) serves to determine the susceptibility of cells transfected with RacB dsRNA (FIG. 4).

In the case of the control dsRNA, no difference between the transfection with the control dsRNA and with water was found in five independent experiments with regard to the penetration efficacy of Bgh.

The deviation of the PE in various genotypes was also studied. To demonstrate the operable linkage with the Mlo gene, an mlo5 genotype (A89, mlo5 ror1, background: Ingrid), which owing to a mutation of the Ror1 gene has only moderate susceptibility to Bgh attack (Freialdenhoven et al. (1996) Plant cell 8:5-14), was employed. In this doubly-mutant genotype, the efficacy of RacB dsRNA was studied in comparison with a wild-type Mlo genotype. However, no prevention of the development of haustoria in A89 was observed in five independent experiments, while in parallel experiments with Pallas and Ingrid the PE was markedly reduced (FIG. 5). Interestingly, the effect of the RacB dsRNA was more pronounced in Pallas than in Ingrid (FIG. 5, Experiments 1 and 2 in comparison with 3, 4 and 5).

To rule out an effect of the dsRNA on the transformation rate or survival rate of the attacked cells, the number of GFP-expressing cells was compared between control and RacB dsRNA experiments (Table 7). The RacB dsRNA had no effect on the total number, or the number of attacked, GFP-expressing cells.

TABLE 7

Transformation rates of barley leaves following bombardment with dsRNA

Number of GFP-expressing cells per bombardment[a]

| Line | Total (Control dsRNA) | Attacked (Control dsRNA) | Total (RacB dsRNA) | Attacked (RacB dsRNA) | n[c] |
|---|---|---|---|---|---|
| Pallas (Mlo Ror1) | 34.3 ± 4.6 | 16.0 ± 2.2 | 33.9 ± 4.8 | 15.5 ± 1.4 | 6 (21) |
| Ingrid (Mlo Ror1) | 51.0 ± 8.9 | 27.6 ± 8.7 | 49.9 ± 5.6 | 31.5 ± 7.8 | 3 (11) |
| A89 (mlo5 ror1) | 34.4 ± 5.4 | 18.1 ± 4.0 | 34.1 ± 5.5 | 16.7 ± 3.8 | 5 (22) |

[a]4 leaves were bombarded per bombardment.
The data shown are means and standard error.
[c]Number of independent experiments (bombardments n in each case for control and RacB dsRNA).

Example 8

Constitutively Active RACB Mutant

A putatively constitutively active barley RACB mutant (substitution G→V at position 15; RacB-V15) was generated and overexpressed in the barley variety Pallas in order to positively identify RACB as susceptibility factor. First, full-length RACB was synthesized via RT-PCR. The following oligonucleotide primers were employed for this purpose:

```
RacB5' BamHI
5'-GGATCCGATGAGCGCGTCCAGGTT-3'    (SEQ ID NO: 31)

RacB3' SalI
5'-GTCGACCTTCGCCCTTGTTCTTTGTC-3'  (SEQ ID NO: 32)
```

The cDNA was cloned into PGEM-T and subsequently excised via the primer cleavage sites and cloned into pGY-1 (Schweizer P et al. (1999) Mol Plant Microbe Interact 12: 647-54; FIG. 7) via BamHI/SalI cleavage sites. The construct is referred to as pGY1-RacB.

The nucleic acid sequence encoding the constitutively active RacB mutant RACB-V15 was generated using the "Transformer® Site-Directed Mutagenesis Kit" (Clonetech, Heidelberg), following the manufacturer's instructions. The starting vector employed was pGY1-RacB. The following oligonucleotide was used as mutagenesis primer:

(SEQ ID NO: 33)
V15
5'-ACCGTGGGGACGTCGCCGTCGGCAAGAC-3'

Then, RACB-V15 was then overexpressed transiently in 5 independent experiments in the barley variety Pallas under the control of the $^{35}$S CamV promoter. The experiments were carried out as described by Schultheiss et al. (Schultheiss H et al. (2002) Plant Physiol 128:1447-1454), except that, after the particle bombardment, 24 hours instead of 4 hours elapsed prior to inoculation. The particles were coated as described in Schweizer et al. (Schweizer P et al. (1999) Mol Plant Microbe Interact 12:647-54).

The expression of a constitutive RacB mutant brings about a significantly increased susceptibility to pathogen attack by powdery mildew of barley in comparison with the controls. Again, these results confirm the key function of RacB in the defense of pathogens. The RACB-V15 effects. (see FIG. 6-A/B) are significant in the t-test when a two-tail paired test is carried out. The relative susceptibility to the fungal pathogen is increased in all cases (FIG. 6-B).

Example 9

Further HvRac Homologs

All full-length sequences were isolated from RNA using specific primers and cloned into PGEM-T and sequenced (Hückelhoven et al. (2001) Plant Mol Biol; Schultheiss et al. (2002) Plant Physiol 128:1447-1454). In some cases, the sequences are very similar to RacB.

a) HvRop6:
LEFT PRIMER
5' -GTGGAGGCGCGGCGAGA-3'           (SEQ ID NO: 25)

RIGHT PRIMER
5' -CCATGCTTCATCTCCATAGTCA-3'      (SEQ ID NO: 26)

b) HvRacD:
LEFT PRIMER
5'-ggatccCGATTCCATCAGGAAAGCAT-3'   (SEQ ID NO: 27)

RIGHT PRIMER
5'-gtcgacGCGAGACACTGCAAAACAAA-3'   (SEQ ID NO: 28)

c) HvRop4:
LEFT PRIMER
5'-GGATCCttctcgtccatttagccggc-3'   (SEQ ID NO: 29)

RIGHT PRIMER
5'-GTCGACtgatcacttgaagcatgccag-3'  (SEQ ID NO: 30)

Example 10

Generation of Sense and Antisense Constructs with the Gene AtRacB for Expression in *Arabidopsis thaliana*

A fragment of the *Arabidopsis* RacB homolog (MIPS-Code: AT4g35950; SEQ ID NO: 53; hereinbelow AtRacB) is isolated via PCR from an *Arabidopsis thaliana* cDNA library. The primer sequences used are:

Fra   5'-ATGAGCGCGTCCAGGTTCATA-3'  (SEQ ID NO: 71)
186:

Fra   5'-ATCAAACACGCCCTTCACGTT-3'  (SEQ ID NO: 72)
187:

The amplification proceeds in a T3 thermocycler from Biometra with the following temperature profile:

35 cycles of 1 min at 95° C., 0.5 min at 59° C. and 3 min at 72° C. Subsequent extension for 5 min at 72° C.

The PCR products is cloned into the vector pCR2.1 (in accordance with the pCR Script Cloning Kit, Stratagene, Heidelberg) following the manufacturer's instructions. A fragment is excised from the vector construct via the restriction enzyme EcoRI (Roche, Mannheim). The fragment can be isolated via gel electrophoresis and subsequent purification using anion exchanger columns (QIAex Purification Kit, Qiagen, Hilden). Accordingly, the binary vector pSUN3-Nit is opened up via the enzymes XmaI and EcoRI and subjected to purification by means of gel electrophoresis followed by elution over anion exchanger columns (QIAex Purification Kit, Qiagen, Hilden).

Since blunt ends have to be generated for the cloning of insert and vector with 5'-overhangs, both the eluted AtRacB fragment and the eluted pSUN3-Nit fragment are treated with 2 µl of dNTP mix I (10 mM each of dATP, dCTP, dGTP, dTTP; Pharmacia, Freiburg) and 1.6 µl of Klenow fragment (USB/Amersham, Braunschweig, 2 U/µl) for filling up the overhang and incubated for 30 min at 37° C. To prevent religation, the vectors are first purified via a QIAquick Spin Column (Qiagen, Hilden), treated with CIAP (Calf Intestinal Alkaline Phosphatase, GibcoBRL, Eggenstein, 1 U/µl) and finally purified via a 0.8% strength agarose gel.

To prepare the following ligation mix in a total volume of 50 µl, 34 µl of H$_2$O, 5 µl of ligation buffer and 1 µl of T4 ligase (Roche, Mannheim) are additionally added to the 10 µl of cut DNA. This mixture is incubated overnight at 16° C. The ligase is subsequently inactivated for 10 min at 65° C. The ligation is now followed by precipitation with 0.1 volume of sodium acetate (pH 5.2) and 2.5 volumes of ethanol. After centrifugation (30 min, 15 000 g, 4° C.), the pellet is dried in 70% ethanol and resuspended in 10 µl of H$_2$O. 2 µl of this pellet are transformed by electroporation (*E. coli* Pulser, Bio-Rad) into *Escherichia coli* bacteria, strain DH5α. The DNA-treated bacteria are plated onto LB plates supplemented with the antibiotic ampicillin (50 mg/l). After incubation for 16 h at 37° C., bacteria are scraped from the colonies which have grown and transferred into tubes containing 3 ml of LB-Amp liquid medium each. After incubation for 16 h at 37° C., the cultures, which have grown to great density, are centrifuged. Plasmid DNA is isolated from the bacterial pellets by means of the QIAprep DNA miniprep kit (Qiagen, Hilden) following the manufacturer's instructions and subjected to analytic digests with various enzyme combinations. These control digests allow the isolation of constructs in which the AtRacB gene is cloned in sense or antisense orientation behind the of the *A. thaliana* nitrilase-1 (nit1) gene, which is constitutively active in plants (GenBank Acc.-No.: Y07648.2, nucleotides 2456-4340, Hillebrand et al. (1996) Gene 170:197-200). These constructs are named pSUN3NIT_AtRacB_s (SEQ ID NO: 73) and pSUN3NIT_atRacB_as (SEQ ID NO: 74) and used for the transformation of *Arabidopsis* plants. The constructs comprise the complete sequence of AtRacB, so that the expression vector pSUN3NIT_HvRacB_s, which comprises the fragment in sense orientation, is capable of expressing a functional AtRacB protein. The vector acts primarily as negative control and leads in most cases to reduced pathogen resistance, but in some cases (see hereinbelow) also to an increase in pathogen resistance, presumably via a cosuppression effect.

Example 11

Generation of Sense and Antisense Constructs with the Gene HvRacB for Expression in *Arabidopsis thaliana*

Various nonfunctional fragments of the gene HvRacB are to be prepared for expression in *Arabidopsis* plants. To this end, the plasmid, which contains the HvRacB gene subcloned into the bacterial vector PGEM-T, is digested with the enzyme combinations BamHI/HindIII (Roche, Mannheim). Overhanging 5'-single strands are filled up by treatment with Klenow polymerase in the presence of a mixture of nucleotides (see above). The resulting HvRacB fragment with these blunt ends is cloned directly into a pSUN3NIT vector, which is opened up with the enzymes BglII and SpeI (Roche, Mannheim) in its multiple cloning site and whose 5'-overhangs are filled up by means of treatment with Klenow polymerase (as described above). For the ligation batches, each of which has a total volume of 50 µl, 34 µl of $H_2O$, 5 µl of ligation buffer and 1 µl of T4 ligase (Roche, Mannheim) are additionally added to the 10 µl of cut DNA. This mixture is incubated overnight at 16° C. The ligase is subsequently inactivated for 10 min at 65° C. The ligation is now followed by precipitation with 0.1 volume of sodium acetate (pH 5.2) and 2.5 volumes of ethanol. After centrifugation (30 min, 15 000 g, 4° C.), the pellet is dried in 70% ethanol and resuspended in 10 µl of $H_2O$. 2 µl of this pellet are transformed by electroporation (*E. coli* Pulser, Bio-Rad) into *Escherichia coli* bacteria, strain DH5α. The DNA-treated bacteria are plated onto LB plates supplemented with the antibiotic ampicillin (50 mg/l). After incubation for 16 h at 37° C., bacteria are scraped from the colonies which have grown and transferred into tubes containing 3 ml of LB-Amp liquid medium each. After incubation for 16 h at 37° C., the cultures, which have grown to great density, are centrifuged. Plasmid DNA is isolated from the bacterial pellets by means of the QIAprep DNA miniprep kit (Qiagen, Hilden) following the manufacturer's instructions and subjected to analytic digests with various enzyme combinations. These control digests allow the identification of constructs in which the appropriate gene construct is cloned in sense or antisense orientation behind the promoter of the *A. thalina* nitrilase-1 gene, which is constitutively active in plants (see above). These constructs are named pSUN3NIT_HvRacB_s (SEQ ID NO: 75) and pSUN3NIT_HvRacB_as (SEQ ID NO: 76) and used for the transformation of *Arabidopsis* plants. The constructs comprise a truncated fragment of hvRacB, so that not even the expression vector pSUN3NIT_HvRacB_s, which comprises the fragment in sense orientation, is capable of expressing a functional HvRacB protein. The vector acts primarily as negative control but leads in some cases (see hereinbelow) also to an increase in pathogen resistance, presumably via a cosuppression effect.

Example 12

Transformation of *Arabidopsis thaliana*, and Analysis of the Fungal Resistance

Wild-type *A. thaliana* plants (Columbia) are with the *Agrabacterium tumefaciens* strain (EHA105) based on a modified method (Steve Clough and Andrew Bent (1998) Plant J 16(6): 735-743) of the vacuum infiltration method of Bechtold et al. (Bechtold N et al. (1993) CR Acad Sci Paris, Life Sciences 316:1194-1199).

The *A. tumefaciens* cells used are previously transformed with the plasmids pSUN3NIT AtRacB_s (SEQ ID NO: 73), pSUN3NIT_atRacB_as (SEQ ID NO: 74), pSUN3NIT_HvRacB_s (SEQ ID NO: 75) and pSUN3NIT_HvRacB_as (SEQ ID NO: 76).

Seeds of the *Agrobacterium*-transformed primary transformants are selected on the basis of their kanamycin resistance. Antibiotic-resistant seedlings are planted in soil and, when grown into fully developed plants, used for biochemical analysis.

To analyze the resistance of the transgenic *Arabidopsis* plants to pathogenic fungi, inoculations with the biotrophic fungi *Peronospora parasitica* and *Erysiphe cichoracearum* are performed.

a) *Peronospora Parasitica*

Plants aged 5 to 8 weeks are sprayed with a conidia spore suspension (approx. 106 spores/ml). The inoculated plants are kept overnight in a refrigerator at approximately 16° C. under dark and damp conditions, being covered with a plastic bag. After one day, the plastic bag is opened slightly and later removed completely. Six days after inoculation, the plants are again covered with the plastic bag overnight, whereby sporulation is induced. On the next day, the leaves are examined for the appearance of conidiophores. Over the next days, the intercellular growth of the fungus leads to the induction of weak chloroses up to severe necroses in the leaves. These symptoms are quantified and tested for significance.

b) *Erysiphe Cichoracearum*

The biotrophic mildew fungus is grown on *Arabidopsis* plants. To infect the 4-week-old transgenic RacB-expressing *Arabidopsis* plants, conidiophores are removed from the leaf surface with a fine brush and applied to the leaves of the transgenic plants. The plants are incubated for 7 days at 20° C. 7 days after the inoculation, the conidiophores appear on the leaves, and chloroses and necroses can be observed over the following days. These symptoms are quantified and tested for significance.

c) Results

The transgenic *Arabidopsis* plants which express antisense sequences for AtRacB or HvRacB are significantly more resistant to *Peronospora parasitica* and to *Erysiphe cichoracearum* than nontransgenic wild-type plants.

The transgenic *Arabidopsis* plants which express sense sequences for the complete AtRacB are in are in most cases significantly more susceptible to both *Peronospora parasitica* and *Erysiphe cichoracearum* than nontransgenic wild-type plants. In some cases, however, an increased resistance can also be observed (presumably via a cosuppression effect).

Transgenic *Arabidopsis* plants which express sense sequences for the an HvRacB fragment are in are in some cases significantly more resistant to both *Peronospora parasitica* and *Erysiphe cichoracearum* than nontransgenic wild-type plants.

We claim:

1. A method of generating or increasing a resistance to at least one pathogen in a plant, which comprises:
reducing an amount, activity or function of an RacB protein in a plant or a tissue, organ, part or cell thereof, wherein the RacB protein is a polypeptide comprising the sequence of SEQ ID NO: 2 or a sequence having at least 90% homology to the sequence of SEQ ID NO: 2; wherein the reducing comprises introducing into the plant, tissue, organ, part or cell thereof: a nucleic acid encoding a double-stranded RacB RNA or an expression cassette comprising said nucleic acid; and wherein the pathogen is selected from the group consisting of Plasmodiophoramycota, Oomycota, Ascomycota, Chytridiomycetes, Zygomycetes, Basidiomycota, Deuteromycetes, and combinations thereof.

2. The method of claim 1, comprising: stably transforming a plant cell with a recombinant expression cassette comprising a nucleic acid encoding;
a double-stranded RacB RNA;
regenerating a plant from the plant cell; and
expressing said nucleic acid in an amount and over a period of time sufficient to generate or increase said resistance.

3. The method of claim 1, wherein the plant is a monocot or dicot.

4. The method of claim 3, wherein the monocot is selected from the group consisting of wheat, oats, millet, barley, rye, maize, rice, buckwheat, sorghum, triticale, spelt, linseed, sugar cane, and combinations thereof.

5. An isolated nucleic acid comprising a nucleic acid sequence encoding a barley RacB protein, wherein the RacB protein is a polypeptide comprising the sequence of SEQ ID NO: 2.

6. An isolated nucleic acid comprising the sequence of SEQ ID NO: 1 or the complement thereof.

7. A recombinant double-stranded RNA molecule for reducing expression of an RacB protein, wherein one of the two RNA strands comprises the sequence of SEQ ID NO: 1 or a sequence having at least 90% homology to the sequence of SEQ ID NO: 1.

8. A recombinant double-stranded RNA molecule for reducing expression of an RacB protein, comprising: a sense strand and an antisense strand, which is essentially complementary to the sense strand; wherein one of the strands comprises the sequence of SEQ ID NO: 1 or a sequence having at least 90% homology to the sequence of SEQ ID NO: 1.

9. The recombinant double-stranded RNA molecule of claim 7, wherein the two RNA strands are linked covalently to each other.

10. An expression cassette comprising a nucleic acid encoding the recombinant double-stranded RNA molecule of claim 7 in operable linkage with a promoter.

11. The expression cassette of claim 10, wherein the promoter is functional in a plant.

12. The expression cassette of claim 11, wherein the promoter is a pathogen-inducible promoter.

13. A vector comprising the expression cassette of claim 10.

14. A transgenic organism comprising the expression cassette of claim 10, wherein the organism is selected from the group consisting of bacteria, yeasts, and plants.

15. The transgenic organism of claim 14, wherein the plants are selected from the group consisting of wheat, oats, millet, barley, rye, maize, rice, buckwheat, sorghum, triticale, spelt, linseed, sugar cane, oil seed rape, canola, cress, Arabidopsis, cabbages, soya, alfalfa, pea, beans, peanut, potato, tobacco, tomato, eggplant, bell pepper, sunflower, Tagetes, lettuce, Calendula, melon, pumpkin, squash and zucchini.

16. A transgenic plant or a tissue, organ, part or cell produced by the method of claim 1.

17. A stably transformed plant produced by the method of claim 2.

18. The method of claim 1, wherein activity comprises GTPase activity of said RacB protein.

19. The method of claim 1, wherein function comprises a substrate-binding capacity of said RacB protein.

20. A method of selecting a plant cell with an increased resistance to a pathogen comprising: introducing into a plant cell a nucleic acid encoding a double stranded RacB RNA or an expression cassette comprising said nucleic acid; said double stranded RNA reduces an amount, activity or function of an RacB protein of the plant cell; and selecting at least one plant cell wherein resistance to a pathogen is increased as compared to an untransformed plant cell; wherein the RacB protein comprises the sequence of SEQ ID NO: 2 or a sequence having at least 90% homology to the sequence of SEQ ID NO: 2; and wherein the pathogen is selected from the group consisting of Plasmodiophoramycota, Oomycota, Ascomycota, Chytridiomycetes, Zygomycetes, Basidiomycota, Deuteromycetes, and combinations thereof.

21. The method of claim 20, wherein the activity comprises GTPase activity of the RacB protein.

22. The method of claim 20, wherein the function comprises a substrate-binding capacity of the RacB protein.

23. An expression cassette comprising a nucleic acid encoding the double-stranded RNA molecule of claim 8 in operable linkage with a promoter.

24. A transgenic organism comprising the expression cassette of claim 23, wherein the organism is selected from the group consisting of bacteria, yeasts, plants.

25. A transgenic organism comprising the vector of claim 13, wherein the organism is selected from the group of organisms consisting of bacteria, yeasts, and plants.

26. A recombinant plant cell wherein an expressed amount, activity or function of an endogenous RacB protein is reduced by stable transformation with a nucleic acid or an expression cassette comprising the nucleic acid as compared to an untransformed plant cell, wherein the nucleic acid comprises a double-stranded RacB RNA; and wherein the nucleic acid comprises the sequence of SEQ ID NO: 1 or a sequence having at least 90% homology to the sequence of SEQ ID NO: 1.

27. The cell of claim 26, wherein the activity comprises GTPase activity of said RacB protein.

28. The cell of claim 26, wherein the function comprises a substrate-binding capacity of said RacB protein.

29. The plant cell of claim 26, wherein the endogenous RacB protein is reduced by at least 60%.

30. The plant cell of claim 26, wherein the endogenous RacB protein is reduced by at least 90%.

31. The plant cell of claim 26, wherein the double-stranded RNA molecule comprises a sense strand and an antisense strand which is essentially complementary to the sense strand.

32. The plant cell of claim 26, wherein the reduction provides the plant cell with an increased resistance to a pathogen as compared to the untransformed plant cell.

33. The cell of claim 32, wherein the pathogen is selected from the group consisting of Plasmodiophoramycota, Oomycota, Ascomycota, Chytridiomycetes, Zygomycetes, Basidiomycota, Deuterormycetes, and combinations thereof.

34. The recombinant double-stranded RNA molecule of claim 8, wherein the two RNA strands are linked covalently to each other.

35. A transgenic organism comprising the dsRNA of claim 8, wherein the organism is selected from the group of organisms consisting of bacteria, yeasts, and plants.

36. A transgenic organism comprising a nucleic acid encoding the double-stranded RNA molecule of claim 7, wherein the organism is selected from the group consisting of bacteria, yeasts, and plants.

37. A plant comprising the transformed plant cell of claim 17.

38. A plant comprising the recombinant plant cell of claim 26.

39. A transformed plant cell obtained by the method of claim 20.

40. A plant comprising the transformed plant cell of claim 39.

41. The method of claim 1, wherein the plant tissue, organ, or part thereof is from a monocot or dicot.

\* \* \* \* \*

UNITED STATES PATENT AND TRADEMARK OFFICE
CERTIFICATE OF CORRECTION

PATENT NO. : 7,456,335 B2 Page 1 of 1
APPLICATION NO. : 10/488222
DATED : November 25, 2008
INVENTOR(S) : Karl-Heinz Kogel et al.

It is certified that error appears in the above-identified patent and that said Letters Patent is hereby corrected as shown below:

In the Claims:

In Claim 35, in column 186, on line 1, "A transgenic organism comprising the dsRNA of claim" should read -- A transgenic organism comprising the recombinant double-stranded RNA of claim --.

Signed and Sealed this

Second Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,456,335 B2  Page 1 of 1
APPLICATION NO. : 10/488222
DATED : November 25, 2008
INVENTOR(S) : Karl-Heinz Kogel et al.

It is certified that error appears in the above-identified patent and that said Letters Patent is hereby corrected as shown below:

Title Pg, Item (22) reading "(22) PCT Filed: Aug. 3, 2002" should read -- (22) PCT Filed: Aug. 30, 2002 --.

Signed and Sealed this

Twenty-third Day of June, 2009

JOHN DOLL
*Acting Director of the United States Patent and Trademark Office*

SEQUENCE LISTING

<160> NUMBER OF SEQ ID NOS: 76

<210> SEQ ID NO 1
<211> LENGTH: 857
<212> TYPE: DNA
<213> ORGANISM: Hordeum vulgare
<220> FEATURE:
<221> NAME/KEY: CDS
<222> LOCATION: (90)..(680)
<220> FEATURE:
<221> NAME/KEY: misc_feature
<222> LOCATION: (780)
<223> OTHER INFORMATION: n is a, c, g or t
<220> FEATURE:
<221> NAME/KEY: misc_feature
<222> LOCATION: (783)
<223> OTHER INFORMATION: n is a, c, g or t

<400> SEQUENCE: 1

```
atcttaacca gctccctacc tccccttctt cttcctcctc ctcccctgtc tcgcccgcag        60
cttcaccggc agcgagggaa agagggagg atg agc gcg tcc agg ttc ata aag        113
                                Met Ser Ala Ser Arg Phe Ile Lys
                                  1               5 tgc gtc acc gtg ggg gac ggc gcc gtc ggc aag acc tgc atg ctc atc        161
Cys Val Thr Val Gly Asp Gly Ala Val Gly Lys Thr Cys Met Leu Ile
         10                  15                  20 tcc tac acc tcc aac acc ttc ccc acc gac tat gtg ccc acg gtg ttt        209
Ser Tyr Thr Ser Asn Thr Phe Pro Thr Asp Tyr Val Pro Thr Val Phe
 25                  30                  35                  40 gac aac ttc agt gct aat gtt gtg gtt gat ggc aac act gtc aac ctt        257
Asp Asn Phe Ser Ala Asn Val Val Val Asp Gly Asn Thr Val Asn Leu
                 45                  50                  55 ggg cta tgg gat act gca ggt cag gaa gac tac aac aga ctg aga ccg        305
Gly Leu Trp Asp Thr Ala Gly Gln Glu Asp Tyr Asn Arg Leu Arg Pro
             60                  65                  70 ctg agt tat cgt gga gct gat gtc ttc ctt ctg gcc ttc tcg ctt atc        353
Leu Ser Tyr Arg Gly Ala Asp Val Phe Leu Leu Ala Phe Ser Leu Ile
         75                  80                  85 agc aag gct agc tat gag aat gtt tca aag aag tgg ata cct gaa ctg        401
Ser Lys Ala Ser Tyr Glu Asn Val Ser Lys Lys Trp Ile Pro Glu Leu
 90                  95                 100 aag cat tat gca cca ggt gtg cct att atc ctc gtg gga aca aag ctt        449
Lys His Tyr Ala Pro Gly Val Pro Ile Ile Leu Val Gly Thr Lys Leu
105                 110                 115                 120 gat ctt cga gat gac aag cag ttc ttt gtg gac cat cct ggt gct gtt        497
Asp Leu Arg Asp Asp Lys Gln Phe Phe Val Asp His Pro Gly Ala Val
                125                 130                 135 cct atc act act gct cag ggg gag gaa cta aaa aag tta ata ggc gca        545
Pro Ile Thr Thr Ala Gln Gly Glu Glu Leu Lys Lys Leu Ile Gly Ala
            140                 145                 150 ccc tac tac atc gaa tgc agc tcg aag acc caa cta aat gtc aag ggt        593
Pro Tyr Tyr Ile Glu Cys Ser Ser Lys Thr Gln Leu Asn Val Lys Gly
        155                 160                 165 gta ttt gat gcg gca ata aag gtg gta ctg cag cca cca aag gca aag        641
Val Phe Asp Ala Ala Ile Lys Val Val Leu Gln Pro Pro Lys Ala Lys
    170                 175                 180 aag aag aaa aag gcg cag agg ggg gct tgc tcc atc ttg tgatctaatc        690
Lys Lys Lys Lys Ala Gln Arg Gly Ala Cys Ser Ile Leu
185                 190                 195 aatcggtaga caaagaacaa gggcgaagtt gccgccatgc tatattattg ttacgtcttg        750
```

```
cttcagcgga gctgcactct catggtcgtn ctnccttccc tcaccccac cccaccctag        810 gttacccacc ggcagctgca acaaggtctc tttgtcgagg catcggg                    857
```

<210> SEQ ID NO 2
<211> LENGTH: 197
<212> TYPE: PRT
<213> ORGANISM: Hordeum vulgare

<400> SEQUENCE: 2

```
Met Ser Ala Ser Arg Phe Ile Lys Cys Val Thr Val Gly Asp Gly Ala
 1               5                  10                  15

Val Gly Lys Thr Cys Met Leu Ile Ser Tyr Thr Ser Asn Thr Phe Pro
            20                  25                  30

Thr Asp Tyr Val Pro Thr Val Phe Asp Asn Phe Ser Ala Asn Val Val
        35                  40                  45

Val Asp Gly Asn Thr Val Asn Leu Gly Leu Trp Asp Thr Ala Gly Gln
    50                  55                  60

Glu Asp Tyr Asn Arg Leu Arg Pro Leu Ser Tyr Arg Gly Ala Asp Val
 65                  70                  75                  80

Phe Leu Leu Ala Phe Ser Leu Ile Ser Lys Ala Ser Tyr Glu Asn Val
                85                  90                  95

Ser Lys Lys Trp Ile Pro Glu Leu Lys His Tyr Ala Pro Gly Val Pro
            100                 105                 110

Ile Ile Leu Val Gly Thr Lys Leu Asp Leu Arg Asp Asp Lys Gln Phe
        115                 120                 125

Phe Val Asp His Pro Gly Ala Val Pro Ile Thr Thr Ala Gln Gly Glu
    130                 135                 140

Glu Leu Lys Lys Leu Ile Gly Ala Pro Tyr Tyr Ile Glu Cys Ser Ser
145                 150                 155                 160

Lys Thr Gln Leu Asn Val Lys Gly Val Phe Asp Ala Ala Ile Lys Val
                165                 170                 175

Val Leu Gln Pro Pro Lys Ala Lys Lys Lys Lys Ala Gln Arg Gly
            180                 185                 190

Ala Cys Ser Ile Leu
        195
```

<210> SEQ ID NO 3
<211> LENGTH: 1113
<212> TYPE: DNA
<213> ORGANISM: Oryza sativa
<220> FEATURE:
<221> NAME/KEY: CDS
<222> LOCATION: (158)..(748)

<400> SEQUENCE: 3

```
ccttgctttg ctcctccttc aaccttcttc tttcttggag tttcttgaga gagagagaga        60
gagagagaga gagagagaga gagagagaga ggggggggag cggtcgcagg aggaggagga       120
cggcggcgtc tgctgcgacc gacggggagc ggcgagg atg agc gcg tcc agg ttc       175
                                         Met Ser Ala Ser Arg Phe
                                           1               5 ata aag tgc gtc acc gtc ggg gac ggc gcc gtc ggc aag acc tgc atg       223
Ile Lys Cys Val Thr Val Gly Asp Gly Ala Val Gly Lys Thr Cys Met
         10                  15                  20 ctc atc tcc tac acc tcc aac acc ttc ccc act gat tat gtt ccg acg       271
Leu Ile Ser Tyr Thr Ser Asn Thr Phe Pro Thr Asp Tyr Val Pro Thr
     25                  30                  35 gtg ttt gac aac ttc agt gcc aac gtc gtg gtt gat ggt aac acc gtc       319
```

```
Val Phe Asp Asn Phe Ser Ala Asn Val Val Asp Gly Asn Thr Val
     40                  45                  50 aac ctc ggg cta tgg gac act gca ggt cag gag gat tac aac aga ctg      367
Asn Leu Gly Leu Trp Asp Thr Ala Gly Gln Glu Asp Tyr Asn Arg Leu
 55                  60                  65                  70 aga cca ctg agt tat cgt gga gct gat gtt ttc ctt ctg gcc ttc tcg      415
Arg Pro Leu Ser Tyr Arg Gly Ala Asp Val Phe Leu Leu Ala Phe Ser
                 75                  80                  85 cta atc agc aag gcc agc tat gag aat gtt tca aag aag tgg ata cct      463
Leu Ile Ser Lys Ala Ser Tyr Glu Asn Val Ser Lys Lys Trp Ile Pro
             90                  95                 100 gag ctg aag cat tat gca cct ggt gtt cct atc atc ctt gtg gga aca      511
Glu Leu Lys His Tyr Ala Pro Gly Val Pro Ile Ile Leu Val Gly Thr
        105                 110                 115 aag ctt gat ctt cga gat gac aag cag ttt ttt gtg gac cat cct ggt      559
Lys Leu Asp Leu Arg Asp Asp Lys Gln Phe Phe Val Asp His Pro Gly
    120                 125                 130 gct gtt cct atc acc act gct cag gga gag gaa cta aga aag caa ata      607
Ala Val Pro Ile Thr Thr Ala Gln Gly Glu Glu Leu Arg Lys Gln Ile
135                 140                 145                 150 ggc gcc cca tac tac atc gaa tgc agc tca aag acc caa cta aac gtc      655
Gly Ala Pro Tyr Tyr Ile Glu Cys Ser Ser Lys Thr Gln Leu Asn Val
                155                 160                 165 aag ggc gtt ttc gat gcg gca ata aag gtg gtg ctg cag cca ccc aag      703
Lys Gly Val Phe Asp Ala Ala Ile Lys Val Val Leu Gln Pro Pro Lys
            170                 175                 180 gcg aag aag aag aaa aag gcg caa agg ggg gcg tgc tcc att ttg           748
Ala Lys Lys Lys Lys Lys Ala Gln Arg Gly Ala Cys Ser Ile Leu
        185                 190                 195 tgatctaatc atcagtagac gacgaagaag aagaacgatg aagttgccag gctttattat    808
tgttgcgtct tgcttcagcg aaacagcatt catggtccgg ggatcctagt ttactggcag    868
ctgcagcaag gcctctttgt cgaggcaatg agcgatccgt tgtttcatt ttctcctttc     928 tgccttgtga ttatctcgtg tgactgacaa gtcgtggcaa ttaggtaact ttcctagatg    988
gtatttcctg tgtttgagaa aaaaaattct tgttatccct gtttcataag tagacatgat   1048
gtaatcgcac tcagtttatt cttttccttc ttatttcact tcaatggaaa attatgtttc   1108
ccttc                                                                1113

<210> SEQ ID NO 4
<211> LENGTH: 197
<212> TYPE: PRT
<213> ORGANISM: Oryza sativa

<400> SEQUENCE: 4

Met Ser Ala Ser Arg Phe Ile Lys Cys Val Thr Val Gly Asp Gly Ala
  1               5                  10                  15

Val Gly Lys Thr Cys Met Leu Ile Ser Tyr Thr Ser Asn Thr Phe Pro
                 20                  25                  30

Thr Asp Tyr Val Pro Thr Val Phe Asp Asn Phe Ser Ala Asn Val Val
             35                  40                  45

Val Asp Gly Asn Thr Val Asn Leu Gly Leu Trp Asp Thr Ala Gly Gln
         50                  55                  60

Glu Asp Tyr Asn Arg Leu Arg Pro Leu Ser Tyr Arg Gly Ala Asp Val
 65                  70                  75                  80

Phe Leu Leu Ala Phe Ser Leu Ile Ser Lys Ala Ser Tyr Glu Asn Val
                 85                  90                  95
```

-continued

```
Ser Lys Lys Trp Ile Pro Glu Leu Lys His Tyr Ala Pro Gly Val Pro
            100                 105                 110

Ile Ile Leu Val Gly Thr Lys Leu Asp Leu Arg Asp Asp Lys Gln Phe
        115                 120                 125

Phe Val Asp His Pro Gly Ala Val Pro Ile Thr Thr Ala Gln Gly Glu
    130                 135                 140

Glu Leu Arg Lys Gln Ile Gly Ala Pro Tyr Tyr Ile Glu Cys Ser Ser
145                 150                 155                 160

Lys Thr Gln Leu Asn Val Lys Gly Val Phe Asp Ala Ala Ile Lys Val
                165                 170                 175

Val Leu Gln Pro Pro Lys Ala Lys Lys Lys Lys Ala Gln Arg Gly
            180                 185                 190

Ala Cys Ser Ile Leu
        195
```

<210> SEQ ID NO 5
<211> LENGTH: 1393
<212> TYPE: DNA
<213> ORGANISM: Zea mays
<220> FEATURE:
<221> NAME/KEY: CDS
<222> LOCATION: (398)..(988)

<400> SEQUENCE: 5

```
gtcgacccac gcgtccgcgg acgcgtgggc ggacgcgtgg gtccccaccc accaccgcgc      60
cgggccacca ccaccactc taccctcccc tccccaccac cactagcacc caccgtcccg     120
gcgcggagac cgcttccctc cctccgcctc cgcaaccctc tcccgcctcg cccgcgcctc     180
cctccatttg tccgcggctc ccctcccctcc cgatcttaac cacccgccac ccggcttcct     240
ctcccccttc ttcctccctc aaaccagacg ctcgcccccc tttcctccac gcctatcttc     300
ttcagacgac cagcaggagg tacgaggaag accacctagg aggcctctct ctctctctcc     360
ccagccaccc ccgtagcgag agggagggcg gaagagg atg agc gcg tcc agg ttc     415
                                         Met Ser Ala Ser Arg Phe
                                          1               5 ata aag tgc gtc acg gtc ggg gac ggc gcc gtc ggc aag acc tgc atg      463
Ile Lys Cys Val Thr Val Gly Asp Gly Ala Val Gly Lys Thr Cys Met
         10                  15                  20 ctc atc tcc tac acc tcc aac acc ttc ccc acc gac tat gtt ccg aca      511
Leu Ile Ser Tyr Thr Ser Asn Thr Phe Pro Thr Asp Tyr Val Pro Thr
     25                  30                  35 gtg ttt gat aac ttc agt gcc aac gtt gtg gtt gat ggt aat act gtc      559
Val Phe Asp Asn Phe Ser Ala Asn Val Val Val Asp Gly Asn Thr Val
 40                  45                  50 aac ctc ggc ctc tgg gac act gca ggt caa gag gat tac aac aga ctg      607
Asn Leu Gly Leu Trp Asp Thr Ala Gly Gln Glu Asp Tyr Asn Arg Leu
 55                  60                  65                  70 aga cca ctg agc tat cgt gga gct gat gtt ttt ctt ctg gct ttc tca      655
Arg Pro Leu Ser Tyr Arg Gly Ala Asp Val Phe Leu Leu Ala Phe Ser
                 75                  80                  85 ctg atc agt aag gcc agc tat gag aat gtt tcg aag aag tgg ata cct      703
Leu Ile Ser Lys Ala Ser Tyr Glu Asn Val Ser Lys Lys Trp Ile Pro
         90                  95                 100 gaa ctg aag cat tat gca cct ggt gtg cca att att ctc gta ggg aca      751
Glu Leu Lys His Tyr Ala Pro Gly Val Pro Ile Ile Leu Val Gly Thr
     105                 110                 115 aag ctt gat ctt cga gac gac aag cag ttc ttt gtg gac cat cct ggt      799
Lys Leu Asp Leu Arg Asp Asp Lys Gln Phe Phe Val Asp His Pro Gly
 120                 125                 130
```

```
gct gtc cct atc act act gct cag gga gag gag cta aga aag caa ata    847
Ala Val Pro Ile Thr Thr Ala Gln Gly Glu Glu Leu Arg Lys Gln Ile
135                 140                 145                 150 ggc gct cca tac tac atc gaa tgc agc tcg aag acc caa cta aac gtg    895
Gly Ala Pro Tyr Tyr Ile Glu Cys Ser Ser Lys Thr Gln Leu Asn Val
                155                 160                 165 aag ggc gtc ttc gat gcg gcg ata aag gtt gtg ctg cag ccg cct aag    943
Lys Gly Val Phe Asp Ala Ala Ile Lys Val Val Leu Gln Pro Pro Lys
            170                 175                 180 gcg aag aag aag aaa aag gtg cag agg ggg gcg tgc tcc att ttg        988
Ala Lys Lys Lys Lys Lys Val Gln Arg Gly Ala Cys Ser Ile Leu
185                 190                 195 tgatctaatc atcggtagat gaagaaacaa gggcgaaggt gccatggctt tatcatcgtc  1048
gcgtcttgct tcagtggaac agcatgaatg gtccccaccc cctctaggtt tactggcggc  1108
tcggctgcag cgagttctca tctctttgtc gaggcattga gcgatatgtt tgtttcattt  1168
tcctccttcc tgccttgtga ttatctggtg tgtgtgtgtg tgtgactgac gaagtcgcgg  1228
cgattaggta actcgcttag aaggtatttc ccgtgtttga gcaaaagaaa gtatccctgt  1288
tatctctgtt ccataagtta gacatgatgt aatcgtacta agtttatttt tacttatttc  1348
acttgaatgg aaaagtatgc ttcccattta aaaaaaaaaa aaaaa                 1393

<210> SEQ ID NO 6
<211> LENGTH: 197
<212> TYPE: PRT
<213> ORGANISM: Zea mays

<400> SEQUENCE: 6

Met Ser Ala Ser Arg Phe Ile Lys Cys Val Thr Val Gly Asp Gly Ala
1               5                   10                  15

Val Gly Lys Thr Cys Met Leu Ile Ser Tyr Thr Ser Asn Thr Phe Pro
                20                  25                  30

Thr Asp Tyr Val Pro Thr Val Phe Asp Asn Phe Ser Ala Asn Val Val
            35                  40                  45

Val Asp Gly Asn Thr Val Asn Leu Gly Leu Trp Asp Thr Ala Gly Gln
        50                  55                  60

Glu Asp Tyr Asn Arg Leu Arg Pro Leu Ser Tyr Arg Gly Ala Asp Val
65                  70                  75                  80

Phe Leu Leu Ala Phe Ser Leu Ile Ser Lys Ala Ser Tyr Glu Asn Val
                85                  90                  95

Ser Lys Lys Trp Ile Pro Glu Leu Lys His Tyr Ala Pro Gly Val Pro
                100                 105                 110

Ile Ile Leu Val Gly Thr Lys Leu Asp Leu Arg Asp Asp Lys Gln Phe
            115                 120                 125

Phe Val Asp His Pro Gly Ala Val Pro Ile Thr Thr Ala Gln Gly Glu
        130                 135                 140

Glu Leu Arg Lys Gln Ile Gly Ala Pro Tyr Tyr Ile Glu Cys Ser Ser
145                 150                 155                 160

Lys Thr Gln Leu Asn Val Lys Gly Val Phe Asp Ala Ala Ile Lys Val
                165                 170                 175

Val Leu Gln Pro Pro Lys Ala Lys Lys Lys Lys Val Gln Arg Gly
                180                 185                 190

Ala Cys Ser Ile Leu
        195
```

<210> SEQ ID NO 7
<211> LENGTH: 197
<212> TYPE: PRT
<213> ORGANISM: Artificial sequence
<220> FEATURE:
<223> OTHER INFORMATION: Description of the artificial sequence: dominant-negative mutant of barley RacB protein
<220> FEATURE:
<221> NAME/KEY: SITE
<222> LOCATION: (20)
<223> OTHER INFORMATION: Thr/Asn mutation for dominant-negative phenotype

<400> SEQUENCE: 7

```
Met Ser Ala Ser Arg Phe Ile Lys Cys Val Thr Val Gly Asp Gly Ala
 1               5                  10                  15

Val Gly Lys Asn Cys Met Leu Ile Ser Tyr Thr Ser Asn Thr Phe Pro
            20                  25                  30

Thr Asp Tyr Val Pro Thr Val Phe Asp Asn Phe Ser Ala Asn Val Val
        35                  40                  45

Val Asp Gly Asn Thr Val Asn Leu Gly Leu Trp Asp Thr Ala Gly Gln
    50                  55                  60

Glu Asp Tyr Asn Arg Leu Arg Pro Leu Ser Tyr Arg Gly Ala Asp Val
65                  70                  75                  80

Phe Leu Leu Ala Phe Ser Leu Ile Ser Lys Ala Ser Tyr Glu Asn Val
                85                  90                  95

Ser Lys Lys Trp Ile Pro Glu Leu Lys His Tyr Ala Pro Gly Val Pro
            100                 105                 110

Ile Ile Leu Val Gly Thr Lys Leu Asp Leu Arg Asp Asp Lys Gln Phe
        115                 120                 125

Phe Val Asp His Pro Gly Ala Val Pro Ile Thr Thr Ala Gln Gly Glu
    130                 135                 140

Glu Leu Lys Lys Leu Ile Gly Ala Pro Tyr Tyr Ile Glu Cys Ser Ser
145                 150                 155                 160

Lys Thr Gln Leu Asn Val Lys Gly Val Phe Asp Ala Ala Ile Lys Val
                165                 170                 175

Val Leu Gln Pro Pro Lys Ala Lys Lys Lys Lys Ala Gln Arg Gly
            180                 185                 190

Ala Cys Ser Ile Leu
        195
```

<210> SEQ ID NO 8
<211> LENGTH: 197
<212> TYPE: PRT
<213> ORGANISM: Artificial sequence
<220> FEATURE:
<223> OTHER INFORMATION: Description of the artificial sequence: : dominant-negative mutant of rice RacB protein
<220> FEATURE:
<221> NAME/KEY: SITE
<222> LOCATION: (20)
<223> OTHER INFORMATION: Thr/Asn mutation for dominant-negative phenotype

<400> SEQUENCE: 8

```
Met Ser Ala Ser Arg Phe Ile Lys Cys Val Thr Val Gly Asp Gly Ala
 1               5                  10                  15

Val Gly Lys Asn Cys Met Leu Ile Ser Tyr Thr Ser Asn Thr Phe Pro
            20                  25                  30

Thr Asp Tyr Val Pro Thr Val Phe Asp Asn Phe Ser Ala Asn Val Val
        35                  40                  45
```

```
Val Asp Gly Asn Thr Val Asn Leu Gly Leu Trp Asp Thr Ala Gly Gln
    50                  55                  60

Glu Asp Tyr Asn Arg Leu Arg Pro Leu Ser Tyr Arg Gly Ala Asp Val
 65                  70                  75                  80

Phe Leu Leu Ala Phe Ser Leu Ile Ser Lys Ala Ser Tyr Glu Asn Val
                 85                  90                  95

Ser Lys Lys Trp Ile Pro Glu Leu Lys His Tyr Ala Pro Gly Val Pro
                100                 105                 110

Ile Ile Leu Val Gly Thr Lys Leu Asp Leu Arg Asp Asp Lys Gln Phe
                115                 120                 125

Phe Val Asp His Pro Gly Ala Val Pro Ile Thr Thr Ala Gln Gly Glu
                130                 135                 140

Glu Leu Arg Lys Gln Ile Gly Ala Pro Tyr Tyr Ile Glu Cys Ser Ser
145                 150                 155                 160

Lys Thr Gln Leu Asn Val Lys Gly Val Phe Asp Ala Ala Ile Lys Val
                165                 170                 175

Val Leu Gln Pro Pro Lys Ala Lys Lys Lys Lys Ala Gln Arg Gly
                180                 185                 190

Ala Cys Ser Ile Leu
        195

<210> SEQ ID NO 9
<211> LENGTH: 197
<212> TYPE: PRT
<213> ORGANISM: Artificial sequence
<220> FEATURE:
<221> NAME/KEY: SITE
<222> LOCATION: (20)
<223> OTHER INFORMATION: Thr/Asn mutation for dominant-negative
      phenotype
<220> FEATURE:
<223> OTHER INFORMATION: Description of the artificial sequence:
      dominant-negative mutant of maize RacB protein

<400> SEQUENCE: 9

Met Ser Ala Ser Arg Phe Ile Lys Cys Val Thr Val Gly Asp Gly Ala
  1               5                  10                  15

Val Gly Lys Asn Cys Met Leu Ile Ser Tyr Thr Ser Asn Thr Phe Pro
                 20                  25                  30

Thr Asp Tyr Val Pro Thr Val Phe Asp Asn Phe Ser Ala Asn Val Val
                 35                  40                  45

Val Asp Gly Asn Thr Val Asn Leu Gly Leu Trp Asp Thr Ala Gly Gln
    50                  55                  60

Glu Asp Tyr Asn Arg Leu Arg Pro Leu Ser Tyr Arg Gly Ala Asp Val
 65                  70                  75                  80

Phe Leu Leu Ala Phe Ser Leu Ile Ser Lys Ala Ser Tyr Glu Asn Val
                 85                  90                  95

Ser Lys Lys Trp Ile Pro Glu Leu Lys His Tyr Ala Pro Gly Val Pro
                100                 105                 110

Ile Ile Leu Val Gly Thr Lys Leu Asp Leu Arg Asp Asp Lys Gln Phe
                115                 120                 125

Phe Val Asp His Pro Gly Ala Val Pro Ile Thr Thr Ala Gln Gly Glu
                130                 135                 140

Glu Leu Arg Lys Gln Ile Gly Ala Pro Tyr Tyr Ile Glu Cys Ser Ser
145                 150                 155                 160

Lys Thr Gln Leu Asn Val Lys Gly Val Phe Asp Ala Ala Ile Lys Val
                165                 170                 175
```

```
Val Leu Gln Pro Pro Lys Ala Lys Lys Lys Lys Val Gln Arg Gly
        180                 185                 190

Ala Cys Ser Ile Leu
        195

<210> SEQ ID NO 10
<211> LENGTH: 24
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 10
ggatccgatg agcgcgtcca ggtt                                              24

<210> SEQ ID NO 11
<211> LENGTH: 26
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 11
gtcgaccttc gcccttgttc tttgtc                                            26

<210> SEQ ID NO 12
<211> LENGTH: 26
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 12
gtgggcacat agtcggtggg gaaggt                                            26

<210> SEQ ID NO 13
<211> LENGTH: 23
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 13
cgactggagc acgaggacac tga                                               23

<210> SEQ ID NO 14
<211> LENGTH: 26
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 14
ggacactgac atggactgaa ggagta                                            26

<210> SEQ ID NO 15
<211> LENGTH: 22
<212> TYPE: DNA
<213> ORGANISM: Artificial sequence
<220> FEATURE:
<223> OTHER INFORMATION: Description of the artificial sequence:
      oligonucleotide primer
```

<400> SEQUENCE: 15
gttcatcaag tgcgtcaccg tg                                22

<210> SEQ ID NO 16
<211> LENGTH: 23
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 16
ttagcttcct cagttcttcc ctg                               23

<210> SEQ ID NO 17
<211> LENGTH: 21
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 17
cgcgccgcag ccgagtacga c                                 21

<210> SEQ ID NO 18
<211> LENGTH: 21
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 18
gtcacaaaaa cacatgtaac c                                 21

<210> SEQ ID NO 19
<211> LENGTH: 20
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 19
ggccgacatg cattcaccag                                   20

<210> SEQ ID NO 20
<211> LENGTH: 21
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 20
catctgatat tgctgggtct g                                 21

<210> SEQ ID NO 21
<211> LENGTH: 21
<212> TYPE: DNA
<213> ORGANISM: Artificial sequence
<220> FEATURE:
<223> OTHER INFORMATION: Description of the artificial sequence:
      oligonucleotide primer

```
<400> SEQUENCE: 21
ccaagatgca gatcttcgtg a                                               21

<210> SEQ ID NO 22
<211> LENGTH: 21
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 22
ttcgcgatag gtaaaagagc a                                               21

<210> SEQ ID NO 23
<211> LENGTH: 18
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 23
gtaaaacgac ggccagtg                                                   18

<210> SEQ ID NO 24
<211> LENGTH: 19
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 24
ggaaacagct atgaccatg                                                  19

<210> SEQ ID NO 25
<211> LENGTH: 17
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 25
gtggaggcgc ggcgaga                                                    17

<210> SEQ ID NO 26
<211> LENGTH: 22
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 26
ccatgcttca tctccatagt ca                                              22

<210> SEQ ID NO 27
<211> LENGTH: 26
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 27
```
ggatcccgat tccatcagga aagcat                                    26

<210> SEQ ID NO 28
<211> LENGTH: 26
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 28
gtcgacgcga gacactgcaa aacaaa                                    26

<210> SEQ ID NO 29
<211> LENGTH: 26
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 29
ggatccttct cgtccattta gccggc                                    26

<210> SEQ ID NO 30
<211> LENGTH: 27
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 30
gtcgactgat cacttgaagc atgccag                                   27

<210> SEQ ID NO 31
<211> LENGTH: 24
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 31
ggatccgatg agcgcgtcca ggtt                                      24

<210> SEQ ID NO 32
<211> LENGTH: 26
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 32
gtcgaccttc gcccttgttc tttgtc                                    26

<210> SEQ ID NO 33
<211> LENGTH: 29
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 33

```
accgtggggg acgtcgccgt cggcaagac                                            29

<210> SEQ ID NO 34
<211> LENGTH: 721
<212> TYPE: DNA
<213> ORGANISM: Hordeum vulgare
<220> FEATURE:
<221> NAME/KEY: CDS
<222> LOCATION: (38)..(673)
<223> OTHER INFORMATION: coding for RacB homologue (Rop6)

<400> SEQUENCE: 34
gtggaggcgc ggcgagagcg gcggaggcgg aggagag atg agc gtg acc aag ttc      55
                                         Met Ser Val Thr Lys Phe
                                           1               5 atc aag tgc gtc acg gtg ggg gac ggc gcc gtc ggc aag acc tgc atg     103
Ile Lys Cys Val Thr Val Gly Asp Gly Ala Val Gly Lys Thr Cys Met
         10                  15                  20 ctc atc tgc tac acc agc aac agg ttc ccc agt gat tac atc ccc acg     151
Leu Ile Cys Tyr Thr Ser Asn Arg Phe Pro Ser Asp Tyr Ile Pro Thr
     25                  30                  35 gtg ttc gac aac ttc agc gcc aac gtc tcc gtc gac ggc aac atc gtc     199
Val Phe Asp Asn Phe Ser Ala Asn Val Ser Val Asp Gly Asn Ile Val
 40                  45                  50 aac ctc ggc cta tgg gac acc gcc ggg caa gaa gac tac agc cgg ctg     247
Asn Leu Gly Leu Trp Asp Thr Ala Gly Gln Glu Asp Tyr Ser Arg Leu
 55                  60                  65                  70 agg ccg ctg agc tac aga ggc gcc gac gtg ttc gtg ctc gcc ttc tcc     295
Arg Pro Leu Ser Tyr Arg Gly Ala Asp Val Phe Val Leu Ala Phe Ser
                 75                  80                  85 ctc atc agc agc gcc agc tac gag aat gtt ctt aag aag tgg atg cca     343
Leu Ile Ser Ser Ala Ser Tyr Glu Asn Val Leu Lys Lys Trp Met Pro
             90                  95                 100 gag ctc cgc cgg ttc gcg ccg aat gtc ccc att gtt ctt gtt ggg acc     391
Glu Leu Arg Arg Phe Ala Pro Asn Val Pro Ile Val Leu Val Gly Thr
         105                 110                 115 aag cta gat ctg cgt gac cac aga gcc tac ctc gcc gac cac ccc ggt     439
Lys Leu Asp Leu Arg Asp His Arg Ala Tyr Leu Ala Asp His Pro Gly
     120                 125                 130 gct tca gca atc aca act gca cag ggt gaa gaa ctt agg aag cag atc     487
Ala Ser Ala Ile Thr Thr Ala Gln Gly Glu Glu Leu Arg Lys Gln Ile
135                 140                 145                 150 ggc gcc gcg gct tac atc gag tgc agc tcc aag aca cag cag aac gtc     535
Gly Ala Ala Ala Tyr Ile Glu Cys Ser Ser Lys Thr Gln Gln Asn Val
                155                 160                 165 aag gct gtg ttt gac acc gcc ata aag gtg gtc ctc cag ccg ccg agg     583
Lys Ala Val Phe Asp Thr Ala Ile Lys Val Val Leu Gln Pro Pro Arg
            170                 175                 180 aga agg gag gtg atg tcc gcc agg aag aaa acc agg cga agc tct gga     631
Arg Arg Glu Val Met Ser Ala Arg Lys Lys Thr Arg Arg Ser Ser Gly
        185                 190                 195 tgc tcc atc aag cac ttg atc tgc ggg agt acg tgc gct gct             673
Cys Ser Ile Lys His Leu Ile Cys Gly Ser Thr Cys Ala Ala
    200                 205                 210 tgaattagca ccatggaggc ctggactgac tatggagatg aagcatgg                721

<210> SEQ ID NO 35
<211> LENGTH: 212
<212> TYPE: PRT
<213> ORGANISM: Hordeum vulgare

<400> SEQUENCE: 35
```

```
Met Ser Val Thr Lys Phe Ile Lys Cys Val Thr Val Gly Asp Gly Ala
  1               5                  10                  15

Val Gly Lys Thr Cys Met Leu Ile Cys Tyr Thr Ser Asn Arg Phe Pro
             20                  25                  30

Ser Asp Tyr Ile Pro Thr Val Phe Asp Asn Phe Ser Ala Asn Val Ser
         35                  40                  45

Val Asp Gly Asn Ile Val Asn Leu Gly Leu Trp Asp Thr Ala Gly Gln
     50                  55                  60

Glu Asp Tyr Ser Arg Leu Arg Pro Leu Ser Tyr Arg Gly Ala Asp Val
 65                  70                  75                  80

Phe Val Leu Ala Phe Ser Leu Ile Ser Ser Ala Ser Tyr Glu Asn Val
             85                  90                  95

Leu Lys Lys Trp Met Pro Glu Leu Arg Arg Phe Ala Pro Asn Val Pro
            100                 105                 110

Ile Val Leu Val Gly Thr Lys Leu Asp Leu Arg Asp His Arg Ala Tyr
            115                 120                 125

Leu Ala Asp His Pro Gly Ala Ser Ala Ile Thr Thr Ala Gln Gly Glu
        130                 135                 140

Glu Leu Arg Lys Gln Ile Gly Ala Ala Tyr Ile Glu Cys Ser Ser
145                 150                 155                 160

Lys Thr Gln Gln Asn Val Lys Ala Val Phe Asp Thr Ala Ile Lys Val
                165                 170                 175

Val Leu Gln Pro Pro Arg Arg Arg Glu Val Met Ser Ala Arg Lys Lys
            180                 185                 190

Thr Arg Arg Ser Ser Gly Cys Ser Ile Lys His Leu Ile Cys Gly Ser
        195                 200                 205

Thr Cys Ala Ala
        210
```

<210> SEQ ID NO 36
<211> LENGTH: 699
<212> TYPE: DNA
<213> ORGANISM: Hordeum vulgare
<220> FEATURE:
<221> NAME/KEY: CDS
<222> LOCATION: (67)..(657)
<223> OTHER INFORMATION: coding for RacB homologue (RacD)
<220> FEATURE:
<221> NAME/KEY: misc_feature
<222> LOCATION: (55)
<223> OTHER INFORMATION: n is a, c, g or t

<400> SEQUENCE: 36

```
ggatcccgat tccatcagga aagcatatag actagcccag taaatagaaa taagnaaaga      60 tcggcg atg agc gca tct cgg ttc atc aag tgc gtg acg gtg ggg gac       108
       Met Ser Ala Ser Arg Phe Ile Lys Cys Val Thr Val Gly Asp
         1               5                  10 ggc gcc gtg gga aag aca tgc ctc ctc atc tca tac aca tcc aac acc      156
Gly Ala Val Gly Lys Thr Cys Leu Leu Ile Ser Tyr Thr Ser Asn Thr
 15                  20                  25                  30 ttc ccc aca gac tat gtc cca aca gtt ttc gac aac ttc agc gct aac      204
Phe Pro Thr Asp Tyr Val Pro Thr Val Phe Asp Asn Phe Ser Ala Asn
                 35                  40                  45 gtc gtg gtt gac ggc agc acc gtc aac ctc gga tta tgg gat act gca      252
Val Val Val Asp Gly Ser Thr Val Asn Leu Gly Leu Trp Asp Thr Ala
             50                  55                  60 gga caa gaa gac tat aat cga cta cgc cca cta agc tac cgt ggt gcc      300
Gly Gln Glu Asp Tyr Asn Arg Leu Arg Pro Leu Ser Tyr Arg Gly Ala
```

```
                    65                  70                  75
gat gtc ttc ctg ctc gcc ttt tct ctc atc agc aaa gca agc tac gag      348
Asp Val Phe Leu Leu Ala Phe Ser Leu Ile Ser Lys Ala Ser Tyr Glu
    80                  85                  90 aat gtc act aag aag tgg att cca gag tta cgg cac tat gct cct ggc      396
Asn Val Thr Lys Lys Trp Ile Pro Glu Leu Arg His Tyr Ala Pro Gly
 95                 100                 105                 110 gtg ccc ata att ctt gtt gga aca aag ctt gat ctg cgg gat gac aag      444
Val Pro Ile Ile Leu Val Gly Thr Lys Leu Asp Leu Arg Asp Asp Lys
                115                 120                 125 cag ttt ttt gtg gat cac cct ggg gcg gtt cct att tcc act gct cag      492
Gln Phe Phe Val Asp His Pro Gly Ala Val Pro Ile Ser Thr Ala Gln
            130                 135                 140 ggt gaa gag ctg aag aag gtg att ggc gcg act gcc tac atc gag tgc      540
Gly Glu Glu Leu Lys Lys Val Ile Gly Ala Thr Ala Tyr Ile Glu Cys
        145                 150                 155 agc tca aaa aca cag cag aac atc aag gcg gtg ttt gat gcg gcg atc      588
Ser Ser Lys Thr Gln Gln Asn Ile Lys Ala Val Phe Asp Ala Ala Ile
    160                 165                 170 aag gtg gtc ctc cag cct ccg aag cag aag cgg aag aag agg aag tca      636
Lys Val Val Leu Gln Pro Pro Lys Gln Lys Arg Lys Lys Arg Lys Ser
175                 180                 185                 190 cag aaa gga tgc agc atc ttg taaagctaaa atccctttg ttttgcagtg          687
Gln Lys Gly Cys Ser Ile Leu
                195 tctcgcgtcg ac                                                        699

<210> SEQ ID NO 37
<211> LENGTH: 197
<212> TYPE: PRT
<213> ORGANISM: Hordeum vulgare

<400> SEQUENCE: 37

Met Ser Ala Ser Arg Phe Ile Lys Cys Val Thr Val Gly Asp Gly Ala
 1               5                  10                  15

Val Gly Lys Thr Cys Leu Leu Ile Ser Tyr Thr Ser Asn Thr Phe Pro
            20                  25                  30

Thr Asp Tyr Val Pro Thr Val Phe Asp Asn Phe Ser Ala Asn Val Val
        35                  40                  45

Val Asp Gly Ser Thr Val Asn Leu Gly Leu Trp Asp Thr Ala Gly Gln
    50                  55                  60

Glu Asp Tyr Asn Arg Leu Arg Pro Leu Ser Tyr Arg Gly Ala Asp Val
 65                 70                  75                  80

Phe Leu Leu Ala Phe Ser Leu Ile Ser Lys Ala Ser Tyr Glu Asn Val
                85                  90                  95

Thr Lys Lys Trp Ile Pro Glu Leu Arg His Tyr Ala Pro Gly Val Pro
            100                 105                 110

Ile Ile Leu Val Gly Thr Lys Leu Asp Leu Arg Asp Asp Lys Gln Phe
        115                 120                 125

Phe Val Asp His Pro Gly Ala Val Pro Ile Ser Thr Ala Gln Gly Glu
    130                 135                 140

Glu Leu Lys Lys Val Ile Gly Ala Thr Ala Tyr Ile Glu Cys Ser Ser
145                 150                 155                 160

Lys Thr Gln Gln Asn Ile Lys Ala Val Phe Asp Ala Ala Ile Lys Val
                165                 170                 175

Val Leu Gln Pro Pro Lys Gln Lys Arg Lys Lys Arg Lys Ser Gln Lys
            180                 185                 190
```

```
Gly Cys Ser Ile Leu
        195

<210> SEQ ID NO 38
<211> LENGTH: 677
<212> TYPE: DNA
<213> ORGANISM: Hordeum vulgare
<220> FEATURE:
<221> NAME/KEY: CDS
<222> LOCATION: (27)..(665)
<223> OTHER INFORMATION: coding for RacB homologue (Rop4)

<400> SEQUENCE: 38
ggatccttct cgtccattta gccggc atg gcg tcc agc gcc tcc cgg ttc atc        53
                              Met Ala Ser Ser Ala Ser Arg Phe Ile
                                1               5 aag tgc gtc acc gtc ggg gac ggc gcc gtc ggc aag acc tgc atg ctc       101
Lys Cys Val Thr Val Gly Asp Gly Ala Val Gly Lys Thr Cys Met Leu
 10                  15                  20                  25 atc tgc tac acc agc aac aag ttc ccc acc gac tac gtg ccc acc gtg       149
Ile Cys Tyr Thr Ser Asn Lys Phe Pro Thr Asp Tyr Val Pro Thr Val
                 30                  35                  40 ttc gac aat ttc agc gcg aac gtg gtg gtg gac ggc acc acc gtg aac       197
Phe Asp Asn Phe Ser Ala Asn Val Val Val Asp Gly Thr Thr Val Asn
             45                  50                  55 ctg ggc ctc tgg gac act gca ggg cag gag gac tac aac aga ttg aga       245
Leu Gly Leu Trp Asp Thr Ala Gly Gln Glu Asp Tyr Asn Arg Leu Arg
         60                  65                  70 ccg ctg agc tac cgg gga gcc gac gtc ttc gtg ctc tcc ttc tcg ctc       293
Pro Leu Ser Tyr Arg Gly Ala Asp Val Phe Val Leu Ser Phe Ser Leu
     75                  80                  85 gtc agc cga gcc agc tac gag aat gtc atg aag aag tgg cta ccg gag       341
Val Ser Arg Ala Ser Tyr Glu Asn Val Met Lys Lys Trp Leu Pro Glu
 90                  95                 100                 105 ctt cag cac cat gca ccc ggc gtg cca aca gtg ctg gtt ggt aca aag       389
Leu Gln His His Ala Pro Gly Val Pro Thr Val Leu Val Gly Thr Lys
                110                 115                 120 cta gat cta cgt gaa gac aag caa tac tta ctt gac cac ccc ggc gtg       437
Leu Asp Leu Arg Glu Asp Lys Gln Tyr Leu Leu Asp His Pro Gly Val
            125                 130                 135 gtg cct gtt act aca gct cag ggg gag gaa ctc cgc aag cac atc ggt       485
Val Pro Val Thr Thr Ala Gln Gly Glu Glu Leu Arg Lys His Ile Gly
        140                 145                 150 gca act tgt tat gtc gaa tgc agc tca aag aca cag cag aat gtc aaa       533
Ala Thr Cys Tyr Val Glu Cys Ser Ser Lys Thr Gln Gln Asn Val Lys
155                 160                 165 gct gtg ttt gat gct gcc atc aag gta gtg atc aaa cct cca aca aag       581
Ala Val Phe Asp Ala Ala Ile Lys Val Val Ile Lys Pro Pro Thr Lys
170                 175                 180                 185 cag agg gaa agg agg aag aag aaa gca cgg caa gga tgt gca tca ttg       629
Gln Arg Glu Arg Arg Lys Lys Lys Ala Arg Gln Gly Cys Ala Ser Leu
                190                 195                 200 ggt acc ctg tca aga agg aag ctg gca tgc ttc aag tgatcagtcg ac         677
Gly Thr Leu Ser Arg Arg Lys Leu Ala Cys Phe Lys
            205                 210

<210> SEQ ID NO 39
<211> LENGTH: 213
<212> TYPE: PRT
<213> ORGANISM: Hordeum vulgare

<400> SEQUENCE: 39
```

```
Met Ala Ser Ser Ala Ser Arg Phe Ile Lys Cys Val Thr Val Gly Asp
 1               5                  10                  15

Gly Ala Val Gly Lys Thr Cys Met Leu Ile Cys Tyr Thr Ser Asn Lys
                20                  25                  30

Phe Pro Thr Asp Tyr Val Pro Thr Val Phe Asp Asn Phe Ser Ala Asn
                35                  40                  45

Val Val Val Asp Gly Thr Thr Val Asn Leu Gly Leu Trp Asp Thr Ala
        50                  55                  60

Gly Gln Glu Asp Tyr Asn Arg Leu Arg Pro Leu Ser Tyr Arg Gly Ala
 65                 70                  75                  80

Asp Val Phe Val Leu Ser Phe Ser Leu Val Ser Arg Ala Ser Tyr Glu
                85                  90                  95

Asn Val Met Lys Lys Trp Leu Pro Glu Leu Gln His His Ala Pro Gly
                100                 105                 110

Val Pro Thr Val Leu Val Gly Thr Lys Leu Asp Leu Arg Glu Asp Lys
                115                 120                 125

Gln Tyr Leu Leu Asp His Pro Gly Val Val Pro Val Thr Thr Ala Gln
130                 135                 140

Gly Glu Glu Leu Arg Lys His Ile Gly Ala Thr Cys Tyr Val Glu Cys
145                 150                 155                 160

Ser Ser Lys Thr Gln Gln Asn Val Lys Ala Val Phe Asp Ala Ala Ile
                165                 170                 175

Lys Val Val Ile Lys Pro Pro Thr Lys Gln Arg Glu Arg Arg Lys Lys
                180                 185                 190

Lys Ala Arg Gln Gly Cys Ala Ser Leu Gly Thr Leu Ser Arg Arg Lys
                195                 200                 205

Leu Ala Cys Phe Lys
        210

<210> SEQ ID NO 40
<211> LENGTH: 945
<212> TYPE: DNA
<213> ORGANISM: Zea mays
<220> FEATURE:
<221> NAME/KEY: CDS
<222> LOCATION: (37)..(672)
<223> OTHER INFORMATION: coding for RacB homologue (Rop6)

<400> SEQUENCE: 40
gagaagaagg gggcctgccg gccggggctg ggagac atg agc gtg acc aag ttc       54
                                        Met Ser Val Thr Lys Phe
                                         1               5 atc aag tgc gtc acg gtg ggc gac ggc gcg gtg ggc aag acc tgc atg      102
Ile Lys Cys Val Thr Val Gly Asp Gly Ala Val Gly Lys Thr Cys Met
         10                  15                  20 ctc atc tgc tac acc agc aac aag ttc ccc acg gac tac atc ccc acg      150
Leu Ile Cys Tyr Thr Ser Asn Lys Phe Pro Thr Asp Tyr Ile Pro Thr
     25                  30                  35 gtg ttc gac aac ttc agc gcc aac gtc tcc gtg gac ggc agc atc gtc      198
Val Phe Asp Asn Phe Ser Ala Asn Val Ser Val Asp Gly Ser Ile Val
 40                  45                  50 aac ctg ggc ctc tgg gac acc gcg ggg caa gag gac tac agc agg ctg      246
Asn Leu Gly Leu Trp Asp Thr Ala Gly Gln Glu Asp Tyr Ser Arg Leu
 55                  60                  65                  70 cgg ccg ctg agc tac agg ggc gcg gac gtg ttc gtg ctg gcc ttc tcc      294
Arg Pro Leu Ser Tyr Arg Gly Ala Asp Val Phe Val Leu Ala Phe Ser
                 75                  80                  85
```

```
ctg atc agc agg gcg agc tac gag aac gtt ctt aag aag tgg gtg cca        342
Leu Ile Ser Arg Ala Ser Tyr Glu Asn Val Leu Lys Lys Trp Val Pro
             90                  95                 100 gag ctt cgc aga ttc gcg ccc aac gtc ccg gtc gtt ctt gtt ggg acc        390
Glu Leu Arg Arg Phe Ala Pro Asn Val Pro Val Val Leu Val Gly Thr
        105                 110                 115 aag tta gat ctc cgc gac cac aga gcc tac ctc gcc gac cat cct gga        438
Lys Leu Asp Leu Arg Asp His Arg Ala Tyr Leu Ala Asp His Pro Gly
    120                 125                 130 gct tca gca gtc acc acg gcg cag ggt gag gaa ctg agg aag cag atc        486
Ala Ser Ala Val Thr Thr Ala Gln Gly Glu Glu Leu Arg Lys Gln Ile
135                 140                 145                 150 ggc gct gcg gcc tac atc gag tgc agt tcc aaa acc cag cag aac gtc        534
Gly Ala Ala Ala Tyr Ile Glu Cys Ser Ser Lys Thr Gln Gln Asn Val
                155                 160                 165 aag tct gtc ttc gat acg gcc atc aaa gtg gtc ctt cag ccc cca cgg        582
Lys Ser Val Phe Asp Thr Ala Ile Lys Val Val Leu Gln Pro Pro Arg
            170                 175                 180 agg agg gag gca gtg cct gcc agg aag aag aac agg cgt ggc tcc gga        630
Arg Arg Glu Ala Val Pro Ala Arg Lys Lys Asn Arg Arg Gly Ser Gly
        185                 190                 195 tgc tct ata atg aac ctt gtg tgt ggc agc aca tgt gct gct                672
Cys Ser Ile Met Asn Leu Val Cys Gly Ser Thr Cys Ala Ala
    200                 205                 210 tagggagtct actagaacac tgaaccggaa gggaggtgaa ggcgtgattc atggtgtgta      732
atgtgctgtg gcaactggca agttagtttg ctatagatga ggatgactgc tgcttttgtt      792
ttccttggcc catctgctgt agttcgtcag gctcttcaag ggctgacttt ttaccagact      852
gcagtgttgt gtaagaagtt tgctagacgc tgtaactgta atgttctccg ctgatgtggt      912
ataactaaga tacgagtaag cttgagcgtg ttc                                   945

<210> SEQ ID NO 41
<211> LENGTH: 212
<212> TYPE: PRT
<213> ORGANISM: Zea mays

<400> SEQUENCE: 41

Met Ser Val Thr Lys Phe Ile Lys Cys Val Thr Val Gly Asp Gly Ala
1               5                   10                  15

Val Gly Lys Thr Cys Met Leu Ile Cys Tyr Thr Ser Asn Lys Phe Pro
            20                  25                  30

Thr Asp Tyr Ile Pro Thr Val Phe Asp Asn Phe Ser Ala Asn Val Ser
        35                  40                  45

Val Asp Gly Ser Ile Val Asn Leu Gly Leu Trp Asp Thr Ala Gly Gln
    50                  55                  60

Glu Asp Tyr Ser Arg Leu Arg Pro Leu Ser Tyr Arg Gly Ala Asp Val
65                  70                  75                  80

Phe Val Leu Ala Phe Ser Leu Ile Ser Arg Ala Ser Tyr Glu Asn Val
                85                  90                  95

Leu Lys Lys Trp Val Pro Glu Leu Arg Arg Phe Ala Pro Asn Val Pro
            100                 105                 110

Val Val Leu Val Gly Thr Lys Leu Asp Leu Arg Asp His Arg Ala Tyr
        115                 120                 125

Leu Ala Asp His Pro Gly Ala Ser Ala Val Thr Thr Ala Gln Gly Glu
    130                 135                 140

Glu Leu Arg Lys Gln Ile Gly Ala Ala Ala Tyr Ile Glu Cys Ser Ser
145                 150                 155                 160
```

```
Lys Thr Gln Gln Asn Val Lys Ser Val Phe Asp Thr Ala Ile Lys Val
                165                 170                 175

Val Leu Gln Pro Pro Arg Arg Arg Glu Ala Val Pro Ala Arg Lys Lys
            180                 185                 190

Asn Arg Arg Gly Ser Gly Cys Ser Ile Met Asn Leu Val Cys Gly Ser
        195                 200                 205

Thr Cys Ala Ala
    210

<210> SEQ ID NO 42
<211> LENGTH: 850
<212> TYPE: DNA
<213> ORGANISM: Oryza sativa
<220> FEATURE:
<221> NAME/KEY: CDS
<222> LOCATION: (112)..(702)
<223> OTHER INFORMATION: coding for RacB homologue    (RACDP / RACD)

<400> SEQUENCE: 42
agcaagcagc agctgaggtg aggtccgtgg cgttggagtg aggactgagg aggaagaaga      60
gggcgggatc tagggtaccg gatgcgctgg ctgtgctgag tgagagtaga g atg agc     117
                                                         Met Ser
                                                          1 gcg tct cgg ttc atc aag tgc gtc acc gtg ggg gac ggc gcc gtg ggc     165
Ala Ser Arg Phe Ile Lys Cys Val Thr Val Gly Asp Gly Ala Val Gly
      5                  10                  15 aag acc tgc atg ctc atc tcc tac acc tcc aac acc ttc ccc acg gac     213
Lys Thr Cys Met Leu Ile Ser Tyr Thr Ser Asn Thr Phe Pro Thr Asp
 20                  25                  30 tat gtt cca act gtt ttt gat aac ttc agt gca aat gtt gtg gtc gat     261
Tyr Val Pro Thr Val Phe Asp Asn Phe Ser Ala Asn Val Val Val Asp
 35                  40                  45                  50 ggg agc act gtg aac ttg ggg ttg tgg gat aca gca gga caa gag gac     309
Gly Ser Thr Val Asn Leu Gly Leu Trp Asp Thr Ala Gly Gln Glu Asp
             55                  60                  65 tac aat agg cta cgc ccg ttg agc tat cgt ggc gct gat gtt ttc ctg     357
Tyr Asn Arg Leu Arg Pro Leu Ser Tyr Arg Gly Ala Asp Val Phe Leu
         70                  75                  80 ctg gcc ttt tct ctg atc agc aaa gca agc tat gag aat gtt tct aaa     405
Leu Ala Phe Ser Leu Ile Ser Lys Ala Ser Tyr Glu Asn Val Ser Lys
         85                  90                  95 aag tgg ata cct gaa tta agg cat tat gct cct ggt gtg cca ata att     453
Lys Trp Ile Pro Glu Leu Arg His Tyr Ala Pro Gly Val Pro Ile Ile
100                 105                 110 ctc gtt gga aca aag ctt gat ctg cgg gat gat aag caa ttt ttc gta     501
Leu Val Gly Thr Lys Leu Asp Leu Arg Asp Asp Lys Gln Phe Phe Val
115                 120                 125                 130 gat cac cct ggt gct gta cct att tcc act gct cag ggc gaa gag ctg     549
Asp His Pro Gly Ala Val Pro Ile Ser Thr Ala Gln Gly Glu Glu Leu
                135                 140                 145 agg aaa ctc att ggt gca gcg gca tac att gaa tgc agt tca aaa aca     597
Arg Lys Leu Ile Gly Ala Ala Ala Tyr Ile Glu Cys Ser Ser Lys Thr
            150                 155                 160 cag caa aac atc aag gca gtt ttc gat gct gcg att aag gtg gtt ctc     645
Gln Gln Asn Ile Lys Ala Val Phe Asp Ala Ala Ile Lys Val Val Leu
        165                 170                 175 cag cct cca aag caa aag aag aag aag aaa aag gcg cag aaa gga tgt     693
Gln Pro Pro Lys Gln Lys Lys Lys Lys Lys Ala Gln Lys Gly Cys
    180                 185                 190
```

```
gcc atc ttg taattaaatg gtagacagtg cagtgcagat cgatgtatcc              742
Ala Ile Leu
195 cttcatttgt agcctctggc ttcaatcgtc gcttgtttgt ataattacgc tagatgccac    802 cggcagaaga tataatatag tcctcctgcc tttgtggtgt tggtctct                850

<210> SEQ ID NO 43
<211> LENGTH: 197
<212> TYPE: PRT
<213> ORGANISM: Oryza sativa

<400> SEQUENCE: 43

Met Ser Ala Ser Arg Phe Ile Lys Cys Val Thr Val Gly Asp Gly Ala
 1               5                  10                  15

Val Gly Lys Thr Cys Met Leu Ile Ser Tyr Thr Ser Asn Thr Phe Pro
                20                  25                  30

Thr Asp Tyr Val Pro Thr Val Phe Asp Asn Phe Ser Ala Asn Val Val
            35                  40                  45

Val Asp Gly Ser Thr Val Asn Leu Gly Leu Trp Asp Thr Ala Gly Gln
        50                  55                  60

Glu Asp Tyr Asn Arg Leu Arg Pro Leu Ser Tyr Arg Gly Ala Asp Val
 65                 70                  75                  80

Phe Leu Leu Ala Phe Ser Leu Ile Ser Lys Ala Ser Tyr Glu Asn Val
                85                  90                  95

Ser Lys Lys Trp Ile Pro Glu Leu Arg His Tyr Ala Pro Gly Val Pro
               100                 105                 110

Ile Ile Leu Val Gly Thr Lys Leu Asp Leu Arg Asp Asp Lys Gln Phe
            115                 120                 125

Phe Val Asp His Pro Gly Ala Val Pro Ile Ser Thr Ala Gln Gly Glu
       130                  135                 140

Glu Leu Arg Lys Leu Ile Gly Ala Ala Ala Tyr Ile Glu Cys Ser Ser
145                 150                 155                 160

Lys Thr Gln Gln Asn Ile Lys Ala Val Phe Asp Ala Ala Ile Lys Val
               165                 170                 175

Val Leu Gln Pro Pro Lys Gln Lys Lys Lys Lys Lys Ala Gln Lys
            180                 185                 190

Gly Cys Ala Ile Leu
        195

<210> SEQ ID NO 44
<211> LENGTH: 1169
<212> TYPE: DNA
<213> ORGANISM: Oryza sativa
<220> FEATURE:
<221> NAME/KEY: CDS
<222> LOCATION: (169)..(813)
<223> OTHER INFORMATION: coding for RacB homologue (Rop 4)

<400> SEQUENCE: 44
aacagttcag agaggaagca tgtgacactt ccctctgtcc ctctctctct ctctagcctc    60
caaccatcgc ttcaccaaga agccatcacc tcctcctctc tatcaagttc tctccctct    120 cttgctgtct ctgcttgctg ctgctgctgc tcgattcggc ggcggcc atg gcg tcc    177
                                                 Met Ala Ser
                                                  1 agc gcg tcg cgg ttc atc aag tgc gtc acg gtc ggg gac ggc gcc gtc    225
Ser Ala Ser Arg Phe Ile Lys Cys Val Thr Val Gly Asp Gly Ala Val
      5                  10                  15
```

| | | |
|---|---|---|
| ggc aag acc tgc atg ctc atc tgc tac acc agc aac aag ttc ccc act<br>Gly Lys Thr Cys Met Leu Ile Cys Tyr Thr Ser Asn Lys Phe Pro Thr<br>20                25                30                35 | 273 |
| gat tac gta ccc act gtt ttt gac aat ttc agt gca aac gtg gtg gtc<br>Asp Tyr Val Pro Thr Val Phe Asp Asn Phe Ser Ala Asn Val Val Val<br>                40                45                50 | 321 |
| gac ggc acc acg gtg aat ttg ggt ctc tgg gat act gca ggg cag gaa<br>Asp Gly Thr Thr Val Asn Leu Gly Leu Trp Asp Thr Ala Gly Gln Glu<br>              55                60                65 | 369 |
| gat tac aac aga ttg agg ccg cta agc tac cgt ggc gcc gat gtc ttt<br>Asp Tyr Asn Arg Leu Arg Pro Leu Ser Tyr Arg Gly Ala Asp Val Phe<br>         70                  75                80 | 417 |
| gtg ctt gcc ttc tcc cta gtg agc cga gct agc tat gag aat gtc atg<br>Val Leu Ala Phe Ser Leu Val Ser Arg Ala Ser Tyr Glu Asn Val Met<br>85                90                95 | 465 |
| aag aag tgg tta cca gag ctt cag cat tat gca cca ggg gtg cca att<br>Lys Lys Trp Leu Pro Glu Leu Gln His Tyr Ala Pro Gly Val Pro Ile<br>100               105              110              115 | 513 |
| gtg ttg gtt ggg acc aaa ttg gat ctt cgt gaa gat aaa cac tac tta<br>Val Leu Val Gly Thr Lys Leu Asp Leu Arg Glu Asp Lys His Tyr Leu<br>               120              125              130 | 561 |
| ctt gac cat cct agc ttg gtg cct gtg act aca gca cag gga gag gaa<br>Leu Asp His Pro Ser Leu Val Pro Val Thr Thr Ala Gln Gly Glu Glu<br>               135              140              145 | 609 |
| ctc cgc aag cac att ggc gca acg tgt tac atc gaa tgc agc tca aag<br>Leu Arg Lys His Ile Gly Ala Thr Cys Tyr Ile Glu Cys Ser Ser Lys<br>         150                155              160 | 657 |
| aca cag cag aat gta aaa gct gtg ttt gat gct gcc atc aag gta gta<br>Thr Gln Gln Asn Val Lys Ala Val Phe Asp Ala Ala Ile Lys Val Val<br>165               170              175 | 705 |
| atc aag cct cca aca aag cag agg gac agg aag aag aag aaa aca cgg<br>Ile Lys Pro Pro Thr Lys Gln Arg Asp Arg Lys Lys Lys Thr Arg<br>180               185              190              195 | 753 |
| cgc gga tgt tct ttc ttc tgc aag ggt gtc atg tcc aga aga agg cta<br>Arg Gly Cys Ser Phe Phe Cys Lys Gly Val Met Ser Arg Arg Arg Leu<br>               200              205              210 | 801 |
| gta tgc ttc aag tgaacaagag gggttctttg atgagcagag cagaggtctg<br>Val Cys Phe Lys<br>         215 | 853 |
| tgagacaaaa tgatgtcttg tgtttgataa ttgctttatc tcaaaagttc cagtttgata | 913 |
| gttgcatttc caacctatat atatcctgtt tggcaattaa ctactacctc cgtcccaaaa | 973 |
| tataacaact tttggctatg aatctgaacg cacagttatc cagattcata gctaaaaata | 1033 |
| cttatatttt gggacggagg gagtactagt agtagattac tatcctgtcc atgtaatgta | 1093 |
| ttaggaaggt taatagcact ccctacatct cagaatggaa gttgttttgg ttttaaaaaa | 1153 |
| aaaaaaaaaa aaaaaa | 1169 |

<210> SEQ ID NO 45
<211> LENGTH: 215
<212> TYPE: PRT
<213> ORGANISM: Oryza sativa

<400> SEQUENCE: 45

Met Ala Ser Ser Ala Ser Arg Phe Ile Lys Cys Val Thr Val Gly Asp
1                5                    10                  15

Gly Ala Val Gly Lys Thr Cys Met Leu Ile Cys Tyr Thr Ser Asn Lys
                  20                    25                    30

Phe Pro Thr Asp Tyr Val Pro Thr Val Phe Asp Asn Phe Ser Ala Asn

-continued

```
                35                  40                  45
Val Val Val Asp Gly Thr Thr Val Asn Leu Gly Leu Trp Asp Thr Ala
     50                  55                  60

Gly Gln Glu Asp Tyr Asn Arg Leu Arg Pro Leu Ser Tyr Arg Gly Ala
 65                  70                  75                  80

Asp Val Phe Val Leu Ala Phe Ser Leu Val Ser Arg Ala Ser Tyr Glu
                 85                  90                  95

Asn Val Met Lys Lys Trp Leu Pro Glu Leu Gln His Tyr Ala Pro Gly
                100                 105                 110

Val Pro Ile Val Leu Val Gly Thr Lys Leu Asp Leu Arg Glu Asp Lys
                115                 120                 125

His Tyr Leu Leu Asp His Pro Ser Leu Val Pro Val Thr Thr Ala Gln
            130                 135                 140

Gly Glu Glu Leu Arg Lys His Ile Gly Ala Thr Cys Tyr Ile Glu Cys
145                 150                 155                 160

Ser Ser Lys Thr Gln Gln Asn Val Lys Ala Val Phe Asp Ala Ala Ile
                165                 170                 175

Lys Val Val Ile Lys Pro Pro Thr Lys Gln Arg Asp Arg Lys Lys Lys
                180                 185                 190

Lys Thr Arg Arg Gly Cys Ser Phe Phe Cys Lys Gly Val Met Ser Arg
            195                 200                 205

Arg Arg Leu Val Cys Phe Lys
        210                 215
```

<210> SEQ ID NO 46
<211> LENGTH: 1127
<212> TYPE: DNA
<213> ORGANISM: Zea mays
<220> FEATURE:
<221> NAME/KEY: CDS
<222> LOCATION: (190)..(831)
<223> OTHER INFORMATION: coding for RacB homologue (RacA)

<400> SEQUENCE: 46

```
gtcgacccac gcgtccgccc agaagtcacg caccaaacac caccaccaaa gaaggcgaga      60
acgtactccg tccctcccct ccccctcccct ccccttcccc tcgaggctcc aggaccgtct    120
cctcgcctgc tcatccgccg ctgcttccct tctctgggct cggagaaccg gagagaagcg    180 cgcgcggcc atg gcg tcc agc gcc tct cgg ttc atc aag tgc gtc acg gtc    231
            Met Ala Ser Ser Ala Ser Arg Phe Ile Lys Cys Val Thr Val
              1               5                  10 ggc gac ggt gcc gtg ggc aag aca tgt atg ctc atc tgc tac acc agc    279
Gly Asp Gly Ala Val Gly Lys Thr Cys Met Leu Ile Cys Tyr Thr Ser
 15                  20                  25                  30 aac aag ttc ccc act gac tac ata cct acg gtg ttc gac aat ttc agt    327
Asn Lys Phe Pro Thr Asp Tyr Ile Pro Thr Val Phe Asp Asn Phe Ser
                 35                  40                  45 gca aat gta gtt gtg gat ggc acc act gtg aat ttg ggc ctt tgg gat    375
Ala Asn Val Val Val Asp Gly Thr Thr Val Asn Leu Gly Leu Trp Asp
             50                  55                  60 acc gct ggg cag gaa gat tac aac cgc ctg agg cct cta agc tac cga    423
Thr Ala Gly Gln Glu Asp Tyr Asn Arg Leu Arg Pro Leu Ser Tyr Arg
 65                  70                  75 ggt gca gat gtt ttc gtg ctt gca ttc tca ctt gtg agc cga gct agc    471
Gly Ala Asp Val Phe Val Leu Ala Phe Ser Leu Val Ser Arg Ala Ser
 80                  85                  90 tat gag aat atc atg aag aag tgg ata cca gag ctt caa cat tat gca    519
Tyr Glu Asn Ile Met Lys Lys Trp Ile Pro Glu Leu Gln His Tyr Ala
```

-continued

```
           95                  100                 105                 110
cct ggg gtg ccc gtt gtt ttg gca ggc aca aaa ttg gat ctt cgt gaa        567
Pro Gly Val Pro Val Val Leu Ala Gly Thr Lys Leu Asp Leu Arg Glu
                115                 120                 125 gac aag cac tac ttg atg gac cat cct gga ttg gtg cct gtt acc act        615
Asp Lys His Tyr Leu Met Asp His Pro Gly Leu Val Pro Val Thr Thr
            130                 135                 140 gca cag ggg gag gaa ctt cgt aga caa att ggt gct atg tat tac att        663
Ala Gln Gly Glu Glu Leu Arg Arg Gln Ile Gly Ala Met Tyr Tyr Ile
        145                 150                 155 gaa tgc agc tca aag aca cag cag aat gtc aaa gct gtg ttc gat gct        711
Glu Cys Ser Ser Lys Thr Gln Gln Asn Val Lys Ala Val Phe Asp Ala
    160                 165                 170 gcc atc aag gta gta atc cag cct cca act aaa ata aga gaa aag aag        759
Ala Ile Lys Val Val Ile Gln Pro Pro Thr Lys Ile Arg Glu Lys Lys
175                 180                 185                 190 aag aaa aaa tca cgc aaa gga tgt tct atg atg aac atc ttc ggt gga        807
Lys Lys Lys Ser Arg Lys Gly Cys Ser Met Met Asn Ile Phe Gly Gly
                195                 200                 205 aga aaa atg cta tgc ttc aag tcc tgaatggttc aagggggtct tacatggact       861
Arg Lys Met Leu Cys Phe Lys Ser
            210 gataccacga gtgtgacccc gagtttgcga agcttgaaat cttgatgtgc tcgttgcgca       921 tgtgtatatt tgcacctttg gttattaatg actagaggta ggtaattgaa actagtctgc       981 ttaagcgttc tgcactgctg gtgtggttag ctctatgagt taagcagttc gacagaggcc      1041 aaaccgacag tgagattttg ttctttcatg gaaatgtgcc aatgtcacag cttttcgtg      1101 aaaaaaaaaa aaaaaaaaaa aaaaaa                                          1127
```

<210> SEQ ID NO 47
<211> LENGTH: 214
<212> TYPE: PRT
<213> ORGANISM: Zea mays

<400> SEQUENCE: 47

```
Met Ala Ser Ser Ala Ser Arg Phe Ile Lys Cys Val Thr Val Gly Asp
 1               5                  10                  15

Gly Ala Val Gly Lys Thr Cys Met Leu Ile Cys Tyr Thr Ser Asn Lys
                20                  25                  30

Phe Pro Thr Asp Tyr Ile Pro Thr Val Phe Asp Asn Phe Ser Ala Asn
            35                  40                  45

Val Val Val Asp Gly Thr Thr Val Asn Leu Gly Leu Trp Asp Thr Ala
        50                  55                  60

Gly Gln Glu Asp Tyr Asn Arg Leu Arg Pro Leu Ser Tyr Arg Gly Ala
 65                  70                  75                  80

Asp Val Phe Val Leu Ala Phe Ser Leu Val Ser Arg Ala Ser Tyr Glu
                85                  90                  95

Asn Ile Met Lys Lys Trp Ile Pro Glu Leu Gln His Tyr Ala Pro Gly
            100                 105                 110

Val Pro Val Leu Ala Gly Thr Lys Leu Asp Leu Arg Glu Asp Lys
        115                 120                 125

His Tyr Leu Met Asp His Pro Gly Leu Val Pro Val Thr Thr Ala Gln
    130                 135                 140

Gly Glu Glu Leu Arg Arg Gln Ile Gly Ala Met Tyr Tyr Ile Glu Cys
145                 150                 155                 160

Ser Ser Lys Thr Gln Gln Asn Val Lys Ala Val Phe Asp Ala Ala Ile
```

165                 170                 175
Lys Val Val Ile Gln Pro Pro Thr Lys Ile Arg Glu Lys Lys Lys
            180                 185                 190

Lys Ser Arg Lys Gly Cys Ser Met Met Asn Ile Phe Gly Gly Arg Lys
        195                 200                 205

Met Leu Cys Phe Lys Ser
    210

<210> SEQ ID NO 48
<211> LENGTH: 901
<212> TYPE: DNA
<213> ORGANISM: Hordeum vulgare
<220> FEATURE:
<221> NAME/KEY: misc_feature
<222> LOCATION: (1)..(901)
<223> OTHER INFORMATION: coding for RacB homologue (RacA)
<220> FEATURE:
<221> NAME/KEY: misc_feature
<222> LOCATION: (826)
<223> OTHER INFORMATION: n is a, c, g or t

<400> SEQUENCE: 48
cccgggctgc aggaattcgg cacgaggcaa gaagtcacgc accaaacacc acccccatc    60 accgccgctc cgctccccag tcccccaccc ctcctccgcc ccttcctcg agccgagctc   120 cggggggaagg aatcggagag gccggcgcgc ggcgagccat ggcgtccagc gcctcccggt   180
tcatcaagtg cgtcacggtg ggcgacggcg ccgtcggcaa gacctgcatg ctcatctgct   240
acaccagcaa caagttcccc accgactaca tacccacggt gttcgacaat ttcagcgcga   300
acgtggtggc ggacggcacc acggtgaatt tgggcctttg gacaccgcc gggcaggagg   360 attacaaccg gctgaggcct ctaagctacc gcggcgccga cgttttcgtg cttgccttct   420
cccttgtgag ccgagctagc tatgagaata tcatgaagaa gtggataccg gagcttcagc   480
attacgcgcc cggcgtacct gttgtgctgg taggcacaaa actggatctt cgtgaagata   540
agcactattt gctggaccac cctgggatga taccgttac cacagcacag ggggaggaac   600
ttcgtaagca agttggtgct ttatattaca tagagtgcag ctcaaagaca caacagaatg   660
tcaaagctgt gtttgatgct gctatcaagg tagtaatcca gccccccact aaacaaagag   720
aaaagaagaa aaagaaacag cgtcggggat gttctatgat gaacttcagc ggaaggaaat   780
gctatgcttc aaatcctgaa tgatgaaaga gaaggttcct tgcctngaac gattgtcacg   840
gttgcgctgc accaatttga caacacctcc aaaccggttg aatgtgctgg attgcaccgt   900
c                                                                  901

<210> SEQ ID NO 49
<211> LENGTH: 594
<212> TYPE: DNA
<213> ORGANISM: Arabidopsis thaliana
<220> FEATURE:
<221> NAME/KEY: CDS
<222> LOCATION: (1)..(591)
<223> OTHER INFORMATION: coding for RacB homologue

<400> SEQUENCE: 49 atg agc gct tcg agg ttc gta aag tgc gtg acg gtt ggt gat gga gct    48
Met Ser Ala Ser Arg Phe Val Lys Cys Val Thr Val Gly Asp Gly Ala
1               5                   10                  15 gtc gga aaa act tgt ttg ttg att tct tac aca agc aac act ttc cct    96
Val Gly Lys Thr Cys Leu Leu Ile Ser Tyr Thr Ser Asn Thr Phe Pro
            20                  25                  30

| | | |
|---|---|---|
| acg gat tat gtg cct acc gtt ttc gat aat ttc agt gcc aat gtt gtg<br>Thr Asp Tyr Val Pro Thr Val Phe Asp Asn Phe Ser Ala Asn Val Val<br>         35                      40                      45 | | 144 |
| gtt aat gga agc act gtg aat ctt gga ttg tgg gac act gca ggg caa<br>Val Asn Gly Ser Thr Val Asn Leu Gly Leu Trp Asp Thr Ala Gly Gln<br>50                      55                      60 | | 192 |
| gag gat tac aat aga tta aga cca ctg agt tac cgt gga gca gat gtt<br>Glu Asp Tyr Asn Arg Leu Arg Pro Leu Ser Tyr Arg Gly Ala Asp Val<br>65                      70                      75                      80 | | 240 |
| ttc att ttg gcc ttc tct ctt atc agt aaa gcc agt tat gaa aac gtc<br>Phe Ile Leu Ala Phe Ser Leu Ile Ser Lys Ala Ser Tyr Glu Asn Val<br>                      85                      90                      95 | | 288 |
| tcc aaa aag tgg atc ccg gag ttg aaa cat tac gcg cct ggt gtc ccc<br>Ser Lys Lys Trp Ile Pro Glu Leu Lys His Tyr Ala Pro Gly Val Pro<br>100                    105                 110 | | 336 |
| atc gtc ctt gtt gga aca aag ctt gat ctt cga gat gat aaa cag ttc<br>Ile Val Leu Val Gly Thr Lys Leu Asp Leu Arg Asp Asp Lys Gln Phe<br>                   115                 120                 125 | | 384 |
| ttt atc gac cat cct ggt gct gtt ccg att act act gct cag gga gag<br>Phe Ile Asp His Pro Gly Ala Val Pro Ile Thr Thr Ala Gln Gly Glu<br>130                    135                 140 | | 432 |
| gag ctg agg aag caa ata gga gca cct act tac atc gaa tgc agt tcc<br>Glu Leu Arg Lys Gln Ile Gly Ala Pro Thr Tyr Ile Glu Cys Ser Ser<br>145                    150                 155                 160 | | 480 |
| aaa act caa gag aat gtg aag gcg gtg ttt gac gca gcc atc cga gtg<br>Lys Thr Gln Glu Asn Val Lys Ala Val Phe Asp Ala Ala Ile Arg Val<br>                   165                 170                 175 | | 528 |
| gtg ttg caa ccg cca aag cag aag aag aag agc aaa gcg cag aag<br>Val Leu Gln Pro Pro Lys Gln Lys Lys Lys Ser Lys Ala Gln Lys<br>180                    185                 190 | | 576 |
| gca tgc tcc att cta tga<br>Ala Cys Ser Ile Leu<br>                   195 | | 594 |

<210> SEQ ID NO 50
<211> LENGTH: 197
<212> TYPE: PRT
<213> ORGANISM: Arabidopsis thaliana

<400> SEQUENCE: 50

Met Ser Ala Ser Arg Phe Val Lys Cys Val Thr Val Gly Asp Gly Ala
1                   5                      10                      15

Val Gly Lys Thr Cys Leu Leu Ile Ser Tyr Thr Ser Asn Thr Phe Pro
                   20                      25                      30

Thr Asp Tyr Val Pro Thr Val Phe Asp Asn Phe Ser Ala Asn Val Val
                   35                      40                      45

Val Asn Gly Ser Thr Val Asn Leu Gly Leu Trp Asp Thr Ala Gly Gln
 50                      55                      60

Glu Asp Tyr Asn Arg Leu Arg Pro Leu Ser Tyr Arg Gly Ala Asp Val
65                   70                      75                      80

Phe Ile Leu Ala Phe Ser Leu Ile Ser Lys Ala Ser Tyr Glu Asn Val
                   85                      90                      95

Ser Lys Lys Trp Ile Pro Glu Leu Lys His Tyr Ala Pro Gly Val Pro
                 100                 105                 110

Ile Val Leu Val Gly Thr Lys Leu Asp Leu Arg Asp Asp Lys Gln Phe
               115                 120                 125

Phe Ile Asp His Pro Gly Ala Val Pro Ile Thr Thr Ala Gln Gly Glu
130                   135                 140

```
Glu Leu Arg Lys Gln Ile Gly Ala Pro Thr Tyr Ile Glu Cys Ser Ser
145                 150                 155                 160

Lys Thr Gln Glu Asn Val Lys Ala Val Phe Asp Ala Ala Ile Arg Val
                165                 170                 175

Val Leu Gln Pro Pro Lys Gln Lys Lys Lys Ser Lys Ala Gln Lys
            180                 185                 190

Ala Cys Ser Ile Leu
        195

<210> SEQ ID NO 51
<211> LENGTH: 594
<212> TYPE: DNA
<213> ORGANISM: Arabidopsis thaliana
<220> FEATURE:
<221> NAME/KEY: CDS
<222> LOCATION: (1)..(591)
<223> OTHER INFORMATION: coding for RacB homologue

<400> SEQUENCE: 51 atg agc gct tcg agg ttc ata aag tgt gtc acc gtt ggc gac gga gct      48
Met Ser Ala Ser Arg Phe Ile Lys Cys Val Thr Val Gly Asp Gly Ala
 1               5                  10                  15 gtt ggt aaa acc tgt ttg ctg att tct tac acc agc aac act ttt cct      96
Val Gly Lys Thr Cys Leu Leu Ile Ser Tyr Thr Ser Asn Thr Phe Pro
            20                  25                  30 acg gat tat gta ccg act gtt ttc gat aac ttt agc gca aat gtg gtt     144
Thr Asp Tyr Val Pro Thr Val Phe Asp Asn Phe Ser Ala Asn Val Val
        35                  40                  45 gtt aat gga gcc act gtg aat ctt ggg cta tgg gat acc gca ggg cag     192
Val Asn Gly Ala Thr Val Asn Leu Gly Leu Trp Asp Thr Ala Gly Gln
    50                  55                  60 gag gat tat aac aga tta aga cct ttg agt tac cgc ggt gct gat gtt     240
Glu Asp Tyr Asn Arg Leu Arg Pro Leu Ser Tyr Arg Gly Ala Asp Val
65                  70                  75                  80 ttc atc tta gca ttc tct ctt atc agt aag gct agt tat gag aat gtc     288
Phe Ile Leu Ala Phe Ser Leu Ile Ser Lys Ala Ser Tyr Glu Asn Val
                85                  90                  95 tcc aag aag tgg atc cca gag ctg aag cat tat gcc cct ggt gtc cct     336
Ser Lys Lys Trp Ile Pro Glu Leu Lys His Tyr Ala Pro Gly Val Pro
            100                 105                 110 ata gtt ctt gtt gga acc aaa cta gat ctt cgg gat gac aaa cag ttc     384
Ile Val Leu Val Gly Thr Lys Leu Asp Leu Arg Asp Asp Lys Gln Phe
        115                 120                 125 ttc att gac cac cct ggc gct gta cca att act act gct cag gga gag     432
Phe Ile Asp His Pro Gly Ala Val Pro Ile Thr Thr Ala Gln Gly Glu
    130                 135                 140 gaa ctg aag aaa cta att gga gct ccc gca tac atc gag tgc agt tca     480
Glu Leu Lys Lys Leu Ile Gly Ala Pro Ala Tyr Ile Glu Cys Ser Ser
145                 150                 155                 160 aaa aca caa gag aac gtg aaa gga gta ttt gat gca gcg atc cga gtg     528
Lys Thr Gln Glu Asn Val Lys Gly Val Phe Asp Ala Ala Ile Arg Val
                165                 170                 175 gtt ctt caa cct cca aag cag aag aaa aag agc aaa gca caa aaa         576
Val Leu Gln Pro Pro Lys Gln Lys Lys Lys Ser Lys Ala Gln Lys
            180                 185                 190 gcc tgc tcc att ttg taa                                             594
Ala Cys Ser Ile Leu
        195

<210> SEQ ID NO 52
<211> LENGTH: 197
```

<212> TYPE: PRT
<213> ORGANISM: Arabidopsis thaliana

<400> SEQUENCE: 52

```
Met Ser Ala Ser Arg Phe Ile Lys Cys Val Thr Val Gly Asp Gly Ala
1               5                   10                  15

Val Gly Lys Thr Cys Leu Leu Ile Ser Tyr Thr Ser Asn Thr Phe Pro
            20                  25                  30

Thr Asp Tyr Val Pro Thr Val Phe Asp Asn Phe Ser Ala Asn Val Val
        35                  40                  45

Val Asn Gly Ala Thr Val Asn Leu Gly Leu Trp Asp Thr Ala Gly Gln
    50                  55                  60

Glu Asp Tyr Asn Arg Leu Arg Pro Leu Ser Tyr Arg Gly Ala Asp Val
65              70                  75                  80

Phe Ile Leu Ala Phe Ser Leu Ile Ser Lys Ala Ser Tyr Glu Asn Val
                85                  90                  95

Ser Lys Lys Trp Ile Pro Glu Leu Lys His Tyr Ala Pro Gly Val Pro
            100                 105                 110

Ile Val Leu Val Gly Thr Lys Leu Asp Leu Arg Asp Asp Lys Gln Phe
        115                 120                 125

Phe Ile Asp His Pro Gly Ala Val Pro Ile Thr Thr Ala Gln Gly Glu
    130                 135                 140

Glu Leu Lys Lys Leu Ile Gly Ala Pro Ala Tyr Ile Glu Cys Ser Ser
145                 150                 155                 160

Lys Thr Gln Glu Asn Val Lys Gly Val Phe Asp Ala Ala Ile Arg Val
                165                 170                 175

Val Leu Gln Pro Pro Lys Gln Lys Lys Lys Ser Lys Ala Gln Lys
            180                 185                 190

Ala Cys Ser Ile Leu
            195
```

<210> SEQ ID NO 53
<211> LENGTH: 594
<212> TYPE: DNA
<213> ORGANISM: Arabidopsis thaliana
<220> FEATURE:
<221> NAME/KEY: CDS
<222> LOCATION: (1)..(591)
<223> OTHER INFORMATION: coding for RacB homologue

<400> SEQUENCE: 53

```
atg agc gca tca agg ttc ata aag tgc gtc acc gtt ggt gat gga gct      48
Met Ser Ala Ser Arg Phe Ile Lys Cys Val Thr Val Gly Asp Gly Ala
1               5                   10                  15 gtt ggt aaa acc tgt ttg ctg att tct tat acc agc aac acc ttt ccc      96
Val Gly Lys Thr Cys Leu Leu Ile Ser Tyr Thr Ser Asn Thr Phe Pro
            20                  25                  30 acg gat tat gtt ccg act gtt ttc gat aac ttt agt gca aat gtg gtt     144
Thr Asp Tyr Val Pro Thr Val Phe Asp Asn Phe Ser Ala Asn Val Val
        35                  40                  45 gtt aat gga gcc acg gtg aat ctt gga ttg tgg gat act gca ggg caa     192
Val Asn Gly Ala Thr Val Asn Leu Gly Leu Trp Asp Thr Ala Gly Gln
    50                  55                  60 gag gac tat aac aga tta aga cct ttg agt tac cgt ggt gct gat gtt     240
Glu Asp Tyr Asn Arg Leu Arg Pro Leu Ser Tyr Arg Gly Ala Asp Val
65              70                  75                  80 ttc att ctt gcc ttc tct ctc att agt aag gct agt tat gag aat gtt     288
Phe Ile Leu Ala Phe Ser Leu Ile Ser Lys Ala Ser Tyr Glu Asn Val
                85                  90                  95
```

```
tcc aag aag tgg att cct gag ttg aag cac tat gct cct ggt gtc cca    336
Ser Lys Lys Trp Ile Pro Glu Leu Lys His Tyr Ala Pro Gly Val Pro
            100                 105                 110 att gtc ctt gtt gga acc aaa cta gat ctt cga gat gac aaa cag ttt    384
Ile Val Leu Val Gly Thr Lys Leu Asp Leu Arg Asp Asp Lys Gln Phe
        115                 120                 125 ttc atc gac cat cct ggt gct gtc cct att acc act gtt cag gga gag    432
Phe Ile Asp His Pro Gly Ala Val Pro Ile Thr Thr Val Gln Gly Glu
130                 135                 140 gag ctg aag aag cta att gga gcg cca gct tac atc gag tgc agt tca    480
Glu Leu Lys Lys Leu Ile Gly Ala Pro Ala Tyr Ile Glu Cys Ser Ser
145                 150                 155                 160 aaa tca caa gag aac gtg aag ggc gtg ttt gat gca gcg atc aga gtg    528
Lys Ser Gln Glu Asn Val Lys Gly Val Phe Asp Ala Ala Ile Arg Val
                165                 170                 175 gtc ctt caa cct cca aag cag aag aaa aag aac aaa gca caa aag        576
Val Leu Gln Pro Pro Lys Gln Lys Lys Lys Asn Lys Ala Gln Lys
                180                 185                 190 gcc tgc tcc atc ttg taa                                            594
Ala Cys Ser Ile Leu
        195
```

<210> SEQ ID NO 54
<211> LENGTH: 197
<212> TYPE: PRT
<213> ORGANISM: Arabidopsis thaliana

<400> SEQUENCE: 54

```
Met Ser Ala Ser Arg Phe Ile Lys Cys Val Thr Val Gly Asp Gly Ala
 1               5                  10                  15

Val Gly Lys Thr Cys Leu Leu Ile Ser Tyr Thr Ser Asn Thr Phe Pro
                20                  25                  30

Thr Asp Tyr Val Pro Thr Val Phe Asp Asn Phe Ser Ala Asn Val Val
            35                  40                  45

Val Asn Gly Ala Thr Val Asn Leu Gly Leu Trp Asp Thr Ala Gly Gln
        50                  55                  60

Glu Asp Tyr Asn Arg Leu Arg Pro Leu Ser Tyr Arg Gly Ala Asp Val
65                  70                  75                  80

Phe Ile Leu Ala Phe Ser Leu Ile Ser Lys Ala Ser Tyr Glu Asn Val
                85                  90                  95

Ser Lys Lys Trp Ile Pro Glu Leu Lys His Tyr Ala Pro Gly Val Pro
            100                 105                 110

Ile Val Leu Val Gly Thr Lys Leu Asp Leu Arg Asp Asp Lys Gln Phe
        115                 120                 125

Phe Ile Asp His Pro Gly Ala Val Pro Ile Thr Thr Val Gln Gly Glu
    130                 135                 140

Glu Leu Lys Lys Leu Ile Gly Ala Pro Ala Tyr Ile Glu Cys Ser Ser
145                 150                 155                 160

Lys Ser Gln Glu Asn Val Lys Gly Val Phe Asp Ala Ala Ile Arg Val
                165                 170                 175

Val Leu Gln Pro Pro Lys Gln Lys Lys Lys Asn Lys Ala Gln Lys
            180                 185                 190

Ala Cys Ser Ile Leu
        195
```

<210> SEQ ID NO 55
<211> LENGTH: 591

<212> TYPE: DNA
<213> ORGANISM: Arabidopsis thaliana
<220> FEATURE:
<221> NAME/KEY: CDS
<222> LOCATION: (1)..(588)
<223> OTHER INFORMATION: coding for RacB homologue

<400> SEQUENCE: 55

```
atg agt gct tcg agg ttt ata aag tgt gtc acc gtc ggc gat ggt gcc      48
Met Ser Ala Ser Arg Phe Ile Lys Cys Val Thr Val Gly Asp Gly Ala
  1               5                  10                  15 gtc gga aaa act tgt atg ctg att tct tac aca agc aac act ttc cct      96
Val Gly Lys Thr Cys Met Leu Ile Ser Tyr Thr Ser Asn Thr Phe Pro
                 20                  25                  30 acg gac tat gtt cca act gtt ttc gac aac ttc agt gct aat gtg gtt     144
Thr Asp Tyr Val Pro Thr Val Phe Asp Asn Phe Ser Ala Asn Val Val
             35                  40                  45 gta gat ggg aac acg gtg aat ctt gga ttg tgg gat aca gct ggt caa     192
Val Asp Gly Asn Thr Val Asn Leu Gly Leu Trp Asp Thr Ala Gly Gln
         50                  55                  60 gaa gac tat aac agg tta aga ccg ttg agt tac cgt ggt gcc gat gtc     240
Glu Asp Tyr Asn Arg Leu Arg Pro Leu Ser Tyr Arg Gly Ala Asp Val
 65                  70                  75                  80 ttc att ctt gca ttc tcg ctt att agc aaa gct agc tac gag aat gta     288
Phe Ile Leu Ala Phe Ser Leu Ile Ser Lys Ala Ser Tyr Glu Asn Val
                 85                  90                  95 gcc aag aag tgg att cct gag ctt agg cat tat gcc cct ggt gtt cct     336
Ala Lys Lys Trp Ile Pro Glu Leu Arg His Tyr Ala Pro Gly Val Pro
                100                 105                 110 ata atc ctc gtt gga acg aaa ctc gat ctt cga gat gac aag caa ttc     384
Ile Ile Leu Val Gly Thr Lys Leu Asp Leu Arg Asp Asp Lys Gln Phe
            115                 120                 125 ttc ata gac cat cct ggt gca gtg cct att act aca aac cag gga gag     432
Phe Ile Asp His Pro Gly Ala Val Pro Ile Thr Thr Asn Gln Gly Glu
130                 135                 140 gaa cta aag aaa ctg ata gga tca cca atc tac att gaa tgt agt tca     480
Glu Leu Lys Lys Leu Ile Gly Ser Pro Ile Tyr Ile Glu Cys Ser Ser
145                 150                 155                 160 aag act cag cag aat gtg aaa gca gtc ttt gac gca gcc ata aaa gtg     528
Lys Thr Gln Gln Asn Val Lys Ala Val Phe Asp Ala Ala Ile Lys Val
                165                 170                 175 gtg ctt cag cca ccg aaa cag aag aag aaa aag aac aag aac cgc         576
Val Leu Gln Pro Pro Lys Gln Lys Lys Lys Lys Asn Lys Asn Arg
                180                 185                 190 tgc gtg ttc ttg tga                                                 591
Cys Val Phe Leu
            195
```

<210> SEQ ID NO 56
<211> LENGTH: 196
<212> TYPE: PRT
<213> ORGANISM: Arabidopsis thaliana

<400> SEQUENCE: 56

```
Met Ser Ala Ser Arg Phe Ile Lys Cys Val Thr Val Gly Asp Gly Ala
  1               5                  10                  15

Val Gly Lys Thr Cys Met Leu Ile Ser Tyr Thr Ser Asn Thr Phe Pro
                 20                  25                  30

Thr Asp Tyr Val Pro Thr Val Phe Asp Asn Phe Ser Ala Asn Val Val
             35                  40                  45

Val Asp Gly Asn Thr Val Asn Leu Gly Leu Trp Asp Thr Ala Gly Gln
```

```
                 50                  55                  60
Glu Asp Tyr Asn Arg Leu Arg Pro Leu Ser Tyr Arg Gly Ala Asp Val
 65                  70                  75                  80

Phe Ile Leu Ala Phe Ser Leu Ile Ser Lys Ala Ser Tyr Glu Asn Val
                 85                  90                  95

Ala Lys Lys Trp Ile Pro Glu Leu Arg His Tyr Ala Pro Gly Val Pro
                100                 105                 110

Ile Ile Leu Val Gly Thr Lys Leu Asp Leu Arg Asp Asp Lys Gln Phe
            115                 120                 125

Phe Ile Asp His Pro Gly Ala Val Pro Ile Thr Thr Asn Gln Gly Glu
        130                 135                 140

Glu Leu Lys Lys Leu Ile Gly Ser Pro Ile Tyr Ile Glu Cys Ser Ser
145                 150                 155                 160

Lys Thr Gln Gln Asn Val Lys Ala Val Phe Asp Ala Ala Ile Lys Val
                165                 170                 175

Val Leu Gln Pro Pro Lys Gln Lys Lys Lys Lys Asn Lys Asn Arg
                180                 185                 190

Cys Val Phe Leu
        195
```

<210> SEQ ID NO 57
<211> LENGTH: 597
<212> TYPE: DNA
<213> ORGANISM: Arabidopsis thaliana
<220> FEATURE:
<221> NAME/KEY: CDS
<222> LOCATION: (1)..(594)
<223> OTHER INFORMATION: coding for RacB homologue

<400> SEQUENCE: 57

```
atg agt gct tca agg ttt atc aag tgt gtc act gtc ggc gac ggt gct       48
Met Ser Ala Ser Arg Phe Ile Lys Cys Val Thr Val Gly Asp Gly Ala
 1               5                  10                  15 gtt gga aag act tgt ctt ctc atc tcc tac act agc aac act ttc ccc       96
Val Gly Lys Thr Cys Leu Leu Ile Ser Tyr Thr Ser Asn Thr Phe Pro
             20                  25                  30 acg gat tat gtg cca act gtg ttc gat aat ttc agt gcc aat gtg att      144
Thr Asp Tyr Val Pro Thr Val Phe Asp Asn Phe Ser Ala Asn Val Ile
         35                  40                  45 gtt gat ggc aac act atc aac ttg gga ttg tgg gat act gca ggg caa      192
Val Asp Gly Asn Thr Ile Asn Leu Gly Leu Trp Asp Thr Ala Gly Gln
     50                  55                  60 gag gac tac aat aga cta aga cct ttg agc tat cgc ggt gca gat gtc      240
Glu Asp Tyr Asn Arg Leu Arg Pro Leu Ser Tyr Arg Gly Ala Asp Val
 65                  70                  75                  80 ttc tta ctt gca ttc tca ctt gtc agc aaa gct agc tat gaa aat gtt      288
Phe Leu Leu Ala Phe Ser Leu Val Ser Lys Ala Ser Tyr Glu Asn Val
                 85                  90                  95 tct aaa aag tgg gtt cct gaa ctg aga cat tat gct cct ggt gtt ccc      336
Ser Lys Lys Trp Val Pro Glu Leu Arg His Tyr Ala Pro Gly Val Pro
            100                 105                 110 atc atc ctc gtt gga aca aag ctt gat ctt cga gat gat aag caa ttc      384
Ile Ile Leu Val Gly Thr Lys Leu Asp Leu Arg Asp Asp Lys Gln Phe
        115                 120                 125 ttt gcc gag cac cct ggt gct gtg cct atc tct acc gct cag ggt gaa      432
Phe Ala Glu His Pro Gly Ala Val Pro Ile Ser Thr Ala Gln Gly Glu
    130                 135                 140 gaa cta aag aag ctg att ggg gcg cct gct tat atc gaa tgc agt gca      480
Glu Leu Lys Lys Leu Ile Gly Ala Pro Ala Tyr Ile Glu Cys Ser Ala
145                 150                 155                 160
```

```
                    145                 150                 155                 160
aaa act caa cag aat gtg aaa gca gtg ttt gat gcg gct atc aag gtc      528
Lys Thr Gln Gln Asn Val Lys Ala Val Phe Asp Ala Ala Ile Lys Val
                        165                 170                 175 gtt ctc cag cca cca aaa aac aag aag aag aag aga aaa tct cag          576
Val Leu Gln Pro Pro Lys Asn Lys Lys Lys Lys Arg Lys Ser Gln
            180                 185                 190 aaa ggt tgt tct ata ctc tga                                          597
Lys Gly Cys Ser Ile Leu
        195

<210> SEQ ID NO 58
<211> LENGTH: 198
<212> TYPE: PRT
<213> ORGANISM: Arabidopsis thaliana

<400> SEQUENCE: 58

Met Ser Ala Ser Arg Phe Ile Lys Cys Val Thr Val Gly Asp Gly Ala
 1               5                  10                  15

Val Gly Lys Thr Cys Leu Leu Ile Ser Tyr Thr Ser Asn Thr Phe Pro
            20                  25                  30

Thr Asp Tyr Val Pro Thr Val Phe Asp Asn Phe Ser Ala Asn Val Ile
        35                  40                  45

Val Asp Gly Asn Thr Ile Asn Leu Gly Leu Trp Asp Thr Ala Gly Gln
    50                  55                  60

Glu Asp Tyr Asn Arg Leu Arg Pro Leu Ser Tyr Arg Gly Ala Asp Val
65                  70                  75                  80

Phe Leu Leu Ala Phe Ser Leu Val Ser Lys Ala Ser Tyr Glu Asn Val
                85                  90                  95

Ser Lys Lys Trp Val Pro Glu Leu Arg His Tyr Ala Pro Gly Val Pro
            100                 105                 110

Ile Ile Leu Val Gly Thr Lys Leu Asp Leu Arg Asp Asp Lys Gln Phe
        115                 120                 125

Phe Ala Glu His Pro Gly Ala Val Pro Ile Ser Thr Ala Gln Gly Glu
    130                 135                 140

Glu Leu Lys Lys Leu Ile Gly Ala Pro Ala Tyr Ile Glu Cys Ser Ala
145                 150                 155                 160

Lys Thr Gln Gln Asn Val Lys Ala Val Phe Asp Ala Ala Ile Lys Val
                165                 170                 175

Val Leu Gln Pro Pro Lys Asn Lys Lys Lys Lys Arg Lys Ser Gln
            180                 185                 190

Lys Gly Cys Ser Ile Leu
        195

<210> SEQ ID NO 59
<211> LENGTH: 588
<212> TYPE: DNA
<213> ORGANISM: Arabidopsis thaliana
<220> FEATURE:
<221> NAME/KEY: CDS
<222> LOCATION: (1)..(585)
<223> OTHER INFORMATION: coding for RacB homologue

<400> SEQUENCE: 59 atg gcg tca agg ttt ata aag tgt gtg acc gtc gga gat ggt gcc gtc      48
Met Ala Ser Arg Phe Ile Lys Cys Val Thr Val Gly Asp Gly Ala Val
 1               5                  10                  15 gga aaa act tgc atg ctc att tct tac act agc aat act ttt cct act      96
Gly Lys Thr Cys Met Leu Ile Ser Tyr Thr Ser Asn Thr Phe Pro Thr
```

|  | 20 |  |  |  | 25 |  |  |  | 30 |  |  |  |  |
|---|---|---|---|---|---|---|---|---|---|---|---|---|---|
| gat | tat | gtg | cca | act | gtt | ttc | gac | aac | ttc | agt | gct | aat | gtg gtt gtt | 144 |
| Asp | Tyr | Val | Pro | Thr | Val | Phe | Asp | Asn | Phe | Ser | Ala | Asn | Val Val Val |  |
|  |  | 35 |  |  |  | 40 |  |  |  | 45 |  |  |  |  | gat ggc aac act gtc aat ctt gga ttg tgg gat act gct ggt caa gag    192
Asp Gly Asn Thr Val Asn Leu Gly Leu Trp Asp Thr Ala Gly Gln Glu
     50                  55                  60 gac tac aac agg tta cga cct ttg agt tac cgt ggt gct gat gtt ttc    240
Asp Tyr Asn Arg Leu Arg Pro Leu Ser Tyr Arg Gly Ala Asp Val Phe
 65                  70                  75                  80 att ctt gct ttc tct ctt att agc aag gct agc tat gag aat ata gcc    288
Ile Leu Ala Phe Ser Leu Ile Ser Lys Ala Ser Tyr Glu Asn Ile Ala
                 85                  90                  95 aag aag tgg att cct gag ctc agg cat tat gct cct ggt gtt ccc att    336
Lys Lys Trp Ile Pro Glu Leu Arg His Tyr Ala Pro Gly Val Pro Ile
            100                 105                 110 atc ctt gtt ggg aca aaa ctc gat ctt cga gat gac aag caa ttc ttt    384
Ile Leu Val Gly Thr Lys Leu Asp Leu Arg Asp Asp Lys Gln Phe Phe
        115                 120                 125 ata gat cat cct ggt gct gtg cca att act aca aac cag gga gag gaa    432
Ile Asp His Pro Gly Ala Val Pro Ile Thr Thr Asn Gln Gly Glu Glu
    130                 135                 140 ctg aag aaa ctg att gga tct gct gtc tac att gaa tgt agt tca aag    480
Leu Lys Lys Leu Ile Gly Ser Ala Val Tyr Ile Glu Cys Ser Ser Lys
145                 150                 155                 160 aca cag cag aac gtg aag gca gtg ttt gat gca gct ata aaa gtg gtg    528
Thr Gln Gln Asn Val Lys Ala Val Phe Asp Ala Ala Ile Lys Val Val
                165                 170                 175 ctt cag cca cca aag cag aag aag aag aaa aag aat aag aac cgt tgc    576
Leu Gln Pro Pro Lys Gln Lys Lys Lys Lys Asn Lys Asn Arg Cys
            180                 185                 190 gcg ttc ttg tga                                                    588
Ala Phe Leu
        195

<210> SEQ ID NO 60
<211> LENGTH: 195
<212> TYPE: PRT
<213> ORGANISM: Arabidopsis thaliana

<400> SEQUENCE: 60

Met Ala Ser Arg Phe Ile Lys Cys Val Thr Gly Asp Gly Ala Val
 1               5                  10                  15

Gly Lys Thr Cys Met Leu Ile Ser Tyr Thr Ser Asn Thr Phe Pro Thr
                20                  25                  30

Asp Tyr Val Pro Thr Val Phe Asp Asn Phe Ser Ala Asn Val Val Val
            35                  40                  45

Asp Gly Asn Thr Val Asn Leu Gly Leu Trp Asp Thr Ala Gly Gln Glu
        50                  55                  60

Asp Tyr Asn Arg Leu Arg Pro Leu Ser Tyr Arg Gly Ala Asp Val Phe
 65                  70                  75                  80

Ile Leu Ala Phe Ser Leu Ile Ser Lys Ala Ser Tyr Glu Asn Ile Ala
                 85                  90                  95

Lys Lys Trp Ile Pro Glu Leu Arg His Tyr Ala Pro Gly Val Pro Ile
            100                 105                 110

Ile Leu Val Gly Thr Lys Leu Asp Leu Arg Asp Asp Lys Gln Phe Phe
        115                 120                 125

Ile Asp His Pro Gly Ala Val Pro Ile Thr Thr Asn Gln Gly Glu Glu

```
                130               135               140
Leu Lys Lys Leu Ile Gly Ser Ala Val Tyr Ile Glu Cys Ser Ser Lys
145                 150                 155                 160

Thr Gln Gln Asn Val Lys Ala Val Phe Asp Ala Ala Ile Lys Val Val
                165                 170                 175

Leu Gln Pro Pro Lys Gln Lys Lys Lys Lys Asn Lys Asn Arg Cys
                180                 185                 190

Ala Phe Leu
        195

<210> SEQ ID NO 61
<211> LENGTH: 606
<212> TYPE: DNA
<213> ORGANISM: Arabidopsis thaliana
<220> FEATURE:
<221> NAME/KEY: CDS
<222> LOCATION: (1)..(603)
<223> OTHER INFORMATION: coding for RacB homologue

<400> SEQUENCE: 61 atg agc aca gca aga ttc att aag tgt gtg act gtc gga gat gga gca    48
Met Ser Thr Ala Arg Phe Ile Lys Cys Val Thr Val Gly Asp Gly Ala
  1               5                  10                  15 gtg gga aag act tgt atg ctc att tca tat acc agc aat acg ttt cct    96
Val Gly Lys Thr Cys Met Leu Ile Ser Tyr Thr Ser Asn Thr Phe Pro
             20                  25                  30 acg gat tat gtt cca aca gtt ttc gac aac ttc agc gca aat gtg gtg   144
Thr Asp Tyr Val Pro Thr Val Phe Asp Asn Phe Ser Ala Asn Val Val
         35                  40                  45 gtc gac ggg agt acc gtg aac ctt ggc ctg tgg gat act gcc ggt cag   192
Val Asp Gly Ser Thr Val Asn Leu Gly Leu Trp Asp Thr Ala Gly Gln
     50                  55                  60 gaa gat tat aat agg ctt agg cct ttg agt tac aga gga gca gat gtc   240
Glu Asp Tyr Asn Arg Leu Arg Pro Leu Ser Tyr Arg Gly Ala Asp Val
 65                  70                  75                  80 ttc tta tta gca ttt tcc ctt ata agc aag gcc agt tac gag aat att   288
Phe Leu Leu Ala Phe Ser Leu Ile Ser Lys Ala Ser Tyr Glu Asn Ile
                 85                  90                  95 cac aaa aag tgg ctt ccg gag ctg aaa cat tat gct cct ggc atc ccc   336
His Lys Lys Trp Leu Pro Glu Leu Lys His Tyr Ala Pro Gly Ile Pro
            100                 105                 110 att gtg ctc gtc gga aca aaa tta gat ttg agg gat gac aag cag ttc   384
Ile Val Leu Val Gly Thr Lys Leu Asp Leu Arg Asp Asp Lys Gln Phe
        115                 120                 125 ttg aag gat cat cca gga gca gct tct ata aca act gct cag gga gaa   432
Leu Lys Asp His Pro Gly Ala Ala Ser Ile Thr Thr Ala Gln Gly Glu
    130                 135                 140 gaa tta agg aaa atg att gga gct gtt agg tac tta gag tgc agc tcc   480
Glu Leu Arg Lys Met Ile Gly Ala Val Arg Tyr Leu Glu Cys Ser Ser
145                 150                 155                 160 aaa acc caa cag aat gtg aag gca gtg ttt gat aca gcg ata agg gta   528
Lys Thr Gln Gln Asn Val Lys Ala Val Phe Asp Thr Ala Ile Arg Val
                165                 170                 175 gct ttg agg cca cca aag gca aag aaa aag ata aaa cca ttg aag act   576
Ala Leu Arg Pro Pro Lys Ala Lys Lys Lys Ile Lys Pro Leu Lys Thr
            180                 185                 190 aag aga tca aga ata tgc ttt ttc cta taa                           606
Lys Arg Ser Arg Ile Cys Phe Phe Leu
        195                 200
```

<210> SEQ ID NO 62
<211> LENGTH: 201
<212> TYPE: PRT
<213> ORGANISM: Arabidopsis thaliana

<400> SEQUENCE: 62

Met Ser Thr Ala Arg Phe Ile Lys Cys Val Thr Val Gly Asp Gly Ala
1               5                   10                  15

Val Gly Lys Thr Cys Met Leu Ile Ser Tyr Thr Ser Asn Thr Phe Pro
            20                  25                  30

Thr Asp Tyr Val Pro Thr Val Phe Asp Asn Phe Ser Ala Asn Val Val
        35                  40                  45

Val Asp Gly Ser Thr Val Asn Leu Gly Leu Trp Asp Thr Ala Gly Gln
    50                  55                  60

Glu Asp Tyr Asn Arg Leu Arg Pro Leu Ser Tyr Arg Gly Ala Asp Val
65                  70                  75                  80

Phe Leu Leu Ala Phe Ser Leu Ile Ser Lys Ala Ser Tyr Glu Asn Ile
                85                  90                  95

His Lys Lys Trp Leu Pro Glu Leu Lys His Tyr Ala Pro Gly Ile Pro
            100                 105                 110

Ile Val Leu Val Gly Thr Lys Leu Asp Leu Arg Asp Asp Lys Gln Phe
        115                 120                 125

Leu Lys Asp His Pro Gly Ala Ala Ser Ile Thr Ala Gln Gly Glu
    130                 135                 140

Glu Leu Arg Lys Met Ile Gly Ala Val Arg Tyr Leu Glu Cys Ser Ser
145                 150                 155                 160

Lys Thr Gln Gln Asn Val Lys Ala Val Phe Asp Thr Ala Ile Arg Val
                165                 170                 175

Ala Leu Arg Pro Pro Lys Ala Lys Lys Ile Lys Pro Leu Lys Thr
            180                 185                 190

Lys Arg Ser Arg Ile Cys Phe Phe Leu
            195                 200

<210> SEQ ID NO 63
<211> LENGTH: 606
<212> TYPE: DNA
<213> ORGANISM: Arabidopsis thaliana
<220> FEATURE:
<221> NAME/KEY: CDS
<222> LOCATION: (1)..(603)
<223> OTHER INFORMATION: coding for RacB homologue

<400> SEQUENCE: 63 atg gct tcg agt gct tca aaa ttc atc aaa tgt gtg act gtt gga gat      48
Met Ala Ser Ser Ala Ser Lys Phe Ile Lys Cys Val Thr Val Gly Asp
1               5                   10                  15 ggt gcc gtt gga aaa act tgt atg ctc atc tgc tac act agc aac aaa      96
Gly Ala Val Gly Lys Thr Cys Met Leu Ile Cys Tyr Thr Ser Asn Lys
            20                  25                  30 ttc cct act gac tac ata cca aca gtt ttt gac aac ttt agt gtt aat     144
Phe Pro Thr Asp Tyr Ile Pro Thr Val Phe Asp Asn Phe Ser Val Asn
        35                  40                  45 gtt gtg gtt gaa ggc atc act gtg aac tta ggc ctt tgg gac act gcc     192
Val Val Val Glu Gly Ile Thr Val Asn Leu Gly Leu Trp Asp Thr Ala
    50                  55                  60 ggg caa gaa gac tat aac aga cta agg cct tta agt tac aga gga gca     240
Gly Gln Glu Asp Tyr Asn Arg Leu Arg Pro Leu Ser Tyr Arg Gly Ala
65                  70                  75                  80 gat gtt ttt gtg ttg gct ttc tca ttg atc agc cga gct agc tat gag     288
Asp Val Phe Val Leu Ala Phe Ser Leu Ile Ser Arg Ala Ser Tyr Glu -continued

```
                Asp Val Phe Val Leu Ala Phe Ser Leu Ile Ser Arg Ala Ser Tyr Glu
                                85                  90                  95 aat gtg ttt aaa aag tgg atc cct gaa ctc caa cac ttt gca cca gga         336
Asn Val Phe Lys Lys Trp Ile Pro Glu Leu Gln His Phe Ala Pro Gly
            100                 105                 110 gtc ccc att gtg ctt gtt ggt acc aaa atg gat ctt cgt gaa gat aga         384
Val Pro Ile Val Leu Val Gly Thr Lys Met Asp Leu Arg Glu Asp Arg
        115                 120                 125 cat tac ttg tct gat cat cct gga ctg tcc ccg gta act aca tca cag         432
His Tyr Leu Ser Asp His Pro Gly Leu Ser Pro Val Thr Thr Ser Gln
130                 135                 140 gga gag gaa ctc cgc aag cat atc gga gcg act tat tac att gaa tgt         480
Gly Glu Glu Leu Arg Lys His Ile Gly Ala Thr Tyr Tyr Ile Glu Cys
145                 150                 155                 160 agc tca aaa act caa cag aat gtg aaa gcc gta ttt gat gct gct att         528
Ser Ser Lys Thr Gln Gln Asn Val Lys Ala Val Phe Asp Ala Ala Ile
                165                 170                 175 aaa gta gta att aaa cca gca gtg aaa caa aag gag aag aag aag aag         576
Lys Val Val Ile Lys Pro Ala Val Lys Gln Lys Glu Lys Lys Lys Lys
            180                 185                 190 cag aag cct cgc agc gga tgt ctc tcg taa                                 606
Gln Lys Pro Arg Ser Gly Cys Leu Ser
        195                 200
```

<210> SEQ ID NO 64
<211> LENGTH: 201
<212> TYPE: PRT
<213> ORGANISM: Arabidopsis thaliana

<400> SEQUENCE: 64

```
Met Ala Ser Ser Ala Ser Lys Phe Ile Lys Cys Val Thr Val Gly Asp
1               5                   10                  15

Gly Ala Val Gly Lys Thr Cys Met Leu Ile Cys Tyr Thr Ser Asn Lys
                20                  25                  30

Phe Pro Thr Asp Tyr Ile Pro Thr Val Phe Asp Asn Phe Ser Val Asn
            35                  40                  45

Val Val Val Glu Gly Ile Thr Val Asn Leu Gly Leu Trp Asp Thr Ala
        50                  55                  60

Gly Gln Glu Asp Tyr Asn Arg Leu Arg Pro Leu Ser Tyr Arg Gly Ala
65                  70                  75                  80

Asp Val Phe Val Leu Ala Phe Ser Leu Ile Ser Arg Ala Ser Tyr Glu
                85                  90                  95

Asn Val Phe Lys Lys Trp Ile Pro Glu Leu Gln His Phe Ala Pro Gly
            100                 105                 110

Val Pro Ile Val Leu Val Gly Thr Lys Met Asp Leu Arg Glu Asp Arg
        115                 120                 125

His Tyr Leu Ser Asp His Pro Gly Leu Ser Pro Val Thr Thr Ser Gln
130                 135                 140

Gly Glu Glu Leu Arg Lys His Ile Gly Ala Thr Tyr Tyr Ile Glu Cys
145                 150                 155                 160

Ser Ser Lys Thr Gln Gln Asn Val Lys Ala Val Phe Asp Ala Ala Ile
                165                 170                 175

Lys Val Val Ile Lys Pro Ala Val Lys Gln Lys Glu Lys Lys Lys Lys
            180                 185                 190

Gln Lys Pro Arg Ser Gly Cys Leu Ser
        195                 200
```

<210> SEQ ID NO 65
<211> LENGTH: 648
<212> TYPE: DNA
<213> ORGANISM: Arabidopsis thaliana
<220> FEATURE:
<221> NAME/KEY: CDS
<222> LOCATION: (1)..(645)
<223> OTHER INFORMATION: coding for RacB homologue

<400> SEQUENCE: 65

| | | | | | | | | | | | | | | | | |
|---|---|---|---|---|---|---|---|---|---|---|---|---|---|---|---|---|
| atg | gct | tca | agt | gct | tca | aag | ttc | atc | aag | tgt | gtg | act | gtt | ggt | gat | 48 |
| Met | Ala | Ser | Ser | Ala | Ser | Lys | Phe | Ile | Lys | Cys | Val | Thr | Val | Gly | Asp | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggt | gct | gtt | ggt | aaa | acc | tgt | atg | ctc | atc | tgc | tac | acc | agc | aat | aaa | 96 |
| Gly | Ala | Val | Gly | Lys | Thr | Cys | Met | Leu | Ile | Cys | Tyr | Thr | Ser | Asn | Lys | |
| | | | 20 | | | | | 25 | | | | | 30 | | | |

| | | | | | | | | | | | | | | | | |
|---|---|---|---|---|---|---|---|---|---|---|---|---|---|---|---|---|
| ttc | ccc | act | gac | tac | ata | cca | aca | gtt | ttt | gac | aac | ttt | agt | gca | aat | 144 |
| Phe | Pro | Thr | Asp | Tyr | Ile | Pro | Thr | Val | Phe | Asp | Asn | Phe | Ser | Ala | Asn | |
| | | 35 | | | | | 40 | | | | | 45 | | | | |

| | | | | | | | | | | | | | | | | |
|---|---|---|---|---|---|---|---|---|---|---|---|---|---|---|---|---|
| gtt | gtt | gtt | gaa | ggc | acc | act | gtc | aat | ttg | ggg | ctt | tgg | gac | act | gct | 192 |
| Val | Val | Val | Glu | Gly | Thr | Thr | Val | Asn | Leu | Gly | Leu | Trp | Asp | Thr | Ala | |
| 50 | | | | | 55 | | | | | 60 | | | | | | |

| | | | | | | | | | | | | | | | | |
|---|---|---|---|---|---|---|---|---|---|---|---|---|---|---|---|---|
| ggg | caa | gaa | gac | tat | aac | aga | tta | agg | cct | tta | agt | tac | agg | gga | gca | 240 |
| Gly | Gln | Glu | Asp | Tyr | Asn | Arg | Leu | Arg | Pro | Leu | Ser | Tyr | Arg | Gly | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gat | gtt | ttc | gtc | ttg | tct | ttc | tca | tta | gtc | agc | cga | gct | agc | tac | gag | 288 |
| Asp | Val | Phe | Val | Leu | Ser | Phe | Ser | Leu | Val | Ser | Arg | Ala | Ser | Tyr | Glu | |
| | | | | 85 | | | | | 90 | | | | | 95 | | |

| | | | | | | | | | | | | | | | | |
|---|---|---|---|---|---|---|---|---|---|---|---|---|---|---|---|---|
| aat | gtt | ttt | aaa | aag | tgg | atc | cct | gaa | ctc | caa | cac | ttt | gct | cca | gga | 336 |
| Asn | Val | Phe | Lys | Lys | Trp | Ile | Pro | Glu | Leu | Gln | His | Phe | Ala | Pro | Gly | |
| | | | 100 | | | | | 105 | | | | | 110 | | | |

| | | | | | | | | | | | | | | | | |
|---|---|---|---|---|---|---|---|---|---|---|---|---|---|---|---|---|
| gtt | ccc | ctt | gtc | ctt | gtt | ggt | acc | aaa | tta | gat | ctt | cgt | gaa | gat | aag | 384 |
| Val | Pro | Leu | Val | Leu | Val | Gly | Thr | Lys | Leu | Asp | Leu | Arg | Glu | Asp | Lys | |
| | | 115 | | | | | 120 | | | | | 125 | | | | |

| | | | | | | | | | | | | | | | | |
|---|---|---|---|---|---|---|---|---|---|---|---|---|---|---|---|---|
| cat | tat | ttg | gct | gat | cat | cct | gga | cta | tcc | cct | gta | act | act | gca | cag | 432 |
| His | Tyr | Leu | Ala | Asp | His | Pro | Gly | Leu | Ser | Pro | Val | Thr | Thr | Ala | Gln | |
| 130 | | | | | 135 | | | | | 140 | | | | | | |

| | | | | | | | | | | | | | | | | |
|---|---|---|---|---|---|---|---|---|---|---|---|---|---|---|---|---|
| gga | gag | gag | ttg | cgt | aag | cta | att | ggt | gcg | acg | tat | tac | att | gag | tgt | 480 |
| Gly | Glu | Glu | Leu | Arg | Lys | Leu | Ile | Gly | Ala | Thr | Tyr | Tyr | Ile | Glu | Cys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| agt | tca | aaa | act | caa | cag | aat | gtg | aaa | gca | gtt | ttt | gat | tct | gcg | ata | 528 |
| Ser | Ser | Lys | Thr | Gln | Gln | Asn | Val | Lys | Ala | Val | Phe | Asp | Ser | Ala | Ile | |
| | | | | 165 | | | | | 170 | | | | | 175 | | |

| | | | | | | | | | | | | | | | | |
|---|---|---|---|---|---|---|---|---|---|---|---|---|---|---|---|---|
| aag | gaa | gtg | atc | aaa | cct | ctg | gtt | aaa | caa | aag | gag | aag | act | aag | aag | 576 |
| Lys | Glu | Val | Ile | Lys | Pro | Leu | Val | Lys | Gln | Lys | Glu | Lys | Thr | Lys | Lys | |
| | | | 180 | | | | | 185 | | | | | 190 | | | |

| | | | | | | | | | | | | | | | | |
|---|---|---|---|---|---|---|---|---|---|---|---|---|---|---|---|---|
| aag | aag | aag | caa | aag | tcg | aat | cac | ggc | tgt | tta | tca | aat | gtt | ctg | tgt | 624 |
| Lys | Lys | Lys | Gln | Lys | Ser | Asn | His | Gly | Cys | Leu | Ser | Asn | Val | Leu | Cys | |
| | | 195 | | | | | 200 | | | | | 205 | | | | |

| | | | | | | | |
|---|---|---|---|---|---|---|---|
| ggg | agg | ata | gtg | act | cgg | cat | tga | 648 |
| Gly | Arg | Ile | Val | Thr | Arg | His | | |
| 210 | | | | | 215 | | | |

<210> SEQ ID NO 66
<211> LENGTH: 215
<212> TYPE: PRT
<213> ORGANISM: Arabidopsis thaliana

<400> SEQUENCE: 66

Met Ala Ser Ser Ala Ser Lys Phe Ile Lys Cys Val Thr Val Gly Asp
1               5                   10                  15

Gly Ala Val Gly Lys Thr Cys Met Leu Ile Cys Tyr Thr Ser Asn Lys

-continued

```
                 20                  25                  30
Phe Pro Thr Asp Tyr Ile Pro Thr Val Phe Asp Asn Phe Ser Ala Asn
         35                  40                  45
Val Val Val Glu Gly Thr Thr Val Asn Leu Gly Leu Trp Asp Thr Ala
 50                  55                  60
Gly Gln Glu Asp Tyr Asn Arg Leu Arg Pro Leu Ser Tyr Arg Gly Ala
 65                  70                  75                  80
Asp Val Phe Val Leu Ser Phe Ser Leu Val Ser Arg Ala Ser Tyr Glu
                 85                  90                  95
Asn Val Phe Lys Lys Trp Ile Pro Glu Leu Gln His Phe Ala Pro Gly
                100                 105                 110
Val Pro Leu Val Leu Val Gly Thr Lys Leu Asp Leu Arg Glu Asp Lys
            115                 120                 125
His Tyr Leu Ala Asp His Pro Gly Leu Ser Pro Val Thr Thr Ala Gln
        130                 135                 140
Gly Glu Glu Leu Arg Lys Leu Ile Gly Ala Thr Tyr Tyr Ile Glu Cys
145                 150                 155                 160
Ser Ser Lys Thr Gln Gln Asn Val Lys Ala Val Phe Asp Ser Ala Ile
                165                 170                 175
Lys Glu Val Ile Lys Pro Leu Val Lys Gln Lys Glu Lys Thr Lys Lys
            180                 185                 190
Lys Lys Lys Gln Lys Ser Asn His Gly Cys Leu Ser Asn Val Leu Cys
        195                 200                 205
Gly Arg Ile Val Thr Arg His
    210                 215

<210> SEQ ID NO 67
<211> LENGTH: 630
<212> TYPE: DNA
<213> ORGANISM: Arabidopsis thaliana
<220> FEATURE:
<221> NAME/KEY: CDS
<222> LOCATION: (1)..(627)
<223> OTHER INFORMATION: coding for RacB homologue

<400> SEQUENCE: 67 atg agt gct tcg aag ttc ata aaa tgt gtt act gtt gga gat ggg gct      48
Met Ser Ala Ser Lys Phe Ile Lys Cys Val Thr Val Gly Asp Gly Ala
 1               5                  10                  15 gtt ggg aag aca tgt atg ctt atc tgt tac act agc aac aag ttt cct      96
Val Gly Lys Thr Cys Met Leu Ile Cys Tyr Thr Ser Asn Lys Phe Pro
             20                  25                  30 act gat tat ata ccg act gtg ttc gac aat ttc agt gcc aat gta gct     144
Thr Asp Tyr Ile Pro Thr Val Phe Asp Asn Phe Ser Ala Asn Val Ala
         35                  40                  45 gtg gat gga caa atc gtt aat tta ggg cta tgg gac act gcc ggt caa     192
Val Asp Gly Gln Ile Val Asn Leu Gly Leu Trp Asp Thr Ala Gly Gln
 50                  55                  60 gaa gat tac agt agg tta aga cca ttg agt tat aga gga gct gat atc     240
Glu Asp Tyr Ser Arg Leu Arg Pro Leu Ser Tyr Arg Gly Ala Asp Ile
 65                  70                  75                  80 ttc gtc tta gcc ttt tcg ctt att agc aag gcg agt tac gaa aat gta     288
Phe Val Leu Ala Phe Ser Leu Ile Ser Lys Ala Ser Tyr Glu Asn Val
                 85                  90                  95 ctc aag aag tgg atg cct gaa ctt cgt cgg ttt gcg cca aat gtt ccc     336
Leu Lys Lys Trp Met Pro Glu Leu Arg Arg Phe Ala Pro Asn Val Pro
            100                 105                 110 ata gtt ctt gtt ggt aca aag cta gat ctc cgg gat gac aag gga tac     384
```

```
Ile Val Leu Val Gly Thr Lys Leu Asp Leu Arg Asp Asp Lys Gly Tyr
            115                 120                 125 ctc gcg gat cac acc aat gtc att acc tct act cag gga gag gaa ttg      432
Leu Ala Asp His Thr Asn Val Ile Thr Ser Thr Gln Gly Glu Glu Leu
        130                 135                 140 agg aag caa att ggt gca gct gct tat att gag tgt agt tcc aag act      480
Arg Lys Gln Ile Gly Ala Ala Ala Tyr Ile Glu Cys Ser Ser Lys Thr
145                 150                 155                 160 caa caa aat gtg aaa gca gtg ttt gat aca gcg atc aag gtg gtt ctt      528
Gln Gln Asn Val Lys Ala Val Phe Asp Thr Ala Ile Lys Val Val Leu
                165                 170                 175 cag cct cca agg agg aaa gag gtc ccg agg agg aag aat cat aga          576
Gln Pro Pro Arg Arg Lys Glu Val Pro Arg Arg Lys Asn His Arg
            180                 185                 190 aga tcc ggt tgc tcc att gcg agt att gtc tgt gga ggt tgc acc gct      624
Arg Ser Gly Cys Ser Ile Ala Ser Ile Val Cys Gly Gly Cys Thr Ala
        195                 200                 205 gct taa                                                              630
Ala
```

<210> SEQ ID NO 68
<211> LENGTH: 209
<212> TYPE: PRT
<213> ORGANISM: Arabidopsis thaliana

<400> SEQUENCE: 68

```
Met Ser Ala Ser Lys Phe Ile Lys Cys Val Thr Val Gly Asp Gly Ala
1               5                   10                  15

Val Gly Lys Thr Cys Met Leu Ile Cys Tyr Thr Ser Asn Lys Phe Pro
            20                  25                  30

Thr Asp Tyr Ile Pro Thr Val Phe Asp Asn Phe Ser Ala Asn Val Ala
        35                  40                  45

Val Asp Gly Gln Ile Val Asn Leu Gly Leu Trp Asp Thr Ala Gly Gln
    50                  55                  60

Glu Asp Tyr Ser Arg Leu Arg Pro Leu Ser Tyr Arg Gly Ala Asp Ile
65                  70                  75                  80

Phe Val Leu Ala Phe Ser Leu Ile Ser Lys Ala Ser Tyr Glu Asn Val
                85                  90                  95

Leu Lys Lys Trp Met Pro Glu Leu Arg Arg Phe Ala Pro Asn Val Pro
            100                 105                 110

Ile Val Leu Val Gly Thr Lys Leu Asp Leu Arg Asp Asp Lys Gly Tyr
        115                 120                 125

Leu Ala Asp His Thr Asn Val Ile Thr Ser Thr Gln Gly Glu Glu Leu
    130                 135                 140

Arg Lys Gln Ile Gly Ala Ala Ala Tyr Ile Glu Cys Ser Ser Lys Thr
145                 150                 155                 160

Gln Gln Asn Val Lys Ala Val Phe Asp Thr Ala Ile Lys Val Val Leu
                165                 170                 175

Gln Pro Pro Arg Arg Lys Glu Val Pro Arg Arg Lys Asn His Arg
            180                 185                 190

Arg Ser Gly Cys Ser Ile Ala Ser Ile Val Cys Gly Gly Cys Thr Ala
        195                 200                 205

Ala
```

<210> SEQ ID NO 69
<211> LENGTH: 600
<212> TYPE: DNA

<213> ORGANISM: Arabidopsis thaliana
<220> FEATURE:
<221> NAME/KEY: CDS
<222> LOCATION: (1)..(597)
<223> OTHER INFORMATION: coding for RacB homologue

<400> SEQUENCE: 69

```
atg gct gca aca tca aca tca tca gca aca gct aca acg ttt ata aag      48
Met Ala Ala Thr Ser Thr Ser Ser Ala Thr Ala Thr Thr Phe Ile Lys
 1               5                  10                  15 tgt gtc act gtt ggc gat gga gct ctt ttg gtg act gtt gag atc ttg      96
Cys Val Thr Val Gly Asp Gly Ala Leu Leu Val Thr Val Glu Ile Leu
             20                  25                  30 tta tta cag gat tat gtt cca aca gtg ttc gac aat ttc aat gct aat     144
Leu Leu Gln Asp Tyr Val Pro Thr Val Phe Asp Asn Phe Asn Ala Asn
         35                  40                  45 gtt tta gtc gat ggt aaa act gtc aat ctg ggt ctc tgg gat act gct     192
Val Leu Val Asp Gly Lys Thr Val Asn Leu Gly Leu Trp Asp Thr Ala
 50                  55                  60 ggt caa gaa gac tac aat agg gtt aga cca ttg agt tac aga gga gca     240
Gly Gln Glu Asp Tyr Asn Arg Val Arg Pro Leu Ser Tyr Arg Gly Ala
 65                  70                  75                  80 gat gtt ttc att ctt gcc ttc tca ctt att agc agg cct agc ttt gag     288
Asp Val Phe Ile Leu Ala Phe Ser Leu Ile Ser Arg Pro Ser Phe Glu
                 85                  90                  95 aac att gct aaa aag tgg gta ccc gag ctg aga cat tat gcc ccg act     336
Asn Ile Ala Lys Lys Trp Val Pro Glu Leu Arg His Tyr Ala Pro Thr
            100                 105                 110 gtg cct att gtt ctt gtg gga acc aaa tca gat cta aga gac aac atg     384
Val Pro Ile Val Leu Val Gly Thr Lys Ser Asp Leu Arg Asp Asn Met
        115                 120                 125 cag ttc cca aag aat tat cca ggt gct tgc aca atc ttc cca gaa cag     432
Gln Phe Pro Lys Asn Tyr Pro Gly Ala Cys Thr Ile Phe Pro Glu Gln
    130                 135                 140 ggt caa gaa cta aga aag gaa ata gga gca tta gca tac ata gag tgc     480
Gly Gln Glu Leu Arg Lys Glu Ile Gly Ala Leu Ala Tyr Ile Glu Cys
145                 150                 155                 160 agc tca aaa gca caa atg aac gta aaa gcc gtg ttt gat gaa gcg atc     528
Ser Ser Lys Ala Gln Met Asn Val Lys Ala Val Phe Asp Glu Ala Ile
                165                 170                 175 aaa gta gtt tta cat cct cct tca aag act aag aag cga aag aga aag     576
Lys Val Val Leu His Pro Pro Ser Lys Thr Lys Lys Arg Lys Arg Lys
            180                 185                 190 atc ggt tta tgc cat gtt ctt tga                                     600
Ile Gly Leu Cys His Val Leu
        195
```

<210> SEQ ID NO 70
<211> LENGTH: 199
<212> TYPE: PRT
<213> ORGANISM: Arabidopsis thaliana

<400> SEQUENCE: 70

```
Met Ala Ala Thr Ser Thr Ser Ser Ala Thr Ala Thr Thr Phe Ile Lys
 1               5                  10                  15

Cys Val Thr Val Gly Asp Gly Ala Leu Leu Val Thr Val Glu Ile Leu
             20                  25                  30

Leu Leu Gln Asp Tyr Val Pro Thr Val Phe Asp Asn Phe Asn Ala Asn
         35                  40                  45

Val Leu Val Asp Gly Lys Thr Val Asn Leu Gly Leu Trp Asp Thr Ala
 50                  55                  60
```

Gly Gln Glu Asp Tyr Asn Arg Val Arg Pro Leu Ser Tyr Arg Gly Ala
 65                  70                  75                  80

Asp Val Phe Ile Leu Ala Phe Ser Leu Ile Ser Arg Pro Ser Phe Glu
                 85                  90                  95

Asn Ile Ala Lys Lys Trp Val Pro Glu Leu Arg His Tyr Ala Pro Thr
            100                 105                 110

Val Pro Ile Val Leu Val Gly Thr Lys Ser Asp Leu Arg Asp Asn Met
        115                 120                 125

Gln Phe Pro Lys Asn Tyr Pro Gly Ala Cys Thr Ile Phe Pro Glu Gln
    130                 135                 140

Gly Gln Glu Leu Arg Lys Glu Ile Gly Ala Leu Ala Tyr Ile Glu Cys
145                 150                 155                 160

Ser Ser Lys Ala Gln Met Asn Val Lys Ala Val Phe Asp Glu Ala Ile
                165                 170                 175

Lys Val Val Leu His Pro Pro Ser Lys Thr Lys Lys Arg Lys Arg Lys
            180                 185                 190

Ile Gly Leu Cys His Val Leu
        195

<210> SEQ ID NO 71
<211> LENGTH: 21
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 71
atgagcgcgt ccaggttcat a                                              21

<210> SEQ ID NO 72
<211> LENGTH: 21
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 72
atcaaacacg cccttcacgt t                                              21

<210> SEQ ID NO 73
<211> LENGTH: 10828
<212> TYPE: DNA
<213> ORGANISM: Artificial sequence
<220> FEATURE:
<223> OTHER INFORMATION: Description of the artificial sequence:
      transgenic expression vector pSUN3NIT_AtRacB_s for expression
      of A-thalianan RacB sense RNA
<220> FEATURE:
<221> NAME/KEY: misc_feature
<222> LOCATION: (2235)
<223> OTHER INFORMATION: n is a, c, g or t

<400> SEQUENCE: 73
ttccatggac atacaaatgg acgaacggat aaaccttttc acgcccttt aaatatccga        60 ttattctaat aaacgctctt ttctcttagg tttacccgcc aatatatcct gtcaaacact      120
gatagtttaa actgaaggcg ggaaacgaca atcagatcta gtaggaaaca gctatgacca      180
tgattacgcc aagcttgcat gcctgcaggt cgactctaga ggatccccca tcaagatctt      240
ggtgatgtag caagagctaa gttgtacttc gatycggttg gacattactc gagaccagat      300

```
gttttacact tgaccgtaaa tgagcacccg aagaaaccgg taacattcat ttcgaaggta      360
gagaaagcgg aagatgactc aaacaagtaa tcggttgtga ttcgtcagtt catgtcactc      420
ctatgaagga gtcaagttca aaatgttatg ttgagtttca aacttttatg ctaaactttt      480
tttcttaatt ttcgttaata atggaagaga accaattctc ttgtatctaa agattatcca      540
tctatcatcc aatttgagtg ttcaattctg gatgttgtgt taccctacat tctacaacca      600
tgtagccaat tattatgaat ctggctttga tttcagttgt gttctttttct tttttctttt      660 gcatatttgc atttagaatg tttaataatt aagttactgt atttccacat acattagttc      720
caagaatata catatattaa tttatttttc ttaaaaatgt tttggaatga ctaatattga      780
caacgaaaat agaagctatg ctaaaccatt acgtatatgt gacttcacat gttgttgttt      840
tacattccct atatatatgg atggctgtca caatcagaaa cgtgatcgaa aaagacaaa       900 cagtgtttgc ataaaaagac tatttcgttt cattgacaat ttgtgtttat ttgtaaagaa      960
aagtggcaaa gtggaatttg agttcctgca agtaagaaag atgaaataaa agacttgagt     1020
gtgtgttttt ttctttttatc tgaaagctgc aatgaaatat tcctaccaag cccgtttgat     1080
tattaattgg ggtttggttt tcttgatgcg aactaattgg ttatataaga aactatacaa     1140
tccatgttaa ttcaaaaatt ttgatttctc ttgtaggaat atgatttact atatgagact     1200
ttcttttcgc caataatagt aaatccaaag atatttgacc ggaccaaaac acattgatct     1260
attttttagt ttatttaatc cagtttctct gagataattc attaaggaaa acttagtatt     1320
aacccatcct aagattaaat aggagccaaa ctcacatttc aaatattaaa taacataaaa     1380
tggatttaaa aaatctatac gtcaaatttt atttatgaca tttcttattt aaatttatat     1440
ttaatgaaat acagctaaga caaaccaaaa aaaaaatact ttctaagtgg tccaaaacat     1500
caattccgtt caatattatt aggtagaatc gtacgaccaa aaaaggtagg ttaatacgaa     1560
attacaaaca tatctatata catagtatat attattaccct attatgagga atcaaaatgc     1620
atcaaatatg gatttaagga atccataaaa gaataaattc tacggaaaaa aaaaaaagaa     1680
taaattcttt taagttttta atttgttttt tatttggtag ttctccattt tgttttattt     1740
cgtttggatt tattgtgtcc aaatactttg taaaccaccg ttgtaattct taaacggggt     1800
tttcacttct tttttatatt cagacataaa gcatcggctg gttaatcaa tcaatagatt      1860 ttatttttct tctcaattat tagtaggttt gatgtgaact ttacaaaaaa aacaaaaaca     1920
aatcaatgca gagaaaagaa accacgtggg ctagtcccac cttgtttcat ttccaccaca     1980
ggttcgatct tcgttaccgt ctccaatagg aaaataaacg tgaccacaaa aaaaaaacaa     2040 aaaaaagtc tatatattgc ttctctcaag tctctgagtg tcatgaacca agtaaaaaa      2100 caaagactcg agtggatccc cggaattcgc ccttatgagc gcatcaaggt tcataaagtg     2160
cgtcaccgtt ggtgatggag ctgttggtaa aacctgtttg ctgatttctt ataccagcaa     2220
cacctttccc acggntattc atcaatcatt ctccctcctt tttttgatat ctgattcatt     2280
tgattctgat tgtgccatat atgaattggg atccatacat actaaaaatg ttgtatacat     2340
ttccattgga acaggattat gttccgactg ttttcgataa ctttagtgca aatgtggttg     2400
tcaatggggc cacggtgaat cttggattgt gggatactgc aggtaaatga atgatgatcc     2460
aattcataat ccttggtgag agagctttcc gtgatgaatc agaggtcgaa attatgtttt     2520
tggtttatgc agggcaagag gactataaca gattaagacc tttgagttac cgtggtgctg     2580
atgttttcat tcttgccttc tctctcatta gtaaggctag ttatgagaat gtttccaaga     2640
```

```
aggtcagttt cgtccgaact ggtcgactat ttaacaattg agagttccaa attttgatgc   2700
ttctttctt ttacagtgga ttcctgagtt gaagcactat gctcctggtg tcccaattgt    2760
ccttgttgga accaaactag gttacttcct cctctcacat ttgtccttgt ttatgcattt   2820
atttatatat atgtctgatt cccatgctta cactgccatt ttccttttca ctttattaag   2880
ctgctctggt ataatatata tcatgacatt agtggacata aaacttcacc ttctcttgat   2940
tgtggttaaa acttgtacat gttcaagatg tattcgttag gtgaaactga gggtagtttt   3000
cagagaatat cattggtcaa caggcttctt cttgtatctt gcacttcttg tgataaagca   3060
accgtatcct ataacacacg cctttaagca tcctccaatg aaatagctac tgtatagcaa   3120
gtgtataccct ttataaaaga cacttgcaag atcttcagtc aactcatgat cctggccttt   3180
ttgattgtct aaccttggtt gttgtcagat cttcgagatg acaaacagtt tttcatcgac   3240
catcctggtg ctgtccctat taccactgtt caggtaagaa tacagttatt tcctcagtgc   3300
aattttatca gctttaccac cgttaagcat tttccctctc tgcatggaag ggagaggagc   3360
tgaagaagct aattggagcg ccagcttaca tcgagtgcag ttcaaaatca caagaggtaa   3420
acgaataaaa gacatctcat gaatcatctt ttcggtgtta gattcttctt tttttgatga   3480
aaacaatgtg actataactg cagaacgtga agggcgtgtt tgataagggc gaattaattc   3540
actggccgtc gttttacaac gactcagagc ttgacaggag gcccgatcta gtaacataga   3600
tgacaccgcg cgcgataatt tatcctagtt tgcgcgctat attttgttttt ctatcgcgta   3660
ttaaatgtat aattgcggga ctctaatcat aaaaacccat ctcataaata acgtcatgca   3720
ttacatgtta attattacat gcttaacgta attcaacaga aattatatga taatcatcgc   3780
aagaccggca acaggattca atcttaagaa actttattgc caaatgtttg aacgatcggg   3840
gatcatccgg gtctgtggcg ggaactccac gaaaatatcc gaacgcagca agatctagag   3900
cttgggtccc gctcagaaga actcgtcaag aaggcgatag aaggcgatgc gctgcgaatc   3960
gggagcggcg ataccgtaaa gcacgaggaa gcggtcagcc cattcgccgc caagctcttc   4020
agcaatatca cgggtagcca acgctatgtc ctgatagcgg tccgccacac ccagccggcc   4080
acagtcgatg aatccagaaa agcggccatt ttccaccatg atattcggca agcaggcatc   4140
gccatgggtc acgacgagat cctcgccgtc gggcatgcgc gccttgagcc tggcgaacag   4200
ttcggctggc gcgagcccct gatgctcttc gtccagatca tcctgatcga caagaccggc   4260
ttccatccga gtacgtgctc gctcgatgcg atgtttcgct tggtggtcga atgggcaggt   4320
agccggatca agcgtatgca gccgccgcat tgcatcagcc atgatggata cttttctcggc   4380
aggagcaagg tgagatgaca ggagatcctg ccccggcact tcgcccaata gcagccagtc   4440
ccttcccgct tcagtgacaa cgtcgagcac agctgcgcaa ggaacgcccg tcgtggccag   4500
ccacgatagc cgcgctgcct cgtcctgcag ttcattcagg gcaccggaca ggtcggtctt   4560
gacaaaaaga accgggcgcc cctgcgctga cagccggaac acggcggcat cagagcagcc   4620
gattgtctgt tgtgcccagt catagccgaa tagcctctcc acccaagcgg ccggagaacc   4680
tgcgtgcaat ccatcttgtt caatcatgcg aaacgatcca gatccggtgc agattatttg   4740
gattgagagt gaatatgaga ctctaattgg ataccgaggg gaatttatgg aacgtcagtg   4800
gagcattttt gacaagaaat atttgctagc tgatagtgac cttaggcgac ttttgaacgc   4860
gcaataatgg tttctgacgt atgtgcttag ctcattaaac tccagaaacc gcggctgag   4920
tggctccttc aacgttgcgg ttctgtcagt tccaaacgta aaacggcttg tcccgcgtca   4980
tcggcggggg tcataacgtg actcccttaa ttctccgctc atgatcagat tgtcgtttcc   5040
```

```
cgccttcagt ttaaactatc agtgtttgac aggatcctgc ttggtaataa ttgtcattag    5100
attgttttta tgcatagatg cactcgaaat cagccaattt tagacaagta tcaaacggat    5160
gttaattcag tacattaaag acgtccgcaa tgtgttatta agttgtctaa gcgtcaattt    5220
gtttacacca caatatatcc tgccaccagc cagccaacag ctccccgacc ggcagctcgg    5280
cacaaaatca ccacgcgtta ccaccacgcc ggccggccgc atggtgttga ccgtgttcgc    5340
cggcattgcc gagttcgagc gttccctaat catcgaccgc acccggagcg ggcgcgaggc    5400
cgccaaggcc cgaggcgtga agtttggccc ccgccctacc ctcacccegg cacagatcgc    5460 gcacgcccgc gagctgatcg accaggaagg ccgcaccgtg aaagaggcgg ctgcactgct    5520
tggcgtgcat cgctcgaccc tgtaccgcgc acttgagcgc agcgaggaag tgacgcccac    5580
cgaggccagg cggcgcggtg ccttccgtga ggacgcattg accgaggccg acgccctggc    5640
ggccgccgag aatgaacgcc aagaggaaca agcatgaaac cgcaccagga cggccaggac    5700
gaaccgtttt tcattaccga agagatcgag gcggagatga tcgcggccgg gtacgtgttc    5760
gagccgcccg cgcacgtctc aaccgtgcgg ctgcatgaaa tcctggccgg tttgtctgat    5820
gccaagctgg cggcctggcc ggccagcttg gccgctgaag aaaccgagcg ccgccgtcta    5880
aaaaggtgat gtgtatttga gtaaaacagc ttgcgtcatg cggtcgctgc gtatatgatg    5940
cgatgagtaa ataaacaaat acgcaagggg aacgcatgaa ggttatcgct gtacttaacc    6000
agaaaggcgg gtcaggcaag acgaccatcg caacccatct agcccgcgcc ctgcaactcg    6060
ccggggccga tgttctgtta gtcgattccg atcccccaggg cagtgccccgc gattgggcgg    6120 ccgtgcggga agatcaaccg ctaaccgttg tcggcatcga ccgcccgacg attgaccgcg    6180
acgtgaaggc catcggccgg cgcgacttcg tagtgatcga cggagcgccc caggcggcgg    6240
acttggctgt gtccgcgatc aaggcagccg acttcgtgct gattccggtg cagccaagcc    6300
cttacgacat atgggccacc gccgacctgg tggagctggt taagcagcgc attgaggtca    6360
cggatggaag gctacaagcg gcctttgtcg tgtcgcgggc gatcaaaggc acgcgcatcg    6420
gcggtgaggt tgccgaggcg ctggccgggt acgagctgcc cattcttgag tcccgtatca    6480
cgcagcgcgt gagctaccca ggcactgccg ccgccggcac aaccgttctt gaatcagaac    6540
ccgagggcga cgctgcccgc gaggtccagg cgctggccgc tgaaattaaa tcaaaactca    6600
tttgagttaa tgaggtaaag agaaaatgag caaaagcaca aacacgctaa gtgccggccg    6660
tccgagcgca cgcagcagca aggctgcaac gttggccagc ctggcagaca cgccagccat    6720
gaagcgggtc aactttcagt tgccggcgga ggatcacacc aagctgaaga tgtacgcggt    6780
acgccaaggc aagaccatta ccgagctgct atctgaatac atcgcgcagc taccagagta    6840
aatgagcaaa tgaataaatg agtagatgaa ttttagcggc taaaggaggc ggcatggaaa    6900
atcaagaaca accaggcacc gacgccgtgg aatgccccat gtgtggagga acgggcggtt    6960
ggccaggcgt aagcggctgg gttgtctgcc ggccctgcaa tggcactgga acccccaagc    7020
ccgaggaatc ggcgtgagcg gtcgcaaacc atcggcccg gtacaaatcg gcgcggcgct    7080
gggtgatgac ctggtggaga agttgaaggc cgcgcaggcc gcccagcggc aacgcatcga    7140
ggcagaagca cgccccggtg aatcgtggca agcggccgct gatcgaatcc gcaaagaatc    7200
ccggcaaccg ccggcagccg gtgcgccgtc gattaggaag ccgcccaagg cgacgcagca    7260
accagatttt ttcgttccga tgctctatga cgtgggcacc cgcgatagtc gcagcatcat    7320
ggacgtggcc gttttccgtc tgtcgaagcg tgaccgacga gctggcgagg tgatccgcta    7380
```

```
cgagcttcca gacgggcacg tagaggtttc gcagggccg gccggcatgg ccagtgtgtg      7440
ggattacgac ctggtactga tggcggtttc ccatctaacc gaatccatga accgataccg      7500
ggaagggaag ggagacaagc ccggccgcgt gttccgtcca cacgttgcgg acgtactcaa      7560
gttctgccgg cgagccgatg gcggaaagca gaaagacgac ctggtagaaa cctgcattcg      7620
gttaaacacc acgcacgttg ccatgcagcg tacgaagaag gccaagaacg gccgcctggt      7680
gacggtatcc gagggtgaag ccttgattag ccgctacaag atcgtaaaga gcgaaaccgg      7740
gcggccggag tacatcgaga tcgagctagc tgattggatg taccgcgaga tcacagaagg      7800
caagaacccg gacgtgctga cggttcaccc cgattacttt ttgatcgatc ccggcatcgg      7860
ccgttttctc taccgcctgg cacgccgcgc cgcaggcaag gcagaagcca gatggttgtt      7920
caagacgatc tacgaacgca gtggcagcgc cggagagttc aagaagttct gtttcaccgt      7980
gcgcaagctg atcgggtcaa atgacctgcc ggagtacgat ttgaaggagg aggcggggca      8040
ggctggcccg atcctagtca tgcgctaccg caacctgatc gagggcgaag catccgccgg      8100
ttcctaatgt acggagcaga tgctagggca aattgcccta gcaggggaaa aaggtcgaaa      8160
aggtctcttt cctgtggata gcacgtacat tgggaaccca aagccgtaca ttgggaaccg      8220
gaacccgtac attgggaacc caaagccgta cattgggaac cggtcacaca tgtaagtgac      8280
tgatataaaa gagaaaaaag gcgattttc cgcctaaaac tctttaaaac ttattaaaac      8340
tcttaaaacc cgcctggcct gtgcataact gtctggccag cgcacagccg aagagctgca      8400
aaaagcgcct acccttcggt cgctgcgctc cctacgcccc gccgcttcgc gtcggcctat      8460
cgcggccgct ggccgctcaa aaatggctgg cctacggcca ggcaatctac cagggcgcgg      8520
acaagccgcg ccgtcgccac tcgaccgccg gcgcccacat caaggcaccc tgcctcgcgc      8580
gtttcggtga tgacggtgaa aacctctgac acatgcagct cccggagacg gtcacagctt      8640
gtctgtaagc ggatgccggg agcagacaag cccgtcaggg cgcgtcagcg ggtgttggcg      8700
ggtgtcgggg cgcagccatg acccagtcac gtagcgatag cggagtgtat actggcttaa      8760
ctatgcggca tcagagcaga ttgtactgag agtgcaccat atgcggtgtg aaataccgca      8820
cagatgcgta aggagaaaat accgcatcag gcgctcttcc gcttcctcgc tcactgactc      8880
gctgcgctcg gtcgttcggc tgcggcgagc ggtatcagct cactcaaagg cggtaatacg      8940
gttatccaca gaatcagggg ataacgcagg aaagaacatg tgagcaaaag gccagcaaaa      9000
ggccaggaac cgtaaaaagg ccgcgttgct ggcgtttttc cataggctcc gcccccctga      9060
cgagcatcac aaaaatcgac gctcaagtca gaggtggcga aacccgacag gactataaag      9120
ataccaggcg tttccccctg gaagctccct cgtgcgctct cctgttccga ccctgccgct      9180
taccggatac ctgtccgcct ttctcccttc gggaagcgtg gcgctttctc atagctcacg      9240
ctgtaggtat ctcagttcgg tgtaggtcgt tcgctccaag ctgggctgtg tgcacgaacc      9300
ccccgttcag cccgaccgct cgccttatc cggtaactat cgtcttgagt ccaacccggt      9360
aagacacgac ttatcgccac tggcagcagc cactggtaac aggattagca gagcgaggta      9420
tgtaggcggt gctacagagt tcttgaagtg gtggcctaac tacggctaca ctagaaggac      9480
agtatttggt atctgcgctc tgctgaagcc agttaccttc ggaaaaagag ttggtagctc      9540
ttgatccggc aaacaaacca ccgctggtag cggtggtttt tttgtttgca agcagcagat      9600
tacgcgcaga aaaaaaggat ctcaagaaga tcctttgatc ttttctacgg ggtctgacgc      9660
tcagtggaac gaaaactcac gttaagggat tttggtcatg catgatatat ctcccaattt      9720
gtgtagggct tattatgcac gcttaaaaat aataaaagca gacttgacct gatagtttgg      9780
```

```
ctgtgagcaa ttatgtgctt agtgcatcta acgcttgagt taagccgcgc cgcgaagcgg    9840
cgtcggcttg aacgaatttc tagctagaca ttatttgccg actaccttgg tgatctcgcc    9900
tttcacgtag tggacaaatt cttccaactg atctgcgcgc gaggccaagc gatcttcttc    9960
ttgtccaaga taagcctgtc tagcttcaag tatgacgggc tgatactggg ccggcaggcg   10020
ctccattgcc cagtcggcag cgacatcctt cggcgcgatt ttgccggtta ctgcgctgta   10080
ccaaatgcgg gacaacgtaa gcactacatt tcgctcatcg ccagcccagt cgggcggcga   10140
gttccatagc gttaaggttt catttagcgc ctcaaataga tcctgttcag gaaccggatc   10200
aaagagttcc tccgccgctg gacctaccaa ggcaacgcta tgttctcttg cttttgtcag   10260
caagatagcc agatcaatgt cgatcgtggc tggctcgaag atacctgcaa gaatgtcatt   10320
gcgctgccat tctccaaatt gcagttcgcg cttagctgga taacgccacg gaatgatgtc   10380
gtcgtgcaca acaatggtga cttctacagc gcggagaatc tcgctctctc caggggaagc   10440
cgaagtttcc aaaaggtcgt tgatcaaagc tcgccgcgtt gtttcatcaa gccttacggt   10500
caccgtaacc agcaaatcaa tatcactgtg tggcttcagg ccgccatcca ctgcggagcc   10560
gtacaaatgt acggccagca acgtcggttc gagatggcgc tcgatgacgc caactacctc   10620
tgatagttga gtcgatactt cggcgatcac cgcttccccc atgatgttta actttgtttt   10680
agggcgactg ccctgctgcg taacatcgtt gctgctccat aacatcaaac atcgacccac   10740
ggcgtaacgc gcttgctgct tggatgcccg aggcatagac tgtaccccaa aaaacagtc   10800 ataacaagcc atgaaaaccg ccactgcg                                      10828

<210> SEQ ID NO 74
<211> LENGTH: 10828
<212> TYPE: DNA
<213> ORGANISM: Artificial sequence
<220> FEATURE:
<223> OTHER INFORMATION: Description of the artificial sequence:
      transgenic expression vector pSUN3NIT_AtRacB_as for
      expression of A-thalianan RacB antisense RNA
<220> FEATURE:
<221> NAME/KEY: misc_feature
<222> LOCATION: (3424)
<223> OTHER INFORMATION: n is a, c, g or t

<400> SEQUENCE: 74
ttccatggac atacaaatgg acgaacggat aaaccttttc acgcccttttt aaatatccga     60 ttattctaat aaacgctctt ttctcttagg tttacccgcc aatatatcct gtcaaacact    120
gatagtttaa actgaaggcg ggaaacgaca atcagatcta gtaggaaaca gctatgacca    180
tgattacgcc aagcttgcat gcctgcaggt cgactctaga ggatccccca tcaagatctt    240
ggtgatgtag caagagctaa gttgtacttc gatycggttg acattactc gagaccagat    300 gttttacact tgaccgtaaa tgagcacccg aagaaaccgg taacattcat ttcgaaggta    360
gagaaagcgg aagatgactc aaacaagtaa tcggttgtga ttcgtcagtt catgtcactc    420
ctatgaagga gtcaagttca aaatgttatg ttgagtttca aacttttatg ctaaactttt    480
tttcttaatt ttcgttaata atggaagaga accaattctc ttgtatctaa agattatcca    540
tctatcatcc aatttgagtg ttcaattctg gatgttgtgt tacccctacat tctacaacca    600 tgtagccaat tattatgaat ctggctttga tttcagttgt gttcttttct ttttttcttt    660
gcatatttgc atttagaatg tttaataatt aagttactgt atttccacat acattagttc    720
caagaatata catatattaa tttatttttc ttaaaaatgt tttggaatga ctaatattga    780
```

```
caacgaaaat agaagctatg ctaaaccatt acgtatatgt gacttcacat gttgttgttt    840
tacattccct atatatatgg atggctgtca caatcagaaa cgtgatcgaa aaagacaaa     900
cagtgtttgc ataaaagac tatttcgttt cattgacaat ttgtgtttat ttgtaaagaa    960
aagtggcaaa gtggaatttg agttcctgca agtaagaaag atgaaataaa agacttgagt  1020
gtgtgttttt ttcttttatc tgaaagctgc aatgaaatat tcctaccaag cccgtttgat  1080
tattaattgg ggtttggttt tcttgatgcg aactaattgg ttatataaga aactatacaa  1140
tccatgttaa ttcaaaaatt ttgatttctc ttgtaggaat atgatttact atatgagact  1200
ttcttttcgc caataatagt aaatccaaag atatttgacc ggaccaaaac acattgatct  1260
atttttagt ttatttaatc cagtttctct gagataattc attaaggaaa acttagtatt   1320
aacccatcct aagattaaat aggagccaaa ctcacatttc aaatattaaa taacataaaa  1380
tggatttaaa aaatctatac gtcaaatttt atttatgaca tttcttattt aaatttatat  1440
ttaatgaaat acagctaaga caaaccaaaa aaaaaatact ttctaagtgg tccaaaacat  1500
caattccgtt caatattatt aggtagaatc gtacgaccaa aaaggtagg ttaatacgaa   1560
attacaaaca tatctatata catagtatat attattaccct attatgagga atcaaaatgc 1620
atcaaatatg gatttaagga atccataaaa gaataaattc tacggaaaaa aaaaaaagaa  1680
taaattcttt taagttttta atttgttttt tatttggtag ttctccattt tgttttattt  1740
cgtttggatt tattgtgtcc aaatactttg taaaccaccg ttgtaattct taaacggggt  1800
tttcacttct tttttatatt cagacataaa gcatcggctg gtttaatcaa tcaatagatt  1860
ttattttct tctcaattat tagtaggttt gatgtgaact ttacaaaaaa aacaaaaaca   1920
aatcaatgca gagaaaagaa accacgtggg ctagtcccac cttgtttcat ttccaccaca  1980
ggttcgatct tcgttaccgt ctccaatagg aaaataaacg tgaccacaaa aaaaaaacaa  2040
aaaaaagtc tatatattgc ttctctcaag tctctgagtg tcatgaacca agtaaaaaa    2100
caaagactcg agtggatccc cggaattcgc ccttatcaaa cacgcccttc acgttctgca  2160
gttatagtca cattgttttc atcaaaaaaa gaagaatcta acaccgaaaa gatgattcat  2220
gagatgtctt ttattcgttt acctcttgtg attttgaact gcactcgatg taagctggcg  2280
ctccaattag cttcttcagc tcctctccct tccatgcaga gagggaaaat gcttaacggt  2340
ggtaaagctg ataaaattgc actgaggaaa taactgtatt cttacctgaa cagtggtaat  2400
agggacagca ccaggatggt cgatgaaaaa ctgtttgtca tctcgaagat ctgacaacaa  2460
ccaaggttag acaatcaaaa aggccaggat catgagttga ctgaagatct tgcaagtgtc  2520
ttttataaag gtatacactt gctatacagt agctatttca ttggaggatg cttaaaggcg  2580
tgtgttatag gatacggttg ctttatcaca agaagtgcaa gatacaagaa gaagcctgtt  2640
gaccaatgat attctctgaa aactaccctc agtttcacct aacgaataca tcttgaacat  2700
gtacaagttt taaccacaat caagagaagg tgaagtttta tgtccactaa tgtcatgata  2760
tatattatac cagagcagct taataaagtg aaaaggaaaa tggcagtgta agcatgggaa  2820
tcagacatat atataaataa atgcataaac aaggacaaat gtgagaggag gaagtaacct  2880
agtttggttc caacaaggac aattgggaca ccaggagcat agtgcttcaa ctcaggaatc  2940
cactgtaaaa gaaagaagc atcaaaattt ggaactctca attgttaaat agtcgaccag   3000
tcggacgaa actgaccttc ttggaaacat tctcataact agccttacta atgagagaga   3060
aggcaagaat gaaaacatca gcaccacggt aactcaaagg tcttaatctg ttatagtcct  3120
cttgccctgc ataaaccaaa aacataattt cgacctctga ttcatcacgg aaagctctct  3180
```

```
caccaaggat tatgaattgg atcatcattc atttacctgc agtatcccac aatccaagat     3240
tcaccgtggc cccattgaca accacatttg cactaaagtt atcgaaaaca gtcggaacat     3300
aatcctgttc caatggaaat gtatacaaca tttttagtat gtatggatcc caattcatat     3360
atggcacaat cagaatcaaa tgaatcagat atcaaaaaaa ggagggagaa tgattgatga     3420
atanccgtgg gaaaggtgtt gctggtataa gaaatcagca aacaggtttt accaacagct     3480
ccatcaccaa cggtgacgca ctttatgaac cttgatcgcg tcataagggc gaattaattc     3540
actggccgtc gttttacaac gactcagagc ttgacaggag gcccgatcta gtaacataga     3600
tgacaccgcg cgcgataatt tatcctagtt tgcgcgctat attttgtttt ctatcgcgta     3660
ttaaatgtat aattgcggga ctctaatcat aaaaacccat ctcataaata acgtcatgca     3720
ttacatgtta attattacat gcttaacgta attcaacaga aattatatga taatcatcgc     3780
aagaccggca acaggattca atcttaagaa actttattgc caaatgtttg aacgatcggg     3840
gatcatccgg gtctgtggcg ggaactccac gaaaatatcc gaacgcagca agatctagag     3900
cttgggtccc gctcagaaga actcgtcaag aaggcgatag aaggcgatgc gctgcgaatc     3960
gggagcggcg ataccgtaaa gcacgaggaa gcggtcagcc cattcgccgc caagctcttc     4020
agcaatatca cgggtagcca acgctatgtc ctgatagcgg tccgccacac ccagccggcc     4080
acagtcgatg aatccagaaa agcggccatt ttccaccatg atattcggca agcaggcatc     4140
gccatgggtc acgacgagat cctcgccgtc gggcatgcgc gccttgagcc tggcgaacag     4200
ttcggctggc gcgagcccct gatgctcttc gtccagatca tcctgatcga caagaccggc     4260
ttccatccga gtacgtgctc gctcgatgcg atgtttcgct tggtggtcga atgggcaggt     4320
agccggatca agcgtatgca gccgccgcat tgcatcagcc atgatggata ctttctcggc     4380
aggagcaagg tgagatgaca ggagatcctg ccccggcact cgcccaata gcagccagtc     4440 ccttcccgct tcagtgacaa cgtcgagcac agctgcgcaa ggaacgcccg tcgtggccag     4500
ccacgatagc cgcgctgcct cgtcctgcag ttcattcagg gcaccggaca ggtcggtctt     4560
gacaaaaaga accgggcgcc cctgcgctga cagccggaac acggcggcat cagagcagcc     4620
gattgtctgt tgtgcccagt catagccgaa tagcctctcc acccaagcgg ccggagaacc     4680
tgcgtgcaat ccatcttgtt caatcatgcg aaacgatcca gatccggtgc agattatttg     4740
gattgagagt gaatatgaga ctctaattgg ataccgaggg gaatttatgg aacgtcagtg     4800
gagcattttt gacaagaaat atttgctagc tgatagtgac cttaggcgac ttttgaacgc     4860
gcaataatgg tttctgacgt atgtgcttag ctcattaaac tccagaaacc cgcggctgag     4920
tggctccttc aacgttgcgg ttctgtcagt tccaaacgta aaacggcttg tcccgcgtca     4980 tcggcgggg tcataacgtg actcccttaa ttctccgctc atgatcagat tgtcgtttcc     5040
cgccttcagt ttaaactatc agtgtttgac aggatcctgc ttggtaataa ttgtcattag     5100
attgttttta tgcatagatg cactcgaaat cagccaattt tagacaagta tcaaacggat     5160
gttaattcag tacattaaag acgtccgcaa tgtgttatta agttgtctaa gcgtcaattt     5220
gtttacacca caatatatcc tgccaccagc cagccaacag ctccccgacc ggcagctcgg     5280
cacaaaatca ccacgcgtta ccaccacgcc ggcggccgc atggtgttga ccgtgttcgc     5340
cggcattgcc gagttcgagc gttccctaat catcgaccgc acccggagcg ggcgcgaggc     5400
cgccaaggcc cgaggcgtga agtttggccc ccgccctacc ctcacccgg cacagatcgc     5460 gcacgcccgc gagctgatcg accaggaagg ccgcaccgtg aaagaggcgg ctgcactgct     5520
```

```
tggcgtgcat cgctcgaccc tgtaccgcgc acttgagcgc agcgaggaag tgacgcccac   5580
cgaggccagg cggcgcggtg ccttccgtga ggacgcattg accgaggccg acgccctggc   5640
ggccgccgag aatgaacgcc aagaggaaca agcatgaaac cgcaccagga cggccaggac   5700
gaaccgtttt tcattaccga agagatcgag gcggagatga tcgcggccgg gtacgtgttc   5760
gagccgcccg cgcacgtctc aaccgtgcgc ctgcatgaaa tcctggccgg tttgtctgat   5820
gccaagctgg cggcctggcc ggccagcttg gccgctgaag aaaccgagcg ccgccgtcta   5880
aaaaggtgat gtgtatttga gtaaaacagc ttgcgtcatg cggtcgctgc gtatatgatg   5940
cgatgagtaa ataaacaaat acgcaagggg aacgcatgaa ggttatcgct gtacttaacc   6000
agaaaggcgg gtcaggcaag acgaccatcg caacccatct agcccgcgcc ctgcaactcg   6060
ccggggccga tgttctgtta gtcgattccg atccccaggg cagtgccgcc gattgggcgg   6120
ccgtgcggga agatcaaccg ctaaccgttg tcggcatcga ccgcccgacg attgaccgcg   6180
acgtgaaggc catcgccgg cgcgacttcg tagtgatcga cggagcgccc caggcggcgg   6240
acttggctgt gtccgcgatc aaggcagccg acttcgtgct gattccggtg cagccaagcc   6300
cttacgacat atgggccacc gccgacctgg tggagctggt taagcagcgc attgaggtca   6360
cggatggaag gctacaagcg gcctttgtcg tgtcgcgggc gatcaaaggc acgcgcatcg   6420
gcggtgaggt tgccgaggcg ctggccgggt acgagctgcc cattcttgag tcccgtatca   6480
cgcagcgcgt gagctaccca ggcactgccg ccgccggcac aaccgttctt gaatcagaac   6540
ccgagggcga cgctgcccgc gaggtccagg cgctggccgc tgaaattaaa tcaaaactca   6600
tttgagttaa tgaggtaaag agaaaatgag caaaagcaca aacacgctaa gtgccggccg   6660
tccgagcgca cgcagcagca aggctgcaac gttggccagc ctggcagaca cgccagccat   6720
gaagcgggtc aactttcagt tgccggcgga ggatcacacc aagctgaaga tgtacgcggt   6780
acgccaaggc aagaccatta ccgagctgct atctgaatac atcgcgcagc taccagagta   6840
aatgagcaaa tgaataaatg agtagatgaa ttttagcggc taaaggaggc ggcatggaaa   6900
atcaagaaca accaggcacc gacgccgtgg aatgccccat gtgtggagga acggcggtt   6960 ggccaggcgt aagcggctgg gttgtctgcc ggccctgcaa tggcactgga accccaagc   7020 ccgaggaatc ggcgtgagcg gtcgcaaacc atcggcccg gtacaaatcg gcgcggcgct   7080
gggtgatgac ctggtggaga gttgaaggc cgcgcaggcc gcccagcggc aacgcatcga   7140
ggcagaagca cgccccggtg aatcgtggca agcggccgct gatcgaatcc gcaaagaatc   7200
ccggcaaccg ccggcagccg gtgcgccgtc gattaggaag ccgcccaagg cgacgagca   7260 accagatttt ttcgttccga tgctctatga cgtgggcacc cgcgatagtc gcagcatcat   7320
ggacgtggcc gttttccgtc tgtcgaagcg tgaccgacga gctggcgagg tgatccgcta   7380
cgagcttcca gacgggcacg tagaggtttc cgcagggccg gccggcatgg ccagtgtgtg   7440
ggattacgac ctggtactga tggcggtttc ccatctaacc gaatccatga accgataccg   7500
ggaagggaag ggagacaagc ccggccgcgt gttccgtcca cacgttgcgg acgtactcaa   7560
gttctgccgg cgagccgatg gcggaaagca gaaagacgac ctggtagaaa cctgcattcg   7620
gttaaacacc acgcacgttg ccatgcagcg tacgaagaag gccaagaacg gccgcctggt   7680
gacggtatcc gagggtgaag ccttgattag ccgctacaag atcgtaaaga gcgaaaccgg   7740
gcggccggag tacatcgaga tcgagctagc tgattggatg taccgcgaga tcacagaagg   7800
caagaacccg gacgtgctga cggttcaccc cgattacttt ttgatcgatc ccggcatcgg   7860
ccgttttctc taccgcctgg cacgccgcgc cgcaggcaag gcagaagcca gatggttgtt   7920
```

```
caagacgatc tacgaacgca gtggcagcgc cggagagttc aagaagttct gtttcaccgt   7980
gcgcaagctg atcgggtcaa atgacctgcc ggagtacgat ttgaaggagg aggcggggca   8040
ggctggcccg atcctagtca tgcgctaccg caacctgatc gagggcgaag catccgccgg   8100
ttcctaatgt acggagcaga tgctagggca aattgcccta gcaggggaaa aaggtcgaaa   8160
aggtctcttt cctgtggata gcacgtacat tgggaaccca aagccgtaca ttgggaaccg   8220
gaacccgtac attgggaacc caaagccgta cattgggaac cggtcacaca tgtaagtgac   8280
tgatataaaa gagaaaaaag gcgatttttc cgcctaaaac tctttaaaac ttattaaaac   8340
tcttaaaacc cgcctggcct gtgcataact gtctggccag cgcacagccg aagagctgca   8400
aaaagcgcct acccttcggt cgctgcgctc cctacgcccc gccgcttcgc gtcggcctat   8460
cgcggccgct ggccgctcaa aaatggctgg cctacggcca ggcaatctac cagggcgcgg   8520
acaagccgcg ccgtcgccac tcgaccgccg gcgcccacat caaggcaccc tgcctcgcgc   8580
gtttcggtga tgacggtgaa aacctctgac acatgcagct cccggagacg gtcacagctt   8640
gtctgtaagc ggatgccggg agcagacaag cccgtcaggg cgcgtcagcg ggtgttggcg   8700
ggtgtcgggg cgcagccatg acccagtcac gtagcgatag cggagtgtat actggcttaa   8760
ctatgcggca tcagagcaga ttgtactgag agtgcaccat atgcggtgtg aaataccgca   8820
cagatgcgta aggagaaaat accgcatcag gcgctcttcc gcttcctcgc tcactgactc   8880
gctgcgctcg tcgttcggc tgcggcgagc ggtatcagct cactcaaagg cggtaatacg   8940
gttatccaca gaatcagggg ataacgcagg aaagaacatg tgagcaaaag gccagcaaaa   9000
ggccaggaac cgtaaaaagg ccgcgttgct ggcgtttttc cataggctcc gcccccctga   9060
cgagcatcac aaaaatcgac gctcaagtca gaggtggcga acccgacag gactataaag   9120
ataccaggcg tttccccctg gaagctccct cgtgcgctct cctgttccga ccctgccgct   9180
taccggatac ctgtccgcct ttctcccttc gggaagcgtg gcgctttctc atagctcacg   9240
ctgtaggtat ctcagttcgg tgtaggtcgt tcgctccaag ctgggctgtg tgcacgaacc   9300
cccgttcag cccgaccgct gcgccttatc cggtaactat cgtcttgagt ccaacccggt   9360
aagacacgac ttatcgccac tggcagcagc cactggtaac aggattagca gagcgaggta   9420
tgtaggcggt gctacagagt tcttgaagtg gtggcctaac tacggctaca ctagaaggac   9480
agtatttggt atctgcgctc tgctgaagcc agttaccttc ggaaaaagag ttggtagctc   9540
ttgatccggc aaacaaacca ccgctggtag cggtggtttt tttgtttgca agcagcagat   9600
tacgcgcaga aaaaaggat ctcaagaaga tcctttgatc ttttctacgg ggtctgacgc   9660
tcagtggaac gaaaactcac gttaagggat tttggtcatg catgatatat ctcccaattt   9720
gtgtagggct tattatgcac gcttaaaaat aataaaagca gacttgacct gatagtttgg   9780
ctgtgagcaa ttatgtgctt agtgcatcta acgcttgagt taagccgcgc cgcgaagcgg   9840
cgtcggcttg aacgaatttc tagctagaca ttatttgccg actaccttgg tgatctcgcc   9900
tttcacgtag tggacaaatt cttccaactg atctgcgcgc gaggccaagc gatcttcttc   9960
ttgtccaaga taagcctgtc tagcttcaag tatgacgggc tgatactggg ccggcaggcg   10020
ctccattgcc cagtcggcag cgacatcctt cggcgcgatt ttgccggtta ctgcgctgta   10080
ccaaatgcgg gacaacgtaa gcactacatt tcgctcatcg ccagcccagt cgggcggcga   10140
gttccatagc gttaaggttt catttagcgc ctcaaataga tcctgttcag gaaccggatc   10200
aaagagttcc tccgccgctg gacctaccaa ggcaacgcta tgttctcttg cttttgtcag   10260
```

```
caagatagcc agatcaatgt cgatcgtggc tggctcgaag atacctgcaa gaatgtcatt    10320
gcgctgccat tctccaaatt gcagttcgcg cttagctgga taacgccacg gaatgatgtc    10380
gtcgtgcaca acaatggtga cttctacagc gcggagaatc tcgctctctc caggggaagc    10440
cgaagtttcc aaaaggtcgt tgatcaaagc tcgccgcgtt gtttcatcaa gccttacggt    10500
caccgtaacc agcaaatcaa tatcactgtg tggcttcagg ccgccatcca ctgcggagcc    10560
gtacaaatgt acggccagca acgtcggttc gagatggcgc tcgatgacgc caactacctc    10620
tgatagttga gtcgatactt cggcgatcac cgcttccccc atgatgttta actttgtttt    10680
agggcgactg ccctgctgcg taacatcgtt gctgctccat aacatcaaac atcgaccac     10740 ggcgtaacgc gcttgctgct tggatgcccg aggcatagac tgtaccccaa aaaacagtc     10800 ataacaagcc atgaaaaccg ccactgcg                                       10828

<210> SEQ ID NO 75
<211> LENGTH: 10036
<212> TYPE: DNA
<213> ORGANISM: Artificial sequence
<220> FEATURE:
<223> OTHER INFORMATION: Description of the artificial sequence:
      transgenic expression vector pSUN3NIT_HvRacB_s for expression
      of barley RacB sense RNA  fragment

<400> SEQUENCE: 75
ttccatggac atacaaatgg acgaacggat aaaccttttc acgccctttt aaatatccga      60
ttattctaat aaacgctctt ttctcttagg tttacccgcc aatatatcct gtcaaacact     120
gatagtttaa actgaaggcg ggaaacgaca atcagatcta gtaggaaaca gctatgacca     180
tgattacgcc aagcttgcat gcctgcaggt cgactctaga ggatccccca tcaagatctt     240
ggtgatgtag caagagctaa gttgtacttc gatycggttg acattactc gagaccagat      300 gttttacact tgaccgtaaa tgagcacccg aagaaaccgg taacattcat ttcgaaggta     360
gagaaagcgg aagatgactc aaacaagtaa tcggttgtga ttcgtcagtt catgtcactc     420
ctatgaagga gtcaagttca aaatgttatg ttgagtttca aacttttatg ctaaactttt     480
tttcttaatt ttcgttaata atggaagaga accaattctc ttgtatctaa agattatcca     540
tctatcatcc aatttgagtg ttcaattctg gatgttgtgt tacccctacat tctacaacca    600 tgtagccaat tattatgaat ctggctttga tttcagttgt gttcttttct tttttctt      660 gcatatttgc atttagaatg tttaataatt aagttactgt atttccacat acattagttc     720
caagaatata catatattaa tttatttttc ttaaaaatgt tttggaatga ctaatattga     780
caacgaaaat agaagctatg ctaaaccatt acgtatatgt gacttcacat gttgttgttt     840
tacattccct atatatatgg atggctgtca caatcagaaa cgtgatcgaa aaaagacaaa     900
cagtgtttgc ataaaaagac tatttcgttt cattgacaat tgtgtttat ttgtaaagaa      960 aagtggcaaa gtggaatttg agttcctgca agtaagaaag atgaaataaa agacttgagt    1020
gtgtgttttt ttcttttatc tgaaagctgc aatgaaatat tcctaccaag cccgtttgat    1080
tattaattgg ggtttggttt tcttgatgcg aactaattgg ttatataaga aactatacaa    1140
tccatgttaa ttcaaaaatt ttgatttctc ttgtaggaat atgatttact atatgagact    1200
ttcttttcgc caataatagt aaatccaaag atatttgacc ggaccaaaac acattgatct    1260
attttttagt ttatttaatc cagtttctct gagataattc attaaggaaa acttagtatt    1320
aacccatcct aagattaaat aggagccaaa ctcacatttc aaatattaaa taacataaaa    1380
tggatttaaa aaatctatac gtcaaatttt atttatgaca tttcttattt aaatttatat    1440
```

```
ttaatgaaat acagctaaga caaaccaaaa aaaaaatact ttctaagtgg tccaaaacat   1500
caattccgtt caatattatt aggtagaatc gtacgaccaa aaaaggtagg ttaatacgaa   1560
attacaaaca tatctatata catagtatat attattaccct attatgagga atcaaaatgc   1620
atcaaatatg gatttaagga atccataaaa gaataaattc tacggaaaaa aaaaaaagaa   1680
taaattcttt taagttttta atttgttttt tatttggtag ttctccattt tgttttattt   1740
cgtttggatt tattgtgtcc aaatactttg taaaccaccg ttgtaattct taaacggggt   1800
tttcacttct tttttatatt cagacataaa gcatcggctg gtttaatcaa tcaatagatt   1860
ttattttcct tctcaattat tagtaggttt gatgtgaact ttacaaaaaa aacaaaaaca   1920
aatcaatgca gagaaaagaa accacgtggg ctagtcccac cttgtttcat ttccaccaca   1980
ggttcgatct tcgttaccgt ctccaatagg aaaataaacg tgaccacaaa aaaaaaacaa   2040 aaaaaagtc tatatattgc ttctctcaag tctctgagtg tcatgaacca agtaaaaaa    2100 caaagactcg agtggatccc cgggccgcca tggccgcggg atggatccga tgagcgcgtc   2160
caggttcata aagtgcgtca cggtcgggga cggcgccgtc ggcaagacct gcatgctcat   2220
ctcctacacc tccaacacct tccccaccga ctatgttccg acagtgtttg ataacttcag   2280
tgccaacgtt gtggttgatg gtaatactgt caacctcggc ctctgggaca ctgcaggtca   2340
agaggattac aacagactga gaccactgag ctatcgtgga gctgatgttt tcttctggc   2400 tttctcactg atcagtaagg ccagctatga gaatgtttcg aagaagtgga tacctgaact   2460
gaagcattat gcacctggtg tgccaattat tctcgtaggg acaaagcttg atcttcgaga   2520
cgacaagcag ttctttgtgg accatcctgg tgctgtccct atcactactg ctcagggaga   2580
ggagctaaga aagcaaatag gcgctccata ctacatcgaa tgcagctcga agacccaact   2640
aaacgtgaag ggcgtcttcg atgcggcgat aaaggttgtg ctgcagccgc ctaaggcgaa   2700
gaagaagaaa aaggtgcaga gggggcgtg ctccattttg tgaaattcac tggccgtcgt    2760
tttacaacga ctcagagctt gacaggaggc ccgatctagt aacatagatg acaccgcgcg   2820
cgataattta tcctagtttg cgcgctatat tttgttttct atcgcgtatt aaatgtataa   2880
ttgcgggact ctaatcataa aaacccatct cataaataac gtcatgcatt acatgttaat   2940
tattacatgc ttaacgtaat tcaacagaaa ttatatgata atcatcgcaa gaccggcaac   3000
aggattcaat cttaagaaac tttattgcca aatgtttgaa cgatcgggga tcatccgggt   3060
ctgtggcggg aactccacga aaatatccga acgcagcaag atctagagct tgggtcccgc   3120
tcagaagaac tcgtcaagaa ggcgatagaa ggcgatgcgc tgcgaatcgg gagcggcgat   3180
accgtaaagc acgaggaagc ggtcagccca ttcgccgcca agctcttcag caatatcacg   3240
ggtagccaac gctatgtcct gatagcggtc cgccacaccc agccggccac agtcgatgaa   3300
tccagaaaag cggccatttt ccaccatgat attcggcaag caggcatcgc catgggtcac   3360
gacgagatcc tcgccgtcgg gcatgcgcgc cttgagcctg gcgaacagtt cggctggcgc   3420
gagcccctga tgctcttcgt ccagatcatc ctgatcgaca gaccggctt ccatccgagt    3480 acgtgctcgc tcgatgcgat gtttcgcttg gtggtcgaat gggcaggtag ccggatcaag   3540
cgtatgcagc cgccgcattg catcagccat gatggatact ttctcggcag gagcaaggtg   3600
agatgacagg agatcctgcc ccggcactto gcccaatagc agccagtccc ttcccgcttc   3660
agtgacaacg tcgagcacag ctgcgcaagg aacgcccgtc gtggccagcc acgatagccg   3720
cgctgcctcg tcctgcagtt cattcagggc accggacagg tcggtcttga caaaagaac   3780
```

```
cgggcgcccc tgcgctgaca gccggaacac ggcggcatca gagcagccga ttgtctgttg   3840
tgcccagtca tagccgaata gcctctccac ccaagcggcc ggagaacctg cgtgcaatcc   3900
atcttgttca atcatgcgaa acgatccaga tccggtgcag attatttgga ttgagagtga   3960
atatgagact ctaattggat accgagggga atttatggaa cgtcagtgga gcattttga    4020 caagaaatat ttgctagctg atagtgacct taggcgactt ttgaacgcgc aataatggtt   4080
tctgacgtat gtgcttagct cattaaactc cagaaaccca cggctgagtg gctccttcaa   4140
cgttgcggtt ctgtcagttc caaacgtaaa acggcttgtc ccgcgtcatc ggcggggtc    4200 ataacgtgac tcccttaatt ctccgctcat gatcagattg tcgtttcccg ccttcagttt   4260
aaactatcag tgtttgacag gatcctgctt ggtaataatt gtcattagat tgttttatg    4320 catagatgca ctcgaaatca gccaatttta gacaagtatc aaacggatgt taattcagta   4380
cattaaagac gtccgcaatg tgttattaag ttgtctaagc gtcaatttgt ttacaccaca   4440
atatatcctg ccaccagcca gccaacagct ccccgaccgg cagctcggca caaaatcacc   4500
acgcgttacc accacgccgg ccggccgcat ggtgttgacc gtgttcgccg gcattgccga   4560
gttcgagcgt tccctaatca tcgaccgcac ccggagcggg cgcgaggccg caaggcccg    4620 aggcgtgaag tttggccccc gccctaccct caccccggca cagatcgcgc acgcccgcga   4680
gctgatcgac caggaaggcc gcaccgtgaa agaggcggct gcactgcttg gcgtgcatcg   4740
ctcgaccctg taccgcgcac ttgagcgcag cgaggaagtg acgcccaccg aggccaggcg   4800
gcgcggtgcc ttccgtgagg acgcattgac cgaggccgac gccctggcgg ccgccgagaa   4860
tgaacgccaa gaggaacaag catgaaaccg caccaggacg gccaggacga accgtttttc   4920
attaccgaag agatcgaggc ggagatgatc gcggccgggt acgtgttcga gccgcccgcg   4980
cacgtctcaa ccgtgcggct gcatgaaatc ctggccggtt tgtctgatgc caagctggcg   5040
gcctggccgg ccagcttggc cgctgaagaa accgagcgcc gccgtctaaa aggtgatgt    5100 gtatttgagt aaaacagctt gcgtcatgcg gtcgctgcgt atatgatgcg atgagtaaat   5160
aaacaaatac gcaaggggaa cgcatgaagg ttatcgctgt acttaaccag aaaggcgggt   5220
caggcaagac gaccatcgca acccatctag cccgcgccct gcaactcgcc ggggccgatg   5280
ttctgttagt cgattccgat ccccagggca gtgcccgcga ttgggcggcc gtgcgggaag   5340
atcaaccgct aaccgttgtc ggcatcgacc gcccgacgat tgaccgcgac gtgaaggcca   5400
tcggccggcg cgacttcgta gtgatcgacg gagcgcccca ggcggcggac ttggctgtgt   5460
ccgcgatcaa ggcagccgac ttcgtgctga ttccggtgca gccaagccct tacgacatat   5520
gggccaccgc cgacctggtg gagctggtta agcagcgcat tgaggtcacg gatggaaggc   5580
tacaagcggc ctttgtcgtg tcgcgggcga tcaaaggcac gcgcatcggc ggtgaggttg   5640
ccgaggcgct ggccgggtac gagctgccca ttcttgagtc ccgtatcacg cagcgcgtga   5700
gctacccagg cactgccgcc gccggcacaa ccgttcttga atcagaaccc gagggcgacg   5760
ctgcccgcga ggtccaggcg ctggccgctg aaattaaatc aaaactcatt tgagttaatg   5820
aggtaaagag aaaatgagca aaagcacaaa acgctaagt gccggccgtc cgagcgcacg    5880
cagcagcaag gctgcaacgt tggccagcct ggcagacacg ccagccatga agcgggtcaa   5940
ctttcagttg ccggcggagg atcacaccaa gctgaagatg tacgcggtac gccaaggcaa   6000
gaccattacc gagctgctat ctgaatacat cgcgcagcta ccagagtaaa tgagcaaatg   6060
aataaatgag tagatgaatt ttagcggcta aggaggcgg catggaaaat caagaacaac   6120
caggcaccga cgccgtggaa tgcccatgt gtggaggaac gggcggttgg ccaggcgtaa   6180
```

```
gcggctgggt tgtctgccgg ccctgcaatg gcactggaac ccccaagccc gaggaatcgg    6240
cgtgagcggt cgcaaaccat ccggcccggt acaaatcggc gcggcgctgg gtgatgacct    6300
ggtggagaag ttgaaggccg cgcaggccgc ccagcggcaa cgcatcgagg cagaagcacg    6360
ccccggtgaa tcgtggcaag cggccgctga tcgaatccgc aaagaatccc ggcaaccgcc    6420
ggcagccggt gcgccgtcga ttaggaagcc gcccaagggc gacgagcaac cagattttt    6480 cgttccgatg ctctatgacg tgggcacccg cgatagtcgc agcatcatgg acgtggccgt    6540
tttccgtctg tcgaagcgtg accgacgagc tggcgaggtg atccgctacg agcttccaga    6600
cgggcacgta gaggtttccg cagggccggc cggcatggcc agtgtgtggg attacgacct    6660
ggtactgatg gcggtttccc atctaaccga atccatgaac cgataccggg aagggaaggg    6720
agacaagccc ggccgcgtgt tccgtccaca cgttgcggac gtactcaagt tctgccggcg    6780
agccgatggc ggaaagcaga aagacgacct ggtagaaacc tgcattcggt taaacaccac    6840
gcacgttgcc atgcagcgta cgaagaaggc caagaacggc cgcctggtga cggtatccga    6900
gggtgaagcc ttgattagcc gctacaagat cgtaaagagc gaaaccgggc ggccggagta    6960
catcgagatc gagctagctg attggatgta ccgcgagatc acagaaggca agaacccgga    7020
cgtgctgacg gttcaccccg attactttt gatcgatccc ggcatcggcc gttttctcta    7080
ccgcctggca cgccgcgccg caggcaaggc agaagccaga tggttgttca agacgatcta    7140
cgaacgcagt ggcagcgccg agagttcaa gaagttctgt ttcaccgtgc gcaagctgat    7200
cgggtcaaat gacctgccgg agtacgattt gaaggaggag gcggggcagg ctggcccgat    7260
cctagtcatg cgctaccgca acctgatcga gggcgaagca tccgccggtt cctaatgtac    7320
ggagcagatg ctagggcaaa ttgccctagc aggggaaaaa ggtcgaaaag gtctctttcc    7380
tgtggatagc acgtacattg gaacccaaa gccgtacatt gggaaccgga acccgtacat    7440
tgggaaccca aagccgtaca ttgggaaccg gtcacacatg taagtgactg atataaaaga    7500 gaaaaaggc gattttccg cctaaaactc tttaaaactt attaaaactc ttaaaacccg    7560
cctggcctgt gcataactgt ctggccagcg cacagccgaa gagctgcaaa aagcgcctac    7620
ccttcggtcg ctgcgctccc tacgccccgc cgcttcgcgt cggcctatcg cggccgctgg    7680
ccgctcaaaa atggctggcc tacggccagg caatctacca gggcgcggac aagccgcgcc    7740
gtcgccactc gaccgccggc gcccacatca aggcaccctg cctcgcgcgt ttcggtgatg    7800
acggtgaaaa cctctgacac atgcagctcc cggagacggt cacagcttgt ctgtaagcgg    7860
atgccgggag cagacaagcc cgtcagggcg cgtcagcggg tgttggcggg tgtcggggcg    7920
cagccatgac ccagtcacgt agcgatagcg gagtgtatac tggcttaact atgcggcatc    7980
agagcagatt gtactgagag tgcaccatat gcggtgtgaa ataccgcaca gatgcgtaag    8040
gagaaaatac cgcatcaggc gctcttccgc ttcctcgctc actgactcgc tgcgctcggt    8100
cgttcggctg cggcgagcgg tatcagctca ctcaaaggcg gtaatacggt tatccacaga    8160
atcaggggat aacgcaggaa agaacatgtg agcaaaaggc cagcaaaagg ccaggaaccg    8220
taaaaaggcc gcgttgctgg cgttttccca taggctccgc cccctgacg agcatcacaa    8280 aaatcgacgc tcaagtcaga ggtggcgaaa cccgacagga ctataaagat accaggcgtt    8340
tccccctgga agctccctcg tgcgctctcc tgttccgacc ctgccgctta ccggatacct    8400
gtccgccttt ctcccttcgg gaagcgtggc gctttctcat agctcacgct gtaggtatct    8460
cagttcggtg taggtcgttc gctccaagct gggctgtgtg cacgaacccc ccgttcagcc    8520
```

-continued

```
cgaccgctgc gccttatccg gtaactatcg tcttgagtcc aacccggtaa gacacgactt      8580
atcgccactg gcagcagcca ctggtaacag gattagcaga gcgaggtatg taggcggtgc      8640
tacagagttc ttgaagtggt ggcctaacta cggctacact agaaggacag tatttggtat      8700
ctgcgctctg ctgaagccag ttaccttcgg aaaaagagtt ggtagctctt gatccggcaa      8760
acaaaccacc gctggtagcg gtggttttttt tgtttgcaag cagcagatta cgcgcagaaa     8820
aaaaggatct caagaagatc ctttgatctt ttctacgggg tctgacgctc agtggaacga     8880
aaactcacgt taagggattt tggtcatgca tgatatatct cccaatttgt gtagggctta     8940
ttatgcacgc ttaaaaataa taaaagcaga cttgacctga tagtttggct gtgagcaatt     9000
atgtgcttag tgcatctaac gcttgagtta agccgcgccg cgaagcggcg tcggcttgaa     9060
cgaatttcta gctagacatt atttgccgac taccttggtg atctcgcctt tcacgtagtg     9120
gacaaattct tccaactgat ctgcgcgcga ggccaagcga tcttcttctt gtccaagata     9180
agcctgtcta gcttcaagta tgacgggctg atactgggcc ggcaggcgct ccattgccca     9240
gtcggcagcg acatccttcg gcgcgatttt gccggttact gcgctgtacc aaatgcggga     9300
caacgtaagc actacatttc gctcatcgcc agcccagtcg ggcggcgagt tccatagcgt     9360
taaggtttca tttagcgcct caaatagatc ctgttcagga accggatcaa agagttcctc     9420
cgccgctgga cctaccaagg caacgctatg ttctcttgct tttgtcagca agatagccag     9480
atcaatgtcg atcgtggctg gctcgaagat acctgcaaga atgtcattgc gctgccattc     9540
tccaaattgc agttcgcgct tagctggata acgccacgga atgatgtcgt cgtgcacaac     9600
aatggtgact tctacagcgc ggagaatctc gctctctcca ggggaagccg aagtttccaa     9660
aaggtcgttg atcaaagctc gccgcgttgt ttcatcaagc cttacggtca ccgtaaccag     9720
caaatcaata tcactgtgtg gcttcaggcc gccatccact gcggagccgt acaaatgtac     9780
ggccagcaac gtcggttcga gatggcgctc gatgacgcca actacctctg atagttgagt     9840
cgatacttcg gcgatcaccg cttcccccat gatgtttaac tttgtttag ggcgactgcc      9900 ctgctgcgta acatcgttgc tgctccataa catcaaacat cgaccacgg cgtaacgcgc     9960 ttgctgcttg gatgcccgag gcatagactg taccccaaaa aacagtcat aacaagccat     10020 gaaaaccgcc actgcg                                                   10036
```

<210> SEQ ID NO 76
<211> LENGTH: 10036
<212> TYPE: DNA
<213> ORGANISM: Artificial sequence
<220> FEATURE:
<223> OTHER INFORMATION: Description of the artificial sequence: transgenic expression vector pSUN3NIT_HvRacB_as for expression of barley RacB anti sense RNA fragment

<400> SEQUENCE: 76

```
ttccatggac atacaaatgg acgaacggat aaaccttttc acgcccttt aaatatccga       60 ttattctaat aaacgctctt ttctcttagg tttacccgcc aatatatcct gtcaaacact      120
gatagtttaa actgaaggcg ggaaacgaca atcagatcta gtaggaaaca gctatgacca     180
tgattacgcc aagcttgcat gcctgcaggt cgactctaga ggatccccca tcaagatctt     240
ggtgatgtag caagagctaa gttgtacttc gatycggttg gacattactc gagaccagat     300
gttttacact tgaccgtaaa tgagcacccg aagaaaccgg taacattcat ttcgaaggta     360
gagaaagcgg aagatgactc aaacaagtaa tcggttgtga ttcgtcagtt catgtcactc     420
ctatgaagga gtcaagttca aaatgttatg ttgagtttca aacttttatg ctaaactttt     480
```

```
tttcttaatt ttcgttaata atggaagaga accaattctc ttgtatctaa agattatcca      540
tctatcatcc aatttgagtg ttcaattctg gatgttgtgt taccctacat tctacaacca      600
tgtagccaat tattatgaat ctggctttga tttcagttgt gttcttttct ttttttcttt      660
gcatatttgc atttagaatg tttaataatt aagttactgt atttccacat acattagttc      720
caagaatata catatattaa tttatttttc ttaaaaatgt tttggaatga ctaatattga      780
caacgaaaat agaagctatg ctaaaccatt acgtatatgt gacttcacat gttgttgttt      840
tacattccct atatatatgg atggctgtca caatcagaaa cgtgatcgaa aaaagacaaa      900
cagtgtttgc ataaaaagac tatttcgttt cattgacaat ttgtgtttat ttgtaaagaa      960
aagtggcaaa gtggaatttg agttcctgca agtaagaaag atgaaataaa agacttgagt     1020
gtgtgttttt ttcttttatc tgaaagctgc aatgaaatat tcctaccaag cccgtttgat     1080
tattaattgg ggtttggttt tcttgatgcg aactaattgg ttatataaga aactatacaa     1140
tccatgttaa ttcaaaaatt ttgatttctc ttgtaggaat atgatttact atatgagact     1200
ttcttttcgc caataatagt aaatccaaag atatttgacc ggaccaaaac acattgatct     1260
attttttagt ttatttaatc cagtttctct gagataattc attaaggaaa acttagtatt     1320
aacccatcct aagattaaat aggagccaaa ctcacatttc aaatattaaa taacataaaa     1380
tggatttaaa aaatctatac gtcaaatttt atttatgaca tttcttattt aaatttatat     1440
ttaatgaaat acagctaaga caaaccaaaa aaaaaatact ttctaagtgg tccaaaacat     1500
caattccgtt caatattatt aggtagaatc gtacgaccaa aaaaggtagg ttaatacgaa     1560
attacaaaca tatctatata catagtatat attattacct attatgagga atcaaaatgc     1620
atcaaatatg gatttaagga atccataaaa gaataaattc tacggaaaaa aaaaaaagaa     1680
taaattcttt taagttttta atttgttttt tatttggtag ttctccattt tgttttattt     1740
cgtttggatt tattgtgtcc aaatactttg taaaccaccg ttgtaattct taaacggggt     1800
tttcacttct tttttatatt cagacataaa gcatcggctg gtttaatcaa tcaatagatt     1860
ttattttct tctcaattat tagtaggttt gatgtgaact ttacaaaaaa aacaaaaaca     1920
aatcaatgca gagaaaagaa accacgtggg ctagtcccac cttgtttcat ttccaccaca     1980
ggttcgatct tcgttaccgt ctccaatagg aaaataaacg tgaccacaaa aaaaaaacaa     2040
aaaaaaagtc tatatattgc ttctctcaag tctctgagtg tcatgaacca agtaaaaaa     2100
caaagactcg agtggatccc cggtcacaaa atggagcacg cccccctctg cacctttttc     2160
ttcttcttcg ccttaggcgg ctgcagcaca acctttatcg ccgcatcgaa gacgcccttc     2220
acgtttagtt gggtcttcga gctgcattcg atgtagtatg gagcgcctat ttgctttctt     2280
agctcctctc cctgagcagt agtgataggg acagcaccag gatggtccac aaagaactgc     2340
ttgtcgtctc gaagatcaag cttttgtccct acgagaataa ttggcacacc aggtgcataa     2400
tgcttcagtt caggtatcca cttcttcgaa acattctcat agctggcctt actgatcagt     2460
gagaaagcca gaagaaaaac atcagctcca cgatagctca gtggtctcag tctgttgtaa     2520
tcctcttgac ctgcagtgtc ccagaggccg aggttgacag tattaccatc aaccacaacg     2580
ttggcactga agttatcaaa cactgtcgga acatagtcgg tggggaaggt gttgagggtg     2640
taggagatga gcatgcaggt cttgccgacg gcgccgtccc cgaccgtgac gcactttatg     2700
aacctggacg cgctcatcgg atccatcccg cggccatggc ggcaattcac tggccgtcgt     2760
tttacaacga ctcagagctt gacaggaggc ccgatctagt aacatagatg acaccgcgcg     2820
```

```
cgataattta tcctagtttg cgcgctatat tttgttttct atcgcgtatt aaatgtataa    2880
ttgcgggact ctaatcataa aaacccatct cataaataac gtcatgcatt acatgttaat    2940
tattacatgc ttaacgtaat tcaacagaaa ttatatgata atcatcgcaa gaccggcaac    3000
aggattcaat cttaagaaac tttattgcca aatgtttgaa cgatcgggga tcatccgggt    3060
ctgtggcggg aactccacga aaatatccga acgcagcaag atctagagct tgggtcccgc    3120
tcagaagaac tcgtcaagaa ggcgatagaa ggcgatgcgc tgcgaatcgg gagcggcgat    3180
accgtaaagc acgaggaagc ggtcagccca ttcgccgcca agctcttcag caatatcacg    3240
ggtagccaac gctatgtcct gatagcggtc cgccacaccc agccggccac agtcgatgaa    3300
tccagaaaag cggccatttt ccaccatgat attcggcaag caggcatcgc catgggtcac    3360
gacgagatcc tcgccgtcgg gcatgcgcgc cttgagcctg gcgaacagtt cggctggcgc    3420
gagcccctga tgctcttcgt ccagatcatc ctgatcgaca gaccggcttc catccgagt     3480 acgtgctcgc tcgatgcgat gtttcgcttg gtggtcgaat gggcaggtag ccggatcaag    3540
cgtatgcagc cgccgcattg catcagccat gatggatact ttctcggcag gagcaaggtg    3600
agatgacagg agatcctgcc ccggcacttc gcccaatagc agccagtccc ttcccgcttc    3660
agtgacaacg tcgagcacag ctgcgcaagg aacgcccgtc gtggccagcc acgatagccg    3720
cgctgcctcg tcctgcagtt cattcagggc accggacagg tcggtcttga caaaaagaac    3780
cgggcgcccc tgcgctgaca gccggaacac ggcggcatca gagcagccga ttgtctgttg    3840
tgcccagtca tagccgaata gcctctccac ccaagcggcc ggagaacctg cgtgcaatcc    3900
atcttgttca atcatgcgaa acgatccaga tccggtgcag attatttgga ttgagagtga    3960
atatgagact ctaattggat accgagggga atttatggaa cgtcagtgga gcattttga     4020 caagaaatat ttgctagctg atagtgacct taggcgactt ttgaacgcgc aataatggtt    4080
tctgacgtat gtgcttagct cattaaactc cagaaacccg cggctgagtg gctccttcaa    4140
cgttgcggtt ctgtcagttc caaacgtaaa acggcttgtc ccgcgtcatc ggcggggtc     4200 ataacgtgac tcccttaatt ctccgctcat gatcagattg tcgtttcccg ccttcagttt    4260
aaactatcag tgtttgacag gatcctgctt ggtaataatt gtcattagat tgtttttatg    4320
catagatgca ctcgaaatca gccaatttta gacaagtatc aaacggatgt taattcagta    4380
cattaaagac gtccgcaatg tgttattaag ttgtctaagc gtcaatttgt ttacaccaca    4440
atatatcctg ccaccagcca gccaacagct ccccgaccgg cagctcggca caaaatcacc    4500
acgcgttacc accacgccgg ccggccgcat ggtgttgacc gtgttcgccg gcattgccga    4560
gttcgagcgt tccctaatca tcgaccgcac ccggagcggg cgcgaggccg ccaaggcccg    4620
aggcgtgaag tttggccccc gcctacccct caccccggca cagatcgcgc acgcccgcga    4680
gctgatcgac caggaaggcc gcaccgtgaa agaggcggct gcactgcttg gcgtgcatcg    4740
ctcgaccctg taccgcgcac ttgagcgcag cgaggaagtg acgcccaccg aggccaggcg    4800
gcgcggtgcc ttccgtgagg acgcattgac cgaggccgac gccctggcgg ccgccgagaa    4860
tgaacgccaa gaggaacaag catgaaaccg caccaggacg ccaggacga accgttttc      4920 attaccgaag agatcgaggc ggagatgatc gcggccgggt acgtgttcga gccgcccgcg    4980
cacgtctcaa ccgtgcggct gcatgaaatc ctggccggtt tgtctgatgc caagctggcg    5040
gcctggccgg ccagcttggc cgctgaagaa accgagcgcc gccgtctaaa aaggtgatgt    5100
gtatttgagt aaaacagctt gcgtcatgcg gtcgctgcgt atatgatgcg atgagtaaat    5160
aaacaaatac gcaaggggaa cgcatgaagg ttatcgctgt acttaaccag aaaggcgggt    5220
```

```
caggcaagac gaccatcgca acccatctag cccgcgccct gcaactcgcc ggggccgatg   5280
ttctgttagt cgattccgat ccccagggca gtgcccgcga ttgggcggcc gtgcgggaag   5340
atcaaccgct aaccgttgtc ggcatcgacc gcccgacgat tgaccgcgac gtgaaggcca   5400
tcggccggcg cgacttcgta gtgatcgacg gagcgcccca ggcggcggac ttggctgtgt   5460
ccgcgatcaa ggcagccgac ttcgtgctga ttccggtgca gccaagccct tacgacatat   5520
gggccaccgc cgacctggtg gagctggtta agcagcgcat tgaggtcacg gatggaaggc   5580
tacaagcggc ctttgtcgtg tcgcgggcga tcaaaggcac gcgcatcggc ggtgaggttg   5640
ccgaggcgct ggccgggtac gagctgccca ttcttgagtc ccgtatcacg cagcgcgtga   5700
gctacccagg cactgccgcc gccggcacaa ccgttcttga atcagaaccc gagggcgacg   5760
ctgcccgcga ggtccaggcg ctggccgctg aaattaaatc aaaactcatt tgagttaatg   5820
aggtaaagag aaaatgagca aaagcacaaa cacgctaagt gccggccgtc cgagcgcacg   5880
cagcagcaag gctgcaacgt tggccagcct ggcagacacg ccagccatga agcgggtcaa   5940 cttcagttg ccggcggagg atcacaccaa gctgaagatg tacgcggtac gccaaggcaa   6000
gaccattacc gagctgctat ctgaatacat cgcgcagcta ccagagtaaa tgagcaaatg   6060
aataaatgag tagatgaatt ttagcggcta aggaggcgg catggaaaat caagaacaac   6120
caggcaccga cgccgtggaa tgccccatgt gtggaggaac gggcggttgg ccaggcgtaa   6180
gcggctgggt tgtctgccgg ccctgcaatg gcactggaac ccccaagccc gaggaatcgg   6240
cgtgagcggt cgcaaaccat ccggcccggt acaaatcggc gcggcgctgg gtgatgacct   6300
ggtggagaag ttgaaggccg cgcaggccgc ccagcggcaa cgcatcgagg cagaagcacg   6360
ccccggtgaa tcgtggcaag cggccgctga tcgaatccgc aaagaatccc ggcaaccgcc   6420
ggcagccggt gcgccgtcga ttaggaagcc gcccaagggc gacgagcaac cagattttt   6480 cgttccgatg ctctatgacg tgggcacccg cgatagtcgc agcatcatgg acgtggccgt   6540
tttccgtctg tcgaagcgtg accgacgagc tggcgaggtg atccgctacg agcttccaga   6600
cgggcacgta gaggtttccg cagggccggc cggcatggcc agtgtgtggg attacgacct   6660
ggtactgatg gcggtttccc atctaaccga atccatgaac cgataccggg aagggaaggg   6720
agacaagccc ggccgcgtgt tccgtccaca cgttgcggac gtactcaagt tctgccggcg   6780
agccgatggc ggaaagcaga aagacgacct ggtagaaacc tgcattcggt taaacaccac   6840
gcacgttgcc atgcagcgta cgaagaaggc caagaacggc cgcctggtga cggtatccga   6900
gggtgaagcc ttgattagcc gctacaagat cgtaaagagc gaaaccgggc ggccggagta   6960
catcgagatc gagctagctg attggatgta ccgcgagatc acagaaggca agaacccgga   7020
cgtgctgacg gttcaccccg attactttt gatcgatccc ggcatcggcc gttttctcta   7080
ccgcctggca cgccgcgccg caggcaaggc agaagccaga tggttgttca agacgatcta   7140
cgaacgcagt ggcagcgccg gagagttcaa gaagttctgt tcaccgtgc gcaagctgat   7200 cgggtcaaat gacctgccgg agtacgattt gaaggaggag gcggggcagg ctggcccgat   7260
cctagtcatg cgctaccgca acctgatcga gggcgaagca tccgccggtt cctaatgtac   7320
ggagcagatg ctagggcaaa ttgccctagc aggggaaaaa ggtcgaaaag gtctctttcc   7380
tgtggatagc acgtacattg ggaacccaaa gccgtacatt gggaaccgga accgtacat   7440 tgggaaccca agccgtaca ttgggaaccg gtcacacatg taagtgactg atataaaaga   7500 gaaaaaggc gatttttccg cctaaaactc tttaaaactt attaaaactc ttaaaacccg   7560
```

```
cctggcctgt gcataactgt ctggccagcg cacagccgaa gagctgcaaa aagcgcctac   7620
ccttcggtcg ctgcgctccc tacgccccgc cgcttcgcgt cggcctatcg cggccgctgg   7680
ccgctcaaaa atggctggcc tacgccagg caatctacca gggcgcggac aagccgcgcc    7740
gtcgccactc gaccgccggc gcccacatca aggcaccctg cctcgcgcgt ttcggtgatg   7800
acggtgaaaa cctctgacac atgcagctcc cggagacggt cacagcttgt ctgtaagcgg   7860
atgccgggag cagacaagcc cgtcagggcg cgtcagcggg tgttggcggg tgtcggggcg   7920
cagccatgac ccagtcacgt agcgatagcg gagtgtatac tggcttaact atgcggcatc   7980
agagcagatt gtactgagag tgcaccatat gcggtgtgaa ataccgcaca gatgcgtaag   8040
gagaaaatac cgcatcaggc gctcttccgc ttcctcgctc actgactcgc tgcgctcggt   8100
cgttcggctg cggcgagcgg tatcagctca ctcaaaggcg gtaatacggt tatccacaga   8160
atcaggggat aacgcaggaa agaacatgtg agcaaaaggc cagcaaaagg ccaggaaccg   8220
taaaaaggcc gcgttgctgg cgttttccca taggctccgc cccectgacg agcatcacaa   8280 aaatcgacgc tcaagtcaga ggtggcgaaa cccgacagga ctataaagat accaggcgtt   8340
tccccctgga agctccctcg tgcgctctcc tgttccgacc ctgccgctta ccggatacct   8400
gtccgccttt ctcccttcgg gaagcgtggc gctttctcat agctcacgct gtaggtatct   8460
cagttcggtg taggtcgttc gctccaagct gggctgtgtg cacgaacccc ccgttcagcc   8520
cgaccgctgc gccttatccg gtaactatcg tcttgagtcc aacccggtaa gacacgactt   8580
atcgccactg gcagcagcca ctggtaacag gattagcaga gcgaggtatg taggcggtgc   8640
tacagagttc ttgaagtggt ggcctaacta cggctacact agaaggacag tatttggtat   8700
ctgcgctctg ctgaagccag ttaccttcgg aaaaagagtt ggtagctctt gatccggcaa   8760
acaaaccacc gctggtagcg gtggtttttt tgtttgcaag cagcagatta cgcgcagaaa   8820
aaaaggatct caagaagatc ctttgatctt ttctacgggg tctgacgctc agtggaacga   8880
aaactcacgt taagggattt tggtcatgca tgatatatct cccaatttgt gtagggctta   8940
ttatgcacgc ttaaaaataa taaaagcaga cttgacctga tagtttggct gtgagcaatt   9000
atgtgcttag tgcatctaac gcttgagtta agccgcgccg cgaagcggcg tcggcttgaa   9060
cgaatttcta gctagacatt atttgccgac taccttggtg atctcgcctt tcacgtagtg   9120
gacaaattct tccaactgat ctgcgcgcga ggccaagcga tcttcttctt gtccaagata   9180
agcctgtcta gcttcaagta tgacgggctg atactgggcc ggcaggcgct ccattgccca   9240
gtcggcagcg acatccttcg gcgcgatttt gccggttact gcgctgtacc aaatgcggga   9300
caacgtaagc actacatttc gctcatcgcc agcccagtcg ggcggcgagt tccatagcgt   9360
taaggtttca tttagcgcct caaatagatc ctgttcagga accggatcaa agagttcctc   9420
cgccgctgga cctaccaagg caacgctatg ttctcttgct tttgtcagca agatagccag   9480
atcaatgtcg atcgtggctg gctcgaagat acctgcaaga atgtcattgc gctgccattc   9540
tccaaattgc agttcgcgct tagctggata acgccacgga atgatgtcgt cgtgcacaac   9600
aatggtgact tctacagcgc ggagaatctc gctctctcca ggggaagccg aagtttccaa   9660
aaggtcgttg atcaaagctc gccgcgttgt ttcatcaagc cttacggtca ccgtaaccag   9720
caaatcaata tcactgtgtg gcttcaggcc gccatccact gcggagccgt acaaatgtac   9780
ggccagcaac gtcggttcga gatggcgctc gatgacgcca actacctctg atagttgagt   9840
cgatacttcg gcgatcaccg cttcccccat gatgtttaac tttgttttag gcgactgcc    9900 ctgctgcgta acatcgttgc tgctccataa catcaaacat cgacccacgg cgtaacgcgc   9960
```

```
ttgctgcttg gatgcccgag gcatagactg taccccaaaa aaacagtcat aacaagccat  10020
gaaaaccgcc actgcg                                                 10036
```